United States Patent [19]
Kyotani et al.

[11] Patent Number: 5,576,324
[45] Date of Patent: Nov. 19, 1996

[54] QUINOLINE DERIVATIVES OR SALT THEREOF AND REMEDY FOR CARDIAC DISEASES CONTAINING THE SAME

[75] Inventors: Yoshinori Kyotani, Higashiyamoto; Tadaaki Ohgiya, Higashimurayama; Tsutomu Toma, Higashimurayama; Yuji Kurihara, Higashimurayama; Takahiro Kitamura, Kiyose; Takashi Yamaguchi, Urawa; Kazuhiro Onogi, Iruma; Seiichi Sato, Tokyo; Hiromichi Shigyo, Huchu; Tomio Ohta, Sayama; Mitsuo Kawada, Tokorozawa; Yasumi Uchida, Ichikawa, all of Japan

[73] Assignee: Kowa Co., Ltd., Nagoya, Japan

[21] Appl. No.: 325,270

[22] PCT Filed: Apr. 28, 1993

[86] PCT No.: PCT/JP93/00566

§ 371 Date: Oct. 27, 1994

§ 102(e) Date: Oct. 27, 1994

[87] PCT Pub. No.: WO93/22317

PCT Pub. Date: Nov. 11, 1993

[30] Foreign Application Priority Data

May 1, 1992 [JP] Japan ................................. 4-112862

[51] Int. Cl.[6] .................... A61K 31/44; C07D 491/04
[52] U.S. Cl. ................... 514/291; 546/89; 546/90
[58] Field of Search .................... 546/89, 90; 514/291

[56] References Cited

PUBLICATIONS

Chemical Abstracts, vol. 106, No. 21, May 25, 1987, AN 176374w, JP-A-61 267588, Nov. 27, 1986, p. 728.

*Primary Examiner*—Alan L. Rotman
*Attorney, Agent, or Firm*—Olbon, Spivak, McClelland, Maier, & Neustadt, P.C.

[57] ABSTRACT

A quinoline derivative represented by general formula (1), a medicinally acceptable salt thereof, and a remedy for cardiac diseases containing the same:

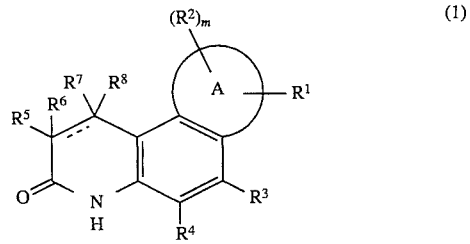

[wherein ring A represents a furan, dihydrofuran or dioxolane ring, and $R^1$ represents an aminoalkyl group].

The compound (1) has a positively inotropic effect on myocardia and an antiarrhythmic effect, and can dilate blood vessels without extremely increasing the heart rate. Therefore, a remedy for cardiac diseases containing the same as the active ingredient is remarkably useful for treating cardiac insufficiency, arrhythmia, and so forth.

7 Claims, No Drawings

QUINOLINE DERIVATIVES OR SALT THEREOF AND REMEDY FOR CARDIAC DISEASES CONTAINING THE SAME

CROSS REFERENCE

This application is a 371 of PCT/JP93/00566, filed Apr. 28, 1993 and published as WO93/22317 Nov. 11, 1993.

TECHNICAL FIELD

The present invention relates to novel quinoline derivatives and medicinally acceptable salts thereof, which have pharmaceutical actions including positive inotropic action, antiarrhythmic action and vasodilating action. The present invention also relates to use of the compounds as medicines.

BACKGROUND ART

Congestive heart failure is a disease in which cardiac output deteriorates because of the malfunction of the heart, outputting only insufficient blood supply for the metabolism of tissue. Recently, J. N. Cohn has described the congestive heart failure as a syndrome caused by failure of the function of the heart which is accompanied by (1) deterioration of motor tolerance capacity, (2) multiple ventricular arrhythmia, and (3) signs indicating unfavorable symptoms (J. N. Cohn: Circulation 78, 1099 (1988)).

To ameliorate the above symptom-complex, diuretic agents, vasodilators, and cardiac tonics such as digitalis have conventionally been employed.

These days, digitalis agents are the most common cardiac tonics. Digoxin, one of the digitalis components, is known to promote the ejection of the heart, thereby preventing the cardiac insufficiency from aggravated. Digoxin has also remarkable advantages in that it lowers the cardiac rate, its effects last long, it does not have drug resistance, and it can be orally dosed. On the other hand, since the effective blood level of digoxin is close to its toxic level, it sometimes induces arrhythmia. Therefore, oral preparations of non-glycoside cardiac tonics have become of interest and, active studies are being made recently.

Accordingly, an object of the present invention is to provide a compound useful for the treatment of heart diseases which is free from the above mentioned drawbacks, and which has positive inotropic action, antiarrhythmic action and vasodilating action.

Under the above mentioned circumstances, the inventors of the present invention have synthesized many compounds, and have carried out screening of the compounds in view of the positive inotropic action, antiarrhythmic action and vasodilating action, and as a result, have found that the novel quinoline derivatives represented by the following formula (1) or their medicinally acceptable salts are suited for the above-mentioned purposes and are useful as medicines for the treatment of heart diseases, leading to completion of the invention.

DISCLOSURE OF THE INVENTION

The present invention provides quinoline derivatives of the following formula (1) and medicinally acceptable salts thereof:

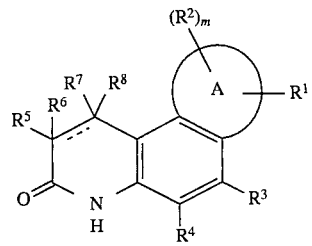

[wherein ring A: a furan ring, a dihydrofuran ring, or a dioxolane ring;

$R^1$: hydroxy, carboxy, alkoxycarbonyl, carbamoyl, alkenyl, formyl, cyano, alkyl which may optionally have a substituent, or a group

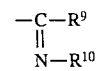

(wherein $R^9$: amino or alkyl, and $R^{10}$: hydrogen or hydroxy);

$R^2$: same or different from each other, and represent hydrogen, alkyl which may optionally have a substituent, alkenyl, acyl, or hydroxy;

$R^3$, $R^4$: same or different from each other, and represent hydrogen, halogen, alkyl which may optionally have a substituent, amino which may optionally have a substituent, alkoxy, alkylthio, carboxy, alkoxycarbonyl, acyl, carbamoyl, cyano, or nitro;

$R^5$, $R^6$, $R^7$, $R^8$: same or different from each other, and represent hydrogen or alkyl;

m: a number from 0 to 3;

----: means that there may be a double bond formed by $R^6$ and $R^8$].

Another object of the present invention is to provide a use of the quinoline derivatives represented by formula (1) and their medicinally acceptable salts.

A further object of the present invention is to provide a therapeutic method for heart diseases characterized by administering the quinoline derivatives represented by formula (1) or their medicinally acceptable salts to a patient suffering from a heart disease.

A still further object of the present invention is to provide a medicine for heart diseases which comprise, as an active component, a quinoline derivative represented by formula (1) or a medicinally acceptable salt thereof.

The quinoline derivatives of formula (1) and their medicinally acceptable salts exhibit positive inotropic action and antiarrhythmic action on heart muscles, and can dilate blood vessels without causing significant increase in the cardiac rate. Accordingly, medicines containing the derivatives or salts as active components are very useful for the treatment of heart diseases such as cardiac insufficiency and arrhythmia.

BEST MODE FOR CARRYING OUT THE INVENTION

In the formula (1), ring A represents a furan ring, a dihydrofuran ring, or a dioxolane ring. Although the rings take several structures according to the position of oxygen atoms which constitute the rings, the following five structures are preferable:

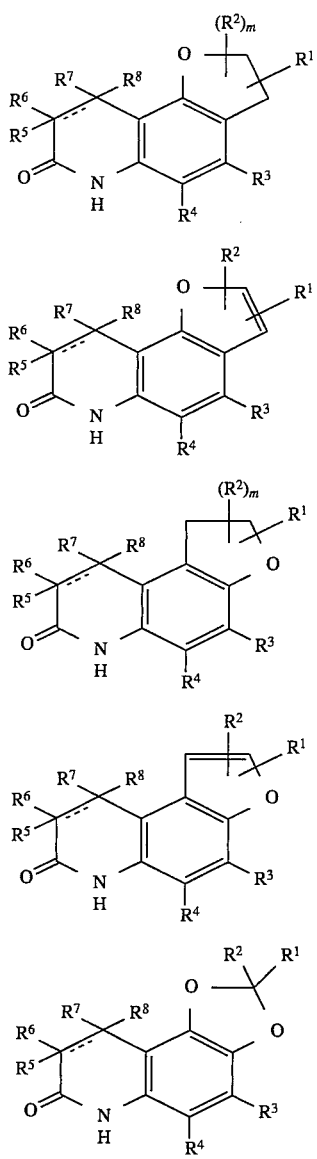

[wherein $R^1, R^2, R^3, R^4, R^5, R^6, R^7, R^8$, and m have the same meaning as defined hereinbefore].

In formula (1), the alkyl groups have 1 to 8, preferably 1 to 5 carbon atoms, and linear, branched or cyclic. The alkenyl groups have 2 to 8, preferably 2 to 5 carbon atoms, and linear or branched. The alkoxy groups have 1 to 8, preferable 1 to 5 carbon atoms, and linear or branched. The halogen atoms are fluorine, chlorine, bromine or iodine. The acyl groups are C1-C6 alkanoyl and aloyl groups such as benzoyl. The alkylthio groups have 1 to 8, preferably 1 to 5 carbon atoms. The alkoxycarbonyl groups have 2 to 9, preferably 2 to 6 carbon atoms, and linear or branched.

Examples of the substituents of "the alkyl which may optionally have a substituent" represented by $R^1$ include halogen, hydroxy, alkoxy which may have a substituent, alkylthio which may have a substituent, acyloxy, alkylsulfonyl, alkylsulfonyloxy, nitroxy, azido, cyano, thiocyanato, amino which may have a substituent, and cyclic amino which may have a substituent. Examples of the alkyl groups which may have substituents include halogenoalkoxy, aminoalkoxy, monoalkyl aminoalkoxy, dialkyl aminoalkoxy, and alkoxy. Examples of the alkylthio groups which may have substituents include halogenoalkylthio, aminoalkylthio, monoalkyl aminoalkylthio, dialkyl aminoalkylthio, and alkylthio. Examples of the acyloxy groups include aroyloxy groups such as C1-C6 alkanoyloxy and benzoyloxy. The alkylsulfonyl groups preferably have 1 to 8, more preferably 1 to 5 carbon atoms. The alkylsulfonyloxy groups preferably have 1 to 8, more preferably 1 to 5 carbon atoms. The amino groups which may have substituents are amino groups which have one or two substituents, and selected from the group consisting of alkyl groups which may have substituents, aralkyl groups which may have substituents, acyl groups which may have substituents, alkoxycarbonyl groups, aryl groups which may have substituents, heterocyclic groups which have substituents,

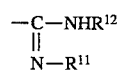

wherein $R^{11}$ is hydrogen or cyano, and $R^{12}$ is hydrogen or alkyl, and —CH=NH. Examples of the cyclic amino groups which may have substituents include pyrrole, pyrrolidine, imidazoline, oxazole, oxazoline, thiazole, thiazoline, piperidine, piperazine and morpholine.

Examples of $R^1$s which are more preferred include hydroxy, carboxy, C2-C6 alkoxycarbonyl, carbamoyl, C2-C5 alkenyl, formyl, cyano, C1-C5 alkyl, C1-C5 halogenoalkyl, C1-C5 hydroxyalkyl, C1-C5 aminoalkyl, C2-C10 mono- or di-alkylaminoalkyl, C2-C10 alkoxyalkyl, C2-C10 hydroxyalkoxyalkyl, C2-C10 aminoalkoxyalkyl, C3-C15 mono- or di- alkylaminoalkoxyalkyl, C2-C10 alkylthioalkyl, C2-C10 halogenoalkylthioalkyl, C2-C10 aminoalkylthioalkyl, C3-C15 mono- or di- alkylaminoalkylthioalkyl, C2-C10 alkanoyloxyalkyl, C2-C10 alkylsulfonylalkyl, C2-C10 alkylsulfonyloxyalkyl, C1-C15 nitroxyalkyl, C1-C5 azidoalkyl, C1-C5 cyanoalkyl, C2-C6 thiocyanato alkyl, C1-C5 aminoalkyl, C2-C10 alkylaminoalkyl, C9-C30 aralkylaminoalkyl, acylaminoalkyl, alkoxycabonylaminoalkyl, arylaminoalkyl, heteroarylaminoalkyl, substituted pyrrolylalkyl, substituted pyrrolydinylalkyl, substituted imidazolylalkyl, substituted oxazolylalkyl, substituted oxazolynylalkyl, substituted thiazolylalkyl, substituted thiazolynylalkyl, substituted piperidinylalkyl, substituted piperazinylalkyl, and substituted morpholinoalkyl.

Groups which may be substituted for the alkyl group of $R^2$ include halogen, hydroxy, amino, mono- or di- alkylamino. Examples of R2s which are preferred include hydrogen, C1-C5 alkyl, C1-C5 halogenoalkyl, C1-C5 aminoalkyl, C2-C10 mono- or di- alkylaminoalkyl, C2-C5 alkenyl, C1-C5 alkanoyl and hydroxy.

In groups $R^3$ and $R^4$, examples of the alkyl groups which may have substituents include alkyl, halogenoalkyl, aminoalkyl, mono- or di- alkylaminoalkyl, and arylalkyl. In these groups of $R^3$ and $R^4$, examples of the amino groups include alkylamino, alkoxycarbonylamino, acylamino, and alkylsulfonylamino.

In formula (1), m is a number from 0 to 3. Preferably, m is 0, 1 or 2.

Examples of the medicinally acceptable salts of the compounds (1) of the present invention include acid addition salts obtained from the use of inorganic or organic acids such as hydrochloric acid, sulfuric acid, nitric acid, fumaric acid, tartaric acid, maleic acid, and succinic acid; alkali metal salts such as sodium salts or potassium salts of carboxyl groups; and alkaline earth metal salts such as calcium salts and magnesium salts.

The compounds (1) of the present invention have optical isomers due to the presence of asymmetric carbon atoms. Optically active compounds and racemic compounds are also part of the present invention. Of course, the present invention encompasses stereochemical isomers.

The compounds (1) of the present invention can be prepared, for example, by the following methods.

[Method 1]

Synthesis (1) of a compound having structure (1a):

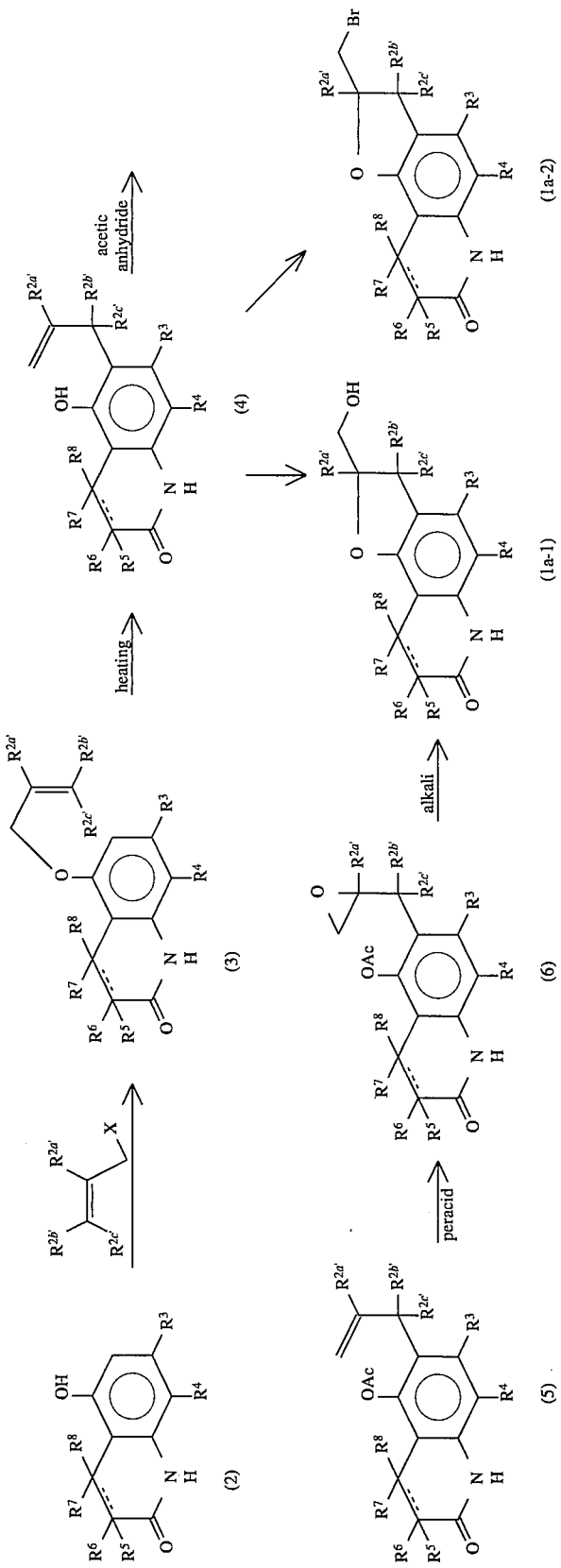

[wherein $R^{11}$ represents hydrogen or lower alkyl, $R^{2a'}$, $R^{2b'}$ and $R^{2c'}$ are the same or different from each other, and each independently represent hydrogen, alkenyl or alkyl which may have a substituent, $R^3$, $R^4$, $R^5$, $R^6$, $R^7$ and $R^8$ have the same meaning as defined herein above, Ac represents acetyl, and X represents halogen].

In this method, quinoline (2) is allowed to react with an allyl halide to obtain compound (3). Compound (3) is heated to undergo Claisen rearrangement, and then allowed to react with acetic acid, obtaining compound (5). Reaction with an peracid yields an epoxy compound (6), which is processed with an alkali to obtain the compound (1a-1) of the present invention. The compound (1a-1) may be directly obtained from the oxidation of compound (4) with an peracid. When a halogenating agent such as N-bromosuccinimide is interacted with compound (4), the compound (1a-2) of the present invention can be prepared.

[Method 2]

Synthesis (2) of a compound having structure (1a):

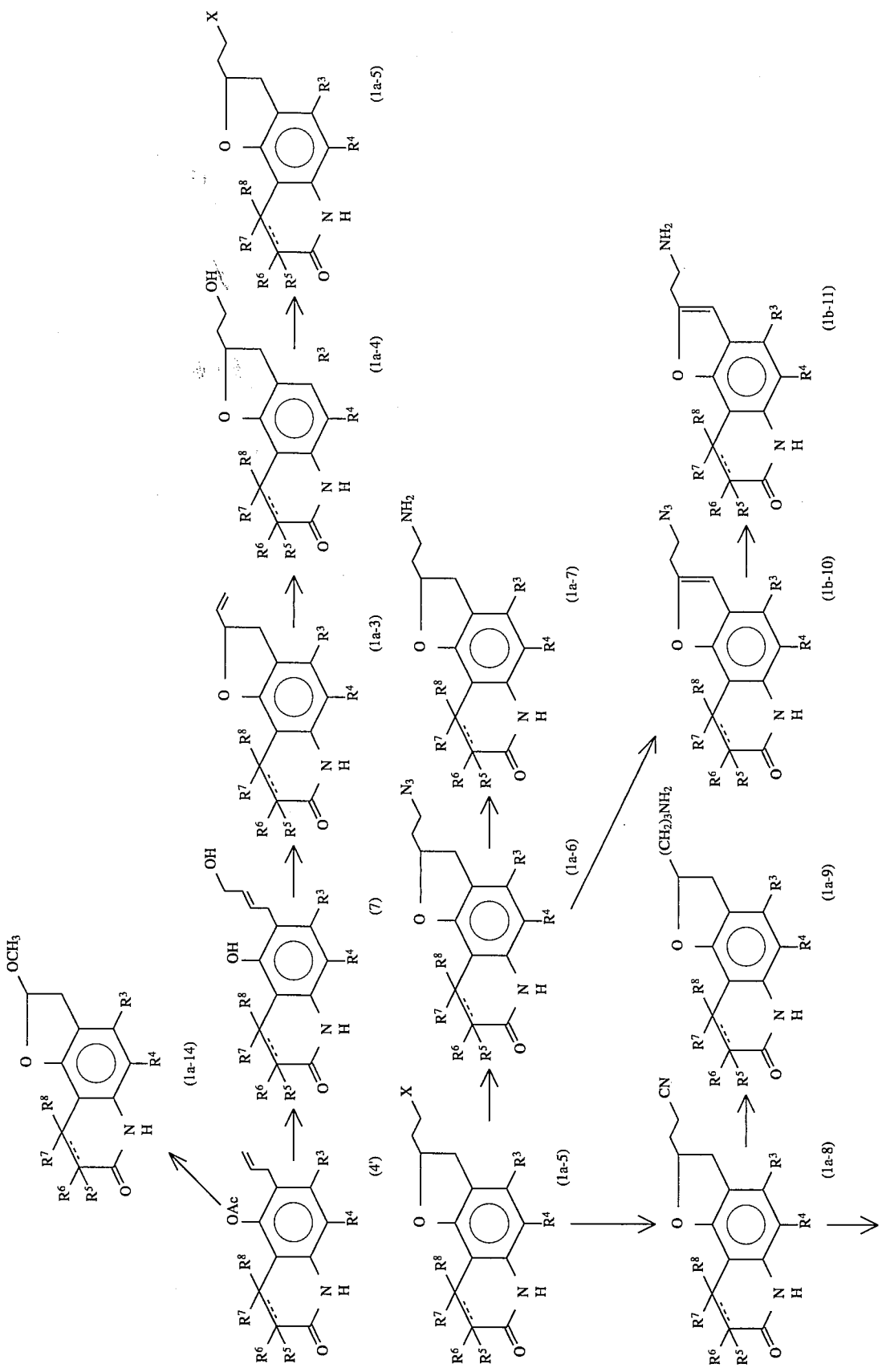

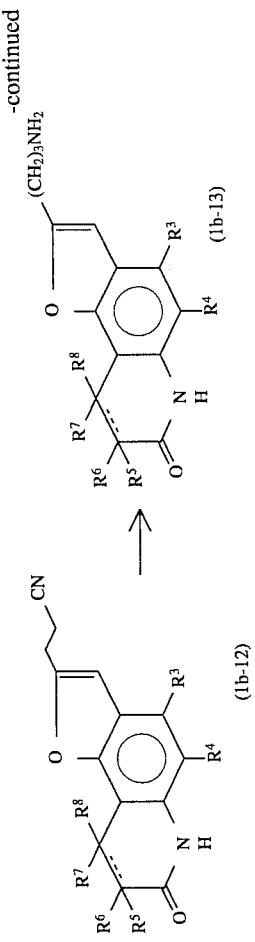

[wherein $R^3$, $R^4$, $R^5$, $R^6$, $R^7$, $R^8$, X and Ac have the same meaning as defined herein above].

In this method, compound (4') is oxidized with ozone, allowed to react with methyl(triphenylphosphoranilidene)-acetate, and then reduced with diisobutylaluminum hydride to obtain compound (7). Compound (7) is cyclized in the presence of a Lewis acid into compound (1a-3), which undergoes hydroboronizing-oxidizing reaction to be converted into compound (1a-4). This compound (1a-4) is halogenated and interacted with an azide into compound (1a-6), which is then reduced to compound (1a-7). If compound (1a-5) is cyanized, compound (1a-8) is obtained, and reduction of compound (1a-8) yields compound (1a-9). Dehydrogenation of compound (1a-6) results in compound (1b-10), and reduction of compound (1b-10) results in compound (1b-11). Dehydrogenation of compound (1a-8) results in compound (1b-12), and reduction of compound (1a-12) results in compound (1b-13).

In the reaction from compound (4') to compound (7), if methanol is used as a solvent, compound (1a-14) is by-produced. Separation of this byproduct and compound (7) can be performed by a conventional method such as recrystallization.

[wherein $R^3$, $R^4$, $R^5$, $R^6$, $R^6$, $R^8$, and Ac have the same meaning as defined herein above].

In this method, compound (2') is allowed to react with trans-1,4-dichloro-2-butene to obtain compound (8), which is acetoxylated, and undergoes a Claisen rearrangement and hydrolysis to obtain compound (10). When compound (10) is cyclized, compound (1a-15) is obtained. Compound (1a-15) is oxidized to cleave, and then reduced to obtain compound (1a-17). Compound (1a-17) is interacted with an azide to compound (1a-18), which is reduced to obtain compound (1a-19). Dehydrogenation of compound (1a-18) results in compound (1b-20), and reduction of compound (1a-20) results in compound (1b-21).

[Method 3]

Synthesis (3) of a compound having structure (1a):

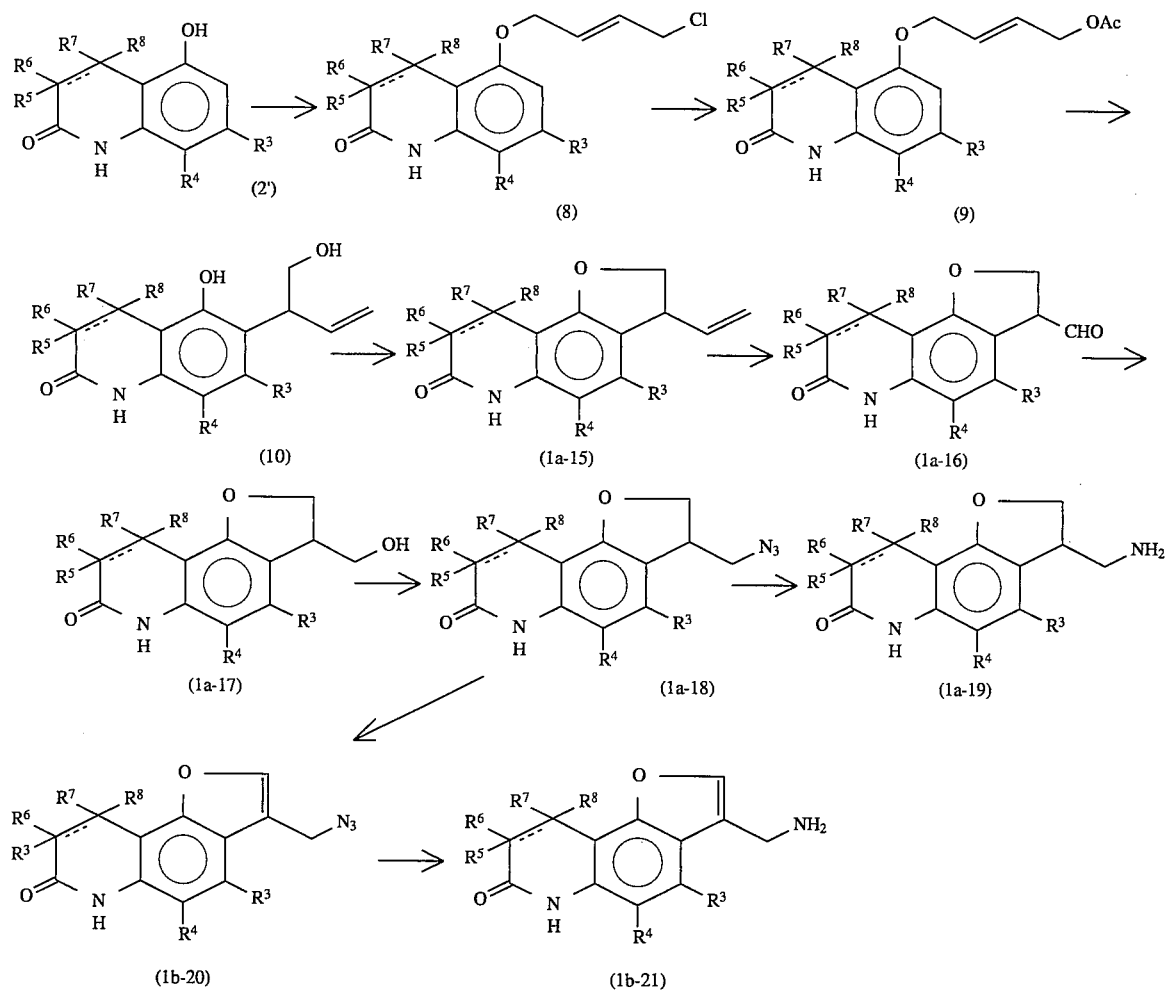

[Method 4]

Synthesis (4) of a compound having structure (1a):

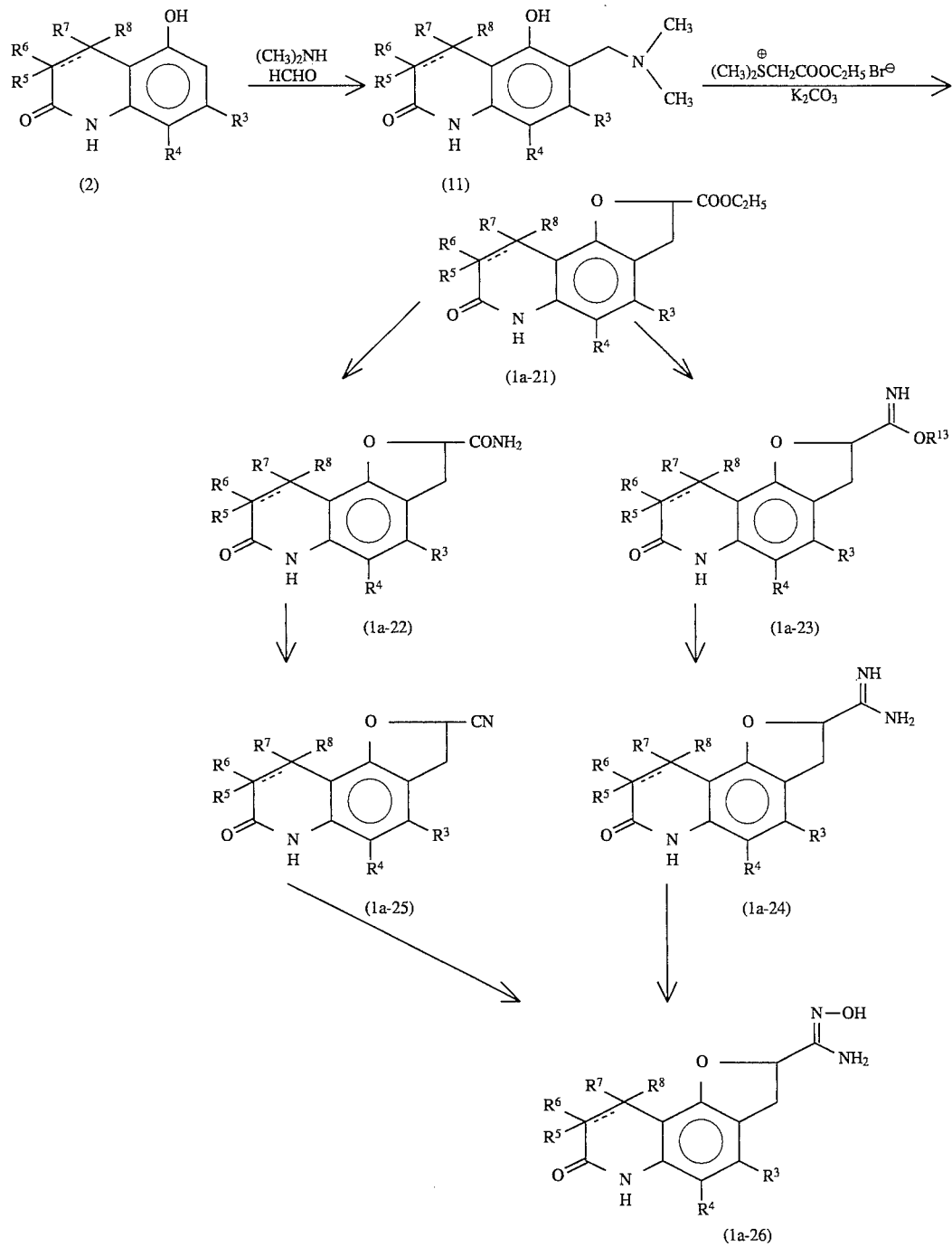

[wherein $R^{13}$ represents alkyl, and $R^3$, $R^4$, $R^5$, $R^6$, $R^7$ and $R^8$ have the same meaning as defined herein above].

In this method, compound (2) is allowed to react with dimethylamine and formaldehyde to obtain compound (11), which is cyclized by interacting with ethyl dimethylthioacetate in the presence of potassium carbonate to yield compound (1a-21). This compound (1a-21) can be converted into compounds (1a-22), (1a-23), (1a-24), (1a-25), and (1a-26).

[Method 5]

Synthesis of a compound having structure (1b):

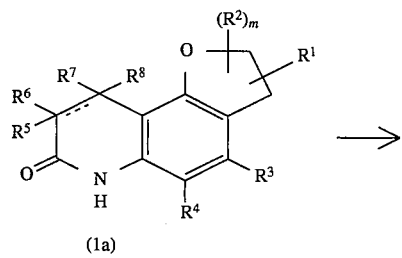

(1a)

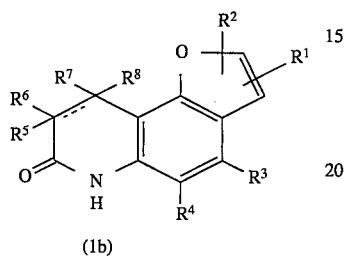

(1b)

[wherein $R^1$, $R^2$, $R^3$, $R^4$, $R^5$, $R^6$, $R^7$ and $R^8$ have the same meaning as defined herein above].

In this method, compound (1a) is allowed to react with a dehydrogenation reagent such as 2,3-dichloro-5,6-dicyano-1,4-benzoquinone (DDQ), during which a double bond is introduced into the ring A, resulting in compound (1b). In the case where groups which may be affected by dehydrogenation are present at $R^1$, $R^2$, etc., they are protected before dehydrogenation is performed, and the protective groups are eliminated after the dehydrogenation reaction.

[Method 6]

Synthesis of a compound having structure (1c) or (1d):

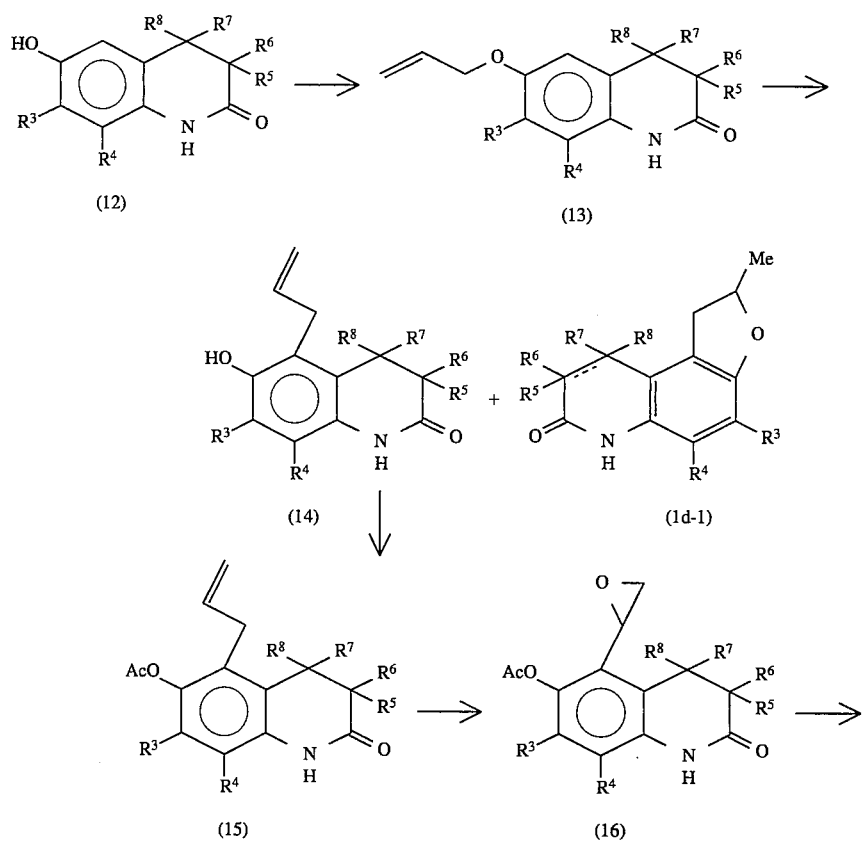

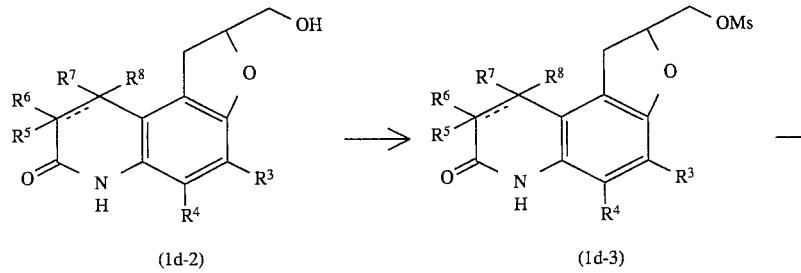

(1d-2) → (1d-3)

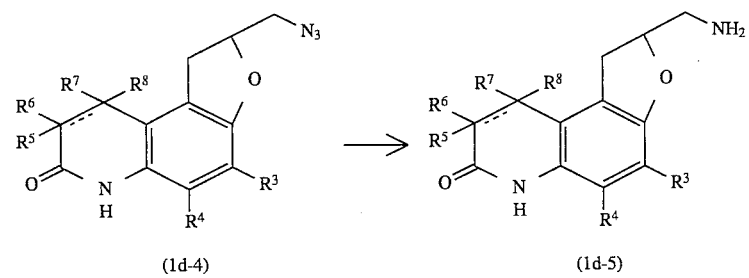

(1d-4) → (1d-5)

[wherein $R^3$, $R^4$, $R^5$, $R^6$ and $R^7$ have the same meaning as defined herein above].

In this method, compound (12) is allowed to react with allylhalide to yield compound (13), followed by a Claisen rearrangement to obtain 5-allyl compound (14). When solvents are not used at the time of the rearrangement reaction, a tricyclic compound (1d-1) is by-produced. Acetic anhydride is reacted with the 5-allyl compound (14), obtaining acetyl compound (15), which is interacted with an peracid to obtain an epoxy compound (16). The epoxy compound (16) is subjected to a ring closure with an alkali, thereby obtaining compound (1d-2). Compound (1d-2) is mesylated, and then interacted with a sodium azide to obtain compound (1d-5).

[Method 7]

Synthesis of a compound having structure (1e):

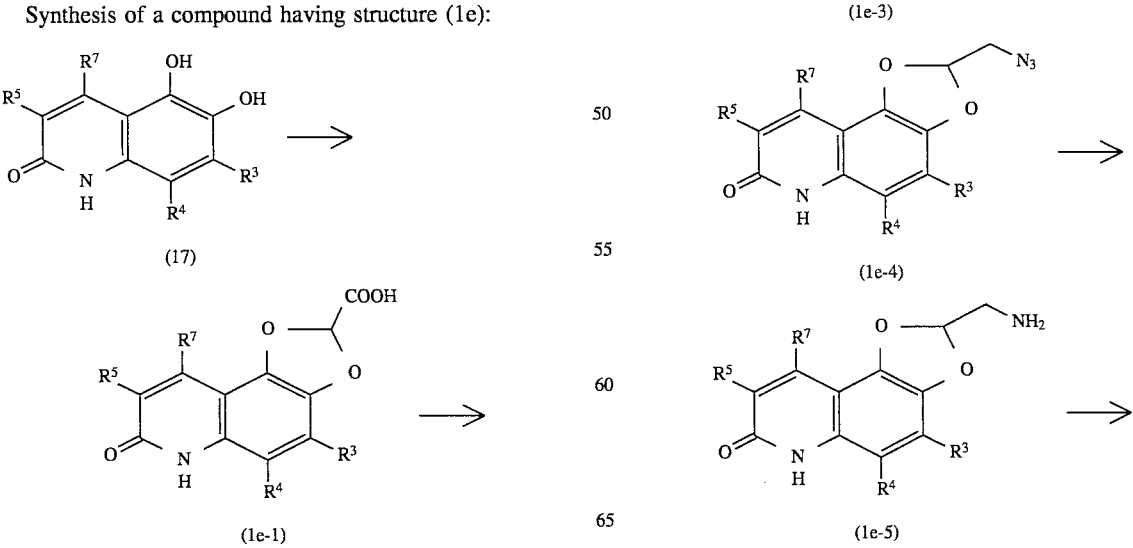

-continued

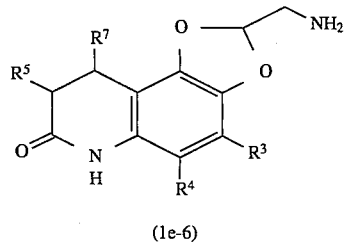

(1e-6)

[wherein Ms represents alkanesulfonyl, and $R^3$, $R^4$, $R^5$ and $R^7$ have the same meaning as defined herein above].

In this method, dihydrocarbostyril (17) is allowed to react with methyldichloroacetate to obtain compound (1e-1). Compound (1e-1) is reduced to obtain compound (1e-2), which is mesylated, interacted with an azide, and then reduced to obtain compound (1e-5). Reduction of compound (1e-5) results in compound (1e-6).

[Method 8]

Synthesis of dihydroquinoline from quinoline:

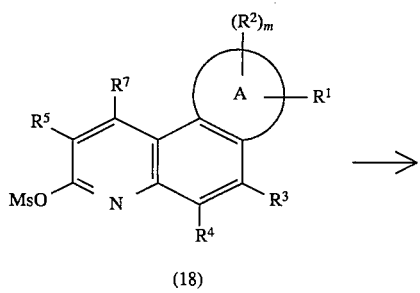

(18)

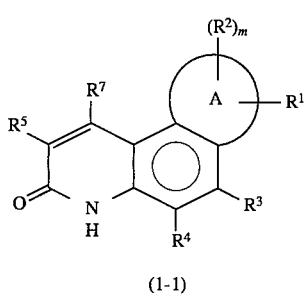

(1-1)

[wherein Ms represents alkanesulfonyl, and $R^1$, $R^2$, $R^3$, $R^4$, $R^5$ $R^7$ m and A have the same meaning as defined herein above].

A quinoline (18) is heated in the presence of a N-fluoro-3,5-dichloropyridinium salt, dihydroquinoline (1-1) can be obtained.

[Method 9]

Synthesis of tetraquinoline ring:

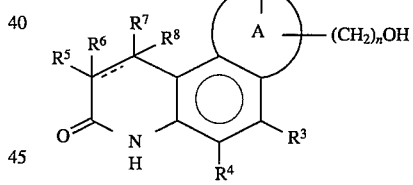

(1-1)

(1-2)

[wherein A, $R^1$, $R^2$, $R^3$, $R^4$, $R^5$, R7, and m have the same meaning as defined herein above].

A dihydroquinoline (1-1) is hydrogenated in the presence of a catalyst such as palladium, tetrahydroquinoline (1-2) can be obtained.

[Method 10]

Conversion (1) of substituent $R^1$:

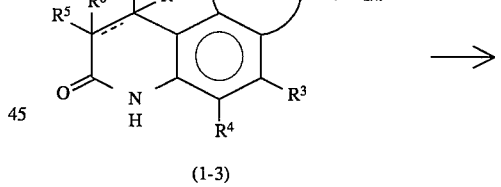

(1-3)

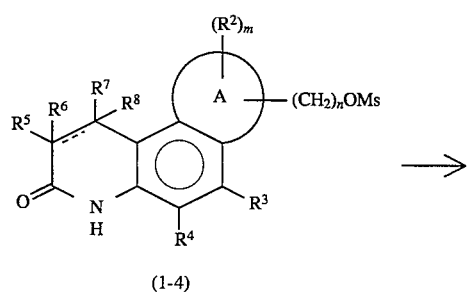

(1-4)

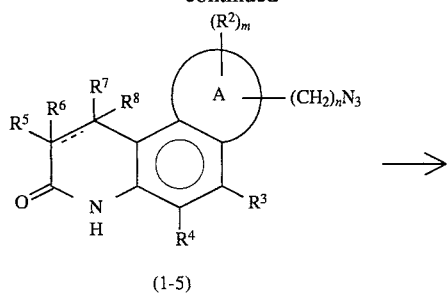

(1-5)

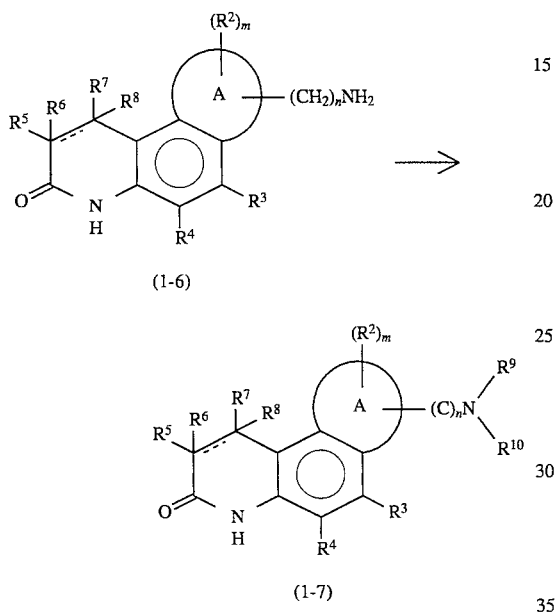

(1-6)

(1-7)

[wherein n is a number from 1 to 5, Ms is alkanesulfonyl, at least one of $R^9$ and $R^{10}$ represent alkyl or acyl which may have a substituent, and the remainder represents hydrogen, A, $R^1$, $R^2$, $R^3$, $R^4$, $R^5$, $R^6$, $R^7$, $R^8$ and m have the same meaning as defined herein above].

Compound (1-3) is interacted with alkanesulfonic halide into compound (1-4), which is interacted with an azide and reduced to obtain compound (1-6). When the amine compound (1-6) is N-alkylated or N-acylated, compound (1-7) can be obtained.

[Method 11]

Conversion (2) of substituent $R^1$:

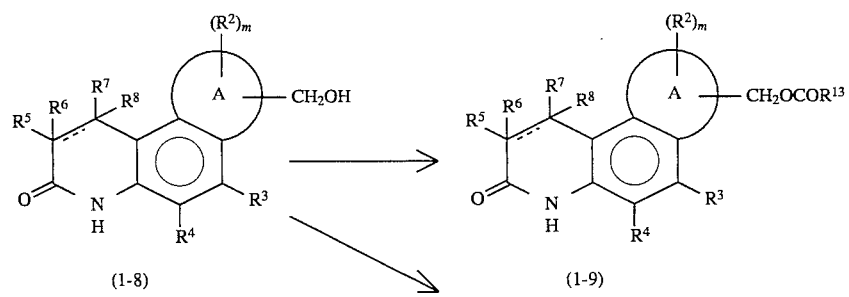

(1-8)    (1-9)

-continued

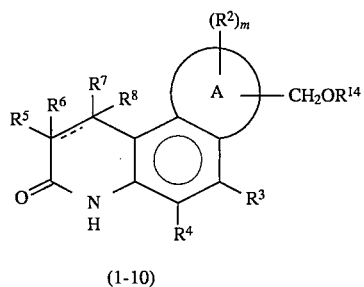
(1-10)

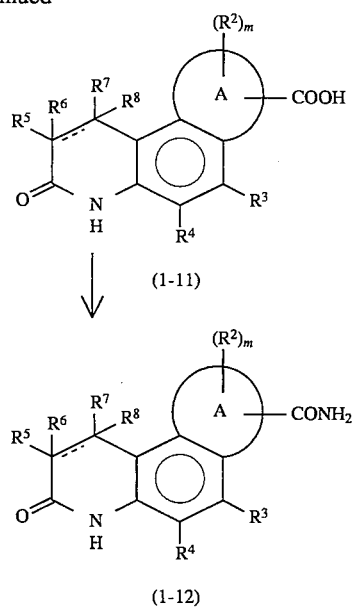
(1-11)

(1-12)

[wherein $R^{13}$ is alkyl which may have a substituent, $R^{14}$ is alkyl which may have a substituent, and $R^2$, $R^3$, $R^4$, $R^5$, R6, $R^7$, $R^8$, A and m have the same meaning as defined herein above].

Interaction between compound (1-8) and an acylating agent such as carboxylic anhydride and carboxylic halide yields compound (1-9). Interaction between compound (1-8) and an alkylating agent such as diazoalkane yields compound (1-10). Oxidation of compound (1-8) results in a carboxylic acid (1-11), which is reacted with an amide to obtain compound (1-12).

[Method 12]

Conversion (3) of substituent $R^1$:

[wherein n is a number from 1 to 5, Ms is alkanesulfonyl, X is a halogen atom, $R^{15}$ is amino which may have a substituent or cyclic amino which may have a substituent, $R^2$, $R^3$, $R^4$, $R^5$, $R^6$, $R^7$, $R^8$, m and A have the same meaning as defined herein above].

Interaction between compound (1-3) and an alkanesulfone halide yields compound (1-4). When compound (1-3) or compound (1-4) is reacted with a halogenating agent such as alkali halide, compound (1-13) is obtained. Reaction between compound (1-4) or compound (1-13) and various amines yields amine-containing compounds such as compound (1-14).

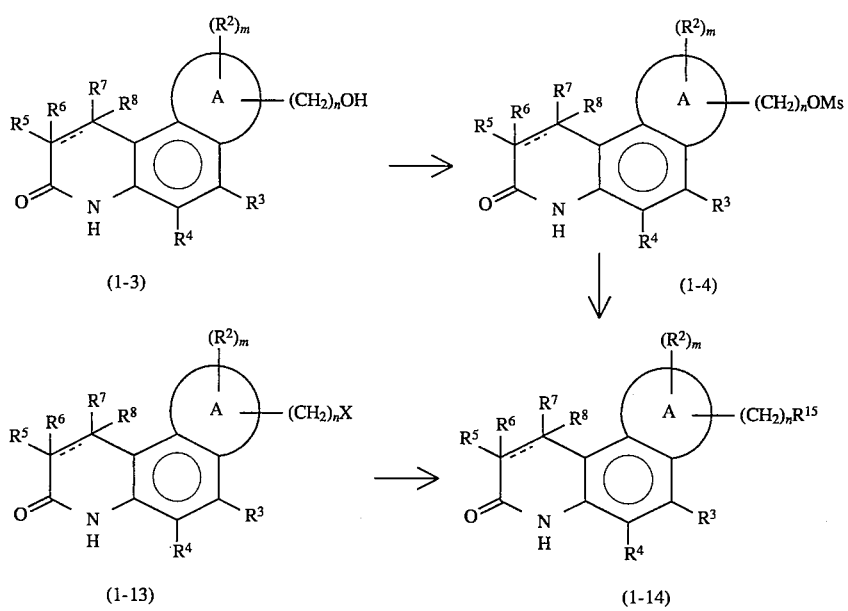

In order to convert $R^2$, $R^3$, $R^4$, $R^5$, or $R^6$ into various substituents, numbers of methods employed in halogenation, cyanization, hydrolysis, oxidation, reduction, etc. may be utilized in accordance with the purposes.

Resolution of the optically active compounds of compound (1) of the present invention may be performed by a method wherein an optical resolution agent is interacted with a racemic compound, and difference in solubility is used for resolution, or by a method wherein a column for separating optical isomers is used.

The thus obtained compounds (1) of the present invention or their medicinally acceptable salts possess excellent antiarrhythmic action, cardiotonic action, and vasodilating action as shown by Test Examples described herein later. Acute toxicity of the compounds investigated by orally dosing the present compounds (1) or their medicinally acceptable salts to rats revealed that the compounds of the present invention have high $LD_{50}$ values (400–1000 mg/kg when orally dosed), proving high safety of the compounds.

Accordingly, the compounds and their medicinally acceptable salts of the present invention are useful as medicines for the treatment of various heart diseases typified by arrhythmia and cardiac insufficiency.

The medicinal compositions according to the present invention comprise the compounds (1) or their medicinally acceptable salts as active components, and carriers for pharmaceutical use as desired, and are prepared by ordinary methods into various formulations such as tablets, powders, capsules, injections, etc. Generally, the compositions of the invention are administered to patients in need thereof orally, subcutaneously, intramuscularly or intravenously.

The dose of the compounds (1) or their medicinally acceptable salts of the present invention is generally from 1 mg to 1 g per day for an adult when it is orally dosed.

EXAMPLES

The present invention will now be described in more detail by way of examples, which should not be construed as limiting the invention.

Reference Example 1:

a) 5-Hydroxy-8-methylcarbostyril:
i) 2-Amino-4-ethoxytoluene:

4-Ethoxy-2-nitrotoluene[1] (10 g, 55.2 mmol) was dissolved in acetic acid (100 ml). To the obtained solution, 10% palladium-on-carbon (3 g) was added, and the mixture was stirred at room temperature in the atmosphere of hydrogen for 2 hours. The catalyst was removed by filtration, and the solution was condensed. Saturated aqueous sodium bicarbonate solution was added to the residue to convert the pH to alkaline, followed by extracting with chloroform. The extract was dried and condensed. As a result, 8.34 g (quantitative yield) of 2-amino-4-ethoxytoluene was obtained as a pale brown oil.

IR(Cap): 3365, 2965, 2930, 1617, 1582, 1508, 1476, 1314, 1281, 1211, 1180, 1138, 1111, 1040 cm$^{-1}$.

$^1$H-NMR(CDCl$_3$)δ: 1.37(3H,t,J=7.1Hz), 2.09(3H,s), 3.52(2H,br), 3.96(2H,q,J=7.1Hz), 6.23–6.31(2H,complex m), 6.92(1H,dd, J=9.3,0.8Hz).

1): Synthesized according to the method described in K. Shibuya, Y. Takahashi, H. Shigyo and T. Ohta; Heterocycles 29, 2199 (1989).

ii) N-(5-Ethoxy-2-methylphenyl)cinnamamide:

2-Amino-4-ethoxytoluene (8.34 g, 55.2 mmol) and pyridine (5.23 g, 66.2 mmol) were dissolved in acetone (150 ml). Cinnamoylchloride (10.15 g, 61.0 mmol) was added to the solution while stirring and cooling. Then the mixture was stirred at room temperature overnight. The solvent was condensed, and dissolved in chloroform, followed by washing, drying and condensing. The resultant residue was purified by alumina column chromatography (eluent:chloroform), and recrystallized (chloroform-n-hexane) to obtain 13.0 g of pale yellow crystals (88.9%).

IR(KBr): 3258, 1654, 1629, 1583, 1533, 1490, 1455, 1446, 1338, 1308, 1270, 1215, 1110, 1046, 963 cm$^{-1}$.

$^1$H-NMR(CDCl$_3$)δ: 1.40(3H,t,J=7.1Hz), 2.25(3H,s), 4.04(2H,q,J=7.1Hz), 6.57(1H,d,J=15.6Hz), 6.66(1H,m), 7.04–7.14(2H,complex m), 7.35–7.44(3H,complex m), 7.50–7.60(2H,complex m), 7.77(1H,d,J=15.6Hz).

iii) Synthesis of 5-hydroxy-8-methylcarbostyril:

Chlorobenzene (28.6 ml) was added to N-(5-ethoxy-2-methylphenyl)cinnamamide (3.9 g, 14.8 mmol). While stirring the mixture in a hot bath (125° C.), aluminum chloride (9.2 g, 69.0 mmol) was added to the mixture, followed by stirring for 30 minutes. After the mixture was cooled, it was poured into ice-water, to which n-hexane was added. Precipitated crystals were collected. The crystals were dissolved in chloroform-methanol (4:1). The solution was dried and condensed. The resultant residue was washed with chloroform, then dissolved in chloroform-methanol (4:1) again. The solution was condensed again. The residue was washed with chloroform and then dissolved in methanol. The resultant solution was treated with activated carbon. 2.4 g of 5-hydroxy-8-methylcarbostyril was obtained as colorless crystals (92.7%).

IR(KBr): 3125, 1640, 1631, 1612, 1564, 1500, 1445, 1384, 1348, 1272, 1238, 1135, 1066, 844, 803 cm$^{-1}$.

$^1$H-NMR(CDCl$_3$:CD$_3$OD:3:1)δ: 2.38(3H,s), 6.61(1H,d, J=9.6Hz), 6.62(1H,d,J=8.1Hz), 7.21 (1H, d, J=8.1Hz), 8.35(1H,d,J=9.6Hz).

b) 7-n-Hexyl-5-hydroxycarbostyril:

A suspension of 3-hydroxy-5-n-hexyl-2-cyclohexene-1-one (29.7 g) in toluene (200 ml) was combined with conc. ammonia water (100 ml), and the mixture was stirred at 130° C. for 3.5 hours in an apparatus equipped with a water separator. After completion of the reaction, ether was added. The precipitate was collected by filtration, and was recrystallized from a solvent mixture of chloroform-ether. 17.0 g of 3-amino-5-n-hexyl-2-cyclohexene-1-one was obtained as pale yellow needles having a melting point of 113° C. (57.5%).

A. Focella, S. Teitle and A. Brossi: J. Org. Chem., 42, 3456 (1977).

The obtained 3-amino-5-n-hexyl-2-cyclohexene-1-one (16.8 g) and acrylic acid (12.4 g) were mixed, and the mixture was stirred at 140° C. for 2 hours. After completion of the reaction, chloroform was added, and the mixture was washed with sodium bicarbonate water, water and aqueous NaCl solution in this order, followed by drying over sodium sulfate. A crude product was obtained when the solvent was evaporated. The crude was purified by silica gel column chromatography (eluent=chloroform:methanol (50:1)). as a result, 11.2 g of 7-n-hexyl-1,2,3,4,5,6,7,8-octahydroquinoline-2,5-dione was obtained as colorless needles having a melting point of 142°–144° C. (52.0%).

The obtained 7-n-hexyl-1,2,3,4,5,6,7,8-octahydroquinoline-2,5-dione (11.0 g) was suspended in decalin (150 ml). To the suspension, 10% palladium-on-carbon (3.7 g) was added, followed by stirring at 200° C. for 17 hours. After completion of the reaction, the insoluble matter was collected by filtration, washed with ether, then extracted with a solvent mixture of chloroform-methanol (2:1). The extract was dried to solidity under reduced pressure. Recrystallization from methanol yielded 9.56 g of 7-n-hexyl-5-hydroxycarbostyril as colorless needles having a melting point of 252°–255° C. (dec.) (87.9%).

IR(KBr): 1623, 1541, 1462, 1405, 1374, 1348, 1288 cm$^{-1}$.

$^1$H-NMR(DMSO-d$_6$)δ: 9.81(1H,br.s), 7.97(1H,d,J=9.6Hz), 6.57(1H,br.s), 6.43(1H,br.s), 6.30(1H,d,J=9.6Hz), 3.38(1H, s), 1.18 . 2.57(10H,m), 0.87(3H, t,J=6.7Hz).

Reference Example 2:

5-Allyloxy-8-methylcarbostyril:

5-Hydroxy-8-methylcarbostyril (6.35 g, 36.3 mmol), allyl iodide (6.07 g, 36.1 mmol), n-tetrabutylammonium bromide (1.16 g, 36.1 mmol) were dissolved in dimethylformamide (108 ml). To the solution, potassium carbonate (10 g, 72.5 mmol) was added, and stirred in a bath of 50° C. for 2 hours. The solvent was evaporated, and the residue, dissolved in chloroform, was washed with water. The washed material was dried and condensed. The resultant residue was purified by silica gel column chromatography (eluent; chloroform). Recrystallization (chloroform-n-hexane) yielded 4.98 g of 5-allyloxy-8-methylcarbostyril as colorless flakes (63.8%).

mp. 193.5°–195° C. IR(KBr): 3153, 3011, 1639, 1607, 1486, 1444, 1303, 1273, 1233, 1144, 1088, 992, 856, 789 cm$^{-1}$.

$^1$H-NMR(CDCl$_3$)δ: 2.36(3H, s), 4.63(2H,m), 5.33(1H, m), 5.46(1H,m), 6.11(1H,m),6.55(1H,d,J=8.1Hz), 6.60(1H, d,J=9.8Hz), 7.24(1H,dd, J=8.1,0.7Hz), 8.23(1H,d,J=9.8Hz), 9.19(1H,br).

Reference Example 3:

6-Allyl-5-hydroxy-8-methylcarbostyril and 2,5-dimethyl2,3,6,7-tetrahydrofuro[2,3-f]quinoline-7-one:

5-Allyloxy-8-methylcarbostyril (3.9 g, 18.1 mmol) was melted in a bath of 200° C. in the atmosphere of nitrogen, and the temperature (200° C.) was maintained for 1 hour. The melt, after cooled, was dissolved in a solvent mixture of chloroform and methanol (4:1), and the solution was extracted with 2N-NaOH. The aqueous phase was washed with chloroform, and then converted to be acidic by conc. HCl. Extraction was performed with a solvent mixture of chloroform and methanol (4:1), followed by drying and condensing. 3.4 g of a crude 6-allyl-5-hydroxy-8-methylcarbostyril was obtained as mud yellow crystals. The obtained crystals were purified by silica gel column chromatography (eluent=chloroform:ethyl acetate=1:1), followed by recrystallization with chloroform-methanol-n-hexane. As a result, 2.7 g of a pure 6-allyl-5-hydroxy-8methylcarboxtyril was obtained as colorless crystals (69.2%). Separately, the organic phase extracted with 2N-NaOH and the phase which had been washed with chloroform were dried and condensed, then purified by silica gel column chromatography. Thereafter, the resultant material was recrystallized from chloroform-n-hexane to obtain 1.2 g of 2,5-dimethyl-2,3,6,7-tetrahydrofuro[2,3-f]quinoline-7-one as slightly brown crystals (30.8%).

6-Allyl-5-hydroxy-8-methylcarbostyril:

mp. 179°–180° C. IR(KBr): 3206, 1628, 1558, 1442, 1353, 1295, 1218, 1154, 833 cm$^{-1}$.

$^1$H-NMR(CDCl$_3$:CD$_3$OD:10:1)δ: 2.34(3H,s), 2.58(2H, br.s, NH, OH), 3.43 (2H, d, J=6.1Hz), 5.11 (1H, dd, J=7.6, 1.2Hz), 5.18(1H,t,J=1.6Hz), 6.00(1H,m), 6.57(1H,d,J=9.8Hz), 7.08(1H, s), 8.24(1H,d,J=9.8Hz).

2,5-Dimethyl-2,3,6,7-tetrahydrofuro[2,3-f]quinoline-7-one:

mp. 217°–221° C. IR(KBr): 3160, 2935, 1646, 1568, 1464, 1445, 1881, 852, 815 cm$^{-1}$.

$^1$H-NMR(CDCl$_3$)δ: 1.50(3H,d,J=6.4Hz), 2.34(3H,s), 2.84(1H, dd, J=15.0,7.6Hz), 3.36(1H,dd,J=15.0,9.0Hz), 5.06(1H,m), 6.56(1H,d,J=9.6Hz), 7.11(1H, s), 7.90(1H,d,J=9.6Hz), 8.91(1H,br.s).

Reference Example 4:

5-Acetoxy-6-allyl-8-methylcarbostyril:

To a solution of 6-allyl-5-hydroxy-8-methylcarbostyril (3.2 g, 14.9 mmol) in pyridine (50 ml), acetic acid (3.5 34.3 mmol) was added and stirred at room temperature for hour. The mixture was condensed and dissolved in chloroform. The resultant solution was washed with saturated aqueous sodium bicarbonate solution, aqueous 2N-HCl solution, and water, and dried and condensed. As a result, 3.5 g of 5-acetoxy-6-allyl-8-methylcarbostyril was obtained as colorless crystals (91.4%).

IR(KBr): 3160, 3010, 1749, 1662, 1603, 1445, 1370, 1213, 1145, 1090, 842, 791 cm$^{-1}$.

$^1$H-NMR(CDCl$_3$)δ: 2.42(6H,s), 3.29(2H,m), 5.07(1H,m), 5.14(1H,m), 5.88(1H,m), 6.65(1H,d,J=9.8Hz), 7.23(1H,s), 7.68(1H,d,J=9.8Hz), 9.07(1H,br.s).

Reference Example 5:

5-Acetoxy-6-(2,3-epoxy)propyl-8-methylcarbostyril:

A solution of 5-acetoxy-6-allyl-8-methylcarbostyril (3.5 g, 13.6 mmol) in chloroform (70 ml) was stirred while cooling, to which m-chloroperbenzoic acid (3.85 g, or 19.4 mmol when the purity is 85%) was added, and the mixture was stirred at room temperature overnight. Subsequently, excessive amount of aqueous 15% sodium sulfite solution was added thereto and stirred thoroughly, followed by washing with saturated aqueous sodium bicarbonate solution, drying and condensing. As a result, 3.7 g (quantitative yield) of 5-acetoxy-6-(2,3-epoxy)propyl-8-methylcarbostyril was obtained as colorless crystals.

IR(KBr): 3160, 3035, 3000, 1743, 1664, 1600, 1447, 1368, 1219, 840 cm$^{-1}$.

$^1$H-NMR(CDCl$_3$)δ: 2.43(3H, s), 2.46(3H,s), 2.54(1H,m), 2.75–2.83(3H,complex m), 3.11(1H,m), 6.67(1H,d,J=9.8Hz), 7.33(1H,s), 7.67(1H,d,J=9.8Hz), 9.07(1H,br.s).

Example 1:

2-Hydroxymethyl-5-methyl-2,3,6,7-tetrahydrofuro[2,3-f]quinoline-7-one:

Aqueous 1N-NaOH solution (41.6 ml) was added to a suspension of epoxy compound (5.7 g, Reference Example 5) in dimethylformamide (125 ml) in the atmosphere of nitrogen, and the mixture was stirred at 50° C. for 50 minutes. Subsequently, the mixture was cooled, and conc. HCl was added to the mixture, followed by condensing under reduced pressure. Water was added to the residue, and precipitated crystals were collected by filtration. When the collected crystals were washed and dried, 2.8 g of the target compound was obtained. Further, the mother liquid was extracted from a solvent mixture of chloroform and methanol (5:1) to obtain 1.1 g of the target compound (yield: 81.3%).

This product was recrystallized from chloroform-methanol-n-hexane, obtaining colorless powdery crystals having a melting point of 240°–242° C.

IR(KBr): 3393, 3259, 3036, 1664, 1643, 1613, 1966, 1050, 829 cm$^{-1}$.

¹H-NMR(CDCl₃, CD₃OD)δ: 8.02(1H,d,J=9.7Hz), 7.19(1H, s), 6.55(1H,d,J=9.7Hz), 5.13–4.96(1H,m), 3.90–3.80(2H,m), 3.20–3.10(1H,m), 3.11(1H,dd,J=7.8, 14.4Hz), 2.37(3H, s).

Example 2:

2-Hydroxymethyl-5-methyl-2,3,6,7-tetrahydrofuro[2,3-f]quinoline-7-one:

Chloroform (1.5 ml) was added to a mixture of 5-hydroxy-6-allyl-8-methylcarbostyril (50.6 mg) and m-chloroperbenzoic acid (61.5 mg). The obtained mixture was stirred at 50° C. for 17 hours. Excessive aqueous sodium sulfite solution was added thereto, and stirring was continued at room temperature for 30 minutes, followed by extracting with a solvent mixture of chloroform and methanol (4:1). The organic phase was dried over sodium sulfate, and condensed. The resultant residue was purified by thin layer chromatography (solvent=chloroform:methanol=10:1), obtaining 20.6 mg of 2-hydroxymethyl-5-methyl-2,3,6,7-tetrahydrofuro[2,3-f]quinoline-7-one (37.9%).

Example 3:

2-Methanesulfonyloxymethyl-5-methyl-2,3,6,7-tetrahydrofuro[2,3-f]quinoline-7-one:

2-Hydroxymethyl-5-methyl-2,3,6,7-tetrahydrofuro[2,3-f]quinoline-7-one (1.2 g) was added to anhydrous pyridine (24 ml). The mixture was stirred on ice, during which methanesulfonylchloride (625 mg) was added thereto, followed by stirring at room temperature for 100 minutes. Methanesulfonylchloride (283 mg) was added again and stirred at the same temperature for 50 minutes. After completion of the reaction, a small amount of ethanol was added, and the mixture was brought to dryness under reduced pressure. The residue was dissolved in a solvent mixture of chloroform and methanol (10:1), washed with diluted HCl, sodium bicarbonate water, and aqueous NaCl solution in this order, and dried. When the solvent was evaporated, 1.6 g (quantitative assay) of the title compound was obtained. This substance was recrystallized from a solvent mixture of chloroform-n-hexane, obtaining colorless powdery crystals having a melting point of 200°–203° C.

IR(KBr): 3369, 1651, 1464, 1350, 1171, 1083, 975, 836 cm⁻¹.

¹H-NMR(CDCl₃)δ: 9.10(1H,br.s),7.88(1H,d,J=9.5Hz), 7.14(1H, s), 6.59(1H,d,J=9.5Hz), 5.20(1H,m), 4.50–4.40(1H,m), 3.41(1H,dd, J=8.9,15.9Hz), 3.20–3.15(1H,m), 3.06(3H, s), 2.36(1H, s).

Example 4:

2-Azidomethyl-5-methyl-2,3,6,7-tetrahydrofuro[2,3-f]quinoline-7-one:

A mesyl compound (Example 3, 1 g) and sodium azide were added to dimethylformamide (20 ml), and the mixture was stirred at 100° C. for 50 minutes. After completion of the reaction, pressure was reduced to concentrate the mixture. The concentrate was diluted with a solvent mixture of chloroform and methanol (5:1), washed with water, and dried. When the solvent was evaporated, 759 mg of the title compound was obtained (91.6%). This substance was recrystallized from a solvent mixture of chloroform-n-hexane, obtaining yellow powdery crystals having a melting point of 192°–194° C.(dec.).

IR(KBr): 3156, 2085, 1629, 1449, 1331, 1271, 1153, 1084, 828, 637, 487 cm⁻¹.

¹H-NMR(CDCl₃)δ: 9.10(1H,br.s), 7.92(1H,d,J=9.7Hz), 7.14(1H,s), 6.59(1H,d,J=9.7Hz), 5.15(1H,m), 3.52(2H,d,J= 5.5Hz), 3.43–3.33(1H,m), 3.04(1H,dd, J:15.4,6.8Hz), 2.36(3H, s).

Example 5:

2-Aminomethyl-5-methyl-2,3,6,7-tetrahydrofuro[2,3-f]quinoline-7-one.HCl:

2-Azidomethyl-5-methyl-2,3,6,7-tetrahydrofuro[2,3-f]quinoline-7-one (759 mg) was dissolved in dimethylformamide (20 ml). To the solution, 10% palladium-on-carbon (455 mg) was added, and the solution was hydrogenated in the atmosphere of hydrogen at ambient temperature and under atmospheric pressure. After completion of the reaction, the catalyst was filtered off. When the solvent was evaporated, 0.7 g of the title compound was obtained as a crude product. This product was purified by silica gel column chromatography to obtain 409 mg of a free base (60.0%). The obtained free base was converted into a hydrochloric acid salt, followed by recrystallizing from a solvent mixture of methanol-diethylether, obtaining yellow powdery crystals having a melting point over 300° C.

IR(KBr): 3396, 2895, 1665, 1456, 1314, 1145, 1080, 931, 837 cm⁻¹.

¹H-NMR(CDCl₃)δ: 8.08(1H,d,J=9.3Hz), 7.29(1H, s), 6.57(1H,d,J=9.3Hz), 5.22(1H,m), 3.51(1H,dd, J=9.8, 15.6Hz), 3.40–3.20(2H,m), 3.06(1H,dd, J=6.8,15.6Hz), 2.39(3H, s).

Example 6:

Optical resolution of 2-aminomethyl-5-methyl-2,3,6,7-tetrahydrofuro[2,3-f]quinoline-7-one:

(±)-2-Aminomethyl-5-methyl-2,3,6,7-tetrahydrofuro[2,3-f]quinoline-7-one (3 g) in methanol and an equimolar amount of L-(+)-tartaric acid in methanol were combined, and the solvent was evaporated. From the resultant crude crystals, 2.5 g was taken and dissolved in methanol (2.5). The solution was filtered and condensed up to ¹/₁₀, followed by allowing to stand at room temperature. The precipitated crystals were collected by filtration to obtain 1.1 g of crystals. The remainder of the crude crystals was recrystallized in a similar manner to obtain 1.92 g in total of a salt of (−)-free base and (+)-tartaric acid. The mother liquids were combined and condensed, to obtain 1.793 g of a salt of (+)-free base and (+)-tartaric acid (1.2 g of second crystals, 423 mg of third crystals and 170 g of fourth crystals).

The salt (1.5 g) of (−)-free base and (+)-tartaric acid was suspended in methanol. The suspension was made into alkaline with aqueous 48% NaOH solution, followed by drying to solidity. The solid was subjected to silica gel column chromatography (eluent=chloroform and ammonia-saturated methanol=10:1) to obtain 854 mg of a free base. This free base and D-10-camphor sulfonate (861 mg) were combined, followed by recrystallizing from methanol. As a result, 816 mg of the salt was obtained as pale yellow crystals.

mp. 256°–258° C. (dec.)

Optical rotation $[\alpha]_D^{22}$=+38.1 (c=1.0, methanol)
IR(KBr): 3410, 2919, 1735, 1670, 1162, 1195, 1038, 943 cm⁻¹.

¹H-NMR(CD₃OD)δ: 8.06(1H,d,J=9.7Hz), 7.28(1H,s), 6.55(1H,d,J=9.7Hz), 5.20(1H,m), 3.60–3.00(6H,m), 2.80–2.60(3H,m), 2.40–2.30(4H,complex m), 2.10–1.30(3H,m), 1.11,0.84(each 3H,each s).

The obtained salt (800 g) was converted into a free base (383 mg) in a similar manner as described above, followed by further converting into a hydrochloric acid salt, which was then recrystallized from a solvent mixture of methanol-ether. As a result, a hydrochloric acid salt of (−)-2-aminomethyl-5-methyl-2,3,6,7-tetrahydrofuro[2,3-f]quinoline-7-one (373 mg) was obtained as pale yellow powdery crystals.

mp. >300° C.

Optical rotation $[\alpha]_D^{22}$=−24.0 (c=0.1, methanol) IR(KBr): 3167, 3027, 2916, 1653, 1458, 1322, 1261, 1142, 1086, 942, 840 cm$^{-1}$.

$^1$H-NMR(CD$_3$OD)δ: 8.08(1H,d,J=9.3Hz), 7.29(1H,s), 6.57(1H,d,J=9.3Hz), 3.51(1H,dd,J=9.8,15.6Hz), 3.06(1H,dd, J=6.8,15.6Hz), 2.39(3H, s).

The salt (1.37 g) of the (+)-free base and (+)-tartaric acid was converted into a free base (798 mg) in a similar manner as described above. The free base was combined with D-10-camphorsulfonic acid (805 mg), followed by recrystallizing from a solvent mixture of methanol-ether (twice). As a result, 1.07 mg of a salt was obtained as light yellow powdery crystals.

mp. 253°–256° C. (dec.)

Optical rotation $[\alpha]_D^{22}$=+6.8 (c=1.0, methanol) IR(KBr): 3408, 3021, 1739, 1657, 1463, 1120, 1086, 1044, 943, 840 cm$^{-1}$.

$^1$H-NMR(CD$_3$OD)δ: 8.06(1H,d,J=9.8Hz), 7.27(1H, s), 6.55(1H,d,J=9.8Hz), 5.20(1H,m), 3.60–3.00(6H,m), 2.80–2.60(3H,m), 2.40–2.30(4H,complex m), 2.10–1.30(3H,m), 1.11,0.84(each 3H,each s).

The obtained salt (1 g) was converted into a fee base (574 mg) in a similar manner as described above, followed by further converting into a hydrochloric acid salt, which was then recrystallized from a solvent mixture of methanol-ether. As a result, a hydrochloric acid salt of (+)-2-aminomethyl-5-methyl-2,3,6,7-tetrahydrofuro[2,3-f]quinoline-7-one (487 mg) was obtained as pale yellow powdery crystals.

mp. >300° C.

Optical rotation $[\alpha]_D^{22}$=+22.0 (c=0.1, methanol) IR(KBr): 3199, 3038, 2984, 1654, 1461, 1322, 1262, 1143, 1086, 942, 840 cm$^{-1}$.

$^1$H-NMR(CD$_3$OD)δ: 8.08(1H,d,J=9.3Hz), 7.29(1H,s), 6.57(1H,d,J=9.3Hz), 5.22(1H,m), 3.51(1H,dd,J=9.8, 15.6Hz), 3.40–3.20(2H,m), 3.06(1H,dd,J=6.8,15.6Hz), 2.39(3H,s).

Example 7:

(+)- And (−)- 2-aminomethyl-2,3,6,7,8,9-hexahydro-5-methylfuro[2,3-f]quinoline-7-one.HCl:

A hydrochloric acid salt (930 mg) of (+)-2-aminomethyl-5-methyl-2,3,6,7-tetrahydrofuro[2,3-f]quinoline-7-one was dissolved in water (18.6 ml). To the solution, 10% palladium-on-carbon (790 mg) was added, and the solution was hydrogenated in the atmosphere of hydrogen under atmospheric pressure. After completion of the reaction, the catalyst was filtered off. The mother liquid was solidified under reduced pressure, followed by recrystallizing from a solvent mixture of methanol and ether. As a result, 320 mg of a hydrochloric acid salt of (+)-2-aminomethyl-2,3,6,7,8,9-hexahydro-5-methylfuro[2,3-f]quinoline-7-one was obtained as colorless powdery crystals having a melting point over 300° C.

Optical rotation $[\alpha]_D^{22}$=+10.2° (c=0.5, methanol) IR(KBr): 3370, 1670, 1472, 1375, 1207, 1082, 936 cm$^{-1}$.

$^1$H-NMR(CD3OD)δ: 6.89(1H, s), 5.05(1H,m), 3.45–3.10(4H,m), 2.91(2H,t,J=7.3Hz), 2.52(2H,t,J=7.3Hz), 2.17(3H, s).

A hydrochloric acid salt of (−)- 2-aminomethyl -2,3,6,7,8,9-hexahydro-5-methylfuro[2,3-f]quinoline-7-one was obtained in a similar manner from a hydrochloric acid salt of (−)- 2-aminomethyl-5-methyl-2,3,6,7-hexahydrofuro[2,3-f]quinoline-7-one.

Yield: 82.9% Colorless powdery crystals, mp. >300° C. (crystallized from methanol-ether) Optical rotation $[\alpha]_D^{22}$=−13.2° (c=0.5 methanol) IR(KBr): 3392, 1671, 1472, 1375, 1208, 1080, 938 cm$^{-1}$.

$^1$H-NMR(CD$_3$OD)δ: 6.89(1H, s), 5.05(1H,m), 3.45–3.10(4H,m), 2.91(2H,t,J=7.3Hz), 2.52(2H,t,J=7.3Hz), 2.17(3H, s).

Example 8:

2,3,6,7,8,9-Hexahydro-2-hydroxymethyl-5-methylfuro[2,3-f]quinoline-7-one:

2-Hydroxymethyl-5-methyl-2,3,6,7-tetrahydrofuro[2,3-f]quinoline-7-one (538 mg) was added to acetic acid (AcOH) (11 ml). To the obtained mixture, 10% palladium-on-carbon (323 mg) was added, and the solution was hydrogenated in the atmosphere of hydrogen at 50° C. under atmospheric pressure. After completion of the reaction, the catalyst was filtered off. The solvent was evaporated, and the residue was dissolved in chloroform. The solution was washed with aqueous sodium bicarbonate solution and water in this order, and dried. Subsequently, the solvent was evaporated to obtain 478 mg of a crude. The obtained crude was purified by silica gel column chromatography (eluent:=chloroform:methanol=100:1), to obtain 395 mg of the target compound (72.8%). This substance was recrystallized from a solvent mixture of chloroform-n-hexane. As a result, colorless powdery crystals having a melting point of 172°–173° C. were obtained.

IR(KBr): 3363, 1648, 1627, 1479, 1391, 1052, 835 cm$^{-1}$.

$^1$H-NMR(CDCl$_3$)δ: 7.20(1H,br.s), 6.83(1H,s), 4.95(1H, m), 4.00–3.85(2H,m), 3.22(1H,dd,J=7.8,14.1Hz), 3.10–2.95(1H,m), 2.90(2H,d,J=7.8Hz), 2.59(2H,d,J=7.8Hz), 2.14(3H,s), 2.00(1H, t, J=6.8Hz).

Example 9:

2,3,6,7,8,9-Hexahydro-2-methanesulfonyloxymethyl-5-methylfuro[2,3-f]quinoline-7-one:

Using 2-hydroxymethyl-5-methyl-2,3,6,7,8,9-hexahydrofuro[2,3-f]quinoline-7-one, the procedure of Example 3 was followed to synthesize the title compound.

Yield: 100% Colorless needles, mp. 156°–157° C.

IR(KBr): 3252, 1671, 1473, 1343, 1177, 1073, 977, 834, 799 cm$^{-1}$.

$^1$H-NMR(CDCl$_3$)δ: 7.35) 1H,br.s), 6.84(1H, s), 5.00(1H, m), 4.39(2H, d, J=4.8Hz), 3.30(1H, dd, J=15.6,9.2Hz), 3.07(3H,s), 3.06–2.85(3H,m), 2.60(2H,d,J=7.8Hz), 2.14(3H,s).

Example 10:

2-Azidomethyl-2,3,6,7,8,9-hexahydro-5-methylfuro[2,3-f]quinoline-7-one:

Using 2,3,.6,7,8,9-hexahydro-2-methanesulfonyloxymethyl-5-methylfuro[2,3-f]quinoline-7-one, the procedure of Example 4 was followed to synthesize the title compound.

Yield: 100% Pale yellow needles, mp. 146°–149° C.

IR(KBr): 3205, 2087, 1668, 1624, 1468, 1378, 1202, 1084, 896, 792 cm$^{-1}$.

$^1$H-NMR(CDCl$_3$)δ: 7.35(1H,br.s), 6.84(1H,s) 5.00(1H, m), 3.45(2H,d,J=3.9Hz), 3.30–2.92(2H,m), 2.91(2H,t,J= 7.8Hz), 2.60(2H,t,J=7.8Hz), 2.15(3H,s).

Example 11:

2-Aminomethyl-2,3,6,7,8,9-hexahydro-5-methylfuro[2,3-f]quinoline-7-one.HCl:

Using 2-azidomethyl-2,3,6,7,8,9-hexahydro-5-methyl-furo[2,3-f]quinoline-7-one, the procedure of Example 5 was followed to synthesize the title compound.

The obtained compound was recrystallized from methanol-diethylether to obtain crystals having a melting point not less than 300° C.

IR(KBr): 3394, 2884, 1671, 1629, 1473, 1302, 1208, 1081, 1023, 830 cm$^{-1}$.

$^1$H-NMR(CDCl$_3$)δ: 6.89(1H,s), 5.05(1H,m), 3.45–3.10(4H,m), 2.91(2H,t,J=7.3Hz), 2.52(2H,t,J=7.3Hz), 2.17(3H, s).

Example 12:

(2RS,3RS) and (2RS, 3SR)-2-Aminomethyl-3,5-dimethyl-2,3,6,7-tetrahydrofuro[2,3-f]quinoline-7-one.HCl:

Using 2-azidomethyl-3,5-dimethyl-2,3,6,7-tetrahydro-furo[2,3-f]quinoline-7-one, the procedure of Example 5 was followed to synthesize a mixture of (2RS,3RS) and (2RS, 3SR)-2-aminomethyl-3,5-dimethyl-2,3,6,7-tetrahydrofuro [2,3-f]quinoline-7-one. The obtained mixture was separated by silica gel column chromatography (eluent=chloroform-:methanol: water=400:25:1), and then converted into a hydrochloric acid salt to obtain (2RS,3SR) and (2SR, 3RS) compounds. The chemical properties are shown in the following Table.

The free base of the (2RS, 3SR) compound was separated by high performance liquid chromatography (ethanol) using a column for optical resolution (Chiralpak AD, by Dicel), and then converted into a hydrochloric acid salt to obtain (+)- and (–)- compounds.

(+)- compound:

Pale yellow powdery crystals, mp. >300° C. (recrystallized from methanol-ether)

Optical rotation $[α]_D^{21}$=–44.0° (c=0.5, methanol)

IR(KBr): 3378, 1661, 1457, 1317, 1067, 931, 831 cm$^1$.

$^1$H-NMR(CD$_3$OD)δ: 8.07(1H,d,J=9.8Hz), 7.28(1H, s), 6.56(1H,d,J=9.8Hz), 5.09(1H,m), 3.87–3.68(1H,m), 3.42–3.07(2H,m), 2.40(3H, s), 1.26(3H,d,J=7.3Hz).

(–)- Compound:

Pale yellow powdery crystals, mp. >300° C. (recrystallized from methanol-ether)

Optical rotation $[α]_D^{21}$=–51.2 ° (c=0.5 methanol)

IR(KBr): 3387, 1661, 1457, 1067, 931, 832 cm$^{-1}$. NMR(CD$_3$OD)δ: 8.07(1H,d,J=9.8Hz), 7.28(1H,s), 6.56(1H, d,J=9.8Hz), 5.09(1H,m), 3.87–3.68(1H,m), 3.42–3.07(2H, m), 2.40(3H,s), 1.26(3H,d,J=7.3Hz).

According to the above Examples, the compounds of the present invention in the following Tables were prepared. The data based on which the compounds were identified are also shown in the same Tables. In the Tables, MeOH, D$_2$O. EtOH, DMSO-d$_6$, ET$_2$O. CHCl$_3$, CDCl$_3$, CD$_3$O represent methanol, heavy water, ethanol, heavy dimethylsulfoxide, ether, chloroform, dichloroform, and dimethanol, respectively. "d" indicates presence of bonding in the broken line, and "s" indicates absence of bonding in the broken line. "*" indicates that the data was obtained on a free base.

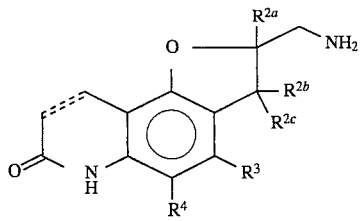

| Ex | Bond by --- | R$^{2a}$ | R$^{2b}$ | R$^{2c}$ | R$^4$ | R$^3$ | Salt | mp. (°C.) | Sol* | IR (cm$^{-1}$) (KBr) | solv. | $^1$H-NMR δ(ppm) |
|---|---|---|---|---|---|---|---|---|---|---|---|---|
| 13 | d | H | H | Me | Me | H | HCl | >300 | MeOH | 3175, 1663, 1271, 1148 | CD$_3$OD | 8.07(1H, d, J=9.8Hz), 7.28 (1H, s), 6.56(1H, d, J= 9.8Hz), 5.09(1H, m), 3.87–3.68(1H, m), 3.42–3.07(2H, m), 2.40(3H, s), 1.26(3H, d, J=7.1Hz) |
| 14 | d | H | Me | H | Me | H | HCl | 300 | MeOH | 3181, 1649, 1150 | CD$_3$OD | 8.06(1H, d, J=9.8Hz), 7.27 (1H, s), 6.56(1H, d, J= 9.8Hz), 4.74–4.60(1H, m), 3.46–3.12(3H, m), 2.40(3H, s), 1.41(3H, d, J=6.8Hz) |
| 15 | s | H | Me | H | Me | H | HCl | 296–299 | EtOH | 2952, 2890, 1684, 1628, 1471, 1442, 1364, 1338 | CD$_3$OD | 6.87(1H, s), 4.49(1H, m), 3.03–3.36(3H, m), 2.80–2.99 (2H, m), 2.49–2.57(2H, m), 2.19(3H, s), 1.34(3H, d, J= 6.4Hz) |
| 16 | d | Me | H | Me | Me | H | HCl | 290 | MeOH EtOH | 3332, 1654, 1502, 1448, 1275, 1138, 1066 | CD$_3$OD | 8.08(1H, d, J=9.7Hz), 7.25 (1H, s), 6.56(1H, d, J= 9.7Hz), 3.51(1H, q, J= 7.5Hz), 3.10–3.35(2H, m), |

-continued

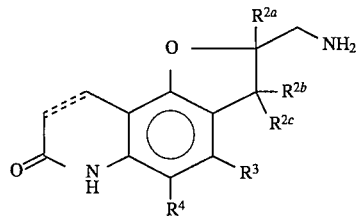

| Ex | Bond by --- | $R^{2a}$ | $R^{2b}$ | $R^{2c}$ | $R^4$ | $R^3$ | Salt | mp. (°C.) | Sol* | IR (cm$^{-1}$) (KBr) | solv. | $^1$H-NMR δ(ppm) |
|---|---|---|---|---|---|---|---|---|---|---|---|---|
| 17 | s | Me | H | Me | Me | H | HCl | >300 | MeOH Et$_2$O | 3214, 2946, 2900, 2865, 1671, 1629, 1507, 1467, 1442, 1389, 1197, 1078, 885 | CD$_3$OD | 2.40(2H, m), 1.64(3H, s), 1.33 (3H, d, J=7.5Hz) 6.84(1H, s), 3.25–3.40(1H, m), 3.16(1H, d, J=13.2Hz), 3.07 (2H, d, J=13.2Hz), 2.87(2H, m), 2.52(2H, t, J=7.3Hz), 2.18(3H, s), 1.57(3H, s), 1.26 (3H, d, J=7.3Hz) |
| 18 | d | Me | Me | H | Me | H | HCl | 287–290 | EtOH | 3000–2500, 1652, 1133 | CD$_3$OD | 8.04(1H, d, J=9.8Hz), 7.26 (1H, s), 6.54(1H, d, J= 9.8Hz), 3.41(1H, q, J= 6.8Hz), 3.26(2H, s), 2.40(3H, s), 1.48(3H, s), 1.33(3H, d, J=6.8Hz) |
| 19 | s | Me | Me | H | Me | H | HCl | 293–296 (dec.) | EtOH | 3100–2400, 1674, 1092, 1050 | CD$_3$OD | 6.83(1H, s), 3.18(2H, s), 3.33–3.06(1H, m), 2.99–2.72(2H, m), 2.52(2H, t, J=7.3Hz), 2.18(3H, s), 1.38(3H, s), 1.26 (3H, d, J=6.8Hz) |
| 20 | d | Me | H | H | Me | H | HCl | 293–296 (dec.) | EtOH | 3156, 1651, 1275, 1069 | CD$_3$OD | 8.03(1H, d, J=9.8Hz), 7.26 (1H, s), 6.53(1H, d, J= 9.8Hz), 3.40–3.30(2H, m), 3.31(1H, d, J=6.1Hz), 2.40–3.30(2H, m), 3.18(1H, d, J= 16.1Hz), 2.38(3H, s), 1.61 (3H, s) |
| 21 | s | Me | H | H | Me | H | HCl | 277–280 (dec.) | EtOH | 3195, 1670, 1201, 1065 | CD$_3$OD | 6.88(1H, s), 3.22(2H, s), 3.18, 3.06(each 1H, each d, J= 15.6Hz), 2.98–2.80(2H, m), 2.65–2.45(2H, m), 2.18(3H, s), 1.54(3H, s) |
| 22 | d | Me | Me | Me | Me | H | HCl | 214–217 | CHCl$_3$ n-Hexane Et$_2$O | 2942, 2836, 2285, 1647, 1603, 1541, 1466, 1327, 1295, 1261, 1156, 1043, 798 | CD$_3$OD | 8.13(1H, d, J=9.5Hz), 7.17 (1H, s), 6.44(1H, d, J= 9.5Hz), 3.19, 3.07(each 1H each d, J=13.4Hz), 2.48, 1.54, 1.32, 1.27(each 3H, each s) |
| 23 | s | Me | Me | Me | Me | H | HCl | >300 | MeOH Et$_2$O | 3386, 3208, 3036, 2908, 1669, 1630, 1470, 1439, 1391, 1374, 1335, 1207 | CD$_3$OD | 6.83(1H, s), 3.15, 3.05 (each 1H, each d, J= 13.2Hz), 2.76–3.00(2H, m), 2.49–2.56(2H, m), 2.20, 1.45, 1.25, 1.20(each 3H, each s) |
| 24 | d | H | H | H | H | H | HCl | >250 | MeOH Et$_2$O | 1646, 1604, 1540, 1511, 1471, 1333, 1277, 1221, 1013, 932, 796 | CD$_3$OD | 8.24(1H, d, J=9.8Hz), 7.50(1H, d, J=8.3Hz), 7.01(1H, d, J=8.3Hz), 6.72(1H, d, J=9.8Hz), 5.29(1H, m), 3.56(1H, dd, J= 15.6, 9.8Hz), 3.20–3.39(2H, m), 3.11(1H, dd, J=15.6, 6.8Hz) |
| 25 | s | H | H | H | H | H | HCl | >250 | MeOH Et$_2$O | 1669, 1603, 1489, 1441, 1381, 1206, 1070, 1028 | CD$_3$OD | 7.00(1H, d, J=7.8Hz), 6.43(1H, d, J=7.8Hz), 5.15–4.98(1H, m), 3.50–3.12(3H, m), 3.03–2.85(3H, m), 2.60–2.46(2H, m) |
| 26 | d | H | H | H | H | Me | HCl | >300 | MeOH Et$_2$O | 3403, 1645, 1575, 1513, 1447, 1386, 1330, 1238, 1143, 1050, 878 | CD$_3$OD | 8.13(1H, d, J=9.8Hz), 6.80 (1H, s), 6.59(1H, d, J= 9.8Hz), 5.26(1H, m), 3.43–3.56(2H, m), 2.99–3.07(2H, m), 2.37(3H, s) |

-continued

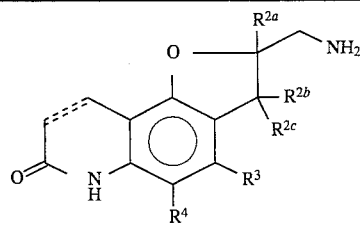

| Ex | Bond by | $R^{2a}$ | $R^{2b}$ | $R^{2c}$ | $R^4$ | $R^3$ | Salt | mp. (°C.) | Sol* | IR (cm$^{-1}$) (KBr) | solv. | $^1$H-NMR δ(ppm) |
|---|---|---|---|---|---|---|---|---|---|---|---|---|
| 27 | s | H | H | H | H | Me | HCl | >300 | MeOH E$_2$O | 3396, 1653, 1591, 1576, 1512, 1441, 1371, 1112, 992, 870, 735, 667, 601 | CD$_3$OD | 6.26(1H, s), 5.06(1H, m), 3.29–3.36(2H, m), 3.17(1H, dd, J=13.2, 9.8Hz), 2.77–2.92(3H, m), 2.50(2H, t, J=7.8Hz), 2.18(3H, s) |
| 28 | d | H | H | H | Me | Me | HCl | 285–290 (dec.) | MeOH | 3336, 1627, 1599, 1448, 1406, 1326 | CD$_3$OD | 8.03(1H, d, J=9.5Hz), 6.49(1H, d, J=9.5Hz), 5.12–5.27(1H, m), 3.51 (1H, dd, J=15.5, 9.6Hz), 3.16–3.42(2H, m), 3.05(1H, dd, J=15.5, 6.7Hz), 2.34(3H, s), 2.31(3H, s) |
| 29 | s | H | H | H | Me | Me | HCl | >300 | MeOH EtOH | 3000–2500, 1654, 1198, 1076 | CDCl$_3$ CD$_3$OD | 5.15–4.96(1H, m), 3.46–3.04 (3H, m), 2.99–2.74(3H, m), 2.60–2.47(2H, m), 2.19(3H, s), 2.10(3H, s) |
| 30 | d | H | H | H | Et | H | HCl | 279–285 (dec.) | MeOH | 3220, 1650, 1610, 1460, 1320, 1260, 1140, 1085, 1010, 950, 840 | CD$_3$OD | 8.06(1H, d, J=9.8Hz), 7.03 (1H, s), 6.54(1H, d, J=9.8Hz), 5.27–5.16(1H, m), 3.52(1H, dd, J=15.6, 9.8Hz), 3.33–3.30(1H, m), 3.23(1H, dd, J=13.7, 9.3Hz), 3.07(1H, dd, J=15.6, 6.8Hz) 2.79(2H, q, J=7.3Hz), 1.25(3H, t, J=7.3Hz) |
| 31 | s | H | H | H | Et | H | HCl | 280–286 (dec.) | MeOH Et$_2$O | 3265, 1665, 1635, 1610, 1465, 1365, 1315, 1205, 1070, 965, 910 | CD$_3$OD | 6.92(1H, s), 5.09–4.98(1H, m), 3.93(1H, dd, J=16.4, 9.3Hz), 3.28(1H, dd, J=13.2, 2.9Hz), 3.14(1H, dd, J=13.2, 9.3Hz), 3.01–2.99(2H, m), 2.84(1H, dd, J=16.4, 7.3Hz), 2.56(2H, q, J=7.3Hz), 2.52(2H, t, J=7.8Hz), 1.15(3H, t, J=7.3Hz) |
| 32 | d | H | H | H | n-Pr | H | HCl | 275–278 (dec.) | MeOH EtOH | 3100–2400, 1629, 1156 | CDCl$_3$ CD$_3$OD | 8.07(1H, d, J=9.8Hz), 7.25 (1H, s), 6.58(1H, d, J=9.8Hz), 5.34–5.15(1H, m), 3.62–2.98(4H, m), 2.73(2H, t, J=7.3Hz), 1.68(2H, sextet, J=7.3Hz), 1.02(3H, t, J=7.3Hz) |
| 33 | s | H | H | H | n-Pr | H | HCl | 283–285 (dec.) | EtOH | 3000–2500, 1670, 1207, 1080 | CD$_3$OD | 6.90(1H, s), 5.12–4.90(1H, m), 3.50–3.05(3H, m), 3.02–2.72(3H, m), 2.52(2H, t, J=7.3Hz), 1.54(2H, sextet, J=7.3Hz), 0.95(3H, t, J=7.3Hz) |
| 34 | d | H | H | H | n-Bu | H | HCl | 260–262 (dec.) | MeOH Et$_2$O | 3009, 2915, 1659, 1608, 1475, 1437, 1271, 1147, 943, 833 | CD$_3$OD | 8.07(1H, d, J=9.8Hz), 7.29 (1H, s), 6.55(1H, d, J=9.8Hz), 5.20(1H, m), 3.52(1H, dd, J=15.6, 9.3Hz), 3.17–3.36(2H, m), 3.06(1H, dd, J=15.6, 7.3Hz), 2.79(2H, t, J=7.6Hz), 1.60(2H, m), 1.41 (2H, m), 0.96(3H, t, J=7.3Hz) |
| 35 | s | H | H | H | n-Bu | H | HCl | 263–265 (dec.) | MeOH Et$_2$O | 3210, 2943, 1670, 1629, 1401, 1382, 1346, 1207, 1083, 968, 938 | CDCl$_3$ | 6.90(1H, s), 5.02(1H, m), 3.05–3.50(6H, m), 2.79–2.97(2H, m), 2.52(2H, t, J=7.3Hz), 1.48(2H, m), 1.38(2H, m), 0.93(3H, t, J=7.3Hz) |
| 36 | s | H | H | H | H | Et | HCl | 282–285 | CHCl$_3$ MeOH | 3414, 2952, 1672, 1615, | CD$_3$OD | 6.30(1H, s), 5.13–4.97(1H, m), 3.43–3.12(3H, m), |

-continued

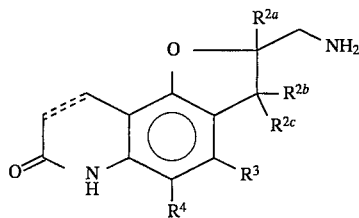

| Ex | Bond by --- | $R^{2a}$ | $R^{2b}$ | $R^{2c}$ | $R^4$ | $R^3$ | Salt | mp. (°C.) | Sol* | IR (cm$^{-1}$) (KBr) | solv. | $^1$H-NMR δ(ppm) |
|---|---|---|---|---|---|---|---|---|---|---|---|---|
| | | | | | | | | (dec.) | Et$_2$O | 1418, 1383, 1205 | | 2.96–2.78(3H, m), 2.57–2.46(4H, m), 1.19(3H, t, J=7.6Hz) |
| 37 | d | H | H | H | H | Et | HCl | >300 | CHCl$_3$ MeOH Et$_2$O | 3383, 1646, 1600, 1542, 1447, 1334, 1160, 903 | CD$_3$OD | 8.18(1H, d, J=9.5Hz), 6.85 (1H, s), 6.64(1H, d, J= 9.5Hz), 5.35–5.23(1H, m), 3.52(1H, dd, J=15.5, 9.6Hz), 3.45–3.23(2H, m), 3.07(1H, dd, J=15.5, 6.9Hz), 2.71 (1H, q, J=7.5Hz), 1.28(3H, t, J=7.5Hz) |
| 38 | d | H | H | H | H | n-Pr | HCl | >300 | MeOH Et$_2$O | 3399, 1646, 1549, 1420, 1339, 1158 | CD$_3$OD | 8.05(1H, d, J=9.3Hz), 6.76 (1H, s), 6.51(1H, d, J= 9.3Hz), 5.31–5.17(1H, m), 3.58–3.18(3H, m), 3.04(1H, dd, J=15.4, 6.5Hz), 2.64 (2H, t, J=7.6Hz), 1.78– 1.61(2H, m), 1.00(3H, t, J= 7.3Hz) |
| 39 | s | H | H | H | H | n-Pr | HCl | 275– 278 (dec.) | CHCl$_3$ MeOH Et$_2$O | 3396, 1672, 1599, 1484, 1420, 1306, 1328, 1204 | CD$_3$OD | 6.29(1H, s), 5.13–4.99(1H, m), 3.43–3.27(2H, m), 3.15(1H, dd, J=13.2, 9.3Hz), 2.98–2.76(3H, m), 2.55–2.43(4H, m), 1.68– 1.52(2H, m), 0.95(3H, t, J=7.3Hz) |
| 40 | d | H | H | H | H | i-Pr | HCl | >300 | MeOH Et$_2$O | 1645, 1600, 1545, 1495, 1420 1365, 1265, 1155, 1070, 970, 860 | CD$_3$OD | 8.11(1H, d, J=9.3Hz), 6.87 (1H, s), 6.57(1H, d, J= 9.3Hz), 5.33–5.22(1H, m), 3.54(1H, dd, J=15.6, 9.8Hz), 3.39(1H, dd, J=13.8, 2.9Hz), 3.26(1H, dd, J=13.8, 9.3Hz), 3.10(1H, dd, J=15.6, 7.3Hz), 3.06–2.93(1H, m), 3.06–1.30 (6H, d, J=6.8Hz) |
| 41 | s | H | H | H | H | i-Pr | HCl | >300 | MeOH | 3020, 1675, 1595, 1510, 1485, 1380, 1310, 1135, 1070, 975, 850 | CD$_3$OD | 6.37(1H, s), 5.12–5.00(1H, m), 3.28–3.43(2H, m), 3.16(1H, dd, J=13.2, 9.3Hz), 2.99–2.77(4H, m), 2.52(2H, t, J=7.6Hz), 1.21(6H, d, J=6.8Hz) |
| 42 | d | H | H | H | H | n-Pen | HCl | 281– 283 (dec.) | MeOH Et$_2$O | 3400, 1647, 1548, 1449, 1386, 1302, 1050, 968, 826, 771, 632 | CD$_3$OD | 8.09(1H, d, J=9.3Hz), 6.78(1H, s), 6.55(1H, d, J= 9.3Hz), 5.25(1H, m), 3.49(1H, dd, J=15.6, 6.8Hz), 3.22(1H, dd, J= 13.7Hz), 3.34(1H, dd, J= 13.7, 2.9Hz), 3.04(1H, dd, J= 15.6, 6.8Hz), 2.65(2H, t, J= 7.8Hz), 1.61–1.68(2H, m), 1.37–1.40(4H, m), 0.92(3H, t, J=6.8Hz) |
| 43 | s | H | H | H | H | n-Pen | HCl | 272– 275 (dec.) | MeOH Et$_2$O | 3414, 1666, 1598, 1447, 1379, 1328, 1107, 1010, 906, 767, 559 | CD$_3$OD | 6.28(1H, s), 3.29–3.38(2H, m) 5.05(1H, m), 3.15(1H, dd, J= 13.2, 9.3Hz), 2.51(2H, t, J= 7.3Hz), 2.76–2.94(3H, m), 2.48(2H, t, J=7.3Hz), 1.53– 1.61(2H, m), 1.32–1.36(4H, m), 0.90(3H, t, J=6.8Hz) |
| 44 | d | H | H | H | H | n-Hex | HCl | 283– 286 (dec.) | MeOH Et$_2$O | 1652, 1615, 1550 1449, 1387, 1341, 1157, 934, 825 | CD$_3$OD | 8.19(1H, d, J=9.8Hz), 6.84 (1H, s), 6.64(1H, d, J= 9.8Hz), 5.36–5.23(1H, m), 3.52(1H, dd, J=15.6, 9.5Hz), 3.44–3.23(2H, m), 3.80(1H, dd, J=15.6, 6.8Hz), 2.68(2H, |

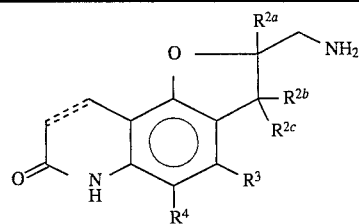

| Ex | Bond by | $R^{2a}$ | $R^{2b}$ | $R^{2c}$ | $R^4$ | $R^3$ | Salt | mp. (°C.) | Sol* | IR (cm$^{-1}$) (KBr) | solv. | $^1$H-NMR δ(ppm) |
|---|---|---|---|---|---|---|---|---|---|---|---|---|
| 45 | s | H | H | H | H | n-Hex | HCl | 266–269 (dec.) | CHCl$_3$ MeOH Et$_2$O | 3394, 1669, 1597, 1473, 1416, 1378, 1326, 1204 | CD$_3$OD | t, J=7.8Hz), 1.74–1.60 (2H, m), 1.47–1.26(6H, m), 0.95–0.86(3H, m) 6.29(1H, s), 5.13–4.98(1H, m), 3.41–3.10(3H, m), 2.97–2.75 (3H, m), 2.56–2.45(4H, m), 1.64–1.49(2H, m), 1.43–1.26(6H, m), 0.95–0.84(3H, m) |
| 46 | d | H | H | H | OMe | H | HCl | 268–270 (dec.) | MeOH Et$_2$O | 3401, 1629, 1603, 1472, 1369, 1342, 1245, 1018 | CD$_3$OD | 8.01(1H, d, J=9.7Hz), 7.12 (1H, s), 6.58(1H, d, J= 9.7Hz), 5.10–5.28(1H, m)3.95(3H, s), 3.54(1H, dd, J=15.6, 9.7Hz), 3.15–3.42 (2H, m), 3.09(1H, dd, J= 15.6, 6.8Hz) |
| 47 | s | H | H | H | OMe | H | HCl | 269–273 | MeOH Et$_2$O | 3405, 1666, 1487, 1443, 1424, 1342, 1195, 1106, 1023 | CD$_3$OD | 6.82(1H, s), 4.80–5.11(1H, m), 3.82(3H, s), 3.41(1H, dd, J=15.5, 9.3Hz), 2.40–3.33(7H, m) |
| 48 | d | H$_2$NCH$_2$ | H | H | Me | H | 2HCl | 293–294 (dec.) | MeOH Et$_2$O | 3378, 1661, 1506, 1461, 1318, 1268, 1143, 832 | CD$_3$OD | 8.12(1H, d, J=9.5Hz), 7.32 (1H, s), 6.59(1H, d, J= 9.5Hz), 3.55(2H, d, J= 13.9Hz), 3.46(2H, d, J= 13.9Hz), 3.45(2H, s), 2.41 (3H, s) |
| 49 | s | H$_2$NCH$_2$ | H | H | Me | H | 2HCl | 275–277 | MeOH Et$_2$O | 3396, 1676, 1476, 1364, 1335, 1207, 1089 | CD$_3$OD | 6.96(1H, s), 3.48(2H, d, J= 13.9Hz), 3.37(2H, d, J= 13.9Hz), 3.48–3.29(2H, m), 3.02–2.93(2H, m), 2.61–2.53(2H, m), 2.19(3H, s) |

Sol*: Solvent used for recrystallization

The following compounds are manufactured in a manner similar to that described in the above-described examples.

Example 50:

2-Aminomethyl-1,2,6,7-tetrahydrofuro[3,2-f]quinoline-7-one:

mp. 233°–236° C. (dec.) (recrystallized from chloroform-methanol-n-hexane)

IR(KBr): 1645, 1623, 1611, 1507, 1441, 1241 cm$^1$.

$^1$H-NMR(DMSO-d$_6$)δ: 7.74(1H,d,J=10.0Hz), 7.09 (1H, d, J=9.0Hz), 6.98 (1H, d, J=9.0Hz), 6.52(1H, d, J=10.0Hz), 4.75–4.92(1H,m), 3.65–3.04(3H,br), 2.81(2H,d,J=6.0Hz).

Example 51:

2-Aminomethyl-1,2,6,7,8,9-hexahydrofuro-[3,2-f]-quinoline-7-one.HCl:

mp. 295° C. (recrystallized from methanol-ether)

IR(KBr): 2893, 1709, 1480, 1449, 1382, 1228, 806 cm$^{-1}$.

$^1$H-NMR(D$_2$O)δ: 6.73(2H,s), 5.04–5.23(1H,m), 3.44(1H, m), 3.34(1H,dd, J=13.4Hz), 3.20(1H,dd,J=13.9Hz), 3.03–2.47(5H,m).

Example 52:

2-Acetoxymethyl-5-methyl-2,3,6,7-tetrahydrofuro-[2,3-f]quinoline-7-one:

To a solution of 2-hydroxymethyl-5-methyl-2,3,6,7-tetrahydrofuro[2,3-f]quinoline-7-one (261 mg) in anhydrous pyridine (7 ml), acetic anhydride (233 mg) was added. The mixture was stirred at room temperature for 1 hour, and further stirred at 50° C. for 1 hour. After completion of the reaction, the solvent was distilled off, and the residue was dissolved in chloroform, and washed with water. After drying, the solvent was distilled off to obtain 305 mg of a crude product. The crude product was purified by silica gel column chromatography (eluent=chloroform:methanol= 70:1) to obtain 247 mg of a target product (80.0%). The product was recrystallized from chloroform-n-hexane, and as a result, colorless powdery crystals were obtained (mp. 197°–200° C.).

Example 53:

2,3,6,7,8,9-Hexahydro-5-methyl-2-nitroxymethylfuro-[2,3-f]quinoline-7-one:

To a solution of 2,3,6,7,8,9-hexahydro-2-methanesulfonyloxymethyl-5-methylfuro-[2,3-f]quinoline-7-one (395 mg) in dimethylformamide (10 ml), tetrabutylammoniumnitrate (2.9 g) was added, and the mixture was stirred at 120° C. for 8 hours. After completion of the reaction, dimethylformamide was distilled off. The residue was dissolved in chloroform, and washed with water and aqueous NaCl solution in this order. After drying, the solvent was distilled off, and the residue was purified by silica gel column chromatography (eluent=chloroform:n-hexane =10:1) to obtain 229 mg of the target product as pale brown crystals (64.9%).

Example 54:

2-Iodomethyl-5-methyl-2,3,6,7-tetrahydrofuro-[2,3-f]quinoline-7-one:

To a solution of 2-methanesulfonyloxymethyl-5-methyl-2,3,6,7-tetrahydrofuro[2,3-f]quinoline-7-one (931 mg) in dimethylformamide (20 ml), sodium iodate (4.5 g) was added, and the mixture was stirred at 100° C. for 2 hours. After completion of the reaction, the solvent was distilled off, and the residue was purified by silica gel column chromatography (eluent: chloroform) to obtain 1 g (assayed quantitatively) of the target compound as a light yellow powder.

Example 55:

Syntheses of 2-(n-butylamino)methyl-5-methyl-2,3,6,7-tetrahydrofuro[2,3-f]quinoline-7-one.HCl and 2-dimethylaminomethyl-5-methyl-2,3,6,7-tetrahydrofuro[2,3-f]quinoline-7-one.HCl (1–17):

To a suspension of 2-methanesulfonyloxymethyl-5-methyl-2,3,6,7-tetrahydrofuro[2,3-f]quinoline-7-one (400 mg) in dimethylformamide (4 ml), n-butylamine (1.28 ml) was added. The mixture was then heated at 100° C. for 10 hours in a sealed vessel. After completion of the reaction, dimethylformamide was distilled off. The residue was dissolved in chloroform, washed with water and aqueous NaCl solution in this order, and dried. The solvent was distilled off, and the residue was purified by silica gel column chromatography (eluent=chloroform:methanol=40:1) to obtain 271 mg of the first free base of the title compound (73.2%) and 58 mg of the second free base of the title compound (17.4%). Both compounds were converted to hydrochloric salts using 4N-HCl/dioxane.

Example 56:

2-Fluoromethyl-5-methyl-2,3,6,7-tetrahydrofuro-[2,3-f]quinoline-7-one:

2-Hydroxymethyl-5-methyl-2,3,6,7-tetrahydrofuro[2,3-f]quinoline-7-one (500 mg) was suspended in anhydrous methylene chloride (20 ml). To the suspension, diethylaminosulfur trifluoride (DAST) (372 mg) was added while stirring and cooling at −78° C. Subsequently, the mixture was stirred at room temperature for 30 minutes. After completion of the reaction, methylene chloride was further added thereto, and washed with aqueous sodium bicarbonate solution, and aqueous NaCl solution in this order. After drying, the solvent was distilled off to obtain 487 mg of a crude product. The crude product was purified by silica gel column chromatography (eluent=chloroform:methanol= 400:1–20:1), and then by separative thin layer chromatography (developer=chloroform:methanol=10:1) to obtain a purified product, which was subjected to recrystallization using a solvent mixture of chloroform and n-hexane to obtain 163 mg of colorless needles (32%).

Example 57:

2,3,6,7,8,9-Hexahydro-2-methoxymethyl-5-methylfuro-[2,3-f]quinoline-7-one:

To a solution of 2,3,6,7,8,9-hexahydro-2-hydroxymethyl-5-methylfuro-[2,3-f]quinoline-7-one (300 mg) in tetrahydrofuran (100 ml), silica gel (10 g) and a solution of diazomethane in ether (200 ml) were added, and stirred at room temperature for 36 hours. After completion of the reaction, the solvent was distilled off, and the residue was purified by silica gel column chromatography to obtain 280 mg of the target product as a pale yellow powder (88%).

Example 58:

2,3,6,7,8,9-Hexahydro-5-methylfuro[2,3-f]quinoline-7-one-2-carboxylic acid and 2,3,6,7,8,9-hexahydro-5-methylfuro[2,3-f]quinoline-7-one-2-carboxamide:

To anhydrous methylene chloride (52 ml), 2,3,6,7,8,9-hexahydro-5-methylfuro[2,3-f]quinoline-7-one (1.2 g), 4-methylmorpholine N-oxide (6.1 g) and a few grains of Molecular Sieves 3A were added and stirred at room temperature for 10 minutes. Subsequently, tetrapropylammoniumperruthenate (183 mg) was added thereto, and the mixture was stirred at room temperature overnight. After completion of the reaction, extraction with aqueous sodium bicarbonate solution was performed, and the aqueous phase was washed with chloroform. After acidifying with HCl, the precipitated crystals were collected by filtration, and washed with water. The crystals were dissolved in a solvent mixture (120 ml) of chloroform and methanol (1:1), and dried. The solvent was distilled off, and the resultant crystals were washed with chloroform to obtain 780 mg of the title carboxylic acid as a pale brown powder (61.4%).

Carboxylic acid (500 mg) thus obtained and urea (600 mg) were mixed, and the mixture was heated at 170° C. for 2 hours while stirring. After completion of the reaction, the reaction mixture was dissolved in a solvent mixture of chloroform and methanol (1:1), and dried. The solvent was then distilled off to obtain 715 mg of a crude product. The crude product was purified by silica gel column chromatography (eluent=chloroform:methanol=100:1) to obtain 310 mg of the title carboxylic amide (58.7%).

Example 59:

2-[(2-Aminoethyl)oxymethyl]-5-methyl-2,3,6,7-tetrahydrofuro[2,3-f]quinoline-7-one.HCl:

6-Benzyl-2-hydroxymethyl-5-methyl-2,3,6,7-tetrahydrofuro[2,3-f]quinoline-7-one (1.5 g), which had been obtained by benzylating 2-hydroxymethyl-5-methyl-2,3,6,7-tetrahydrofuro[2,3-f]quinoline-7-one, was dissolved in dioxane (47 ml). 2-(t-Butoxy)ethyl iodide (1.6 g), potassium hydroxide (375 mg) and tetrabutylammonium bromide (469 mg) were added to the mixture, and the mixture was stirred at 90° C. for 75 minutes. Further, the above-mentioned iodide (1.6 g) and potassium hydroxide (370 were added, and the mixture was stirred at the same temperature for 2.5 hours, followed by addition of potassium hydroxide (375 mg). After 1 hour had elapsed, the above-mentioned iodide (1.5 g) and potassium hydroxide (375 were added again and stirred at the same temperature for 2 hours. After completion of the reaction, the insoluble matter was removed by filtration, and the solvent was distilled off to obtain a crude product. The crude product was purified by silica gel column chromatography (eluent:chloroform) to obtain 1.5 g of a product. This product was dissolved in a solution (15 ml) of 25% hydrobromic acid and acetic acid, and stirred at room temperature overnight. After completion of the reaction, the mixture was condensed under reduced pressure, to which aqueous sodium bicarbonate solution was added. Extraction with a solvent mixture of chloroform and methanol (10:1) was carried out, and the extract was washed with water and dried. The solvent was then distilled off to obtain 1.1 g of a crude product. The crude product was dissolved in methanol (60 ml), to which aqueous solution (6 mg) of aqueous 1N-sodium hydroxide solution was added. The mixture was stirred at room temperature for 5 minutes, and condensed. The condensed mixture was then dissolved along with a solvent mixture of chloroform and methanol (10:1), and was washed with diluted HCl, aqueous sodium bicarbonate solution, and aqueous NaCl solution in this order. After drying, the solvent was distilled off, and chloroform was added. The precipitated crystals were collected by filtration, and as a result, 621 mg of 2-[(2-hydroxyethyl)oxymethyl]-5-methyl-2,3,6,7-tetrahydrofuro[2,3-f]quinoline-7-one was obtained. This product was converted into a mesyl, and then an azido, which was then hydrogenated in a similar manner as in Examples 5, 9 and 10 to obtain a target product.

Example 60:

2-(3,4-Dimethoxybenzoylaminomethyl-5-methyl-2,3,6,7-tetrahydrofuro[2,3-f]quinoline-7-one:

2-Aminomethyl-5-methyl-2,3,6,7-tetrahydrofuro-[2,3-f]quinoline-7-one (78 mg) was dissolved in a solvent mixture (10 ml) of dimethylformamide and pyridine (1:1). To the mixture, 3,4-dimethoxybenzoylchloride (81.6 mg) was added, and stirred at 50° C. for 12 hours. After condensing, the reaction mixture was diluted with chloroform, washed with diluted HCl, and dried. The solvent was distilled off to obtain a crude product. The crude product was purified by separative thin layer chromatography (eluent=chloroform-:methanol=10:1) to obtain 86 mg of the target product as a pale yellow powder (64%).

Example 61:

5-Methyl-2-[3-(4-methylphenoxy)-2 -hydroxypropyl]aminomethyl-2,3,6,7-tetrahydrofuro[2,3-f]quinoline-7-one-.HCl:

4-(2,2-Dioxo-1,3,2-dioxathia-4-yl)methyloxytoluene (400 mg) was suspended in a solvent mixture (16 ml) of tetrahydrofuran and methanol (1:1), to which a solution of 2-aminomethyl-5-methyl-2,3,6,7-tetrahydrofuro[2,3-f]-quinoline-7-one (453 mg) in tetrahydrofuran (4 ml) was added. The mixture was stirred at room temperature for 1 hour, and further stirred at 50° C. for 2 hours. Hydrated sulfuric acid (conc. sulfuric acid: 2 ml, water: 0.8 ml) was added to the mixture, and was stirred at 50° C. for 3 hours. After completion of the reaction, water was added, and the pH was turned to alkaline with potassium carbonate, and condensed under reduced pressure. Then, extraction was carried out using chloroform, and the chloroform phase was washed with aqueous NaCl solution. After drying, the solvent was distilled off, and the residue thus obtained was purified by silica gel column chromatography (eluent=chloroform:methanol=50:1–30:1) to obtain 452 mg of a free base (70.0%). The free base was converted into a hydrochloric acid salt and was recrystallized from methanol to obtain the title compound as colorless powdery crystals (mp. 256°–261° C. (dec.)).

Example 62:

2,5-Dimethyl-2-isopropylaminomethyl-2,3,6,7-tetrahydrofuro[2,3-f]quinoline-7-one.HCl:

2,5-Dimethyl-[(2-propylideneamine)methyl]-2,3,6,7-tetrahydrofuro[2,3-f]quinoline-7-one (0.739 g), which had been obtained by recrystallizing 2-aminomethyl-2,5-dimethyl -2,3,6,7-tetrahydrofuro[2,3-f]quinoline-7-one from acetone, was dissolved in methanol (84 ml), to which sodium borohydride (0.197 g) was added. The mixture was then refluxed for 30 minutes while heating. After completion of the reaction, the solvent was distilled off under reduced pressure. After adding water, extraction was performed with a solvent mixture of chloroform-methanol (10:1). The extract was washed with water, and dried. The solvent was then distilled off, and the residue was subjected to recrystallization using a solvent mixture of tetrahydrofuran-n-hexane to obtain 0.518 g of a fee base (69.7%). The free base was converted into a hydrochloric acid salt and was recrystallized from a solvent mixture of ethanol-ether to obtain pale yellow powdery crystals (mp. 295°–298° C. (dec.)).

Example 63:

2-(t-Butoxycarbonyl)aminomethyl-2,3,6,7-tetrahydrofuro[2,3-f]quinoline-7-one:

2-Aminomethyl-2,3,6,7-tetrahydrofuro[2,3-f]quinoline-7-one (600 mg) and di-t-butyldicarbonate (1.1 g) were dissolved in tetrahydrofuran (131 ml), and stirred at room temperature for 2 hours. After another addition of di-t-butylcarbonate (500 mg), the mixture was stirred at room temperature for 100 minutes. After completion of the reaction, the solvent was distilled off, and the residue was purified by silica gel column chromatography (eluent=chloroform:methanol=70:1) to obtain 668 mg of 2-(t -butoxycarbonyl)-aminomethyl-2,3,6,7-tetrahydrofuro[2,3-f]quinoline-7-one (76.0%). This compound was recrystallized from a solvent mixture of chloroform-n-hexane to obtain colorless powdery crystals (mp.: 193°–196° C.).

IR(KBr): 3351, 1658, 1442, 1271, 1163, 1072, 861 cm$^{-1}$.

$^1$H-NMR(CDCl$_3$)δ: 7.94(1H,d, J=9.7Hz), 7.26(1H,d,J=8.3Hz), 6.85(1H,d,J=8.3Hz), 6.61(1H,d,J=9.7Hz), 5.10–4.90(2H,m), 3.70–3.25(4H,m), 3.01(1H,dd, J=15.1, 7.3Hz), 1.46(9H, s).

Example 64:

2-(t-Butoxycarbonyl)aminomethyl-5-iodo-2,3,6,7-tetrahydrofuro[2,3-f]quinoline-7-one:

2-(t-Butoxycarbonyl)aminomethyl-2,3,6,7-tetrahydrofuro[2,3-f]quinoline-7-one (882 mg) and N-iodosuccinimide (756 mg) were dissolved in a solvent mixture (44 ml) of chloroform-methanol (5:1). After refluxing for 2.5 hours with heat, N-iodosuccinimide (756 mg) was added to the mixture, followed by further 2 hour refluxing with heat. Further, N-iodosuccinimide (400 mg) was added to the mixture, which was then refluxed for 1.5 hours with heat. After completion of the reaction, the solvent was distilled off, and the residue was purified by silica gel column chromatography (eluent=chloroform:methanol=200:1) to obtain 903 mg of 2-(t-butoxycarbonyl)aminomethyl-5-iodo -2,3,6,7-tetrahydrofuro[2,3-f]quinoline-7-one (73.2%). This compound was recrystallized from a solvent mixture of chloroform-n-hexane to obtain pale yellow powdery crystals (mp.: 173°–174° C.).

IR(KBr): 3326, 1658, 1456, 1278, 1190, 1162, 830 cm$^{-1}$.

¹H-NMR(CDCl₃)δ: 8.79(1H,br.s), 7.79(1H,d,J=9.8Hz), 7.66(1H, s), 6.56(1H,d,J=9.8Hz), 5.15–4.90(2H,m), 3.70–3.25(4H,m), 3.02(1H,dd, J=15.4,7.3Hz), 1.58(9H, s).

Example 65:

2-Aminomethyl-5-chloro-2,3,6,7-tetrahydrofuro[2,3-f]quinoline-7-one.HCl:

2-(t-Butoxycarbonyl)aminomethyl-2,3,6,7-tetrahydrofuro[2,3-f]quinoline-7-one (416 mg) was dissolved in tetrahydrofuran (8.8 ml), to which 6N-HCl (2.2 ml) was added. The mixture was refluxed for 30 minutes while heating. After completion of the reaction, the mixture was dried to solidity under reduced pressure. The residue was subjected to recrstallization with a solvent mixture of methanol-ether to obtain 265 mg of a hydrochloric acid salt of 2-aminomethyl-5-chloro-2,3,6,7-tetrahydrofuro[2,3-f]quinoline-7-one as light yellow powdery crystals (79.6%, mp.: >300° C.).

Example 66:

2-(t-Butoxycarbonyl)aminomethyl-5-cyano-2,3,6,7-tetrahydrofuro[2,3-f]quinoline-7-one:

2-(t-Butoxycarbonyl)aminomethyl-5-iodo-2,3,6,7-tetrahydrofuro[2,3-f]quinoline-7-one (610 mg) and cuprous cyanide (134 mg) were dissolved in dimethylformamide (30.5 ml), and stirred at 150° C. for 1 hour. After completion of the reaction, the solvent was distilled off, and the residue was purified by silica gel column chromatography (eluent=chloroform:methanol=70:1). As a result, 347 mg of 2-(t-butoxycarbonyl)aminomethyl-5-cyano-2,3,6,7-tetrahydrofuro[2,3-f]quinoline-7-one was obtained (73.7%). This compound was recrystallized from a solvent mixture of chloroform-n-hexane to obtain pale yellow powdery crystals (mp.: 200°–202° C. (dec.)).

IR(KBr): 3306, 2209, 1676, 1466, 1364, 1161, 1096, 833 cm⁻¹.

¹H-NMR(CDCl₃)δ: 8.96(1H,br.s), 7.86(1H,d,J=9.8Hz), 7.51(1H,s), 6.62(1H,d,J=9.8Hz), 5.20–4.90(2H,m), 3.70–3.30(4H,m), 3.06(1H,dd, J=15.1,7.3Hz), 1.45(9H, s).

Example 67:

2-Aminomethyl-5-cyano-2,3,6,7-tetrahydrofuro[2,3-f]quinoline-7-one.HCl:

The title compound was synthesized from 2-(t -butoxycarbonyl)aminomethyl-5-cyano-2,3,6,7-tetrahydrofuro[2,3-f]quinoline-7-one in a manner similar to that described in Example 65.

Example 68:

2-Azidomethyl-5-iodo-2,3,6,7-tetrahydrofuro[2,3-f]quinoline-7-one:

The title compound was synthesized from 2-azidomethyl-2,3,6,7-tetrahydrofuro[2,3-f]quinoline-7-one in a manner similar to that described in Example 64.

colorless needles, mp.: 175° C. (acetone-n-hexane)

IR(KBr): 2075, 1653, 1592, 1457, 1275, 1147 cm⁻¹.

¹H-NMR(CDCl₃)δ: 8.79(1H,br.s), 7.80(1H,d,J=9.8Hz), 7.68(1H,s), 6.57(1H,d,Jm9.8Hz), 3.58(1H, dd, Jm14.0, 3.9Hz), 3.51(1H,dd, J=14.0, 5.4Hz), 3.41(1H,dd,J=15.6, 9.5Hz), 3.10(1H,dd,J=15.6,6.8Hz).

Example 69:

2-Azidomethyl-5-cyano- 2,3,6,7-tetrahydrofuro[2,3-f]quinoline-7-one:

The title compound was synthesized from 2-azidomethyl-5-iodo-2,3,6,7-tetrahydrofuro[2,3-f]quinoline-7-one in a manner similar to that described in Example 64.

colorless prisms, mp.: 213°–215° C. (chloroform-methanol)

IR(KBr): 2200, 2129, 2092, 1670, 1603, 1460, 1287, 1263 cm⁻¹.

¹H-NMR(CDCl₃-CD₃OD)δ: 7.99(1H,d,J=10.0Hz), 7.66(1H, s), 6.67(1H,d,J=10.0Hz), 4.42(1H,br.s), 3.74(1H, dd, Jm13.6,3.5Hz), 3.58(1H, dd, J=13.6,5.6Hz), 3.49(1H,dd, J-15.6,9.5Hz), 3.18(1H, dd, Jm15.6,7.0Hz).

Example 70:

2-Azidomethyl-5-ethoxycarbonyl-2,3,6,7-tetrahydrofuro[2,3-f]quinoline-7-one and 2-azidomethyl-5-carbamoyl-2,3,6,7-tetrahydrofuro[2,3-f]quinoline-7-one:

2-Azidomethyl-5-cyano-2,3,6,7-tetrahydrofuro[2,3-f]quinoline-7-one (3.4 g) was suspended in 95% ethanol (85 ml). Concentrated sulfuric acid (32 ml) was added to the mixture, and the mixture was refluxed for 5 hours while heating. 30% potassium carbonate was added to the reaction mixture to turn the pH of the mixture alkaline. Extraction was performed using a solvent mixture of chloroform-methanol (8:1), and the extract was dried. The solvent was distilled off, and the resultant residue was washed with chloroform to obtain 0.232 g of 2-azidomethyl-5-carbamoyl -2,3,6,7-tetrahydrofuro[2,3-f]quinoline-7-one as a pale brown solid (6.4%, mp.: 220°–223° C. (dec.)). The chloroform used to wash the above-described residue was dried to solidity under reduced pressure, and the obtained crude product was purified by silica gel column chromatography (eluent=chloroform) to obtain 1.64 g of 2-azidomethyl-5-ethoxycarbonyl-2,3,6,7-tetrahydrofuro[2,3-f]quinoline-7-one (41.1%). The purified product was recrystallized from acetone to obtain colorless needles (mp.: 173° C.).

2-Azidomethyl-5-ethoxycarbonyl-2,3,6,7-tetrahydrofuro[2,3-f]quinoline-7-one:

IR(KBr): 2089, 1728, 1656, 1603, 1466, 1280, 1180, 1149 cm⁻¹.

¹H-NMR(CDCl₃-CD₃OD)δ: 9.12(1H, br.s), 8.10(1H, s), 7.94(1H, d, J=9.7Hz), 6.64(1H, d, J=9.7Hz), 5.36–5.18(1H, m), 4.42 (2H, q, J=7.0Hz), 3.73–3.38(3H,m), 3.14(1H, dd, J=15.9,6.1Hz), 1.43 (3H, t, J=7.0Hz).

2-Azidomethyl-5-carbamoyl-2,3,6,7-tetrahydrofuro[2,3-f]quinoline-7-one:

IR(DBr): 2091, 1644, 1469, 1421, 1286, 1150 cm⁻¹.

¹H-NMR(CDCl₃-CD₃OD)δ: 8.12(1H,br.s), 7.98(1H,d,J= 9.8Hz), 7.85(1H,s), 6.30(1H, d,J=9.8Hz), 5.23–5.38(1H,m), 4.21(2H,br.s), 3.35–3.76(3H,m), 3.16(1H, dd, J=15.6, 6.8Hz).

Example 71:

2-Aminomethyl-5-ethoxycarbonyl-2,3,6,7-tetrahydrofuro[2,3-f]quinoline-7-one.HCl and 2-aminomethyl-5-carbamoyl-2,3,6,7-tetrahydrofuro[2,3-f]quinoline-7-one.HCl:

The title compounds were synthesized from the corresponding azide compounds in a manner similar to that described in Example 5.

Example 72:

2-Aminomethyl-5-ethoxycarbonyl-2,3,6,7-hexafuro[2,3-f]quinoline-7-one.HCl:

The title compounds was synthesized from the corresponding tetrahydro compound in a manner similar to that described in Example 7.

Example 73:

2-Acetyl-2-methanesulfonyloxymethyl-2,3,6,7-tetrahydrofuro[2,3-f]quinoline-7-one:

2-Hydroxymethyl-2,3,6,7-tetrahydrofuro[2,3-f]quinoline-7-one (1.066 g) was added to pyridine (20 ml). Methanesulfonyl chloride (0.85 ml) was added to the mixture at room temperature while stirring, followed by further stirring overnight at room temperature. After completion of the reaction, the solvent was distilled off. After adding aqueous sodium dicarbonate solution for alkalifying, extraction was performed with chloroform. After drying the chloroform phase, the solvent was distilled off, and the residue was purified by silica gel column chromatography (eluent=chloroform), thereby obtaining 1.3 g of a purified product. Trifluoro acetic anhydride (2 ml) and acetic acid (0.7 ml) were added to the purified product, and the mixture was stirred at 60° C. for 6 hours. After completion of the reaction, aqueous sodium bicarbonate solution was added for neutralization, followed by extraction with chloroform. The chloroform phase was washed with water, and dried. The solvent was then distilled off to obtain 1.23 g of 2-acetyl-2-methanesulfonyloxymethyl-2,3,6,7-tetrahydrofuro[2,3-f]quinoline-7-one as crystals (61.5%, mp.: 233°–236° C. (dec.).

IR(KBr): 1658, 1355, 1160, 834 cm$^1$.

$^1$H-NMR(DMSO-d$_6$)δ: 8.25(1H,s), 7.93(1H,d,J=9.9Hz), 6.54(1H,d,J=9.9Hz), 5.4–5.5(1H,m), 4.6–4.7(2H,m), 3.45(2H,d,J=4.9Hz), 3.23(3H,s), 2.64(3H, s).

Example 74:

5-Acetyl-2-azidomethyl-2,3,6,7-tetrahydrofuro[2,3-f]quinoline-7-one.ethyleneacetal:

2-Acetyl-2-azidomethyl-2,3,6,7-tetrahydrofuro[2,3-f]quinoline-7-one (228 mg) was suspended in benzene (20 ml), to which ethylene glycol (4 ml) and p-tolenesulfonic acid (20 mg) were added. A water separator was attached to a vessel containing the mixture, and reflux was performed for 5 hours while heating. Chloroform was then added to the mixture, and washed with aqueous sodium bicarbonate solution, water and aqueous NaCl solution in this order. After drying, the solvent was distilled off, and the obtained crude product was purified by silica gel separative thin layer chromatography (eluent=chloroform:methanol=15:1). As a result, 129 mg of 2-acetyl-2-azidomethyl -2,3,6,7-tetrahydrofuro[2,3-f]quinoline-7-one.ethyleneacetal was obtained as pale yellow crystals (49.0%, mp.: 130°–132° C.).

IR(KBr): 3287, 2088, 1662, 1150, 1032, 780 cm$^{-1}$.

$^1$H-NMR(CDCl$_3$)δ: 10.38(1H,br.s), 7.88(1H,d,J=9.2Hz), 7.44(1H,s), 6.57(1H,d,J=9.2Hz), 5.20–5.10(1H,m), 4.12(2H,t,J=7.0Hz), 3.85(2H,t,J=7.0Hz), 3.54(2H,d,J=6.3Hz), 3.38(1H, dd, J–15.0,9.0Hz), 3.06(1H,dd,J=15.0, 7.0Hz), 1.68(3H,s).

Example 75:

2-Hydroxymethyl-nitro-2,3,6,7-tetrahydrofuro[2,3-f]quinoline-7-one:

70% Nitric acid (10 ml, d=1.42) was added dropwise to 2-hydroxymethyl-2,3,6,7-tetrahydrofuro[2,3-f]quinoline-7-one while cooling on ice, and the mixture was stirred at the same temperature for 20 minutes. The reaction mixture was poured into ice and water (200 ml), and precipitated crystals were collected by filtration. After drying with air, recrystallization was performed using methanol to obtain 3.0 g of 2-hydroxymethyl-nitro-2,3,6,7-tetrahydrofuro[2,3-f]quinoline-7-one as yellowish brown prisms (75.3%, mp. 215°–218° C.).

IR(KBr): 3350, 1650, 1595, 1560, 1515, 1450, 1315, 1270, 1230, 1150, 1090, 960, 845, 825 cm$^{-1}$.

$^1$H-NMR(DMSO-d$_6$)δ: 11.24(1H,br.s), 8.36(1H,s), 7.96(1H,d,J=9.9Hz), 6.61(1H,d,J=9.9Hz), 5.25(1H,m), 5.13(1H,t,J=5.3Hz), 3.78(1H, ddd, J=12.5,5.3,3.3Hz), 3.62(1H,dt,J=12.5,5.3Hz), 3.37(1H,dd, J=15.9,9.2Hz), 3.16(1H, dd, J-15.9,5.8Hz).

The following compounds were manufactured in a manner similar to that described in Examples 52–75.

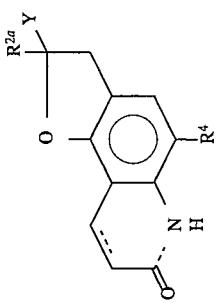

| Ex | Bond by | R²ᵃ | R⁴ | Y | Salt | mp. (°C.) | Sol* | IR (cm⁻¹) (KBr) | solv. | ¹H-NMR δ(ppm) |
|---|---|---|---|---|---|---|---|---|---|---|
| 76 | d | H | Me | CH₂NEt₂ | HCl | 244–246 (dec.) | MeOH–Et₂O | 3426, 1637, 1465, 1444, 1152, 1086, 1025, 840, 638 | CDCl₃ CD₃OD | 7.91(1H, d, J=9.7Hz), 7.37(1H, s), 6.61(1H, d, J=9.7Hz), 5.60(1H, m), 3.80–3.25(7H, m), 3.02(1H, d, J=7.4, 15.6Hz), 2.39 (3H, s), 1.45(6H, t, J=7.4Hz) |
| 77 | s | H | Me | CH₂NEt₂ | HCl | 230–234 (dec.) | MeOH–Et₂O | 3380, 3252, 2922, 2635, 1682, 1408, 1364, 1243, 1205, 1096, 1055, 1019 | CDCl₃ CD₃OD | 6.86(1H, s), 5.45(1H, m), 3.55–3.20(5H, m), 3.00–3.70(5H, m), 2.59(2H, t, J=7.3Hz), 2.16(3H, s), 1.44(3H, t, J=7.3Hz), 1.43(3H, t, J=7.3Hz) |
| 78 | d | H | Me | CH₂NHMe | HCl | >270 | MeOH | 3165, 1645, 1570, 1465, 1445, 1335, 1270, 1250, 1215, 1165, 1070, 840 | CD₃OD | 8.05(1H, d, J=9.3Hz), 7.29(1H, s), 6.56(1H, d, J=9.3Hz), 5.22–5.33 (1H, m), 3.53(1H, dd, J=9.3, 15.6Hz), 3.36–3.39(2H, m), 3.05(1H, dd, J=7.1, 15.6Hz), 2.83(3H, s), 2.39(3H, s) |
| 79 | s | H | Me | CH₂NHMe | HCl | >270 | MeOH | 3225, 1675, 1625, 1480, 1470, 1445, 1390, 1375, 1200, 1085, 1050, 855 | CD₃OD | 6.90(1H, s), 5.04–5.14(1H, m), 3.39(1H, dd, J=9.3, 15.4Hz), 3.23–3.33(2H, m), 2.85–2.97(3H, m), 2.80(3H, s), 2.52(2H, t, J=7.8Hz), 2.17(3H, s) |
| 80 | d | H | Me | CH₂N(morpholine) | HCl | >280 | MeOH–n-Hexane | *3156, 3023, 2847, 1641, 1569, 1460, 1271, 1157, 1114 | *CDCl₃ | 8.60(1H, brs), 7.89(1H, d, J=9.7Hz), 7.12(1H, s), 6.55(1H, d, J=9.7Hz), 5.08–5.13(1H, m), 3.72–3.76(2H, m), 3.02–3.36(4H, m), 2.51–2.83(4H, m), 2.32(3H, s), 1.59(4H, m) |
| 81 | s | H | Me | CH₂N(morpholine) | HCl | 281–285 | MeOH–n-hexane | 3212, 2885, 1663, 1634, 1465, 1201, 1113, 1089 | *CDCl₃ | 8.07(1H, brs), 6.82(1H, s), 4.96–4.98(1H, m), 2.50–3.75(12H, m), 2.13(3H, s), 1.57(4H, m) |

-continued

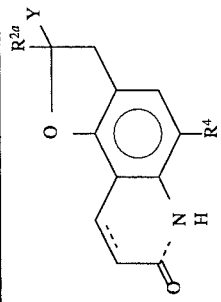

| Ex | Bond by --- | R2a | R4 | Y | Salt | mp. (°C.) | Sol* | IR (cm⁻¹) (KBr) | solv. | ¹H-NMR δ(ppm) |
|---|---|---|---|---|---|---|---|---|---|---|
| 82 | d | H | Me | <br>CH₂N⟨cyclohexyl⟩ | HCl | 287–300 | MeOH-n-Hexane | 3374, 2930, 2709, 1642, 1614, 1455, 1316, 1247, 1145, 1092 | *CDCl₃ | 8.70(1H, brs), 7.92(1H, d, J=9.7Hz), 7.12(1H, s), 6.55(1H, d, J=9.7Hz), 5.07–5.13(1H, m), 2.96–3.35(2H, m), 2.46–2.87(8H, m), 2.32(3H, s), 1.38–1.75(4H, m) |
| 83 | s | H | Me | CH₂N⟨cyclohexyl⟩ | HCl | 272–274 | MeOH-n-Hexane | 3382, 2934, 2637, 1666, 1631, 1472, 1377, 1288, 1205, 1079 | *CDCl₃ | 7.29(1H, brs), 6.81(1H, s), 4.97(1H, m), 3.21(1H, dd, J=15.6, 8.8Hz), 2.72 (1H, dd, J=14.2, 6.8Hz), 2.82–3.96 (3H, m), 2.40–2.66(7H, m), 2.13(3H, s), 1.52–1.68(4H, m), 1.40–1.50(2H, m) |
| 84 | d | H | Me | CH₂N⟨pyrrolidinyl⟩ | — | 188–190 | Column chromatography | 3150, 3007, 2823, 2762, 1645, 1569, 1463, 1327, 1266, 1241, 1149 | CDCl₃ | 9.58(1H, brs), 7.93(1H, d, J=9.7Hz), 7.12(1H, s), 6.55(1H, d, J=9.7Hz), 5.05–5.16(1H, m), 2.97–3.37(2H, m), 2.84–2.86(2H, m), 2.63–2.75(4H, m), 2.33(3H, s), 1.81–1.85(4H, m) |
| 85 | s | H | Me | CH₂N⟨pyrrolidinyl⟩ | HCl | 255–257 | MeOH-n-Hexane | 3227, 2930, 1668, 1628, 1471, 1379, 1283, 1203, 1089 | CDCl₃ | 6.81(1H, s), 4.95–5.05(1H, m), 2.35–3.28(12H, m), 2.13(3H, s), 1.65–1.81(4H, m) |
| 86 | d | H | Me | CH₂NHCH₂φ | HCl | 282–285 (dec.) | MeOH | 3160, 3020, 1670, 1635, 1610, 1455, 1490, 1430, 1260, 1245, 1065, 840 | CD₃OD | 8.05(1H, d, J=9.8Hz), 7.52–7.57(2H, m), 7.45–7.50(3H, m), 7.27(1H, s), 6.55 (1H, d, J=9.8Hz), 5.24–5.35(1H, m), 4.35(2H, s), 3.35–3.40(2H, m), 3.30(1H, dd, J=7.0, 15.8Hz), 2.38(3H, s) |
| 87 | s | H | Me | CH₂NHCH₂φ | HCl | 234–238 (dec.) | MeOH–Et₂O | 3220, 1685, 1630, 1485, 1470, 1440, 1205, 745, 700 | CD₃OD | 7.46–7.55(5H, m), 6.89(1H, s), 4.32(2H, s), 3.23–3.43(3H, m), 2.85–2.95(3H, m), 2.52(2H, t, J=7.8Hz), 2.17(3H, s) |

-continued

| Ex | Bond by | R²ᵃ | R⁴ | Y | Salt | mp. (°C.) | Sol* | IR (cm⁻¹) (KBr) | solv. | ¹H-NMR δ(ppm) |
|---|---|---|---|---|---|---|---|---|---|---|
| 88 | d | H | Me | CH₂N—CH₂φ<br>\|<br>CH₃ | — | 152–153 | EtOH–Et₂O | 3145, 1640, 1615, 1570, 1450, 1265, 1220, 1150, 1085, 1025, 865, 845 | CD₃OD | 8.80(1H, brs), 7.92(1H, d, J=9.8Hz), 7.20–7.30(5H, m), 7.10(1H, s), 6.55(1H, d, J=9.8Hz), 5.04–5.15(1H, m), 3.62–3.69(2H, m), 3.28(1H, dd, J=9.3, 15.1Hz), 2.99(1H, dd, J=7.3, 15.1Hz), 2.81(1H, dd, J=6.4, 13.2Hz), 2.66(1H, dd, J=5.4, 13.2Hz), 2.37(3H, s), 2.33(1H, s) |
| 89 | d | H | Me | [imidazole with CH₂N linker] | HCl | >270 | MeOH–Et₂O | 3110, 2930, 2795, 1630, 1610, 1575, 1540, 1460, 1435, 1400, 1330, 1310 | CD₃OD | 9.10–9.11(1H, m), 8.24(1H, d, J=9.3Hz), 7.78–7.80(1H, m), 7.58–7.59(1H, m), 7.38(1H, s), 6.78(1H, d, J=9.3Hz), 5.36–5.46(1H, m), 4.74 (1H, dd, J=2.9, 14.7Hz), 4.60(1H, dd, J=7.8, 14.7Hz), 3.60(1H, dd, J=9.8, 16.1Hz), 3.17(1H, dd, J=6.8, 16.1Hz), 2.43(3H, s) |
| 90 | d | H | Me | [dimethoxyphenyl with CH₃/CH₂N(CH₂)₂] | HCl | 268–272 (dec.) | MeOH–Et₂O | 3180, 1680, 1655, 1590, 1465, 1420, 1390, 1325, 1260, 1235, 1080, 825 | CD₃OD | 7.97(1H, d, J=9.8Hz), 7.28(1H, s), 6.82–6.96(3H, m), 6.54(1H, d, J=9.8Hz), 5.41–5.52 (1H, m), 3.80(6H, s), 3.50–3.70(4H, m), 3.14(3H, s), 2.99–3.11(4H, m), 2.38(3H, s) |
| 91 | s | H | Me | [dimethoxyphenyl with CH₃/CH₂N(CH₂)₂] | HCl | 227–230 (dec.) | MeOH–Et₂O | 3220, 1670, 1630, 1470, 1420, 1370, 1335, 1235, 1200, 1155, 1140, 1020 | CD₃OD | 6.84–6.91(4H, m), 5.22–5.33(1H, m), 3.82(3H, s), 3.81(3H, s), 3.38–3.62(5H, m), 3.10(3H, s), 3.00–3.08(2H, m), 2.81–2.96(3H, m), 2.47–2.53(2H, m), 2.17(3H, s) |

-continued

| Ex | Bond by - - - | R$^{2a}$ | R$^4$ | Y | Salt | mp. (°C.) | Sol* | IR (cm$^{-1}$)(KBr) | solv. | $^1$H-NMR δ(ppm) |
|---|---|---|---|---|---|---|---|---|---|---|
| 92 | d | H | Me | CH$_2$NH-C$_6$H$_{11}$ | HCl | >270 | MeOH–Et$_2$O | 3180, 1675, 1635, 1610, 1455, 1330, 1310, 1270, 1240, 1220, 1150, 835 | CD$_3$OD | 8.05(1H, d, J=9.8Hz), 7.28(1H, s), 6.52(1H, d, J=9.8Hz), 5.21–5.32 (1H, m), 3.53(1H, dd, J=9.3, 15.6Hz), 3.38–3.41(2H, m), 3.06(1H, dd, J=6.8, 15.6Hz), 2.38(3H, s), 2.14–2.22 (2H, m), 1.87–1.94(2H, m), 1.69–1.78 (1H, m), 1.18–1.52(6H, m) |
| 93 | s | H | Me | CH$_2$NH-C$_6$H$_{11}$ | HCl | 268–273 (dec.) | MeOH | 3235, 1675, 1630, 1470, 1440, 1390, 1370, 1340, 1285, 1205, 1080, 1025 | CD$_3$OD | 6.90(1H, s), 5.04–5.14(1H, m), 3.39 (1H, dd, J=8.8, 15.6Hz), 3.12–3.32 (2H, m), 2.80–2.98(1H, m), 2.52 (2H, t, J=7.8Hz), 2.17(3H, s), 2.10–2.20 (2H, m), 1.84–1.95(2H, m), 1.68–1.78 (1H, m), 1.16–1.51(5H, m) |
| 94 | d | H | Me | CH$_2$NH$^n$Bu | HCl | >270 | MeOH | 3170, 1650, 1615, 1565, 1445, 1325, 1310, 1265, 1215, 1150, 1085, 835 | CD$_3$OD | 8.05(1H, s), 7.28(1H, s), 6.56(1H, d, J=9.8Hz), 5.22–5.33(1H, m), 3.52(1H, dd, J=9.8, 15.6Hz), 3.36–3.39(2H, m), 3.00–3.16(3H, m), 2.38(3H, s), 1.68–1.81(2H, m), 1.39–1.53 (2H, m), 1.01(3H, t, J=7.3H) |
| 95 | s | H | Me | CH$_2$NH$^n$Bu | HCl | 258–260 (dec.) | MeOH–Et$_2$O | 3220, 1675, 1625, 1470, 1375, 1740, 1285, 1340, 1205, 1085, 1055, 1025 | CD$_3$OD | 6.90(1H, s), 5.04–5.15(1H, m), 3.22–3.44 (3H, m), 3.07–3.13(2H, m), 2.85–2.97 (3H, m), 2.52(2H, t, J=7.8Hz), 2.17 (3H, s), 1.67–1.79(2H, m), 1.39–1.52 (2H, m), 1.01(3H, t, J=7.3Hz) |
| 96 | d | H | Me | CH$_2$N(piperazinyl)NCH$_2$φ | 2HCl | 267–270 | MeOH–n-Hexane | *3394, 2961, 2359, 1660, 1461, 1323, 1259, 1149, 1083 | *CDCl$_3$ | 8.78(1H, brs), 7.89(1H, d, J=9.3Hz), 7.26–7.33(5H, m), 7.11(1H, s), 6.54(1H, d, J=9.3Hz), 5.04–5.14(1H, m), 3.53(2H, m), 2.41–3.39(12H, m), 2.32(3H, s) |
| 97 | d | H | Me | CH$_2$N(piperazinyl)NH | 2HCl | >300 | MeOH–n-Hexane | 3389, 2626, 2634, 1649, 1568, 1461, 1310, 1268, 1150, 1062 | *CDCl$_3$ | 7.90(1H, d, J=9.3Hz), 7.12(1H, s), 6.55(1H, d, J=9.3Hz), 5.05–5.16(1H, m), 2.50–3.35(12H, m), 2.35(3H, s) |

-continued

| Ex | Bond by | R$^{2a}$ | R$^4$ | Y | Salt | mp. (°C.) | Sol* | IR (cm$^{-1}$) (KBr) | solv. | $^1$H-NMR δ(ppm) |
|---|---|---|---|---|---|---|---|---|---|---|
| 98 | d | H | Me | CH$_2$N-φ<br>\|<br>Me | — | 203–205 | MeOH—CHCl$_3$—Et$_2$O | 3150, 3005, 2985, 1635, 1605, 1570, 1500, 1445, 1370, 1250, 1150, 825 | CDCl$_3$ | 9.60(1H, brs), 7.84(1H, d, J=9.8Hz), 7.20–7.27(2H, m), 7.12(1H, s), 6.71–6.77(3H, m), 6.56(1H, d, J=9.8Hz), 5.16–5.27(1H, m), 3.60–3.62(2H, m), 3.33(1H, dd, J=9.3, 15.1Hz), 3.07 (3H, s), 2.95(1H, dd, J=6.8, 15.1Hz), 2.39(3H, s) |
| 99 | d | H | Me | CH$_2$NH(CH$_2$)$_2$-(3,4-dimethoxyphenyl) | HCl | 247–253 (dec.) | MeOH—Et$_2$O | 3170, 1650, 1615, 1590, 1515, 1460, 1255, 1235, 1150, 1085, 1025, 835 | CD$_3$OD | 8.02(1H, d, J=9.8Hz), 7.28(1H, s), 6.82–6.92(3H, m), 6.55(1H, d, J=9.8Hz), 5.24–5.35(1H, m), 3.83 (3H, s), 3.81(3H, s), 3.52(1H, dd, J=9.5, 15.6Hz), 3.35–3.42(4H, m), 2.99–3.09(3H, m), 2.38(3H, s) |
| 100 | d | H | Me | CH$_2$N-piperidinyl-NCO-(3,4-dimethoxyphenyl) | — | 245–248 | Column chromatography | 3382, 1722, 1699, 1634, 1463, 1117 | CDCl$_3$ | 8.89(1H, brs), 7.89(1H, d, J=9.8Hz), 7.10(1H, s), 6.86–6.99(1H, m), 6.84 (1H, d, J=9.8Hz), 5.04–5.10(1H, m), 3.94(3H, s), 3.97(3H, s), 2.33–3.83 (12H, m), 2.29(3H, s) |
| 101 | d | H | Me | CH$_2$NMe$_2$ | HCl | >270 | MeOH—Et$_2$O | 3225, 1660, 1635, 1615, 1475, 1460, 1320, 1260, 1215, 1080, 970, 830 | CD$_3$OD | 8.04(1H, d, J=9.8Hz), 7.27(1H, s), 6.54(1H, d, J=9.8Hz), 5.38–5.48(1H, m), 3.45–3.68(3H, m), 3.30–3.34 (1H, m), 3.08(3H, s), 3.05(3H, s), 2.37(3H, s) |
| 102 | s | H | Me | CH$_2$NMe$_2$ | HCl | >270 | MeOH—EtOH | 3465, 3240, 1655, 1625, 1475, 1420, 1340, 1230, 1210, 1165, 1050, 845 | CD$_3$OD | 6.90(1H, s), 5.18–5.29(1H, m), 3.37–3.54(3H, m), 3.02(6H, s), 2.86–2.94(3H, m), 2.52(2H, t, J=7.8Hz), 2.17(3H, s) |
| 103 | d | H | Me | CH$_2$OAc | — | 197–200 | CHCl$_3$ n-Hexane | 3395, 3158, 3024, 1749, 1674, 1646, 1450, 1267, 1042, 838 | CDCl$_3$ | 8.95(1H, brs), 7.92(1H, d, J=9.5Hz), 7.13(1H, s), 6.58(1H, d, J=9.5Hz), 5.10(1H, m), 4.40–4.20(2H, m), 3.36 (1H, dd, J=9.3, 15.5Hz), 3.02(1H, dd, J=7.4, 15.5Hz), 2.35(3H, s), |

-continued

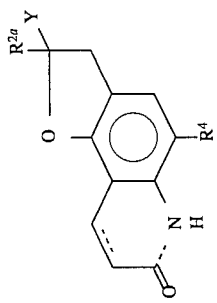

| Ex | Bond by ... | R²ᵃ | R⁴ | Y | Salt | mp. (°C.) | Sol* | IR (cm⁻¹) (KBr) | solv. | ¹H-NMR δ(ppm) |
|---|---|---|---|---|---|---|---|---|---|---|
| 104 | s | H | Me | CH₂OAc | — | 183–184 | CHCl₃ n-Hexane | 3229, 1735, 1678, 1482, 1456, 1387, 1246, 1037, 650 | CDCl₃ | 2.10(3H, s), 7.35(1H, brs), 6.83(1H, s), 5.00(1H, m), 4.40–4.20(2H, m), 3.25(1H, dd, J=4.3, 15.3Hz), 3.00–2.90(4H, m), 2.59(2H, t, J=7.8Hz), 2.14(3H, s), 2.10(3H, s) |
| 105 | s | H | Me | CH₂ONO₂ | — | 160–163 | CHCl₃ n-Hexane | 3215, 1660, 1630, 1480, 1470, 1440, 1370, 1340, 1275, 1205, 1080, 1055, 845 | CDCl₃ | 8.10(1H, brs), 6.85(1H, s), 5.00–5.11 (1H, m), 4.66(1H, dd, J=6.4, 11.7 Hz), 4.59(1H, dd, J=4.4, 11.7Hz), 3.33(1H, dd, J=9.3, 15.9Hz), 2.96(1H, dd, J=6.6, 15.9Hz), 2.85–2.91(2H, m), 2.57–2.26(2H, m), 2.15(3H, s) |
| 106 | d | H | Me | CH₂I | — | 230–233 | Column chromatography | 3144, 3007, 1624, 1569, 1445, 1326, 1268, 1230 1147, 1081, 926 | CDCl₃ | 7.97(1H, d, J=9.7Hz), 7.18(1H, s), 6.58(1H, d, J=9.7Hz), 5.00–5.07(1H, m), 3.05–3.53(4H, m), 2.37(3H, s) |
| 107 | d | H | Me | CH₂F | — | 136–141 | CHCl₃ n-Hexane | 3391, 1658, 1465, 1347, 1083, 938, 832 | CDCl₃ | 8.80(1H, brs), 7.93(1H, d, J=9.7Hz), 7.14(1H, s), 5.15(1H, m), 4.80–4.45 (2H, m), 6.58(1H, d, J=9.7Hz), 3.36(1H, dd, J=7.8, 15.1Hz), 3.11 (1H, dd, J=7.8, 15.1Hz), 2.34(3H, s) |
| 108 | s | H | Me | CH₂F | — | 170–177 | CHCl₃ n-Hexane | 3395, 1670, 1482, 1457, 1388, 1205, 1083, 938, 822 | CDCl₃ | 7.30(1H, brs), 6.84(1H, s), 5.00(1H, m), 4.68(1H, s), 4.45(1H, m), 3.40–2.90(4H, m), 2.59(2H, t, J=7.8Hz), 2.14(3H, s) |
| 109 | d | H | Me | CH₂OMe | — | 181–184 | CHCl₃ n-Hexane | 3151, 3010, 1646, 1572, 1465, 1329, 1245, 1121, 1089 | CDCl₃ | 8.59(1H, brs), 7.95(1H, d, J=9.7Hz), 7.13(1H, s), 6.55(1H, d, J=9.7Hz), 5.04–5.14(1H, m), 3.63–3.69(2H, m), 3.45(3H, s), 3.01–3.34(2H, m), 2.32(3H, s) |
| 110 | s | H | Me | CH₂OMe | — | 237–242 | Column chromatography | 3215, 2636, 1667, 1627, 1469, 1384, 1204, 1095, 1051 | CDCl₃ | 6.84(1H, s), 4.95(1H, m), 4.08(2H, m), 3.61(2H, m), 3.45(3H, s), 2.89(2H, m), 2.56(2H, m), 2.16(3H, s) |

-continued

| Ex | Bond by ... | R²ᵃ | R⁴ | Y | Salt | mp. (°C.) | Sol* | IR (cm⁻¹) (KBr) | solv. | ¹H-NMR δ(ppm) |
|---|---|---|---|---|---|---|---|---|---|---|
| 111 | s | H | Me | COOH | — | 278–283 | Note¹ | 3284, 1714, 1634, 1610, 1474, 1419, 1247, 1054 | CDCl₃ CD₃OD | 6.86(1H, s), 5.20(1H, s), 5.20(1H, dd, J=6.8, 10.7 Hz), 3.60–2.80(4H, m), 2.55(2H, t, J=7.3Hz), 2.17(3H, s) |
| 112 | s | H | Me | CONH₂ | — | 264–266 | CHCl₃ MeOH n-Hexane | 3334, 1601, 1479, 1439, 1387, 1284, 1205, 1087, 1050, 939 | CDCl₃ CD₃OD | 6.87(1H, s), 5.12(1H, dd, J=6.8, 11.5Hz), 3.60–2.85(4H, m), 2.58(2H, t, J=7.8Hz), 2.19(3H, s) |
| 113 | d | H | Me | CH₂O—⟨phenyl⟩—NH₂ | HCl | >300 | MeOH Et₂O | 3394, 1670, 1648, 1481, 1451, 1310, 1277, 1116, 939 | CD₃OD | 8.01(1H, d, J=9.7Hz), 7.25(1H, s), 6.55(1H, d, J=9.7Hz), 5.15(1H, m), 3.90–3.70(4H, m), 3.40–3.00(4H, m), 2.38(3H, s) |
| 114 | s | H | Me | CH₂NHMs | — | 217–219 | CHCl₃ n-Hexane | 3275, 1669, 1471, 1390, 1332, 1206, 1133, 1078, 973 | CDCl₃ | 7.40(1H, brs), 6.82(1H, s), 3.01(1H, s), 5.14(1H, brt, J=5.9Hz), 4.95 (1H, m), 3.60–2.80(6H, m), 2.58 (2H, t, J=7.3Hz), 2.10(3H, s) |
| 115 | d | H | Me | CH₂NHCO—⟨phenyl(OMe)(OMe)⟩ | — | 245–248 | Separative TLC | 3266, 3026, 1652, 1620, 1507, 1463, 1309, 1269, 1230, 1143, 1084 | CDCl₃ | 8.78(1H, brs), 7.92(1H, d, J=9.3Hz), 7.38(1H, d, J=2.0Hz), 7.21(1H, dd, J=2.0, 6.3Hz), 7.14(1H, s), 6.84(1H, d, J=8.3Hz), 6.59(1H, d, J=9.3Hz), 6.46(1H, m), 5.15(1H, m), 3.95(3H, s), 3.92(3H, s), 3.72–3.92(2H, m), 3.01–3.39(2H, m), 2.33(3H, s) |
| 116 | d | H | Me | CH₂NH—CH₂—CH(OH)—CH₂O—⟨phenyl⟩—Me | HCl | 256–261 (dec.) | MeOH | 3265, 1655, 1635, 1610, 1505, 1480, 1450, 1245, 1145, 1085, 1065, 1040, 1020, 835 | CD₃OD | 8.01(1H, d, J=9.8Hz), 7.28(1H, s), 7.08(2H, d, J=8.8Hz), 6.844, 6.841 (altogether, 2H, each d, J=8.8Hz), 6.50, 6.49(altogether, 1H, each d, J=9.8Hz), 5.41–5.38 (1H, m), 4.38–4.28 (1H, m), 4.10–3.95(2H, m), 3.58–3.33 (4H, m), 3.10–3.01(1H, m), 2.38(3H, s), 2.26(3H, s) |

-continued

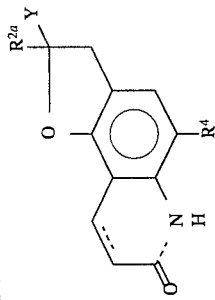

| Ex | Bond by --- | $R^{2a}$ | $R^4$ | Y | Salt | mp. (°C.) | Sol* | IR (cm$^{-1}$) (KBr) | solv. | $^1$H-NMR δ(ppm) |
|---|---|---|---|---|---|---|---|---|---|---|
| 117 | d | Me | Me | CH$_2$NH$^i$Pr | HCl | 295–298 | EtOH Et$_2$O | 2900–2300, 1653, 1076 | CDCl$_3$ CD$_3$OD | 7.96(1H, d, J=9.3Hz), 7.22(1H, s), 6.55(1H, d, J=9.3Hz), 3.58–3.40 (1H, m), 3.44(1H, d, J=16.1Hz), 3.16(1H, d, J=16.1Hz), 3.34(1H, d, J=13.3Hz), 3.27(1H, d, J=13.3Hz), 2.36(3H, s), 1.67(3H, s), 1.43(3H, s), 1.40(3H, s) |
| 118 | s | Me | Me | CH$_2$NH$^i$Pr | HCl | 268–270 (dec.) | EtOH Et$_2$O | 3282, 1662, 1072 | CD$_3$OD | 6.89(1H, s), 3.47(1H, q, J=6.8Hz), 3.37–3.20(2H, m), 3.20(1H, d, J=15.6 Hz, 3.07(1H, d, J=15.6Hz), 2.94–2.80 (2H, m), 2.60–2.45(2H, s), 2.18(3H, s), 1.59(3H, s), 1.38(3H, s), 1.35(3H, s) |
| 119 | d | Me | Me | CH$_2$NHCH$_2$– (3,4-diOMe-phenyl) | HCl | 268–269 (dec.) | EtOH MeOH | 1652, 1264, 1080, 1022 | CDCl$_3$ CD$_3$OD | 7.95(1H, d, J=9.8Hz), 7.22(1H, s), 7.10 (1H, d, J=2.0Hz), 7.04(1H, d, J=2.0Hz), 7.00(1H, d, J=2.0Hz), 6.89(1H, d, J=8.2 Hz), 6.55(1H, d, J=9.8Hz), 4.27(1H, d, J=13.2Hz), 4.19(1H, d, J=13.2Hz), 3.84(3H, s), 3.83(3H, s), 3.27(2H, s), 3.25(1H, d, J=15.6Hz), 3.15(1H, d, J=15.6Hz), 2.38(3H, s), 1.63(3H, s) |
| 120 | d | H | Cl | CH$_2$NH$_2$ | HCl | >300 | MeOH Et$_2$O | 3478, 1668, 1646, 1461, 1304, 1084, 1021, 775 | CD$_3$OD | 8.03(1H, d, J=9.7Hz), 7.50(1H, s), 5.25(1H, m), 6.60(1H, d, J=9.7Hz), 3.65–3.20(3H, m), 3.10(1H, dd, J=15.4, 6.5Hz) |
| 121 | s | H | Cl | CH$_2$NH$_2$ | HCl | 278–282 (dec.) | MeOH Et$_2$O | 3385, 1684, 1635, 1475, 1205, 1179, 1104 | CD$_3$OD | 7.14(1H, s), 5.10(1H, m), 3.50–2.90(6H, m), 2.90(2H, t, J=7.8Hz), 2.57(2H, t, J=7.8Hz) |
| 122 | d | H | I | CH$_2$NH$_2$ | HCl | 273–276 (dec.) | MeOH | 3399, 1659, 1608, 1456, 1150, 1081, 632 | D$_2$O | 7.84(1H, d, J=9.7Hz), 7.81(1H, s), 6.50(1H, d, J=9.7Hz), 5.34(1H, m), 3.78–3.27(3H, m), 3.07(1H, dd, J=16.1, 6.8Hz) |
| 123 | s | H | I | CH$_2$NH$_2$ | HCl | 165 (dec.) | MeOH | 3388, 1665, 1496, 1211, 1022, 616 | D$_2$O | 7.52(1H, s), 5.17(1H, m), 3.60–2.90 (4H, m), 2.87(2H, t, J=7.3Hz), 2.56 (2H, t, J=3Hz) |
| 124 | d | H | CN | CH$_2$NH$_2$ | HCl | 290–295 | MeOH | 3399, 2200, | CD$_3$OD | 8.04(1H, d, J=9.8Hz), 7.76(1H, s), |

-continued

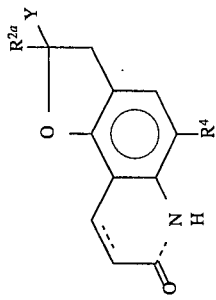

| Ex | Bond by ... | R²ᵃ | R⁴ | Y | Salt | mp. (°C.) | Sol* | IR (cm⁻¹) (KBr) | solv. | ¹H-NMR δ(ppm) |
|---|---|---|---|---|---|---|---|---|---|---|
| | | | | | | (dec.) | Et₂O | 1668, 1604, 1464, 1291, 937 | | 6.63(1H, d, J=9.8Hz), 5.35(1H, m), 3.65–3.30(3H, m), 3.09(1H, dd, J=10.2, 9.8Hz) |
| 125 | s | H | CN | CH₂NH₂ | HCl | 173–177 (dec.) | MeOH Et₂O | 3408, 2213, 1673, 1623, 1473, 1369, 1209, 1097 | CD₃OD | 7.37(1H, s), 3.60–2.80(6H, m), 5.20(1H, m), 2.60(2H, t, J=7.8Hz) |
| 126 | d | H | COOEt | CH₂NH₂ | HCl | 273–275 (dec.) | MeOH Et₂O | 1731, 1648, 1603, 1462, 1298, 1234, 1183 | D₂O | 7.85(1H, s), 7.80(1H, d, J=9.8Hz), 6.43(1H, d, J=9.8Hz), 5.28–5.47(1H, m), 4.29(2H, q, J=7.1Hz), 3.30–3.59(3H, m), 3.04(1H, dd, J=16.1, 6.8Hz), 1.44(3H, t, J=7.1Hz) |
| 127 | s | H | COOEt | CH₂NH₂ | HCl | 269–273 (dec.) | MeOH Et₂O | 1662, 1614, 1471, 1438, 1343, 1280, 1215, 1175 | D₂O | 7.68(1H, s), 5.15–5.32(1H, m), 4.27 (2H, q, J=7.1Hz), 3.28(1H, dd, J=13.6, 9.4Hz), 2.98(1H, dd, J=16.6, 7.1Hz), 2.52–3.52(6H, m), 1.40(3H, t, J=7.1Hz) |
| 128 | d | H | CONH₂ | CH₂NH₂ | HCl | >300 | MeOH Et₂O | 3304, 1641, 1505, 1467, 1429, 1382, 1286 | D₂O | 7.66(1H, d, J=9.8Hz), 7.48(1H, s), 6.31(1H, d, J=9.8Hz), 5.24–5.42(1H, m), 2.85–3.75(4H, m) |
| 129 | d | H | Ac | CH₂NH₂ | HCl | 272 (dec.) | MeOH Et₂O | 1661, 1645, 1621, 1597 | DMSO-d₆ | 12.51(1H, brs), 8.32(1H, brs), 8.26 (1H, s), 7.98(1H, d, J=9.2Hz), 6.61(1H, dd, J=10.0, 2.0Hz), 5.30–5.50(1H, m), 3.50(1H, dd, J=15.9, 9.2Hz), 3.20–3.40 (2H, m), 3.12(1H, dd, J=15.9, 5.9Hz), 2.65(3H, s) |
| 130 | d | H | NH₂ | CH₂NH₂ | 2HCl | >300 | MeOH Et₂O | 3390, 1665, 1615, 1560, 1470, 1435, 1390, 1325, 1275, 1225, 1095, 935, 830, 770 | CD₃OD | 8.15(1H, d, J=9.7Hz) 7.52(1H, s), 6.75(1H, d, J=9.7Hz) 5.37–5.26(1H, m), 3.60(1H, dd, J=16.6, 9.8Hz), 3.39(1H, dd, J=13.7, 3.4Hz), 3.28(1H, dd, J=13.7, 9.5Hz), 3.16(1H, dd, J=16.6, 7.8Hz) |
| 131 | d | H | NHMs | CH₂NH₂ | HCl | >300 | MeOH Et₂O | 3290, 3260, 1660, 1615, 1575, 1515, 1465, 1400, | CD₃OD | 8.04(1H, d, J=9.8Hz), 7.47(1H, s), 6.58(1H, d, J=9.8Hz), 5.33–5.23(1H, m), 3.57(1H, dd, J=15.9, 9.3Hz), |

-continued
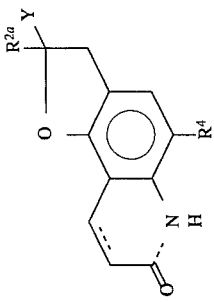
| Ex | Bond by | $R^{2a}$ | $R^4$ | Y | Salt | mp. (°C.) | Sol* | IR (cm$^{-1}$) (KBr) | solv. | $^1$H-NMR δ(ppm) |
|---|---|---|---|---|---|---|---|---|---|---|
| | | | | | | | | 1260, 1215, 1140, 1015, 930, 800 | | 3.37(1H, dd, J=13.0, 3.4Hz), 3.27(1H, dd, J=13.0, 8.6Hz), 3.12(1H, dd, J=15.9, 6.6Hz), 3.05(3H, S) |
| 132 | s | H | NHMs | CH$_2$NH$_2$ | HCl | >300 | MeOH Et$_2$O | 3380, 1685, 1630, 1480, 1470, 1435, 1420, 1355, 1315, 1205, 1145, 1015, 990, 800 | CD$_3$OD | 7.08(1H, s), 5.18–5.07(1H, m), 3.41 (1H, dd, J=16.1, 9.3Hz), 3.31(1H, dd, J=13.7, 2.9Hz), 3.19(1H, dd, J=13.7, 9.3Hz), 3.07(3H, s), 2.94(1H, dd, J=16.1, 6.4Hz), 2.83(t, J=7.8Hz), 2.82(t, J=7.8Hz)(altogether, 2H), 2.53(2H, t, J=7.8Hz) |
Sol*: Solvent used for recrystallization
Note$^1$: Recrystallization could not be performed due to its very slight solubility

Example 133:

2-(N-Acetylaminomethyl)-6,7-dihydro-5-methylfuro-[2,3-f]-quinoline-7-one:

2-(N-Acetylaminomethyl)-5-methyl-2,3,6,7-tetrahydrofuro[2,3-f]quinoline-7-one (750 mg) was suspended in acetic acid (15 ml), to which 2,3-dichloro-5,6-dicyano -1,4-benzoquinone (782 mg) was added. The mixture was stirred at 60° C. for 1 hour. The solvent was distilled off under reduced pressure. To the residue, aqueous 1N NaOH solution (50 ml) was added. Precipitated crystals were collected. As a result, 553 mg of 2-(N-acetylaminomethyl) -6,7-dihydro-5-methylfuro[2,3-f]quinoline-7-one (74.3%) was obtained.

This product was recrystallized from methanol to obtain pale brown prisms (m.p. 300° C.).

IR(KBr): 3270, 1675, 1640, 1600, 1570, 1535, 1440, 1380, 1345, 1265, 1220, 1100, 1070, 850 cm$^{-1}$.

$^1$H-NMR(DMSO-d$_6$)δ: 11.00(1H,br.s), 8.46(1H,t,J=5.6Hz), 8.17(1H,d,J=9.3Hz), 7.54(1H, s), 6.71(1H,s), 6.62(1H,d,J=9.3Hz), 4.44(2H,d,J=5.6Hz), 2.46(3H,s), 1.89(3H, s).

Example 134:

2-Aminomethyl-6,7-dihydro-5-methylfuro[2,3-f]quinoline-7-one.HCl:

2-(N-Acetylaminomethyl)-6,7-dihydro-5 -methylfuro[2,3-f]quinoline-7-one (475 mg) was suspended in methanol (4 mg), to which KOH (1.16 g) in water (1 ml) was added. The mixture was stirred at 90° C. for 11 hours. After completion of the reaction, the solvent was removed under reduced pressure, and water (50 ml) was added. The resulting mixture was made into acidic with 2N-HCl. The aqueous phase was washed with chloroform. Potassium carbonate was added thereto up to definite alkaline pH, followed by extraction with chloroform. The chloroform phase was washed with aqueous NaCl solution, and dried. After the solvent was removed under reduced pressure, 306 mg of 2-aminomethyl-6,7-dihydro-5-methylfuro[2,3-f]quinoline-7-one (76.3%) was obtained. This product was converted into a hydrochloride, and recrystallized from methanol. As a result, a hydrochloric acid salt of 2-aminomethyl-6,7-dihydro-5-methylfuro[2,3-f]quinoline-7-one was obtained as pale yellow prisms (mp.: higher than 300° C.).

Example 135:

2-Methoxy-5-methyl-2,3,6,7-tetrahydrofuro[2,3-f]quinoline-7-one and 5-hydroxy-6-(E-4-hydroxy-2-butenyl)-8-methylcarbostyril:

5-Acetoxy-6-allyl-8-methylcarbostyril (13.0 g) was dissolved in a solvent mixture (4 1) of ethyl acetate-methanol (1:3). The obtained mixture was allowed to react at −5° to 0° C. for 5 hours while oxygen was blown in. The reaction mixture was then subjected to nitrogen atmosphere, and dimethylsulfide (50 ml) was added thereto. The temperature of the system was raised at 50° C., and stirred for 1 hour. Subsequently, the reaction mixture was condensed under reduced pressure, to which methanol (2 1) and methyl(triphenylphosphoranilidene)acetate (33 g) were added in this order. The resultant mixture was stirred at room temperature for 12.5 hours. The reaction liquid was condensed under reduced pressure, and the residue was purified by column chromatography (eluent:chloroform:ethyl acetate=4:1). The purified product was recrystallized from methanol, and as a result, crystals (11.85 g) were obtained. Part of the crystals (6.14 g) was taken therefrom, and suspended in tetrahydrofuran (246 Diisobutylaluminum hydride (1.0 mol, in toluene, 123 ml) was added to the suspension and stirred for 3 hours. 2N-HCl was added to the reaction mixture to bring the pH of the mixture 4, followed by extraction with a solvent mixture of chloroform-methanol (4:1). The organic phase was washed with aqueous 2N-NaOH solution, and dried. The residue obtained after condensation under reduced pressure was recrystallized from a chloroform-methanol-ether solvent mixture. As a result, 1.65 g of 2-methoxy-5-methyl-2,3,6,7-tetrahydrofuro[2,3-f]quinoline-7-one (27.3%) was obtained as colorless flakes. Next, conc. HCl was added to the aqueous NaOH phase to bring the pH to 4, followed by extraction with a solvent mixture of chloroform-methanol (4:1). After drying and condensing, the residue was recrystallized from a methanol-ether solvent mixture to obtain 4.0 g of 5-hydroxy-6-(E-4-hydroxy-2-butenyl)-8-methylcarbostyril as pale yellow prisms (62.3%).

2-Methoxy-5-methyl-2,3,6,7-tetrahydrofuro[2,3-f]quinoline-7-one:

mp. 278°–279° C.

IR(KBr): 3155, 1654, 1574, 1465, 1452, 1428, 1363, 1333, 1209, 1092, 1074, 1007, 900, 832 cm$^1$.

$^1$H-NMR(CD$_3$OD)δ: 8.04(1H,d,J=9.8Hz), 7.22(1H,s), 6.59(1H,d,J=9.8Hz), 5.81(1H,dd, J=6.8,2.4Hz), 3.58(3H, s), 3.42(1H,dd,J=16.1,6.8Hz), 3.07(1H,dd, J=16.1,2.4Hz), 2.39(3H,s).

5-Hydroxy-6-(E-4-hydroxy-2-butenyl)-8-methylcarbostyril:

mp. 201°–203° C.

$^1$H-NMR(CD$_3$OD)δ: 8.27(1H,d,J=9.8Hz), 7.13(1H,s), 6.50(1H,d,J=9.8Hz), 5.56–5.70(2H,m), 4.27(2H,d,J=5.4Hz), 3.45(2H,d,J=6.5Hz), 2.33(3H, s).

The 2-Methoxy compound was converted into a hexahydro compound in accordance with Example 6.

2,3,6,7,8,9-Hexahydro-2-methoxy-5-methylfuro[2,3-f]quinoline-7-one:

mp. 232°–234° C.

IR(KBr): 3223, 1664, 1629, 1471, 1445, 1345, 1344, 1100, 1051, 966, 861, 700, 725 cm$^{-1}$.

$^1$H-NMR(CDCl$_3$)δ: 7.76(1H,br.s), 6.85(1H, s), 5.64(1H, dd, J=6.4,2.0Hz), 3.51(3H, s), 3.29 (1H, dd, J=16.1,6.4Hz), 2.84–3.00 (3H, m), 2.61(2H,t,J=7.3Hz), 2.14(3H, s).

Example 136:

5-Methyl-2,3,6,7-tetrahydro-2-vinylfuro[2,3-f]quinoline-7-one:

5-Hydroxy-6-(trans-4-hydroxy-2-butenyl)-8-methylcarbostyril (2.6 g) was suspended in 1,2-dichloroethane (50 ml). Boron trifluoride.ether complex (7.5 ml) was added to the suspension, and the mixture was stirred at 60° C. for 5 hours. After the reaction, saturated sodium bicarbonate (50 ml) was added thereto, followed by stirring at room temperature for 1.5 hours. Water was added thereto and extraction was performed with chloroform. The extract was dried and condensed under reduced pressure, and the residue was recrystallized from a solvent mixture of chloroform-ether. As a result, 2.35 g of 5-methyl-2,3,6,7-tetrahydro-2-vinylfuro[2,3-f]quinoline-7-one was obtained as pale brown powdery crystals (97.6%).

mp. 253°–255° C(dec.)

IR(KBr): 3405, 1646, 1631, 1570, 1465, 1445, 1424, 1323, 1237, 1216, 1151, 1083, 923, 830 cm$^{-1}$.

¹H-NMR(CDCl₃)δ: 9.05(1H,br.s), 7.94(1H,d,J=9.3Hz), 7.12(1H, s), 6.57(1H,d,J=9.3Hz), 6.04(1H, ddd, J=17.1, 10.3,6.8Hz), 5.41(1H, d, J=17.1Hz), 5.33(1H, ddd, J=9.3, 7.3,6.8Hz), 5.26(1H, d, J=10.3Hz), 3.42(1H,dd, J=15.1, 9.3Hz), 3.03(1H,dd,J=15.1,7.3Hz), 2.35(3H,s).

Example 137:

2-(2-Hydroxyethyl)-5-methyl-2,3,6,7-tetrahydrofuro[2,3-f]quinoline-7-one:

5-Methyl-2,3,6,7-tetrahydro-2-vinylfuro[2,3-f]quinoline-7-one (2.17 g) was suspended in tetrahydrofuran (40 ml). 9-Borabicyclo[3.3.1]nonan (0.5 mol, tetrahydrofuran solution, 80 ml) was added thereto while cooling on ice, and the mixture was stirred for 5.5 hours. Subsequently, aqueous 3N-NaOH solution (20 ml) and aqueous 35% hydrogen peroxide (20 ml) were added to the mixture in this order, and the temperature was raised to room temperature. After stirring for 30 minutes, extraction was performed with a solvent mixture of chloroform-methanol (4:1). The organic phase was dried and condensed under reduced pressure. The residue was recrystallized from a solvent mixture of chloroform-ethyl acetate-ether to obtain 1.7 g of 2-(2-hydroxyethyl)-5-methyl-2,3,6,7-tetrahydrofuro[2,3-f]quinoline-7-one as pale yellow powdery crystals (72.6%).

mp. 224°–227° C.

IR(KBr): 3380, 1647, 1564, 1463, 1385, 1310, 1236, 1152, 1045, 871, 689, 585 cm⁻¹.

¹H-NMR(CD₃OD)δ: 7.99(1H,d,J=9.3Hz), 7.23(1H,s), 6.51(1H,d,J=9.3Hz), 5.09(1H,m), 3.74–3.82(2H,m), 3.38(1H,dd,J=15.1,8.8Hz), 2.95(1H,dd,J=15.1,8.8Hz), 2.36(3H,s).

Example 138:

2-(2-Chloroethyl)-5-methyl-2,3,6,7-tetrahydrofuro[2,3-f]quinoline-7-one:

2-(2-Hydroxyethyl)-5-methyl-2,3,6,7-tetrahydrofuro[2,3-f]quinoline-7-one (1.65 g) was suspended in dimethylformamide (20 ml). To the suspension, pyridine (20 ml) and methanesulfonyl chloride (1.5 ml) were added thereto, and the mixture was stirred for 6 hours. When the reaction was completed, methanol (20 ml) was added while cooling the mixture on ice, followed by mixing for 20 minutes. Subsequently, the reaction mixture was condensed under reduced pressure, to which water was added and extracted with chloroform. The chloroform phase was dried and condensed under reduced pressure. The resultant residue was recrystallized from a solvent mixture of chloroform-ether to obtain 1.75 of 2-(2-chloroethyl)-5-methyl-2,3,6,7-tetrahydrofuro[2,3-f]quinoline-7-one as pale yellow needles (98.6%).

mp. 209°–211° C.

IR(KBr): 3400, 1675, 1645, 1630, 1482, 1450, 1306, 1249, 1179, 1109, 1044, 794, 690 cm⁻¹.

¹H-NMR(CDCl₃)δ: 8.72(1H,br.s), 7.92(1H,d,J=9.8Hz), 7.14(1H, s), 6.58(1H,d,J=9.8Hz), 5.14(14H,m), 3.78–3.72(2H,m), 3.42(1H,dd,J=15.1,7.3Hz), 2.91(1H,dd, J=15.1,6.8Hz), 2.33(3H, s), 2.28(1H,m), 2.17(1H,m).

Example 139:

2-(2-Cyanoethyl)-5-methyl-2,3,6,7-tetrahydrofuro[2,3-f]quinoline-7-one:

2-(2-Chloroethyl)-5-methyl-2,3,6,7-tetrahydrofuro[2,3-f]quinoline-7-one (1.5 g) was dissolved in dimethylformamide (50 ml). To the solution, potassium cyanide (2.0 g) was added and stirred at 100° C. for three hours. After the reaction was completed, the reaction liquid was condensed under reduced pressure. Water was added thereto and extraction was performed with chloroform. The chloroform phase was dried and condensed under reduced pressure. The residue was recrystallized from a solvent mixture of chloroform-ether to obtain 1.4 g of 2-(2-cyanoethyl)-5-methyl-2,3,6,7-tetrahydrofuro[2,3-f]quinoline-7-one as pale yellow prisms (96.8%).

mp. 188°–190° C.

IR(KBr): 3405, 1656, 1634, 1570, 1462, 1424, 1321, 1147, 1082, 1063, 878, 835 cm⁻¹.

¹H-NMR(CDCl₃)δ: 8.79(1H,br.s), 7.99(1H,d,J=9–8Hz), 7.13(1H,s), 6.58(1H,d,J=9.8Hz), 5.05(1H,m), 3.44(1H, dd, J=15.1,9.3Hz), 2.93(1H, dd, J=15.1,6.8Hz), 2.66–2.57(2H, m), 2.16–2.07(2H,m), 2.34(3H, s).

Example 140:

2-(3-Aminopropyl)-5-methyl-2,3,6,7-tetrahydrofuro[2,3-f]quinoline-7-one.HCl 2-(2-Cyanoethyl)-5-methyl-2,3,6,7-tetrahydrofuro[2,3-f]quinoline-7-one (1.35 g) was dissolved in tetrahydrofuran (100 ml), to which lithium aluminum hydride (1.4 g) was added and stirred at 30° C. for 2 hours. To the reaction liquid, methanol (20 ml) was added and stirred for 10 minutes, then filtered through cerite. The filtrate was condensed under reduced pressure, and the resultant crude product was purified by alumina column chromatography (eluent: first, chloroform:ethyl acetate=1:1; later, chloroform:methanol=3:1). Crude crystals (1.05 g) was obtained. These crude crystals were converted into a hydrochloride, which was then recrystallized from a solvent mixture of chloroform-ethanol-ether to obtain 1.53 g of a hydrochloric acid salt of 2-(3-aminopropyl)-5-methyl-2,3,6,7-tetrahydrofuro-[2,3-f]quinoline-7-one as yellow needles (73.4%).

Example 141:

2-(2-Cyanoethyl-6,7-dihydro-5-methylfuro[2,3-f]quinoline-7-one:

This compound was synthesized in a manner similar to that described in Example 133 from 2-(2-cyanoethyl)-5-methyl-2,3,6,7-tetrahydrofuro[2,3-f]quinoline -7-one.

mp. 261°–263° C. (dec.) (Recrystallized from a solvent mixture of chloroform-ether)

IR(KBr): 3408, 2220, 1647, 1569, 1443, 1425, 1350, 1272, 1218, 1151, 802, 772, 478 cm⁻¹.

¹H-NMR(CDCl₃)δ: 8.23(1H,d,J=9.8Hz), 7.48(1H, s), 6.76(1H,d,J=9.8Hz), 6.60(1H, s), 3.20(2H,t,J=7.3Hz), 2.83(2H,t,J=7.3Hz), 2.51(3H,s).

Example 142:

2-(3-Aminopropyl)-6,7-dihydro-5-methylfuro[2,3-f]quinoline-7-one.HCl

This compound was synthesized in a manner similar to that described in Example 140 from 2-(2-cyanoethyl-6,7-dihydro-5-methylfuro[2,3-f]quinoline-7-one. The melting point was higher than 300 ° C. (recrystallized from a solvent mixture of methanol-ethanol-ether).

IR(KBr): 3395, 1655, 1627, 1560, 1505, 1479, 1442, 1347, 1270, 1220, 1151, 831, 772, 650 cm⁻¹.

¹H-NMR(CD₃OD)δ: 8.37(1H,d,J=9.5Hz), 7.59(1H,s), 6.74(1H,d,J=9.5Hz), 6.62(1H,s), 2.95-3.10(4H,m), 2.54(3H, s), 2.14(2H,quintet,J=8.5Hz).

Reference Example 6:

5-[(E-4-Acetoxy-2-butenyl)oxy]-8-methylcarbostyril:

5-[(E-4-Chloro-2-butenyl)oxy]-8-methylcarbostyril (16.15 g) was dissolved in dimethylformamide (200 ml), to which sodium acetate (35.0 g) was added and stirred at 120° C. for 6 hours. After the reaction was completed, the reaction mixture was condensed under reduced pressure. Water was added to the condensate and extracted with chloroform. The chloroform phase was dried, and the solvent was removed. The residue was recrystallized from a solvent mixture of chloroform-ether to obtain 11.80 g of 5-[(E-4-acetoxy-2butenyl)oxy]-8-methylcarbostyril as colorless powdery crystals (67.1%).

mp. 178°–181° C.

IR(BKr): 3416, 1743, 1688, 1647, 1606, 1572, 1491, 1453, 1384, 1344, 1304, 1178, 1100, 999 cm$^{-1}$.

$^1$H-NMR(CDCl$_3$)δ: 9.55(1H,br.s), 8.23(1H,d,J=9.8Hz), 7.22(1H,d,J=8.8Hz), 6.61(1H,d,J=9.8Hz), 6.52(1H,d,J= 8.8Hz), 6.03–6.01(2H,m), 4.64–4.63(4H,m), 2.40(3H,s), 2.10(3H, s).

Reference Example 7:

5-Hydroxy-6-(2-hydroxy-1-vinylethyl)-8-methylcarbostyril:

This compound was synthesized in a manner similar to that described in Reference Example 3 from 5-[(E-4-acetoxy-2-butenyl)oxy]-8-methylcarbostyril.

Yield: 73.8%. Pale yellow needles, m.p: 170°–172° C. (recrystallized from methanol-ether).

IR(BKr): 3378, 1636, 1560, 1488, 1465, 1445, 1394, 1337, 1306, 1275, 1255, 1234, 1092, 793 cm$^{-1}$.

$^1$H-NMR(CD$_3$OD)δ: 8.32(1H,d,J=9.8Hz), 7.15(1H, s), 6.52(1H, d, J=9.8Hz), 6.14 (1H, ddd, J=17.1,10.3,6.3Hz), 5.14(1H,dt,J=10.3,1.5Hz), 5.05(1H, dr, J=17.1,1.5Hz) ,n2.36(3H, s).

Example 143:

5-Methyl-2,3,6,7-tetrahydro-3-vinylfuro[2,3-f]quinoline-7-one:

5-Hydroxy-6-(2-hydroxy-1-vinylethyl)-8methylcarbostyril (7.2 g) was dissolved in pyridine (50 ml), to which triphenylphosphine (25.0 g) and carbon tetrachloride (15 ml) were added in this order, followed by stirring at 60° C. for 3 hours. Methanol (50 ml) was added thereto and stirred for 1 hour. The reaction mixture was filtered. The filtrate was condensed under reduced pressure, to which 1N-HCl was added. Extraction was performed with chloroform. The chloroform phase was dried, and the solvent was evaporated. The residue was recrystallized from a solvent mixture of chloroform-ethyl acetate-ether to obtain 6.4 g of 5-methyl-2,3,6,7-tetrahydro-3-vinylfuro[2,3-f]quinoline-7-one as colorless powdery crystals (95.9%).

mp. 275°–277° C. (dec.)

IR(BKr): 3398, 1647, 1610, 1566, 1467, 1444, 1328, 1269, 1218, 1143, 1078, 923, 831, 634 cm$^{-1}$.

$^1$H-NMR(CDCl$_3$)δ: 8.96(1H,br.s), 7.90(1H,d,J=9.3Hz), 7.09(1H, s), 6.58(1H,d,J=9.3Hz), 5.85(1H, ddd, J=17.6,11.2, 8.3Hz), 5.22(1H,d,J=17.6Hz), 5.17(1H,d,J=11.2Hz), 4.85(1H,t,J=8.3Hz), 4.38(1H,t,J=8.3Hz), 4.17(1H,q,J= 8.3Hz), 2.35(3H, s).

Example 144:

3-Formyl-5-methyl-2,3,6,7-tetrahydrofuro[2,3-f]quinoline-7-one:

5-Methyl-2,3,6,7-tetrahydro-3-vinylfuro[2,3-f]quinoline-7-one (1.75 g) was dissolved in a mixture of butanol-acetone-water (3:3:1, 350 ml), to which sodium periodate (11.5 g) and osmium tetraoxide (350 mg) were added, followed by stirring at room temperature for 24 hours. The reaction mixture was filtered, and the filtrate was subjected to distillation to remove the solvent. The residue was recrystallized from a solvent mixture of chloroform-ether to obtain 1.05 g of 3-formyl-5-methyl-2,3,6,7-tetrahydrofuro[2,3-f] quinoline-7-one as pale yellow needles (59.5%).

mp. 230°–232° C.

IR(KBr): 3182, 1655, 1616, 1568, 1472, 1447, 1425, 1400, 1333, 1310, 1271, 1040, 927, 776 cm$^{-1}$.

$^1$H-NMR(CDCl$_3$)δ: 9.72(1H,d,J=2.0Hz), 9.23(1H,br.s), 7.90(1H,d,J=9.8Hz), 7.25(1H, s), 6.61(1H,d,J=9.8Hz), 5.13 (1H, dd, J=9.3,5.4Hz), 4.81 (1H, t, J=9.3Hz), 4.27(1H,m), 2.39(3H,s).

Example 145:

3-Hydroxymethyl-5-methyl-2,3,6,7-tetrahydrofuro[2,3-f] quinoline-7-one:

To 3-formyl-5-methyl-2,3,6,7-tetrahydrofuro[2,3-f] quinoline-7-one (1.0 g) in methanol (80 ml), sodium borohydride (1.0 g) was added and stirred at room temperature for 30 minutes. After completion of the reaction, water was added and extracted with chloroform-methanol (4:1). The extract was dried and the solvent was evaporated. The residue was recrystallized from methanol-ether to obtain 0.59 g of 3-hydroxymethyl-5-methyl-2,3,6,7-tetrahydrofuro [2,3-f]quinoline-7-one was obtained as colorless needles (58.5%).

mp. 234°–236° C.

IR(KBr): 3370, 1637, 1612, 1565, 1472, 1444, 1403, 1305, 1217, 1104, 1073, 940, 874, 782, 648 cm$^{-1}$.

$^1$H-NMR(CD$_3$OD)δ: 7.99(1H,d,J=9.3Hz), 7.29(1H,s), 6.51(1H,d,J=9.3Hz), 4.75(1H,t,J=8.8Hz), 4.58 (1H, dd, J=8.8,4.4Hz), 3.74(1H,m), 3.64–3.62(2H,m), 2.37 (3H, s).

The compounds of the present invention shown in Tables below were prepared. The identification data are given in the Tables.

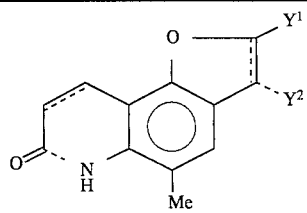

| Ex. | 2,3-bond | 8,9-bond | Y¹ | Y² | Salt | mp. (°C.) | Sol* | IR (cm⁻¹) (KBr) | ¹H-NMR solv. | δ(ppm) |
|---|---|---|---|---|---|---|---|---|---|---|
| 146 | d | d | $CH_2NH_2$ | H | HCl | >300 | MeOH | 1650, 1620, 1535, 1495, 1435, 1420, 1370, 1350, 1220, 1150, 1085, 930, 805, 785, | $CD_3OD$ | 8.36(1H, d, J=9.8Hz), 7.64(1H, s), 7.02(1H, s), 6.74(1H, d, J=9.8Hz), 4.39(2H, s), 2.52(3H, s) |
| 147 | d | d | $CH_2NH_2$ | Me | HCl | 292–297 (dec.) | MeOH $Et_2O$ | 3140, 1650, 1625, 1555, 1540, 1440, 1380, 1350, 1260, 1220, 1170, 1040, 830, 810 | $CD_3OD$ | 8.34(1H, d, J=9.8Hz), 7.60(1H, s), 6.72(1H, d, J=9.8Hz), 4.38(2H, s), 2.52(3H, s), 2.34(3H, s) |
| 148 | s | d | $(CH_2)_2NH_2$ | H | HCl | >300 | MeOH $Et_2O$ | 3396, 1635, 1548, 1464, 1443, 1395, 1321, 1310, 1245, 1144, 1115, 1089, 957, 873 | $CD_3OD$ | 8.25(1H, d, J=9.8Hz), 7.37(1H, s), 6.73(1H, d, J=9.8Hz), 5.12(1H, m), 3.51(1H, dd, 14.2, 8.8Hz), 3.21–3.35(2H, m), 3.03(1H, dd, J=17.6, 7.3Hz), 2.44(3H, s) 2.12–2.20(2H, m), |
| 149 | s | s | $(CH_2)_2NH_2$ | H | HCl | >300 | MeOH $Et_2O$ | 3409, 2914, 1652, 1627, 1471, 1438, 1045 | $CD_3OD$ | 6.86(1H, s), 4.88(1H, m), 3.32(1H, m), 3.14–3.20(2H, m), 2.82–2.90(3H, m), 2.51(2H, t, J=7.8Hz), 2.16(3H, s), 2.03–2.11(2H, m) |
| 150 | s | d | $(CH_2)_3NH_2$ | H | HCl | 277–279 (dec.) | $CHCl_3$ EtOH $Et_2O$ | 3394, 1645, 1462, 1327, 1307, 1241, 1152, 1091, 1065, 1007, 975, 874, 833 | $CD_3OD$ | 8.11(1H, d, J=9.8Hz), 7.31(1H, s), 6.64(1H, d, J=9.8Hz), 5.04(1H, m), 3.44(1H, dd, J=15.1, 9.3Hz), 2.93–3.06(3H, m), 2.41(3H, s), 1.17–1.98(4H, m) |
| 151 | s | s | $(CH_2)_3NH_2$ | H | HCl | >300 | MeOH $Et_2O$ | 3396, 1669, 1623, 1471, 1442, 1376, 1303, 1283, 1238, 1122, 1049, 996, 779, 725 | $CD_3OD$ | 6.84(1H, s), 4.85(1H, m), 3.29(1H, m), 3.01–3.05(2H, m), 2.79–2.87(3H, m), 2.51(2H, t, J=7.8Hz), 2.15(3H, s), 1.81–1.87(4H, m) |
| 152 | s | d | H | $CH_2NH_2$ | HCl | >300 | MeOH $Et_2O$ | 3387, 1664, 1615, 1471, 1460, 1443, 1416, 1384, 1317, 1234, 1006, 933, 833, 649 | $CD_3OD$ | 8.07(1H, d, J=9.8Hz), 7.39(1H, s), 6.61(1H, d, J=9.8Hz), 4.84(1H, dd, J=9.8, 8.8Hz), 4.66(1H, dd, J=9.8, 4.9Hz), 3.87(1H, m), 3.12–3.34(2H, m) 2.42(3H, s) |
| 153 | s | s | H | $CH_2NH_2$ | HCl | >300 | MeOH $Et_2O$ | 3395, 1669, 1658, 1628, 1482, 1470, 1376, 1340, 1285, 1205, 1059, 773, 650, 495 | $CD_3OD$ | 6.99(1H, s), 4.64(1H, dd, J=9.8, 8.8Hz), 4.46(1H, dd, J=9.8, 4.9Hz), 3.72(1H, m), 3.21(1H, dd, J=13.2, 4.9Hz), 3.08(1H, dd, J=13.2, 8.8Hz), 2.84(2H, t, J=7.3Hz), 2.51(2H, t, J=7.3Hz), 2.19(3H, s) |
| 154 | d | d | H | $CH_2NH_2$ | HCl | >300 | MeOH $Et_2O$ | 3395, 1651, 1623, 1444, 1383, 1351, 1257, 834 | $CD_3OD$ | 8.39(1H, d, J=9.8Hz), 8.02(1H, s), 7.81(1H, s), 6.76(1H, d, J=9.8Hz), 4.33(2H, s), 2.58(3H, s) |

Sol*: Solvent used for recrystallization

Reference Example 8:

N-(4-Methoxyphenyl)cinnamamide:

p-Anisidine (25 g, 0.203 mol) was suspended in acetone (400 ml), to which pyridine (19.7 ml, 0.244 mol) was added. While cooling on ice, cinnamoyl chloride (37.2 g, 0.223 mol) was further added, followed by stirring at ambient temperature for 20 minutes. As a result, a uniform solution was obtained. The solvent was condensed under reduced pressure. To the residue, ethyl acetate and water were added. The sediment was collected by filtration, washed with ethyl acetate and water, and dried with air. 50.4 g of the title compound was obtained as pale greenish brown powder (98.0%, mp.: 147°–150° C.).

IR(KBr): 1658, 1623, 1508, 1228, 1171, 1037, 905, 826 cm$^{-1}$.

$^1$H-NMR(DMSO-d$_6$)δ: 3.75(3H,s), 6.82(1H,d,J=15Hz), 6.93(2H,d,J=9Hz), 7.50(1H,d,J=15Hz), 7.45(2H,d,J=9Hz), 7.35–7.70(5H,m), 10.10(1H, s,NH).

Reference Example 9:

6-Hydroxycarbostyril:

The compound obtained in Reference Example 8 (50.4 g, 0.199 mol) was suspended in chlorobenzene (350 ml), to which aluminum chloride (132.7g, 0.995 mol) was added and stirred at 125° C. for 1 hour. As a result, a uniform solution was. obtained. The solution was cooled and poured into ice-water. The insoluble matter was collected by filtration, followed by washing with water, n-hexane, and chloroform in this order. After drying with air, 26.3 g of the title compound was obtained as a brown solid (82.0%, mp.: over 60° C.).

IR(KBr): 1653, 1625, 1605, 1506, 1427, 1409, 1294, 1121, 851 cm$^{-1}$.

$^1$H-NMR(DMSO-d$_6$)δ: 6.44(1H,d,J=9Hz), 6.90–7.06(2H, m), 7.17(1H,d,J=7Hz), 7.77(1H,d,J=9Hz), 9.42(1H,s,OH), 11.55(1H,s,NH).

Reference Example 10:

6-Allyloxycarbostyril:

The compound obtained in Reference Example 9 (17.8 g, 0.11 mol), potassium carbonate (30.5 g, 0.22 mol), tetra-n-butylammoniumbromide (3.56 g, 11 mol) were suspended in dimethylformamide (270 ml), to which allyl iodide (22.3 g, 0.133 mol) was added by dropwise and stirred at 50° C. for 2 hours. The reaction mixture was condensed under reduced pressure, and the resultant residue was combined with water. The insoluble matter was collected by filtration, washed with water and chloroform in this order, followed by drying. As a result, 13.7 g of the title compound was obtained as brown powder (61.6%, mp. 180°–182° C.)

IR(KBr): 1646, 1617, 1500, 1431, 1361, 1285, 1237, 1178, 1119 cm$^{-1}$.

$^1$H-NMR(DMSO-d$_6$)δ: 4.60(2H,dt,J=6,1.5Hz), 5.31(1H, dq, J=11,1.5Hz), 5.44(1H,dq,J=16,1.5Hz), 6.10(1H, ddt, J=16,12,6Hz), 6.52(1H,d,J=9Hz), 7.16–7.36(3H,m), 7.88(1H,d,J=9Hz), 11.70(1H,s,NH).

Reference Example 11:

5-Allyl-6-hydroxycarbostyril:

The compound obtained in Reference Example 10 (7.0 g, 34.8 mmol) was suspended in N,N-dimethylaniline (35 ml). The suspension was stirred at 200° C. for 1 hour in the atmosphere of nitrogen. After completion of the reaction, the reaction system was cooled. n-Hexane was added thereto and the precipitate was collected by filtration, followed by washing with chloroform. 5.06 g of the title compound was obtained as a yellow solid (72.3%, mp. 285° C. (dec.)).

IR(KBr): 1644, 1602, 1495, 1407, 1333, 1284, 1063, 827 cm$^{-1}$.

$^1$H-NMR(DMSO-d$_6$)δ: 3.62(2H,d,J=6Hz), 4.87–5.03(2H, m), 5.92(1H,ddt,J=16,10,6Hz), 6.48(1H,d,J=9Hz), 7.10(2H, s), 7.95(1H,d,J=9Hz), 9.35(1H, s,OH), 11.57(1H, s,NH).

Example 155:

2-Methyl-1,2,6,7-tetrahydrofuro[3,2-f]quinoline-7-one:

The compound obtained in Reference Example 10 (4.0 g, 19.9 mmol) was stirred at 200° C. for 1 hour in the atmosphere of nitrogen. The reaction mixture was cooled, then it was dissolved in 2N-NaOH solution (40 ml). Extraction was performed with a solvent mixture of chloroform-:methanol (10:1), then the solvent was evaporated over sodium sulfate. The residue was condensed under reduced pressure, followed by washing with chloroform. As a result, 0.235 g of the title compound was obtained as a yellow solid (5.9%), which was recrystallized from a solvent mixture of chloroform-methanol-ether to obtain pale yellow prisms of the title compound (mp.: 268°–270° C. (dec.)).

IR(KBr): 1645, 1442, 1262, 1238, 1053, 820 cm$^{-1}$.

$^1$H-NMR(CDCl$_3$:CD$_3$OD 10:1)δ: 1.54(3H,d,J=7Hz), 3.00(1H, dd, J=15,8Hz), 3.54(1H,dd,J=12,8Hz), 4.98–5.19 (1H,m), 6.72(1H, d, J=10Hz), 7.02(1H,d,J=10Hz), 7.18(1H, d,J=9Hz), 7.70(1H,d,J=10Hz).

Reference Example 12:

6-Acetoxy-5-allyl-1,2-carbostyril:

The compound obtained in Reference Example 11 (9.62 g, 47.8 mmol) was dissolved in pyridine (200 ml), to which acetic anhydride (6.77 ml, 71.7 mmol) was added dropwise. The mixture was stirred for 1 hour. After completion of the reaction, methanol was added and then condensed under reduced pressure. The residue was washed with chloroform. 10.8 g of the title compound was obtained as white powder (92.6%, mp. 228°–230° C. (dec.)).

IR(KBr): 1753, 1663, 1430, 1207, 1188 cm$^{-1}$.

$^1$H-NMR(CDCl$_3$)δ: 2.34(3H, s), 3.59(2H,dt,J=6,2Hz), 4.96(1H, dq, J=17,2Hz), 5.08(1H, dq, J=10,2Hz), 5.80–6.01(1H,m), 6.76(1H,d,J=10Hz), 7.23(1H,d,J=9Hz), 7.38(1H,d,J=9Hz), 8.00(1H,d,J=10Hz).

Reference Example 13:

6-Acetoxy-5-(2,3-epoxypropyl)carbostyril:

The compound obtained in Reference Example 12 (10.8 g, 44.4 mol) was dissolved in chloroform (550 ml), to which m-chloroperbenzoic acid (70% purity) (13.8 g, 79.7 mmol) was added, followed by stirring at ambient temperature for 24 hours. m-Chloroperbenzoic acid (6.9 g, 40 mmol) was further added, and reaction was allowed to proceed for 15 hours. The reaction mixture was washed with aqueous 5% sodium sulfite, saturated sodium bicarbonate solution, aqueous NaCl solution in this order, and dried over sodium sulfate. The solvent was distilled off under reduced pressure, and the residue was washed with a small amount of chloroform. 8.21 g of the tile compound was obtained as white powder (71.5%, mp. 218°–223° C. (dec.)).

IR(KBr): 1759, 1662, 1431, 1202 cm$^{-1}$.

$^1$H-NMR(CDCl$_3$)δ: 2.37(3H, s), 2.48(1H,dd,J=5,2Hz), 2.76(1H,t,J=5Hz), 3.00–3.28(3H,m), 6.78(1H,d,J=10Hz), 7.25(1H,d,J=9Hz), 7.38(1H,d,J=9Hz), 8.10(1H,d,J=10Hz).

Example 156:

2-hydroxymethyl-1,2,6,7-tetrahydrofuro[3,2-f]quinoline-7-one:

The compound obtained in Reference Example 13 (4.0 g, 15.4 mmol) was suspended in dimethylformamide (50 ml), to which 1N-NaOH (30.9 ml) was added. The compound was dissolved while generating heat. The solution was stirred at 50° C. for 40 minutes, then condensed under reduced pressure. The residue was combined with water. The precipitate was collected by filtration. The title compound was obtained as pale brown powder (2.97 g, 88.6%). The obtained compound was recrystallized from a solvent mixture of chloroform-methanol-ether. Pale yellow prisms of the title compound was obtained (mp.: 265°–268° C. (dec.)).

IR(KBr): 3383, 1641, 1509, 1431, 1354, 1245, 1057, 973 cm$^{-1}$.

$^1$H-NMR(CDCl$_3$:CD$_3$OD 5:1)δ: 3.24(1H,dd, J=16,8Hz), 3.49(1H,dd,J=16,10Hz), 3.77(1H,dd,J=12,6Hz), 3.85(1H,dd, J=12,4Hz), 4.96–5.12(1H,m), 6.69(1H,d,J=10Hz), 7.05(1H,d,J=9Hz), 7.15(1H,d,J=9Hz), 7.77(1H,d,J=10Hz).

Example 157

2-Methanesulfonyloxymethyl-1,2,6,7-tetrahydrofuro-[3,2-f]quinoline-7-one:

The compound obtained in Example 156 (2.11 g, 9.71 mmol) was suspended in pyridine (130 ml), to which methanesulfonyl chloride (1.67 g, 14.6 mmol) was added and stirred at ambient temperature for 1.5 hours. The reaction mixture was combined with methanol, and condensed under reduced pressure. The residue was washed with chloroform. 2.01 g of the tile compound was obtained as white powder (70.1%, mp.: 222°–224° C. (dec.)).

$^1$H-NMR(DMSO-d$_6$) δ: 3.21 (1 H, dd, J=17, 7 Hz), 3.25 (3 H, s), 3.57 (1 H, dd, J=17, 11 Hz), 4.34–4.56 (2 H, m), 5.20 (1 H, m), 6.54 (1 H, d, J=10 Hz), 7.05 (1 H, d, J=9 Hz), 7.13 (1 H, d, J=9 Hz), 7.77 (1 H, d, J=10 Hz), 8.33 (1 H, br.s).

Example 158

2-Azidomethyl-1,2,6,7-tetrahydrofuro-[3,2-f]quinoline-7-one:

The compound obtained in Example 157 (1.0 g, 3.37 mmol) and sodium azide (1.9 g, 33.7 mmol) were suspended in dimethylformamide (20 ml). The suspension was stirred at 100° C. for 2 hours, followed by cooling. The reaction mixture was combined with water, and the precipitated crystals were collected by filtration and washed with water. 0.733 g of the title compound was obtained as pale brown crystals (89.4%, mp.: 194° C. (dec.)).

IR(KBr): 2083, 1647, 1624, 1440, 1256, 1237, 1218 cm$^{-1}$.

$^1$H-NMR(DMSO-d$_6$) δ: 3.16 (1 H, dd, J=17, 7 Hz), 3.53 (1 H, dd, J=17, 9 Hz), 3.56 (1 H, dd, J=13, 6 Hz), 3.70 (1 H, dd, J=13, 4 Hz), 5.04–5.20 (1 H, m), 6.55 (1 H, d, J=10 Hz), 7.05 (1 H, d, J=9 Hz), 7.14 (1 H, d, J=9 Hz), 7.77 (1 H, d, J=10 Hz).

Example 159

2-Aminomethyl-1,2,6,7-tetrahydrofuro-[2,3-f]quinoline-7-one:

The compound obtained in Example 158 (0.50 g, 2.06 mmol) dissolved in dimethylformamide (12 ml) was combined with 10% palladium-carbon (0.30 g), then stirred in the stream of hydrogen for 1.5 hour. From the reaction mixture, palladium-carbon was filtered off. The filtrate was condensed under reduced pressure, and purified by silica gel column chromatography (eluent; chloroform: ammonia=methanol 15:1). 0.33 g of the tile compound was obtained as pale yellow crystals (74.0%). They were recrystallized from a solvent mixture of chloroform—methanol—n-hexane to obtain pale yellow prisms of the title compound (mp.: 233°–236° C. (dec.)).

IR(KBr): 1645, 1623, 1611, 1507, 1441, 1241 cm$^{-1}$.

$^1$H-NMR(DMSO-d$_6$-D$_2$O) δ: 2.81 (2 H, d, J=6 Hz), 3.18 (1 H, dd, J=16, 8 Hz), 3.42 (1 H, dd, J=16, 9 Hz), 4.86 (1 H, m), 6.52 (1 H, d, J=10 Hz), 6.98 (1 H, d, J=9 Hz), 7.09 (1 H, d, J=9 Hz), 7.74 (1 H, d, J=10 Hz).

Example 160

1,2,6,7,8,9-Hexahydro-2-methanesulfonyloxymethylfuro-[3,2-f]quinoline-7-one:

The compound obtained in Example 157 (0.85 g, 2.88 mmol) dissolved in dioxane (50 ml) was combined with 10% palladium-carbon (1.55 g), then stirred in the stream of hydrogen at 60° for 16 hours. From the reaction mixture, palladium-carbon was filtered off. The filtrate was condensed under reduced pressure, and the reside was washed with ether. 0.726 g of the tile compound was obtained as pale brown crystals (84.8%). They were recrystallized from a solvent mixture of chloroform—methanol—ether to obtain colorless prisms of the title compound (mp.: 209°–210° C. (dec.)).

IR(KBr): 1660, 1477, 1449, 1388, 1321, 1265, 1222, 1173, 943 cm$^{-1}$.

$^1$H-NMR(CDCl$_3$) δ: 1.38 (2 H, br.s), 2.54–3.02 (7 H, m), 3.19 (1 H, dd, J=16, 9 Hz), 4.83 (1 H, m), 6.57 (2 H, s), 8.70 (1 H, br.s).

Example 161

2-Azidomethyl-1,2,6,7,8,9-hexahydrofuro-[3,2-f]quinoline-7-one:

The compound obtained in Example 160 (0.691 g, 2.32 mmol) and sodium azide (1.51 g) were suspended in dimethylformamide (14 ml) and stirred at 120° C. for 2 hours. The suspension was cooled and poured into water, followed by extraction with chloroform. The chloroform phase was washed with water and dried over sodium sulfate. When the solvent was distilled off under reduced pressure, 0.553 g of the pale yellow crystals of the title compound was obtained (97.4%, mp.: 157°–158° C.).

IR(KBr): 2092, 1650, 1478, 1438, 1383, 1223 cm$^{-1}$.

$^1$H-NMR(CDCl$_3$) δ: 2.61 (1 H, dd, J=8, 2 Hz), 2.65 (1 H, d, J=8 Hz), 2.85 (1 H, d, J=8 Hz), 2.89 (1 H, d, J=8 Hz), 2.96 (1 H, dd, J=16, 7 Hz), 3.26 (1 H, dd, J=16, 9 Hz), 3.47 (1 H, dd, J=13, 6 Hz), 3.57 (1 H, dd, J=13, 4 Hz), 4.92–5.07 (1 H, m), 6.59 (1 H, d, J=8 Hz), 6.64 (1 H, d, J=8 Hz), 8.71 (1 H, br.s, NH).

Example 162

2-Aminomethyl-1,2,6,7,8,9-hexahydrofuro-[3,2-f]quinoline-7-one:

The compound obtained in Example 161 (0.53 g, 2.17 mmol) dissolved in tetrahydrofuran (26 ml) was combined with 10% palladium-carbon (0.32 g), then stirred in the stream of hydrogen at ambient temperature for 1.5 hour. After completion of the reaction, palladium-carbon was filtered off from the reaction mixture. The palladium-carbon was washed with tetrahydrofuran and then methanol. The filtrate was condensed under reduced pressure, and the residue was purified by silica gel column chromatography (eluent: chloroform: ammonia/methanol=20:1). 0.385 g of the tile compound was obtained as colorless crystals (87.9%, mp.: 162°–163° C.).

IR(KBr): 3171, 3046, 1712, 1666, 1476, 1382, 1225 cm$^{-1}$.

$^1$H-NMR(CDCl$_3$) δ: 1.38 (2 H, br.s, NH2), 2.54–3.02 (7 H, m), 3.19 (1 H, dd, J=16, 9 Hz), 4.83 (1 H, m), 6.57 (2 H, s), 8.70 (1 H, br.s, NH).

Hydrochloric acid salt of this compound:

The above compound (0.36 g, 1.65 mmol) was dissolved in methanol (5 ml), to which 4N-HCl/dioxane solution (0.49 ml) was added. The solvent was distilled off under reduced pressure, and the residue was recrystallized from a solvent mixture of methanol—ether to obtain 0.302 g of the hydrochloric acid salt of the title compound (71.9%, colorless prisms, mp.: 295° C. (dec.)).

IR(KBr): 2893, 1709, 1480, 1449, 1382, 1228, 806 cm$^{-1}$.

$^1$H-NMR(D$_2$O) δ: 2.59 (2 H, br.t, J=8 Hz), 2.75–3.03 (3 H, m), 3.20 (1 H, dd, J=13, 9 Hz), 3.34 (1 H, dd, J=13, 4 Hz), 3.32–3.52 (1 H, m), 5.04–5.23 (1 H, m), 6.73 (2 H, s).

Example 163

(2RS,3SR)-2-Aminomethyl-3,5-dimethyl-2,3,6,7,8,9-hexahydrofuro-[2,3-f]quinoline-7-one.HCl The hydrochloric acid salt of (2RS,3SR)-2-aminomethyl-3,5-dimethyl-2,3,6,7-tetrahydrofuro-[2,3-f]quinoline-7-one obtained in Example 12 (575 mg, 2.05 mmol) in water (20 ml) was combined with 10% palladium-carbon (600 mg), then stirred in the presence of hydrogen gas at 80° C. for 4 hours. From the reaction mixture, palladium-carbon was filtered off. Water was distilled off under reduced pressure, and the residue was recrystallized from a solvent mixture of methanol—ether. As a result, 416 mg of a hydrochloric acid salt of (2 RS, 3 SR)-2-aminomethyl-3,5-dimethyl-2,3,6,7,8,9-hexahydrofuro-[2,3-f]quinoline-7-one was obtained as colorless crystals (71.8%). mp. >300° C.

IR(KBr): 3225, 3000, 2950, 2865, 1665, 1625, 1485, 1470, 1440, 1420, 1390, 1365, 1340, 1320, 1285, 1235, 1200, 1175, 1085, 1060, 1040, 980, 950, 820, 790, 765, 740 cm$^{-1}$.

$^1$H-NMR(CD$_3$OD) δ: 6.88 (1 H, s), 4.97–4.88 (1 H, m), 3.63 (1 H, d, t, J=7.3, 7.3 Hz), 3.29 (1 H, dd, J=2.9, 13.2 Hz), 3.17 (1 H, dd, J=10.7, 13.2 H), 2.96 (1 H, dd, J=7.6, 16.1 Hz), 2.84 (1 H, dd, J=7.6, 16.1 Hz), 2.52 (2 H, t, J=7.6 Hz), 2.19 (3 H, s), 1.22 (3 H, d, J=7.3 Hz).

Example 164

2-Bromomethyl-5-methyl-2,3,6,7-tetrahydrofuro-[2,3-f]quinoline-7-one:

A suspension of 5-hydroxy-8-methyl-6-(2-propenyl) carbostyril (64.57 g) in chloroform (2000 ml) was combined with N-bromosuccinimide (56.47 g) and refluxed with heat for 3 hours while stirring. The reaction mixture became yellow uniform solution. The reaction solution was washed with water, dried and condensed. n-Hexane was added to the concentrate, and crystallized. 91.40 g of the title compound was obtained as white powder.

Yield: 95.3% mp. 248°–250° C. (dec.)

$^1$H-NMR(CDCl$_3$) δ: 9.10 (1 H, br.s), 7.91 (1 H, d, J=9.8 Hz), 7.13 (1 H, s), 6.58 (1 H, d, J=9.8 Hz), 5.15 (1 H, m), 3.65 (1 H, dd, J=10.3, 4.4 Hz), 3.58 (1 H, dd, J=10.3, 6.6 Hz), 3.43 (1 H, dd, J=16.1, 9.1 Hz), 3.17 (1 H, dd, J=16.1, 6.3 Hz), 2.36 (3 H, s).

IR(KBr): 3144, 1627, 1150, 1080 cm$^{-1}$.

Example 165

5-Methyl-2-[1-(2-thienylmethylamino)methyl]-2,3,6,7,8,9-hexahydrofuro-[2,3-f]quinoline-7-one.HCl A mixture of 2-methanesulfonyloxymethyl- 5-methyl-2,3,6,7,8,9-hexahydrofuro-[2,3-f]quinoline-7-one (1350 g) and 2-aminomethylthiophene (7.06 g) was stirred in a hot bath (150° C.) for 1 hour in the stream of argon. The solvent was distilled off under reduced pressure, and the residue was dissolved in chloroform The obtained solution was washed with sodium bicarbonate water and water, then dried. When crystallized from ethanol, 0.790 g of a free base of the title compound was obtained in pale yellow prisms (mp.: 151°–153° C., yield: 55.5%).

$^1$H-NMR(CDCl$_3$) δ: 7.36 (1 H, s), 7.12 (1 H, m), 6.97–6.91 (2 H, m), 6.81 (1 H, s), 4.94 (1 H, m), 4.07 (2 H, s), 3.20 (1 H, dd, J=15.6, 9.3 Hz), 2.99–2.80 (5 H, m), 2.63–2.54 (2 H, m), 2.13 (3 H, s).

IR(KBr): 3197, 1665, 1369, 1194 cm$^{-1}$.

Hydrochloric acid salt:

$^1$H-NMR(CD$_3$OD) δ: 7.57 (1 H, d, J=6.1, 1.0 Hz), 7.34 (1 H, d, J=3.4 Hz), 7.13, 7.10 (1 H, dd, J=3.4 Hz), 6.89 (1 H, s), 5.11 (1 H, m), 4.56 (2 H, s), 3.48–3.18 (3 H, m), 3.00–2.75 (3 H, m), 2.52 (2 H, t, J=7.3 Hz), 2.16 (3 H, s).

IR(KBr): 3210, 3000–2200, 1674, 1479, 1428, 1374, 1201, 697 cm$^{-1}$.

Example 166

2-Aminomethyl-2-ethyl-5-methyl-2,3,6,7-tetrahydrofuro-[2,3-f]quinoline-7-one.HCl:

The title compound was prepared in a manner similar to that described in Example 5.

mp. 281°–283° C. (dec.)

$^1$H-NMR(CD$_3$OD) δ: 8.08 (1 H, d, J=9.8 Hz), 7.27 (1 H, s), 6.55 (1 H, d, J=9.8 Hz), 3.49 (1 H, dd, J=14.2 Hz, 7.3 Hz), 3.65–3.20 (3 H, m), 2.39 (3 H, s), 2.05–1.80 (2 H, m), 1.00 (3 H, t, J=7.3 Hz).

IR(KBr): 3386, 2957, 1651, 1464, 1317, 1086, 834 cm$^{-1}$.

Example 167

2-Aminomethyl-5-ethyl-2,3,6,7,8,9-hexahydro-5-methyl-furo-[2,3-f]quinoline-7-one.HCl:

The title compound was prepared in a manner similar to that described in Example 163.

mp. 281°–283° C. (dec.)

$^1$H-NMR(CD$_3$OD) δ: 6.88 (1 H, s), 3.55–2.80 (6 H, m), 2.52 (2 H, t, J=7.3 Hz), 2.17 (3 H, s), 1.95–1.70 (2 H, m), 0.97 (3 H, t, J=7.3 Hz).

IR(KBr): 3199, 2937, 1670, 1483, 1387, 1203, 1075 cm$^{-1}$.

Example 168

5-Methyl-2-methylthiomethyl-2,3,6,7-tetrahydrofuro-[2,3-f]quinoline-7-one:

A solution of 2-bromomethyl-5-methyl-2,3,6,7-tetrahydrofuro-[2,3-f]quinoline-7-one (2.942 g) in dimethylformamide (120 ml) was combined with aqueous 15% sodium thiomethoxide (9.4 ml), and stirred at room temperature for 1 hour. The solvent was distilled off under reduced pressure. Water was added to the residue, and extracted with chloroform. The chloroform extract was washed with diluted hydrochloric acid, diluted caustic soda and water in this order, and dried. The resultant material was crystallized from tetrahydrofuran to obtain 2.355 g of the title compound as colorless prisms (mp. 203°–206° C.) (yield: 90.1%).

$^1$H-NMR(CDCl$_3$) δ: 9.42 (1 H, br.s), 7.89 (1 H, d, J=9.8 Hz), 7.13 (1 H, s), 6.57 (1 H, d, J=9.8 Hz), 5.10 (1 H, m), 3.44, 3.36 (1 H, dd, J=8.8 Hz), 3.14, 3.06 (1 H, dd, J=7.3 Hz), 2.97, 2.90 (1 H, dd, J=5.9 Hz), 2.84, 2.77 (1 H, dd, J=6.4 Hz), 2.38 (3 H, s), 2.22 (3 H, s).

IR(KBr): 1650, 1447, 1266, 1144, 1082, 813, 640 cm$^{-1}$.

Example 169

5-Methyl-2-methylsulfonylmethyl-2,3,6,7-tetrahydrofuro-[2,3-f]quinoline-7-one:

To a solution of 5-methyl-2-methylthiomethyl-2,3,6,7-tetrahydrofuro-[2,3-f]quinoline-7-one (0.784 g) in chloroform (100 ml), a solution of methachloroperbenzoic acid (1.47 g) in chloroform (50 ml) was added dropwise while cooling on ice, and stirred for 1 hour. The reaction mixture was washed with saturated sodium bicarbonate water and water in this order, and then dried and condensed. The residue was crystallized from chloroform—methanol to obtain 0.627 g of the title compound as colorless prisms (yield: 71.2%, mp.: 294°–297° C. (dec.)).

$^1$H-NMR(CDCl$_3$-CD$_3$OD) δ: 7.93 (1 H, d, J=9.3 Hz), 7.24 (1 H, s), 6.60 (1 H, d, J=9.3 Hz), 5.46 (1 H, m), 3.79–3.50 (2 H, m), 3.46–3.07 (2 H, m), 3.17 (3 H, s), 2.41 (3 H, s).

IR(KBr): 1662, 1466, 1300, 1123, 1081, 832.

Example 170

Dimethyl[[5-methyl-7-oxo-2,3,6,7-tetrahydrofuro [2,3-f]quinoline]-2-methyl]sulfonium iodide A mixture of 5-methyl-2-methylthiomethyl-2,3,6,7-tetrahydrofuro-[2,3-f]quinoline-7-one (0.523 g), methyliodide (2.893 g) and nitromethane (20 ml) was stirred at room temperature for 7 days. The sediment was collected by filtration, and dried. The resulting yellow powder was recrystallized from methanol to obtain 0.498 g of the title compound as flakes (mp.: 199°–202° C.).

$^1$H-NMR(CDCl$_3$) δ: 8.00 (1 H, d, J=9.8 Hz), 7.30 (1 H, s), 6.57 (1 H, d, J=9.8 Hz), 5.48 (1 H, m), 3.85 (2 H, d, J=6.3 Hz), 3.63 (1 H, m), 3.19 (1 H, m), 3.09 (3 H, s), 3.08 (3 H, s), 2.39 (3 H, s).

IR(KBr): 1667, 1628, 1472, 1391, 1207, 1081, 1023, 830 cm$^{-1}$.

Example 171

5-Methyl-2-thiocyanato-2,3,6,7-tetrahydrofuro-[2,3-f]quinoline-7-one:

A mixture of 2-bromomethyl-5-methyl-2,3,6,7-tetrahydrofuro-[2,3-f]quinoline-7-one (0.882 g), potassium thiocyanate (2.915 g) and dimethylformamide (40 ml) was stirred in a hot bath at 100° C. for 5 hours. The solvent was distilled off under reduced pressure. The residue was combined with water and extracted with chloroform. The chloroform extract liquid was washed with water, dried and condensed. The residue was crystallized from chloroform—n-hexane to obtain 0.683 g of the title compound as white powder (mp.: 227°–229° C. (dec.)).

Yield: 83.6%

$^1$H-NMR(CDCl$_3$-CD$_3$OD) δ: 7.99 (1 H, d, J=9.3 Hz), 7.19 (1 H, s), 6.59 (1 H, d, J=9.3 Hz), 5.26 (1 H, m), 3.55 (1 H, dd, J=15.6, 9.5 Hz), 3.33 (2 H, d, J=5.9 Hz), 3.14 (1 H, dd, J=15.6, 6.4 Hz), 2.38 (3 H, s).

IR(KBr): 2140, 1669, 1646, 1449, 1269, 1147, 1083, 837 cm$^{-1}$.

Example 172

2-[2-(Dimethylamino)ethylthiomethyl]-5-methyl-2,3,6,7-tetrahydrofuro-[2,3-f]quinoline-7-one:

To a suspension of 2-bromomethyl-5-methyl- 2,3,6,7-tetrahydrofuro-[2,3-f]quinoline-7-one (1. 765 g) in dimethylformamide (60 ml), hydrochloric acid salt of 2 (dimethylamino)ethylmercaptan (4.25 g) and caustic soda (2.40 g) in water (20 ml) were added and stirred at room temperature for 1 hour. The solvent was distilled off under reduced pressure. The residue was combined with water, and extracted with chloroform. The extract was washed with NaCl solution twice and dried and condensed. The residue was crystallized from chloroform—n-hexane to obtain 1.741 g of the title compound as white powder (mp.: 163°–165° C.).

Yield: 91.1%

$^1$H-NMR(CDCl$_3$) δ: 9.00 (1 H, br.s), 7.89 (1 H, d, J=9.8 Hz), 7.13 (1 H, s), 6.56 (1 H, d, J=9.8 Hz), 5.10 (1 H, m), 3.39 (1 H, dd, J=15.1, 9.3 Hz), 3.10 (1 H, dd, J=15.1, 6.8 Hz), 2.98 (1 H, dd, J=13.7, 9.5 Hz), 2.84 (1 H, dd, J=13.7, 6.8 Hz), 2.80–2.68 (2 H, m), 2.59–2.45 (2 H, m), 2.35 (3 H, s), 2.24 (6 H, s)

IR(KBr): 1652, 1610, 1462, 1142, 1083, 1063, 919, 642 cm$^{-1}$.

Example 173

2-[2-(Dimethylamino)ethylthiomethyl]-5-methyl-2,3,6,7-tetrahydrofuro-[2,3-f]quinoline-7-one.HCl The compound obtained in Example 172 was allowed to reacted with HCl to obtain a hydrochloric acid salt.

Yield: 85.5%, pale yellow powder, mp. 258–260 (dec.)

$^1$H-NMR(CD$_3$OD) δ: 7.97 (1 H, d, J=9.8 Hz), 7.23 (1 H, s), 6.53 (1 H, d, J=9.8 Hz), 5.19 (1 H, m), 3.51–3.27 (3 H, m), 3.20–2.93 (5 H, m), 2.88 (6 H, m), 2.34 (3 H, s).

IR(KBr): 2720–2250, 1648, 1464, 1141, 1081 cm$^{-1}$.

Example 174

2-[1-(2-Aminoethylthio)methyl]-5-methyl-2,3,6,7-tetrahydrofuro-[2,3-f]quinoline-7-one:

To a suspension of 2-bromomethyl-5-methyl-2,3,6,7-tetrahydrofuro-[2,3-f]quinoline-7-one (0.882 g) in dimethylformamide (40 ml), cysteamine hydrochloride (3.41 g) and caustic soda (2.40 g) in water (20 ml) were added and stirred at room temperature for 1 hour. The solvent was distilled off under reduced pressure. The residue was combined with water, and extracted with chloroform. The extract was washed with water and dried. The solvent was evaporated and the residue was crystallized from chloroform—n-hexane to obtain 0.714 g of the title compound as pale yellow prisms (mp.: 182°–184° C.).

Yield: 82.0%

$^1$H-NMR(CDCl$_3$) δ: 9.10 (1 H, br.s), 7.89 (1 H, d, J=9.8 Hz), 7.13 (1 H, s), 6.57 (1 H, d, J=9.8 Hz), 5.09 (1 H, m), 3.30 (1 H, dd, J=15.1, 9.3 Hz), 3.11 (1 H, dd, J=15.1, 6.8 Hz), 3.03–2.83 (4 H, m), 2.83–2.67 (2 H, m), 2.35 (3 H, s), 1.62 (2 H, br.s).

IR(KBr): 3362, 3152, 1648, 1462, 1327, 1149, 1084, 835 cm$^{-1}$.

Example 175

2-[1-(2-Aminoethylthio)methyl]-5-methyl-2,3,6,7-tetrahydrofuro-[2,3-f]quinoline-7-one.HCl The compound obtained in Example 174 was allowed to reacted with HCl to obtain a hydrochloric acid salt.

Yield: 70.6%, yellow prisms, mp. 272–274 (dec.)

$^1$H-NMR(CD$_3$OD) δ: 7.97 (1 H, d, J=9.8 Hz), 7.22 (1 H, s), 6.53 (1 H, d, J=9.8 Hz), 5.15 (1 H, m), 3.24–3.07 (4 H, m), 3.07–2.85 (4 H, m), 2.37 (3 H, s).

IR(KBr): 3300–2400, 1671, 1645, 1450, 1146, 1085, 837 cm$^{-1}$,

Example 176

5-Methyl-2-[1-(2-thienylmethylamino)methyl]-2,3,6,7-tetrahydrofuro-[2,3-f]quinoline-7-one:

A mixture of 2-bromomethyl-5-methyl-2,3,6,7-tetrahydrofuro-[2,3-f]quinoline-7-one (2.942 g) and 2-aminomethylthiophene (4.528 g) was stirred in a hot bath at 150° C. in the stream of argon gas for 4 hours. The solvent was distilled off under reduced pressure. Chloroform was added to the residue, and washed with sodium bicarbonate water, and water in this order. After dried, the residue was crystallized from ethanol to obtain 2.712 g of a free base of the title compound as pale yellow prisms (mp.: 163°–165° C.).

Yield: 83.1%

$^1$H-NMR(CDCl$_3$) δ: 9.03 (1 H, br.s), 7.91 (1 H, d, J=9.8 Hz), 7.21 (1 H, m), 7.12 (1 H, s), 7.00–6.89 (2 H, m), 6.56 (1 H, d, J=9.8 Hz), 5.08 (1 H, m), 4.08 (2 H, s), 3.32 (1 H, dd, J=15.1, 9.8 Hz), 3.03 (1 H, dd, J=15.1, 7.3 Hz), 2.97 (2 H, d, J=5.4 Hz), 2.34 (3 H, s).

IR(KBr): 3149, 1646, 1448, 1147, 1062, 832 cm$^{-1}$.

Hydrochloric acid salt: pale yellow prisms, mp.: 275°–277° C. (dec.)

$^1$H-NMR(CD$_3$OD) δ: 8.04 (1 H, d, J=9.8 Hz), 7.57 (1 H, dd, J=5.0, 1.5 Hz), 7.35 (1 H, d, J=3.4 Hz), 7.27 (1 H, s), 7.12 (1 H, dd, J=5.0, 3.4 Hz), 6.55 (1 H, d, J=9.8 Hz), 5.29 (1 H, m), 4.59 (2 H, s), 3.51 (1 H, dd, J=15.6, 9.8 Hz), 3.43–3.38 (2 H, m), 3.04 (1 H, dd, J=15.6, 6.3 Hz), 2.38 (3 H, s).

IR(KBr): 3000–2266, 1659, 1451, 1387, 1146, 1069, 866 cm$^{-1}$.

Example 177

5-Methyl-2-[1-(3-thiazolinyl)methyl]-2,3,6,7-tetrahydrofuro-[2,3-f]quinoline-7-one.HCl:

A mixture of 2-bromomethyl-5-methyl-2,3,6,7-tetrahydrofuro-[2,3-f]quinoline-7-one (4.802 g) and thiazoline (5.815 g) was stirred at 150° C. in the stream of argon gas for 4 hours. The solvent was distilled off under reduced pressure. Chloroform was added to the residue, and extracted with 1N-HCl. After the extract was washed with chloroform, 1N-NaOH was added to bring the pH basic. Extraction was performed with chloroform, followed by washing with water. After dried, the residue was crystallized from methanol to obtain 1.885 g of a free base of the title compound as pale yellow powder (mp.: 196°–199° C.).

Yield: 38.2%

$^1$H-NMR(CDCl$_3$) δ: 9.12 (1 H, br.s), 7.93 (1 H, d, J=9.8 Hz), 7.13 (1 H, s), 6.57 (1 H, d, J=9.8 Hz), 5.06 (1 H, m), 4.18 (1 H, d, J=9.8 Hz), 4.15 (1 H, d, J=9.8 Hz), 3.35 (1 H, dd, J=15.1, 9.3 Hz), 3.21–3.12 (2 H, m), 3.04 (1 H, dd, J=15.1, 7.3 Hz), 2.91 (2 H, t, J=5.9 Hz), 2.79 (1 H, dd, J=13.7, 6.8 Hz), 2.66 (1 H, dd, J=13.7, 4.4 Hz), 2.36 (3 H, s).

IR(KBr): 1647, 1463, 829 cm$^{-1}$.

Hydrochloric acid salt: pale yellow powder, mp.: 252°–254° C. (dec.)

$^1$H-NMR(D$_2$O) δ7.74 (1 H, d, J=9.8 Hz), 7.13 (1 H, s), 6.39 (1 H, d, J=9.8 Hz), 5.38 (1 H, m), 4.70 (1 H, d, J=10.3 Hz), 4.65 (1 H, d, J=10.3 Hz), 3.91 (2 H, t, J=6.8 Hz), 3.83–3.64 (2 H, m), 3.49 (1 H, dd, J=16.1, 9.8 Hz), 3.39 (2 H, t, J=6.8 Hz), 2.98 (1 H, dd, J=16.1, 7.5 Hz), 2.14 (3 H, s).

IR(KBr): 3193, 2700–2100, 1659, 1464, 1206, 1140, 828 cm$^{-1}$.

Example 178

2-[4-(2-Methoxyphenyl)-1-piperazinomethyl]-5-methyl-2,3,6,7-tetrahydrofuro-[2,3-f]quinoline-7-one.HCl A mixture of 2-bromomethyl-5-methyl-2,3,6,7-tetrahydrofuro-[2,3-f]quinoline-7-one (3.824 g) and 1-(2-methoxyphenyl)piperazine (5.000 g) was stirred in a hot bath at 150° C. in the stream of argon gas for 1 hour. The reaction product was dissolved in a solvent mixture of chloroform and methanol (5:1), and washed with sodium bicarbonate water, and water in this order. After dried and condensed, n-hexane was added to the residue, and the mixture was allowed to stand. As a result, 4.349 g of a free base of the title compound was obtained as pale yellow flakes (mp.: 245°–247° C. (dec.)).

Yield: 82.5%

$^1$H-NMR(CDCl$_3$) δ: 8.67 (1 H, br.s), 7.94 (1 H, d, J=9.8 Hz), 7.26 (1 H, s), 7.08–6.82 (4 H, m) 6.57 (1 H, d, J=9.8 Hz), 5.16 (1 H, m), 3.88 (3 H, s), 3.34 (1 H, dd, J=15.1, 8.8 Hz), 3.21–2.67 (11 H, m), 2.33 (3 H, s).

IR(KBr): 3152, 1641, 1497, 1461, 1237, 1155, 938, 848, 745 cm$^{-1}$.

Hydrochloric acid salt: Colorless flakes, mp.: 268°–270° C. (dec.)

$^1$H-NMR(CD$_3$OD-D$_2$O) δ: 8.14 (1 H, d, J=9.8 Hz), 7.34 (1 H, s), 7.24–6.94 (4 H, m), 6.62 (1 H, d, J=9.8 Hz), 5.49 (1 H, m), 3.92 (3 H, s), 3.85–3.24 (11 H, m), 3.12 (1 H, dd, J=16.0, 7.3 Hz), 2.40 (3 H, s).

IR(KBr): 3142, 2600–2000, 1653, 1452, 760 cm$^{-1}$.

Example 179

2-[4-(2-Methoxyphenyl)-1-piperazinomethyl]-5-methyl-2,3,6,7-tetrahydrofuro-[2,3-f]quinoline-7-one.HCl The title compound was prepared in a manner similar to that described in Example 163.

Colorless flakes, mp.: 163°–166° C.

$^1$H-NMR(CD$_3$OD) δ: 7.15–6.82 (5 H, m), 5.31 (1 H, m), 3.87 (3 H, s), 3.72–3.20 (1 H, m), 3.05–2.80 (3 H, m), 2.53 (2 H, t, J=7.8 Hz), 2.18 (3 H, s).

IR(KBr): 2600–2000, 1668, 1471, 1236, 1019, 746 cm$^{-1}$.

Example 180

5-Methyl-2-[4-[5-(3,4,5-trimethoxyphenyl)phenyl]homopiperazino-1-methyl]-2,3,6,7-tetrahydrofuro-[2,3-f]quinoline-7-one.2 HCl:

A mixture of 2-bromomethyl-5-methyl-2,3,6,7-tetrahydrofuro-[2,3-f]quinoline-7-one (4.412 g) and 1-[5 (3,4,5-trimethoxyphenyl)pentyl]homopiperazine (19.46 g) was stirred in a hot bath at 200° C. in the stream of argon gas for 3 hours. The reaction product was dissolved in chloroform, and extracted with concentrated HCl solution. The extract was washed with chloroform. NaOH solution was added until the pH became basic, followed by extraction with chloroform. The resultant extract was washed with water, dried, and purified by silica gel chromatography (developer= chloroform: methanol=50:1–40:1). As a result, 1.64 g of a free base of the title compound was obtained as brown oil.

Yield: 19.9%

$^1$H-NMR(CDCl$_3$) δ: 8.82 (1 H, br.s), 7.90 (1 H, d, J=9.8 Hz), 7.12 (1 H, s), 6.55 (1 H, d, J=9.8 Hz), 6.39 (2 H, s), 5.06 (1 H, m), 3.85 (6 H, s), 3.82 (3 H, s), 3.30 (1 H, dd, J=15.1, 8.8 Hz), 3.10–2.42 (15 H, m), 2.33 (3 H, s), 1.90–1.22 (8 H, m). IR (KBr): 2914, 1645, 1586, 1457, 1233, 1123 cm$^{-1}$.

Hydrochloric acid salt: Yellow powder, mp.: 220°–222° C. (dec.) Yield: 94.2%

$^1$H-NMR(CD$_3$OD) δ: 8.24 (1 H, d, J=9.8 Hz), 7.31 (1 H, s), 6.62 (1 H, d, J=9.8 Hz), 6.50 (2 H, s), 5.53 (1 H, br.s), 4.30–3.15 (13 H, m), 3.06 (1 H, dd, J=16.9, 6.8 Hz), 3.82 (6 H, s), 3.73 (3 H, s), 2.68–2.25 (4 H, m), 2.39 (3 H, s), 1.95–1.33 (6 H, m).

IR(KBr): 2720–2100, 1651, 1455, 1233, 1118 cm$^{-1}$.

Example 181

2-Benzoxyhydrazinomethyl-5-methyl-2,3,6,7-tetrahydrofuro-[2,3-f]quinoline-7-one:

2-Bromomethyl-5-methyl-2,3,6,7-tetrahydrofuro-[2,3-f]quinoline-7-one (6.0 g, 20.4 mmol) was dissolved in dimethylformamide (100 ml), to which carbobenzoxyhydrazine (15.9 g, 95.7 mmol) was added, followed by stirring at 150° C. for 2 hours. The reaction mixture was poured into water, and the insoluble matter was collected by filtration, washed with water and ethanol in this order to obtain 3.38 g of the title compound as a white solid (yield: 43.7%). This solid was recrystallized from a solvent mixture of chloroform—methanol—ether to obtain colorless needles (mp.: 210°–214° C.).

$^1$H-NMR(CDCl$_3$: CD$_3$OD 10:1) δ: 2.37 (3 H, s), 3.01 (1 H, dd, J=7.2, 15.6 Hz), 3.12–3.50 (3 H, m), 5.12 (1 H, m), 5.17 (2 H, s), 6.57 (1 H, d, J=9.7 Hz), 7.17 (1 H, s), 7.37 (5 H, s), 7.97 (1 H, d, J=9.7 Hz).

IR(KBr): 3279, 1689, 1654, 1519, 1451, 1312, 1268, 1142 cm$^{-1}$.

Example 182

2-Hydrazinomethyl-5-methyl-2,3,6,7-tetrahydrofuro-[2,3-f]quinoline-7-one.HCl:

The compound obtained in Example 181 (3.25 g, 8.57 mmol) was dissolved in a mixture of dimethylformamide (60 ml), methanol (60 ml) and 5% HCl methanol solution (8.3 ml), to which 10% palladium-carbon (1.3 g) was added and stirred at ambient temperature in the stream of hydrogen gas for 1 hour. After completion of the reaction, the solvent was distilled off under reduced pressure. The residue was washed with a solvent mixture of ethanol and ether to obtain 2.32 g of the title compound as a pale yellow solid (yield: 96.1%). This solid was recrystallized from a solvent mixture of methanol—ether. As a result, the title compound was obtained as pale yellow needles (mp.: 248° C. (dec.)).

$^1$H-NMR(DMSO-d$_6$) δ: 2.32 (3 H, s), 2.98 (1 H, dd, J=6.8, 15.6 Hz), 3.08–3.60 (3 H, m), 3.41 (2 H, br), 5.15 (1 H, m), 6.49 (1 H, d, J=9.7 Hz), 7.22 (1 H, s), 7.93 (1 H, d, J=9.7 Hz), 9.27 (1 H, br), 10.88 (1 H, br.s).

IR(KBr): 1653, 1457, 1447, 1310, 1146, 1082 cm$^{-1}$.

Example 183

2-[(1,1-Bis(ethoxycarbonyl)methylidenhydrazino]methyl-5-methyl-2,3,6,7-tetrahydrofuro-[2,3-f]quinoline-7-one:

The compound obtained in Example 182 (0.50 g, 1.77 mmol) was suspended in chloroform (10 ml), to which diethylketomaronic acid (1.38 g, 7.92 mmol) and triethylamine (0.36 g, 3.56 mmol) were added, and stirred at ambient temperature for 15 hours. The reaction mixture was washed with water and dried. The solvent was evaporated and the residue was crystallized from chloroform—ether. 0.404 g of the title compound was obtained as pale yellow needles (yield: 56.7%, mp.: 189°–192° C.).

$^1$H-NMR(CDCl$_3$) δ: 1.34 (6 H, t, J=7.1 Hz), 2.35 (3 H, s), 3.03 (1 H, dd, J=6.7, 15.6 Hz), 3.41 (1 H, dd, J=9.3, 15.6 Hz), 3.83–3.96 (2 H, m), 4.28 (2 H, q, J=7.1 Hz), 4.31 (2 H, q, J=7.1 Hz), 5.18 (1 H, m), 6.62 (1 H, d, J=9.7 Hz), 7.15 (1 H, s), 7.94 (1 H, d, J=9.7 Hz), 8.94 (1 H, br.s), 11.46 (1 H, br).

IR(KBr): 1717, 1645, 1568, 1520, 1462, 1270, 1190, 1083 cm$^{-1}$.

Example 184

5-Methyl-2-(α-phenylamino)methyl-2,3,6,7-tetrahydrofuro-[2,3-f]quinoline-7-one.HCl:

A mixture of 2-bromomethyl-5-methyl-2,3,6,7-tetrahydrofuro-[2,3-f]quinoline-7-one (50.0 g, 170 mmol) and D-(+)-α-phenethylamine (61.8 g, 510 mmol) was stirred in a hot bath at 150° C. for 3 hours. The reaction product was condensed under reduced pressure to remove excessive starting amines. Thereafter, the resultant material was dissolved in methanol (600 ml), to which 4N-HCl in 1,4-dioxane solution (70 ml) was added. The solvent was removed under reduced pressure to yield 52.7 g (83.6%) of a crude target material as a mixture of 2 types of diastereomers which are different at the position C-2. This product was suspended in ethanol—water (95:5 v/v%, 800 g) and refluxed with heat for 18 hours. The insoluble matter was collected by filtration, and washed with a small amount of ethanol. As a result, 29.3 g of a first diastereomer of the title compound was obtained (55.6%, 73.8% d.e.). The similar procedure was repeated twice using a mixture of ethanol—water (95:5 v/v%, 200 ml). The resultant material was dissolved in a solvent mixture of ethanol—water (95:5 v/v%, 2000 ml), and then concentrated to 400 ml under atmospheric pressure. The insoluble matter was collected by filtration, and washed with a small amount of ethanol. As a result, 23.9 g of a second diastereomer of the title compound was obtained as colorless needles (45.3%, >99% d.e.). mp.: 281°–283° C.

$^1$H-NMR(CD$_3$OD) δ: 8.11 (1 H, d, J=9.8 Hz), 7.37–7.16 (6 H, m), 6.58 (1 H, d, J=9.8 Hz), 5.10 (1 H, m), 3.88 (1 H, q, J=6.3 Hz), 3.44–3.27 (1 H, m), 2.94 (1 H, dd, J=6.8, 15.6 Hz), 2.84–2.67 (2 H, m), 2.39 (3 H, s), 1.44 (3 H, d, J=6.8 Hz).

IR(KBr): 3155, 3015, 1646, 1568, 1461, 1269, 1149, 829, 697 cm$^{-1}$.

Optical rotation $[\alpha]_D^{22}$=+14.4 (c=1.02 methanol)

Example 185

5-Methyl-2-(1-α-naphthylethylamino)methyl-2,3,6,7-tetrahydrofuro-[2,3-f]quinoline-7-one:

A mixture of 2-bromomethyl-5-methyl-2,3,6,7-tetrahydrofuro-[2,3-f]quinoline-7-one (1.48 g, 5.04 mmol) and S-(–)-1-(1-naphthyl)ethylamine (1.75 g, 10.2 mmol) was stirred in a hot bath at 150° C. for 3 hours. The reaction product was subjected to silica gel column chromatography (developer=chloroform: methanol=50:1) to obtain 1.78 g (91.9%) of a crude target material as a mixture of 2 types of diastereomers which are different at the position C-2. This product was further subjected to silica gel column chromatography (developer=chloroform: methanol=100:1), and the first eluted fraction was condensed under reduced pressure. As a result, 535 mg of a first diastereomer of the title compound was obtained as pale yellow powder (27.6%)

$^1$H-NMR(CDCl$_3$) δ: 8.54 (1 H, br), 8.23 (1 H, d, J=9.8 Hz), 7.93–7.84 (2 H, m), 7.79–7.71 (2 H, m), 7.55–7.44 (3 H, m), 7.07 (1 H, s), 6.55 (1 H, d, J=9.8 Hz), 5.12 (1 H, m), 4.75 (1 H, m), 3.26 (1 H, dd, J=9.3, 15.6 Hz), 3.00–2.77 (3 H, m), 2.29 (3 H, s), 1.58 (3 H, br.).

This isomer was dissolved in methanol (30 ml), to which 4N-HCl in 1,4-dioxane (0.4 ml) was added and stirred. The solvent was distilled off under reduced pressure, and recrystallized from methanol—ether to obtain 561 mg of a hydrochloric salt of the title compound as colorless needles (95.8%, >99% d.e.). mp. 254°–256° C. (dec.)

$^1$H-NMR(CD$_3$OD-CDCl$_3$) δ: 8.27 (1 H, d, J=9.3 Hz), 8.08–7.98 (3 H, m), 7.85 (1 H, d, J=7.3 Hz), 7.73–7.61 (3 H, m), 7.28 (1 H, s), 6.58 (1 H, d, J=9.3 Hz), 5.60 (1 H, q, J=6.8 Hz), 3.60–3.35 (3 H, m), 2.99 (1 H, dd, J=6.8, 15.6 Hz), 2.41 (3 H, s), 1.92 (3 H, d, J=6.8 Hz).

IR(KBr): 3390, 2955, 1661, 1576, 1462, 1246, 1144, 1080, 774 cm$^{-1}$.

Further, the second elution fraction was condensed under reduced pressure. As a result, 330 mg of a second diastereomer was obtained as pale yellow powder (17.0%).

$^1$H-NMR(CDCl$_3$) δ: 8.33 (1 H, d, J=9.3 Hz), 8.26 (1 H, d, J=7.3 Hz), 8.01 (1 H, d, J=8.3 Hz), 7.89 (1 H, dd, J=1.0, 6.84 Hz), 7.84 (1 H, d, J=7.8 Hz), 7.65–7.50 (3 H, m), 6.79 (1 H, s), 6.62 (1 H, d, J=9.8 Hz), 5.70 (1 H, m), 5.33 (1 H, m), 3.29–2.95 (3 H, m), 2.69 (1 H, dd, J=7.8, 15.1 Hz), 2.20 (3 H, s), 2.19 (3 H, d).

This product was dissolved in methanol (20 ml), and 4N-HCl in 1,4-dioxane (0.3 ml) was added thereto. The mixture was stirred, and the solvent was distilled off under reduced pressure. The residue was recrystallized from methanol—ether. As a result, 171 mg of a hydrochloric acid salt of the title compound was obtained as pale brown needles (47.4%>99% d.e.).

mp. 256°–258° C. (dec.)

$^1$H-NMR(CD$_3$OD-CDCl$_3$) δ: 8.22 (1 H, d, J=8.3 Hz), 8.10 (1 H, d, J=9.3 Hz), 8.04–7.94 (2 H, m), 7.78 (1 H, d, J=7.2 Hz), 7.74–7.52 (3 H, m), 7.25 (1 H, s), 6.63 (1 H, d, J=9.3 Hz), 5.47 (1 H, q, J=6.8 Hz), 5.30 (1 H, m), 3.64–3.06 (3 H, m), 2.40 (3 H, s). 1.87 (3 H, d, J=6.8 Hz).

IR(KBr): 3263, 1654, 1538, 1451, 1147, 1084, 839, 790 cm$^{-1}$.

Example 186

5-Methyl-2-[(S)-N-(1-phenethyl)aminomethyl]-2,3,6,7-tetrahydrofuro-[2,3-f]quinoline-7-one.HCl A mixture of 2-bromomethyl-5-methyl-2,3,6,7-tetrahydrofuro-[2,3-f]quinoline-7-one (5.883 g,), (S)-1-phenethylamine (9.428 g) and dimethylformamide (50 ml) was stirred in at 150° C. for 3 hours. The solvent was distilled off under reduced pressure. Chloroform was added to the residue, and extracted with 2N-HCl four times. The extract was washed with chloroform, to which conc. caustic soda was added until basic. Extraction was performed with chloroform. The extract was washed with water, dried, and subjected to silica gel chromatography (developer=chloroform: methanol= 40:1). As a first component of the chromatography, 0.685 g of a free base of a first diastereomer of the title compound was obtained.

Yield: 10.2%, yellow flakes, mp. 161°–163° C.

$^1$H-NMR(CDCl$_3$) δ: 9.12 (1 H, br.s), 7.93 (1 H, d, J=9.8 Hz), 7.40–7.16 (5 H, m), 7.09 (1 H, s), 6.57 (1 H, d, J=9.8 Hz), 5.00 (1 H, m), 3.82 (1 H, q, J=6.4 Hz), 3.25 (1 H, dd, J=15.1, 9.3 Hz), 2.96–2.75 (2 H, m), 2.66 (1 H, dd, J=12.2, 3.9 Hz), 2.34 (3 H, s), 1.80 (1 H, br.s), 1.40 (3 H, d, J=6.4 Hz).

IR(KBr): 3150, 1653, 1461, 1147, 1083, 1063, 828, 699 cm$^{-1}$.

Hydrochloric acid salt: Pale yellow powder, mp.288°–289° C. (dec.)

$^1$H-NMR(CD$_3$OD) δ: 8.07 (1 H, d, J=9.8 Hz), 7.58–7.40 (5 H, m), 7.24 (1 H, s), 6.57 (1 H, d, J=9.8 Hz), 5.19 (1 H, m), 4.53 (1 H, q, J=6.8 Hz), 3.52–2.86 (4 H, m), 2.37 (3 H, s), 1.76 (3 H, d, J=6.8 Hz).

IR(KBr): 3000–2500, 1658, 1636, 1457 cm$^{-1}$. Optical rotation [α]$_D^{22}$=–14.8 (c=0.5 methanol)

As a latter component of the chromatography, 0.507 g of a free base of a second diastereomer of the title compound was obtained.

Yield: 7.6% Pale yellow powder, mp. 143°–144° C.

$^1$H-NMR(CDCl$_3$) δ: 9.02 (1 H, br.s), 7.92 (1 H, d, J=9.8 Hz), 7.38–7.16 (5 H, m), 7.10 (1 H, s), 6.57 (1 H, d, J=9.8 Hz), 5.03 (1 H, m), 3.85 (1 H, q, J=6.4 Hz), 3.23 (1 H, dd, J=15.1, 9.3 Hz), 3.00 (1 H, dd, J=15.1, 7.5 Hz), 2.86 (1 H, dd, J=12.7, 3.9 Hz), 2.73 (1 H, dd, J=12.7, 7.3 Hz), 2.34 (3 H, s), 1.79 (1 H, br.s), 1.37 (3 H, d, J=6.4 Hz).

IR(KBr): 3155, 1652, 1461, 1148, 1083, 829, 697 cm$^{-1}$.

Hydrochloric acid salt: Pale yellow powder mp. 288°–289° C. (dec.)

$^1$H-NMR(CD$_3$OD) δ: 8.04 (1 H, d, J=9.8 Hz), 7.56–7.33 (5 H, m), 7.21 (1 H, s), 6.56 (1 H, d, J=9.8 Hz), 5.26 (1 H, m), 4.53 (1 H, q, J=6.8 Hz), 3.55–2.84 (4 H, m), 2.35 (3 H, s), 1.76 (3 H, d, J=6.8 Hz).

IR(KBr): 3050–2600, 1653, 1612, 1450, 1147, 1082 cm$^{-1}$. Optical rotation [α]$_D^{22}$=–44.7 (c=0.38 methanol)

Example 187

(+)-5-Methyl-2-[(R)-N-(1-phenethyl)aminomethyl]2,3,6,7-tetrahydrofuro-[2,3-f]quinoline-7-one.HCl:

A mixture of 2-bromomethyl-5-methyl-2,3,6,7-tetrahydrofuro-[2,3-f]quinoline-7-one (5.883 g) and (R)-(+)-1-phenethylamine (7.271 g) was stirred in a hot bath at 150° C. for 3 hours. Excessive (R)-(+)-1-phenethylamine on product was removed under reduced pressure, and then the residue was dissolved in chloroform, to which was added saturated sodium bicarbonate solution to bring the pH basic. After washing with water and drying, the solvent was evaporated. n-Hexane was added to the residue and crystallized. 5.947 g of yellow powder was obtained. yield: 88.9%. This powder was dissolved in methanol (80 ml), and 4N-HCl-dioxane (7.5 ml) was added thereto. The solvent was distilled off under reduced pressure. The residue was recrystallized from ethanol—water (95:5) three times to obtain 1.71 g of the title compound as white powder (mp: 281°–282° C. (dec.)).

Yield: 25.9%

$^1$H-NMR(CD$_3$OD) δ: 8.07 (1 H, d, J=9.8 Hz), 7.58–7.40 (5 H, m), 7.24 (1 H, s), 6.57 (1 H, d, J=9.8 Hz), 5.19 (1 H, m), 4.53 (1 H, q, J=6.8 Hz), 3.52–2.86 (4 H, m), 2.37 (3 H, s), 1.76 (3 H, d, J=6.8 Hz).

IR(KBr): 3386, 3168, 3000–2400, 1656, 1459, 1152, 1083, 834 cm$^{-1}$. Optical rotation [α]$_D^{22}$=+13.6 (c=0.5 methanol)

Example 188

(2R*, 3S*)-2-[1-((S)-1-Phenethylamino)methyl]-2,3,5-trimethyl-2,3,6,7-tetrahydrofuro-[2,3-f]quinoline-7-one.HCl (2R*, 3S*)-2-Iodomethyl-2,3,5-trimethyl-2,3,6,7-tetrahydrofuro-[2,3-f]quinoline-7-one (2.966 g) and (S)-1-phenylethylamine (9.73 g) were stirred in a hot bath at 180° C. in the stream of argon gas for 3 hours. The solvent was distilled off under reduced pressure, and the residue was dissolved in chloroform, then washed with saturated sodium bicarbonate solution and water in this order and dried. The solvent was evaporated. The residue was subjected to silica gel column chromatography (developer=chloroform: methanol=100:1). As a first component of the chromatography, 0.347 g of a free base of a first diastereomer of the title compound. Yield: 11.9%

$^1$H-NMR(CDCl$_3$) δ: 8.82 (1 H, br.s), 7.95 (1 H, d, J=9.3 Hz), 7.40–7.13 (5 H, m), 7.02 (1 H, s), 6.58 (1 H, d, J=9.3 Hz), 3.74 (1 H, q, J=6.4 Hz), 3.22 (1 H, q, J=7.3 Hz), 2.83 (1 H, d, J=12.2 Hz), 2.38 (1 H, d, J=12.2 Hz), 2.34 (3 H, s), 1.57 (3 H, s), 1.35 (3 H, d, J=6.4 Hz), 1.13 (3 H, d, J=7.3 Hz).

Hydrochloric acid salt: Colorless flakes mp. 273°–274° C. (dec.)

$^1$H-NMR(CD$_3$OD) δ: 8.01 (1 H, d, J=9.8 Hz), 7.55–7.30 (5 H, m), 7.18 (1 H, s), 6.57 (1 H, d, J=9.8 Hz), 4.53 (1 H, q, J=6.8 Hz), 3.42 (1 H, q, J=7.3 Hz), 3.91 (1 H, d, J=13.2 Hz), 2.97 (1 H, d, J=13.2 Hz), 2.39 (3 H, s), 1.73 (3 H, d, J=6.8 Hz), 1.59 (3 H, s), 1.20 (3 H, d, J=7.3 Hz).

IR(KBr): 3100–2250, 1637, 1564, 1443, 1132, 1071, 702 cm$^{-1}$. Optical rotation $[\alpha]_D^{22}$=−68.0 (c=0.025, methanol)

As a latter component of the chromatography, 0.772 g of a free base of a second diastereomer of the title compound was obtained. Yield: 26.5%

$^1$H-NMR(CDCl$_3$) δ: 8.98 (1 H, br.s), 7.94 (1 H, d, J=9.8 Hz), 7.39–7.10 (5 H, m), 7.02 (1 H, s), 6.58 (1 H, d, J=9.8 Hz), 3.73 (1 H, q, J=6.4 Hz), 3.27 (1 H, q, J=7.3 Hz), 2.72 (1 H, d, J=12.2 Hz), 2.63 (1 H, d, J=12.2 Hz), 2.34 (3 H, s), 1.57 (3 H, s), 1.33 (3 H, d, J=6.4 Hz), 1.23 (3 H, d, J=7.3 Hz).

Hydrochloric acid salt: White powder, mp. >300° C.

$^1$H-NMR(CD$_3$OD) δ: 8.05 (1 H, d, J=9.8 Hz), 7.40–7.32 (2 H, m), 7.24–7.13 (3 H, m), 7.80 (1 H, s), 6.63 (1 H, d, J=9.8 Hz), 4.39 (1 H, q, J=6.8 Hz), 3.45 (1 H, q, J=7.3 Hz), 3.22 (1 H, d, J=13.2 Hz), 2.83 (1 H, d, J=13.2 Hz), 2.33 (3 H, s), 1.74 (3 H, d, J=6.8 Hz), 1.71 (3 H, s), 1.20 (3 H, d, J=7.3 Hz).

IR(KBr): 3000–2250, 1653, 1451 cm$^{-1}$. Optical rotation $[\alpha]_D^{22}$=+225.0 (c=0.02, methanol)

Example 189

(−)-(2 R*, 3 R*)-2-Aminomethyl-2,3,6,7-tetrahydro-2,3,5-trimethylfuro-[2,3-f]quinoline-7-one.HCl:

A racemic compound of 2-aminomethyl-2,3,6,7-tetrahydro-2,3,5-trimethylfuro-[2,3-f]quinoline-7-one (3.8 g) was resolved by high performance liquid chromatography using Chiralpak AD (a column for optical resolution, by Dicel Co.). As a second peak, 1.27 g of pale brown powder was obtained (1.27 g, 33.4%). This powder was converted into a hydrochloric acid salt to yield 0.941 g of the title compound as pale brown crystals (yield: 64.9%). The crystals were recrystallized from isopropanol to obtain pale brown prisms of the title compound (mp.: 291–296 (dec.)).

Optical rotation $[\alpha]_D^{20}$=−3.8° C. (c=0.5, methanol)
$^1$H-NMR(CD$_3$OD) δ: 1.32 (3 H, d, J=6.8 Hz), 1.47 (3 H, s), 2.40 (3 H, s), 3.26 (2 H, s), 3.41 (1 H, g, J=6.8 Hz), 6.55 (1 H, d, J=9.8 Hz), 7.27 (1 H, s), 8.05 (1 H, d, J=9.8 Hz).

IR(KBr): 1656, 1500, 1440, 1393, 1263, 1135, 1088, 1063 cm$^{-1}$.

Example 190

(−)-(2R*, 3R*)-2-Aminomethyl-2,3,6,7,8,9-hexahydro-2,3,5-trimethylfuro-[2,3-f]quinoline-7-one.HCl:

The compound obtained in Example 189 (0.40 g, 1.36 mmol), water (8 ml) and 10% palladium-carbon (0.40 g) were allowed to react at 80° C. in the stream of hydrogen gas for 7 hours. Subsequently, palladium-carbon was removed by filtration. 0.355 g of the title compound was yielded as a white solid (yield: 88.2%). The solid was recrystallized from methanol—ether to obtain the title compound as colorless needles (mp.: 286°–290° C. (dec.)).

Optical rotation $[\alpha]_D^{20}$=−8.0° C. (c=0.5, methanol)
$^1$H-NMR(CD$_3$OD) δ: 1.26 (3 H, d, J=7.3 Hz), 1.39 (3 H, s), 2.18 (3 H, s), 2.45–2.97 (4 H, m), 3.20–3.40 (3 H, m), 6.86 (1 H, s).

IR(KBr): 1677, 1629, 1497, 1468, 1438, 1355, 1334, 1202, 1092 cm$^{-1}$.

Example 191

(−)-(2R*,3R*)-2-Aminomethyl-3,5-dimethyl-2,3,6,7-tetrahydrofuro-[2,3-f]quinoline-7-one.HCl:

The procedure for optical resolution described in Example 189 was followed.
mp. >300° C.

IR(KBr): 3175, 3045, 2920, 2810, 1650, 1610, 1460, 1440, 1325, 1270, 1215, 1150, 1090, 1060, 985, 955, 900, 835, 785 cm$^{-1}$.

$^1$H-NMR(CD$_3$OD) δ: 8.10 (1 H, d, J=9.8 Hz), 7.28 (1 H, s), 6.59 (1 H, d, J=9.8 Hz), 4.71 (1 H, m), 3.41–3.31 (2 H, m), 3.22 (1 H, dd, J=9.3, 13.2 Hz), 2.41 (3 H, s), 1.42 (3 H, d, J=6.8 Hz).

Optical rotation $[\alpha]_D^{22}$=−63.0 (c=0.1 methanol)

Example 192

(−)-(2R*,3R*)-2-Aminomethyl-3,5-dimethyl-2,3,6,7,8,9-hexahydrofuro-[2,3-f]quinoline-7-one.HCl:

The compound of Example 191 was prepared in a manner similar to that described in Example 190.
mp. >300° C.

IR(KBr): 3215, 3110, 3010, 2950, 2800, 1660, 1630, 1615, 1470, 1440, 1375, 1340, 1210, 1095, 1050, 985, 955, 740, 715 cm$^{-1}$.

$^1$H-NMR(CD$_3$OD) δ: 6.88 (1 H, s), 4.49 (1 H, m), 3.32 (1 H, m), 3.23 (1 H, m), 3.14 (1 H, dd, J=9.3, 13.7 Hz), 2.99–2.80 (2 H, m), 2.53 (2 H, t, J=7.3 Hz), 2.19 (3 H, s), 1.35 (3 H, m, J=6.8 Hz).

Optical rotation $[\alpha]_D^{22}$=−55 (c=0.1 methanol)

Example 193

(+)-(2R*,3R*)-2-Aminomethyl-2,3,6,7,8,9-hexahydro-2,3,5-trimethylfuro-[2,3-f]quinoline-7-one.HCl:

The title compound was prepared in a manner similar to that described in Example 190.
mp. 296°–298° C.

$^1$H-NMR(CD$_3$OD) δ: 6.86 (1 H, s), 3.40–3.20 (3 H, m), 2.97–2.78 (2 H, m), 2.52 (2 H, t, J=7.8 Hz), 2.19 (3 H, s), 1.39 (3 H, s), 1.27 (3 H, d, J=6.8 Hz).

IR(KBr): 2954, 1678, 1629, 1497, 1468, 1354, 1251, 1092, 1052, 888 cm$^{-1}$.

Optical rotation $[\alpha]_D^{22}$=+9.4 (c=0.5, methanol)

Example 194

(+)-(2 R*, 3 R*)-2-Aminomethyl-2,3,5-trimethyl-2,3,5,6,7-tetrahydrofuro-[2,3-f]quinoline-7-one.HCl:

The title compound was optically resolved in a manner similar to that described in Example 189.
mp. 292°–296° C. (dec.)

$^1$H-NMR(CD$_3$OD) δ: 8.12 (1 H, d, J=9.3 Hz), 7.32 (1 H, s), 6.62 (1 H, d, J=9.3 Hz), 3.45 (1 H, q, J=7.3 Hz), 3.33 (1 H, m), 2.45 (3 H, s), 1.52 (3 H, s), 1.37 (3 H, d, J=7.3 Hz).

IR(KBr): 2951, 2865, 1662, 1636, 1502, 1456, 1263, 1136, 1088, 831 cm$^{-1}$.

Optical rotation $[\alpha]_D^{22}$=+4.0 (c=0.5 , methanol)

Example 195

(−)-2-Hydroxymethyl-5-methyl-2,3,6,7-tetrahydrofuro-[2,3-f]quinoline-7-one:

The title compound was optically resolved in a manner similar to that described in Example 189.
mp. 237°–238° C.

$^1$H-NMR(CDCl$_3$-CD$_3$OD) δ: 8.02 (1 H, d, J=9.8 Hz), 7.18 (1 H, s), 6.54 (1 H, d, J=9.8 Hz), 5.04 (1 H, m), 3.87–3.73 (2 H, m), 3.31 (1 H, dd, J=9.3, 15.7 Hz), 3.07 (1 H, dd, J=7.8, 15.7 Hz), 2.36 (3 H, s).

IR(KBr): 3200, 1643, 1563, 1465, 1448, 1313, 1268, 1161, 851 cm$^{-1}$.

Optical rotation $[\alpha]_D^{22}$=−5 (c=0.1 methanol)

Example 196

(+)-(2 R*, 3 R*)-2-Aminomethyl-3,5-dimethyl- 2,3,6,7-tetrahydrofuro-[2,3-f]quinoline-7-one.HCl:

The title compound was optically resolved in a manner similar to that described in Example 189.

Yield: 86.4%, pale yellow powder mp. >300° C.

$^1$H-NMR(CD$_3$OD) δ: 8.06 (1 H, d, J=9.3 Hz), 7.26 (1 H, Gs), 6.57 (1 H, d, J=9.3 Hz), 4.67 (1 H, m), 3.46–3.12 (3 H, m), 2.41 (3 H, s), 1.41 (3 H, d, J=6.8 Hz). IR (KBr): 3000–2200, 1650, 1467, 955, 866 cm$^{-1}$.

Optical rotation $[\alpha]_D^{22}$=+65.0 (c=0.1, methanol)

Example 197

(−)-2,3,6,7,8,9-Hexahydro-2-hydroxymethyl-5methylfuro-[2,3-f]quinoline-7-one:

The title compound was prepared in a manner similar to that described in Example 190.

Colorless needles mp. 186°–187° C.

$^1$H-NMR(CDCl$_3$) δ: 7.43 (1 H, br.s), 6.83 (1 H, s), 4.91 (1 H, m), 3.94–3.64 (2 H, m), 3.20 (1 H, dd, J=15.6, 9.3 Hz), 2.98 (1 H, dd, J=15.6, 6.8 Hz), 2.95–2.80 (2 H, m), 2.67–2.52 (2 H, m), 2.14 (3 H, s), 2.09 (1 H, t, J=6.8 Hz). IR(KBr): 3286, 1647, 1470, 1388, 1201, 1049 cm$^{-1}$.

Optical rotation $[\alpha]_D^{23}$=−12.0 (c=1.0 methanol)

Example 198

(+)-2,3,6,7,8,9-Hexahydro-2-hydroxymethyl-5-methylfuro-[2,3-f]quinoline-7-one:

The title compound was prepared in a manner similar to that described in Example 190.

Colorless needles mp. 186°–187° C.

Optical rotation $[\alpha]_D^{23}$=+10.7 (c=1.0, methanol)

$^1$H-NMR and IR data were the same as Example 197.

Example 199

(+)-2-Hydroxymethyl-5-methyl-2,3,6,7-tetrahydrofuro-[2,3-f]quinoline-7-one:

The title compound was obtained by following the optical resolution described in Example 189.

White powder, mp. 239°–241° C. (dec.)

$^1$H-NMR(CDCl$_3$-CD$_3$OD) δ: 8.04 (1 H, d, J=9.8 Hz), 7.20 (1 H, s), 6.55 (1 H, d, J=9.8 Hz), 5.04 (1 H, m), 3.89–3.70 (2 H, m), 3.53 (1 H, m), 3.08 (1 H, dd, J=15.1, 7.3 Hz), 2.38 (3 H, s).

IR(KBr): 3400, 1649 cm$^{-1}$.

Optical rotation $[\alpha]_D^{22}$=+4.0 (c=0.1, methanol)

Example 200-1

(−)-(2 R*, 3 S*)-2-Aminomethyl-2,3,6,7-tetrahydro-2,3,5trimethylfuro-[2,3-f]quinoline-7-one.HCl:

The title compound was obtained by following the optical resolution described in Example 189.

Yield: 43.5%, Pale yellow powder, mp. 238°–289° C. (dec.)

$^1$H-NMR(CDCl$_3$-CD$_3$OD) δ: 8.07 (1 H, d, J=9.8 Hz), 7.18 (1 H, s), 6.59 (1 H, d, J=9.8 Hz), 3.50 (1 H, q, J=7.3 Hz), 3.19 (1 H, d, J=13.2 Hz), 3.10 (1 H, d, J=13.2 Hz), 2.42 (3 H, s), 1.65 (3 H, s), 1.34 (3 H, d, J=7.3 Hz).

IR(KBr): 3000–2400, 1652, 1458, 1065 cm$^{-1}$.

Optical rotation $[\alpha]_D^{22}$=−20.0 (c=0.1, methanol)

Example 200-2

(+)-(2R*,3S*)-2-Aminomethyl-2,3,6,7-tetrahydro-2,3,5-trimethylfuro-[2,3-f]quinoline-7-one.HCl:

The title compound was obtained by following the optical resolution described in Example 189.

Yield: 62.2%, Pale yellow powder, mp. 290°–293° C. (dec.)

Optical rotation $[\alpha]_D^{22}$=+21.0 (c=0.1 methanol)

$^1$H-NMR and IR data were the same as Example 200.

Example 201

(+)-(2R*,3R*)-2-Aminomethyl-3,5-dimethyl-2,3,6,7,8,9-hexahydrofuro-[2,3-f]quinoline-7-one.HCl:

The title compound was obtained by a method similar to that described in Example 190.

Colorless prisms, mp. >300° C., Yield: 50.5%

$^1$H-NMR(CD$_3$OD) δ: 6.88 (1 H, s), 4.49 (1 H, m), 3.26–3.10 (3 H, m), 2.98–2.80 (2 H, m), 2.52 (2 H, t, J=7.3 Hz), 2.18 (3 H, s), 1.34 (3 H, d, J=6.4 Hz).

IR(KBr): 3000–2400, 1661, 1472, 1387, 1208, 1049, 986, 958 cm$^{-1}$.

Optical rotation $[\alpha]_D^{22}$=+52.0 (c=0.1, methanol)

Example 202

(−)-Aminomethyl-2,5-dimethyl-2,3,6,7-tetrahydrofuro-[2,3-f]quinoline-7-one.HCl:

The title compound was obtained as described in Example 189.

Yield: 68.3%, mp. >297°–300° C. (dec.)

$^1$H-NMR(CD$_3$OD) δ: 8.03 (1 H, d, J=9.8 Hz), 7.26 (1 H, s), 6.53 (1 H, d, J=9.8 Hz), 3.40–3.24 (5 H, m), 3.31 (1 H, d, J=16.1 Hz), 3.18 (1 H, d, J=16.1 Hz), 2.38 (3 H, s), 1.61 (3 H, s).

IR(KBr): 3000–2300, 1651, 1562, 1457, 1317, 1293, 1083, 1014, 832, 797 cm$^{-1}$.

Optical rotation $[\alpha]_D^{23}$=−10.0 (c=1.0, methanol)

Example 203

(+)-2-Aminomethyl-2,5-dimethyl-2,3,6,7-tetrahydrofuro-[2,3-f]quinoline-7-one.HCl:

The title compound was obtained as described in Example 189.

Yield: 58.9%, Pale yellow flakes, mp. 286°–288° C.

Optical rotation $[\alpha]_D^{22}$=+6.6 (c=0.5, methanol)

$^1$H-NMR and IR data were the same as Example 202.

Example 204

(−)-2-Aminomethyl-2,5-dimethyl-2,3,6,7,8,9hexahydro-furo-[2,3-f]quinoline-7-one.HCl:

The title compound was obtained as described in Example 190.

Colorless flakes, mp. 278°–280° C. (dec.), Yield: 53.0%

$^1$H-NMR(CD$_3$OD) δ: 6.88 (1 H, s), 3.22 (2 H, s), 3.17 (1 H, d, J=16.1 Hz), 3.06 (1 H, d, J=16.1 Hz), 2.96–2.76 (2 H, m), 2.52 (2 H, t=7.8 Hz), 2.17 (3 H, s), 1.53 (3 H, s).

IR(KBr): 3000–2400, 1670, 1474, 1389, 1285, 1211, 1050 cm$^{-1}$.

Optical rotation $[\alpha]_D^{23}$=−20.2 (c=0.5, methanol)

Example 205

(+)-2-Aminomethyl-2,5-dimethyl-2,3,6,7,8,9-hexahydro-furo-[2,3-f]quinoline-7-one.HCl:

The title compound was obtained as described in Example 190.

Yield: 57.7%, Colorless flakes, mp. 277°–281° C. (dec.)

Optical rotation $[\alpha]_D^{22}$=+21.0 (c=0.5, methanol)

$^1$H-NMR and IR data were the same as Example 204.

Example 206

(−)-2-Aminomethyl-2-ethyl-5-methyl- 2,3,6,7-tetrahydrofuro-[2,3-f]quinoline-7-one.HCl:

The title compound was obtained as described in Example 189.

Yield: 47.4%, Yellow powder

Optical rotation $[\alpha]_D^{22}$=−6.6 (c=0.1, methanol)

$^1$H-NMR(CD$_3$OD) δ: 8.08 (1 H, d, J=9.8 Hz), 7.27 (1 H, s), 6.55 (1 H, d, J=9.8 Hz), 3.40 (1 H, dd. J=14.2, 7.3 Hz), 3.65–3.20 (3 H, m, C3-H), 2.39 (3 H, s), 2.80–2.05 (2 H, m), 1.00 (3 H, t, J=7.3 Hz).

IR(KBr): 3386, 2957, 1651, 1464, 1317, 1086, 834 cm$^{-1}$.

Example 207

(2 RS, 3 RS)-2-Aminomethyl-3-ethyl-5-methyl-2,3,6,7-tetrahydrofuro-[2,3-f]quinoline-7-one.HCl:

The title compound was obtained as described in Example 12.

mp. 300° C.

IR(KBr): 3155, 2995, 2950, 2850, 1645, 1615, 1560, 1460, 1440, 1330, 1265, 1220, 1155, 1095, 1065, 1000, 955, 930, 835, 800 cm$^{-1}$.

$^1$H-NMR(CD$_3$OD) δ: 8.13 (1 H, d, J=9.8 Hz), 7.31 (1 H, s), 6.60 (1 H, d, J=9.8 Hz), 4.88 (1 H, m), 3.29–3.12 (3 H, m), 2.42 (3 H, s), 1.93–1.65 (2 H, m), 1.00 (3 H, t, J=7.3 Hz).

Example 208

(2 RS, 3 RS)-2-Aminomethyl-3-ethyl-5-methyl-2,3,6,7,8,9-tetrahydrofuro-[2,3-f]quinoline-7-one.HCl:

The title compound was obtained as described in Example 190.

mp. 300° C.

IR(KBr): 3195, 3110, 2950, 2910, 2830, 1660, 1630, 1610, 1470, 1440, 1390, 1375, 1340, 1210, 1095, 1055, 995, 980, 945, 905, 745 cm$^{-1}$.

$^1$H-NMR(CD$_3$OD) δ: 6.90 (1 H, s), 4.66 (1 H, m), 3.31 (1 H, dd. J=2.9, 13.8 Hz), 3.12–3.03 (2 H, m), 3.01–2.89 (2 H, m), 2.53 (2 H, t, J=7.3 Hz), 2.18 (3 H, s), 1.85–1.58 (2 H, m), 0.99 (3 H, t, J=7.3 Hz).

Example 209

(2 RS, 3 SR)-2-Aminomethyl-3-ethyl-5-methyl-2,3,6,7-tetrahydrofuro-[2,3-f]quinoline-7-one.HCl:

The title compound was obtained as described in Example 5.

mp. >300° C.

IR(KBr): 3155, 3000, 2950, 2910, 1660, 1610, 1570, 1560, 1505, 1465, 1455, 1400, 1330, 1300, 1275, 1230, 1155, 1075, 985, 835, 820, 810 cm$^{-1}$.

$^1$H-NMR(CD$_3$OD) δ: 8.07 (1 H, d, J=9.8 Hz), 7.31 (1 H, s), 6.56 (1 H, d, J=9.8 Hz), 5.08 (1 H, m), 3.53 (1 H, dd, J=15.1, 7.3 Hz), 3.43 (1 H, dd, J=15.1, 2.9 Hz), 3.32 (1 H, m), 2.41 (3 H, s), 1.73–1.61 (2 H, m), 1.07 (3 H, t, J=7.3 Hz).

Example 210

(2 RS, 3 SR)-2-Aminomethyl-3-ethyl-5-methyl-2,3,6,7,8,9-tetrahydrofuro-[2,3-f]quinoline-7-one.HCl:

The title compound was obtained as described in Example 163.

mp. 294°–298° C. (dec.)

IR(KBr): 3210, 3110, 2950, 2950, 2860, 1665, 1630, 1615, 1470, 1440, 1385, 1375, 1340, 1305, 1205, 1095, 1070, 990, 975, 945, 925, 770, 740 cm$^{-1}$.

$^1$H-NMR(CD$_3$OD) δ: 6.92 (1 H, s), 4.87 (1 H, m), 3.41–3.17 (3 H, m), 3.00–2.79 (2 H, m), 2.53 (3 H, t, J=7.3 Hz), 2.19 (3 H, s), 1.69–1.52 (2 H, m), 1.05 (3 H, t, J=7.3 Hz).

Example 211

2-Guadininomethyl-5-methyl-2,3,6,7-tetrahydrofuro-[2,3-f]quinoline-7-one.HCl:

2-Aminomethyl5-methyl-2,3,6,7-tetrahydrofuro-[2,3-f]quinoline-7-one (1.1 g, 4.78 mmol) and a nitric acid salt of 3,5-dimethylpyrazole-1-carboxysamidine (0.96 g, 4.78 mmol) were dissolved in dimethylformamide (40 ml), and the solution was stirred at 100° C. for 15 hours. After completion of the reaction, the solvent was distilled off under reduced pressure, and the residue was dissolved in water (35 ml). Saturated sodium bicarbonate water was added thereto and neutralized. Subsequently, extraction was performed with n-butanol. The solvent was distilled off under reduced pressure to obtain 0.703 g of a free base of the title compound as pale yellow powder (54.0%). This was converted into a hydrochloric acid salt, followed by recrystallizing with methanol—ethanol. As a result, 0.609 g of the title compound was obtained as colorless needles (41.2%, mp.: 173° C.).

$^1$H-NMR(CD$_3$OD) δ: 2.37 (3 H, s), 3.04 (1 H, dd, J=7.0, 15.6 Hz), 3.30–3.72 (3 H, m), 5.15 (1 H, m), 6.56 (1 H, d, J=9.7 Hz), 7.29 (1 H, s), 8.02 (1 H, d, J=9.7 Hz).

IR(KBr): 3320, 1645, 1564, 1463, 1443, 1310, 1151, 1084 cm$^{-1}$.

Example 212

2-(3-Cyano-2-methyl-1-isothioureido)methyl-5-methyl-2,3,6,7-tetrahydrofuro-[2,3-f]quinoline-7-one:

To a solution of 2-aminomethyl-5-methyl-2,3,6,7-tetrahydrofuro-[2,3-f]quinoline-7-one (1.0 g, 4.35 mmol) in ethanol (100 ml), dimethyl N-cyanoiminodithiocarbonate (1.27 g, 8.7 mmol) was added, and the mixture was stirred for 15 hours. Crystals precipitated from the reaction solution were collected by filtration, and washed with ethanol. 1.24 g of the title compound was obtained as while crystals (86.8%). They were recrystallized from chloroform—methanol to obtain the title compound as colorless needles.

mp. 275°–277° C. (dec.)

$^1$H-NMR(DMSO-d$_6$) δ: 2.32 (3 H, s), 2.56 (3 H, s), 2.96 (1 H, dd, J=6.0, 15.6 Hz), 3.35 (1 H, m), 3.58 (2 H, d, J=6.0 Hz), 5.14 (1 H, m), 6.46 (1 H, d, J=9.7 Hz), 7.23 (1 H, s), 7.83 (1 H, d, J=9.7 Hz), 8.62 (1 H, br.s), 10.74 (1 H, br).

IR(KBr): 3225, 2165, 1652, 1611, 1542, 1506, 1429, 1346, 1278 cm$^{-1}$.

Example 213-1

2-(2-Cyano-3-methylguanidino)methyl-5-methyl-2,3,6,7-tetrahydrofuro-[2,3-f]quinoline-7-one:

The compound obtained in Example 212 (0.66 g, 2.01 mmol) was dissolved in a mixture of ethanol (30 ml) and dimethylformamide (50 ml). To the obtained solution, 30% methylamine in ethanol (25 ml) was added and stirred at 80° C. for 1.5 hours. The solvent was distilled off under reduced pressure, and the residue was washed with ethanol. 0.626 g (assayed quantitatively) of the title compound was obtained as a pale yellow solid. The solid was recrystallized from chloroform—methanol—ether, to obtain the title compound as colorless needles (mp. 262°–265° C. (dec.)).

$^1$H-NMR(DMSO-d$_6$) δ: 2.32 (3 H, s), 2.68 (3 H, d, J=4.7 Hz), 2.97 (1 H, dd, J=6.0, 15.7 Hz), 3.16–3.52 (3 H, m), 5.07 (1 H, m), 6.46 (1 H, d, J=9.7 Hz), 7.16 (1 H, q, J=4.7 Hz), 7.24 (1 H, s), 7.26 (1 H, br), 7.84 (1 H, d, J=9.7 Hz), 10.85 (1 H, br.s).

IR(KBr): 3264, 2147, 1653, 1567, 1448, 1405, 1366, 1308 cm$^{-1}$.

Example 213-2

2-(3-Cyano-2-methyl-1-isothioureido)methyl-2,3,6,7,8,9-hexahydro-5-methylfuro-[2,3-f]quinoline-7-one:

The procedure of Example 212 was followed using 2-aminomethyl-2,3,6,7,8,9-hexahydro-5-methylfuro-[2,3-f]quinoline-7-one (0.60 g, 2.59 mmol), dimethyl-N-cyanoiminodithiocarbonate (0.76 g, 5.2 mmol), and ethanol (30 ml). 0.692 g of the title compound was obtained (80.4%). The obtained compound was recrystallized from chloroform—methanol—ether to obtain the title compound as colorless needles (mp. 243°–244° C. (dec.)).

$^1$H-NMR(DMSO-d$_6$) δ: 2.12 (3 H, s), 2.34–2.82 (4 H, m), 2.51 (3 H, s), 2.86 (1 H, dd, J=6.0, 15.6 Hz), 3.14–3.60 (3 H, m), 4.95 (1 H, m), 6.85 (1 H, s), 8.55 (1 H, br s), 9.34 (1 H, s).

IR(KBr): 3227, 2167, 1671, 1630, 1545, 1480, 1469, 1425, 1269 cm$^{-1}$.

Example 214

2-(2-Cyano-2-methylguanidino)methyl-2,3,6,7,8,9-hexahydro-5-methylfuro-[2,3-f]quinoline-7-one:

The procedure of Example 213-2 was followed using the compound obtained in Example 213-1 (0.68 g, 2.06 mmol), 30% methylamine in ethanol (15 ml) and dimethylformamide (10 ml). 0.638 g of the title compound was obtained as a white solid (98.9%). The obtained compound was recrystallized from chloroform—methanol—ether to obtain the title compound as colorless needles (mp. 246°–247° C. (dec.)).

$^1$H-NMR(DMSO-d$_6$) δ: 2.12 (3 H, s), 2.34–2.78 (4 H, m), 2.68 (3 H, d, J=4.6 Hz), 2.86 (1 H, dd, J=6.3, 15.7 Hz), 3.10–3.52 (3 H, m), 4.89 (1 H, m), 6.85 (1 H, s), 7.10 (1 H, q, J=4.6 Hz), 7.16 (1 H, t, J=5.4 Hz), 9.33 (1 H, s).

IR(KBr): 3230, 2155, 1654, 1603, 1578, 1472, 1371, 1341, 1201 cm$^{-1}$.

Example 215

2-[4-(3,4-Dimethoxybenzoyl)-1-piperazinomethyl]-5-methyl-2,3,6,7,8,9-hexahydrofuro-[2,3-f]quinoline-7-one.HCl To a solution of 5-methyl-2-(1-piperazinomethyl)-2,3,6,7,8,9-hexahydrofuro-[2,3-f]quinoline-7-one (1.474 g) in pyridine (40 ml), a solution of 3,4-dimethoxybenzoyl chloride (1.003 g) in pyridine (20 ml) was added dropwise while cooling on ice. Subsequently, stirring was continued at room temperature for 1 hour. The solvent was distilled off under reduced pressure. The residue was combined with water, and extracted with chloroform. The extract was washed with sodium bicarbonate water and water in this order, and dried and concentrated. The residue was crystallized from chloroform—n-hexane to obtain 2.163 g of a free base of the title compound as colorless prisms (mp. 190°–191° C.).

Yield: 95.0%

$^1$H-NMR(CDCl$_3$) δ: 7.35 (1 H, br.s), 7.01 (1 H, s), 6.90–6.78 (3 H, m), 4.92 (1 H, m), 3.91 (6 H, s), 3.66 (4 H, br.s), 3.23 (1 H, dd, J=15.6, 9.3 Hz), 2.91 (1 H, dd, J=15.6, 7.8 Hz), 2.87 (2 H, t, J=7.3 Hz), 2.80–2.45 (8 H, m), 2.14 (3 H, s).

IR(KBr): 3201, 1664, 1613, 1471, 1446, 1262, 1226, 1132 cm$^{-1}$.

Hydrochloric acid salt: Colorless prisms, mp. 253°–254° C. (dec.).

$^1$H-NMR(CD$_3$OD) δ: 7.17–6.98 (3 H, m), 6.90 (1 H, s), 5.31 (1 H, m), 4.70–3.22 (11 H, m), 3.88 (3 H, s), 3.87 (3 H, s), 3.02–2.80 (3 H, m), 2.52 (2 H, t, J=7.8 Hz), 2.17 (3 H, s).

IR(KBr): 3000–2100, 1669, 1641, 1450, 1029 cm$^{-1}$.

Example 216

5-Methyl-2-(1-piperazino)methyl- 2,3,6,7,8,9-hexahydrofuro-[2,3-f]quinoline-7-one.2 HCl To an aqueous solution of 2-[1-(4-Benzyl-1-piperazino)methyl]-5-methyl-2,3,6,7-tetrahydrofuro-[2,3-f]quinoline-7-one.2 HCl, 10% palladium-on-carbon catalyst (0.75 g) was added, and stirred in a hot bath of 80° C. for 3 hours in the stream of hydrogen gas. The catalyst was removed by filtration, and the solvent was distilled off under reduced pressure. The residue was crystallized from methanol to obtain 0.839 g of the title compound (mp. 273°–276° C. (dec.)).

Yield: 69.2%

$^1$H-NMR(D$_2$O) δ: 6.97 (1 H, s), 5.45–5.25 (1 H, m), 3.78 (8 H, d, J=7.8 Hz), 3.61 (2 H, d, J=6.4 Hz), 3.47 (1 H, dd, J=16.1, 9.3 Hz), 2.96 (1 H, dd, J=16.1, 6.8 Hz), 2.83–2.75 (2 H, m), 2.53 (2 H, t, J=7.3 Hz), 2.13 (3 H, s).

IR(KBr): 3201, 2800–2100, 1668, 1475, 1439, 1384, 1201 cm$^{-1}$.

Example 217

2-[4-(3,4-dimethoxybenzoyl)-1-piperazinomethyl]-5-methyl-2,3,6,7-tetrahydrofuro-[2,3-f]quinoline-7-one.HCl To a suspension of 5-methyl-2-(1-piperazino)methyl-2,3,6,7,-hexahydrofuro-[2,3-f]quinoline-7-one (1.124 g) in pyridine (40 ml), a solution of 3,4-dimethoxybenzoyl chloride (0.803 g) in pyridine (20 ml) was added dropwise while cooling on ice, and stirred at room temperature for 1 hour. The solvent was distilled off under reduced pressure. The residue was dissolved in chloroform, washed with sodium bicarbonate water and water in this order, and dried. The residue was crystallized from a solvent mixture of chloroform—n-hexane to obtain 1.327 g of a free base of the title compound as white powder (mp. 243°–244° C.)

Yield: 76.3%

$^1$H-NMR(CDCl$_3$) δ: 8.87 (1 H, s), 7.88 (1 H, d, J=9.8 Hz), 7.13 (1 H, s), 7.01 (1 H, s), 6.98 (1 H, dd, J=9.3, 2.0 Hz), 6.86 (1 H, d, J=8.8 Hz), 6.56 (1 H, d, J=9.8 Hz), 5.11 (1 H, m), 3.91 (6 H, s), 3.85–3.46 (4 H, m), 3.32 (1 H, dd, J=15.1, 9.3 Hz), 3.03 (1 H, dd, J=15.1, 8.8 Hz), 2.92–2.50 (6 H, m), 2.34 (3 H, s).

IR(KBr): 3150, 1647, 1615, 1459, 1424, 1263, 1145, 1024, 1000, 939, 867, 826 cm$^{-1}$.

Hydrochloric acid salt: White powder, mp. 261°–263° C. (dec.).

$^1$H-NMR(CD$_3$OD-D$_2$O) δ: 8.12 (1 H, d, J=9.8 Hz), 7.36 (1 H, s), 7.13 (3 H, s), 6.63 (1 H, d, J=9.8 Hz), 5.48 (1 H, m), 4.10–3.80 (4 H, m), 3.91 (3 H, s), 3.89 (3 H, s), 3.76–3.36 (7 H, m), 2.96 (1 H, m), 2.39 (3 H, s).

IR(KBr): 3187, 2700–2200, 1664, 1645, 1452, 1262, 1023 cm$^{-1}$.

Example 218

2-[1-(4-(3,4-dimethoxybenzoyl)homopiperazino]methyl]-5-methyl-2,3,6,7-tetrahydrofuro-[2,3-f]quinoline-7-one, oxalate:

To a solution of 2-(1-homopiperazino)methyl-5-methyl-2,3,6,7-tetrahydrofuro-[2,3-f]quinoline-7-one (0.940 g) in pyridine (40 ml), a solution of 3,4-dimethoxybenzoyl chloride (0.644 g) in pyridine (20 ml) was added dropwise. After the addition was completed, the mixture was stirred at room temperature for 1 hour. The solvent was distilled off under reduced pressure. The residue was dissolved in chloroform, washed with saturated sodium bicarbonate water and water in this order, and dried and concentrated. The residue was crystallized from ethyl acetate to obtain 0.872 g of a free base of the title compound as white powder (mp. 143°–145° C.).

Yield: 60.9%

$^1$H-NMR(CDCl$_3$) δ: 8.82 (1 H, s), 7.85 (1 H, m), 7.12 (1 H, s), 7.03–6.72 (3 H, m), 6.55 (1 H, d, J=9.3 Hz), 5.07 (1 H, m), 3.90 (6 H, s), 3.95–2.70 (11 H, m), 2.33 (3 H, s), 2.14–1.60 (3 H, m).

IR(KBr): 1651, 1461, 1261, 1143, 1023 cm$^{-1}$.

Oxalic acid salt: White powder, mp. 148°–150° C.

$^1$H-NMR(CD$_3$OD) δ: 8.05 (1 H, br.s), 7.25 (1 H, s), 7.15–6.82 (3 H, m), 6.55 (1 H, d, J=9.8 Hz), 5.40 (1 H, br.s), 4.08–3.42 (11 H, m), 3.31 (6 H, s), 2.99 (1 H, m), 2.38 (3 H, s), 2.30–2.15 (2 H, br.s).

IR(KBr): 2800–2100, 1712, 1651, 1629, 1444, 1232, 1133, 1017, 832 cm$^{-1}$.

Example 219

(−)-2-Formylaminomethyl-5-methyl-2,3,6,7-tetrahydro-furo-[2,3-f]quinoline-7-one:

To a suspension of (−)-aminomethyl-5-methyl-2,3,6,7-tetrahydrofuro-[2,3-f]quinoline-7-one (965 mg, 4.19 mmol) in a mixture of tetrahydrofuran (30 ml) and chloroform (30 ml), acetic anhydride—formic anhydride (1.83 g, 20.8 mmol) was added and refluxed with heat in a bath of 70° C. for 3 hours. The temperature of the reaction mixture was returned to room temperature. Ether was added to the mixture and insoluble matter was collected by filtration. Recrystallization from chloroform—methanol—ether yielded 410 mg of the title compound as colorless powder (37.9%).

mp. 282°–284° C.

$^1$H-NMR(CD$_3$OD) δ: 8.14 (1 H, s), 8.02 (1 H, d, J=9.8 Hz), 7.21 (1 H, s), 6.56 (1 H, d, J=9.8 Hz), 5.07 (1 H, m), 3.68 (1 H, dd, J=4.4, 14.7 Hz), 3.54 (1 H, dd, J=6.8, 14.7 Hz), 3.36 (1 H, complex m), 3.01 (1 H, dd, J=7.3, 16.1 Hz), 2.39 (3 H, s).

IR(KBr): 3262, 1655, 1539, 1452, 1311, 1269, 1243, 1147, 839, 790 cm$^{-1}$.

Example 220

(−)-5-methyl-2-methylamino-2,3,6,7-tetrahydrofuro-[2,3-f]quinoline-7-one:

(−)-2-Formylaminomethyl-5-methyl-2,3,6,7-tetrahydro-furo-[2,3-f]quinoline-7-one (410 mg, 1.59 mmol) was dissolved in dry tetrahydrofuran (100 ml), and aluminum lithium hydride (302 mg, 7.95 mmol) was added thereto. The mixture was dried while stirring in a bath of 50° C. in the stream of nitrogen gas for 18 hours. The reaction mixture was cooled. A small amount of ethyl acetate was added. The solvent was distilled off under reduced pressure. 2N-caustic soda solution was added to the residue, and extracted with a solvent mixture of chloroform: methanol=10:1. The extract was dried, and the solvent was distilled off under reduced pressure. 342 mg of the title compound was obtained as a crude product (88.2%). The crude was dissolved in methanol. 4N-HCl in 1,4-dioxane solution (0.4 ml) was added to the methanol solution of the crude, and the solution was concentrated. The resultant concentrate was recrystallized from methanol—ether, obtaining 310 mg of a hydrochloric acid salt of the title compound (78.8%) as yellow powder.

mp. 293°–296° C. (dec.)

$^1$H-NMR(CD$_3$OD) δ: 8.07 (1 H, d, J=9.8 Hz), 7.29 (1 H, s), 6.57 (1 H, d, J=9.8 Hz), 5.26 (1 H, m), 3.53 (1 H, dd, J=9.7, 15 Hz), 3.48–3.29 (2 H, complex m), 3.05 (1 H, dd, J=6.8, 15.6 Hz), 2.82 (3 H, s), 2.39 (3 H, s).

IR(KBr): 2920, 1654, 1462, 1311, 1261, 1215, 1145, 1085, 834 cm$^{-1}$.

Optical rotation $[\alpha]_D^{22}$=−19.2 (c=0.5 methanol)

Example 221

(+)-2-Formylaminomethyl-5-methyl-2,3,6,7-tetrahydro-furo-[2,3-f]quinoline-7-one:

(+)-2-Aminomethyl-5-methyl-2,3,6,7-tetrahydrofuro-[2,3-f]quinoline-7-one (1.17 g, 5.08 mmol) was suspended in tetrahydrofuran (30 ml)—chloroform (30 ml). To the suspension, acetic anhydride—formic anhydride (2.24 g, 25.4 mmol) was added, and refluxed with heat in a bath of 70° C. for 3 hours. The resulting reaction mixture was cooled at room temperature, and combined with ether. The insoluble matter, which was collected by filtration, was recrystallized from chloroform—methanol—ether. As a result, 460 mg of the title compound was obtained as colorless powder (35.1%).

mp. 282°–284° C.

$^1$H-NMR(CD$_3$OD) δ: 8.14 (1 H, s), 8.02 (1 H, d, J=9.8 Hz), 7.21 (1 H, s), 6.56 (1 H, d, J=9.8 Hz), 5.07 (1 H, m), 3.68 (1 H, dd, J=4.4, 14.7 Hz), 3.54 (1 H, dd, J=6.8, 14.7 Hz), 3.38 (1 H, complex m), 3.02 (1 H, dd, J=7.3, 16.1 Hz), 2.39 (3 H, s).

IR(KBr): 3262, 3036, 1654, 1539, 1451, 1383, 1310, 1269, 1243, 1147, 839 cm$^{-1}$.

Example 222

(+)-5-Methyl-2-methylaminomethyl-2,3,6,7-tetrahydro-furo-[2,3-f]quinoline-7-one.HCl (+)-2-Formylaminomethyl-5-methyl-2,3,6,7-tetrahydro-furo-[2,3-f]quinoline-7-one (460 mg, 1.78 mM) was dissolved in dry tetrahydrofuran (100 ml). To the solution, aluminum lithium hydride (135 mg, 3.57 mM) was added thereto. The mixture was dried while stirring in a bath of 50° C. in the atmosphere of nitrogen for 18 hours. The reaction mixture was cooled. A small amount of ethyl acetate was added. The solvent was distilled off under reduced pressure. 2N-caustic soda solution was added to the residue, followed by extraction with a solvent mixture of chloroform: methanol=10:1. The extract was dried, and the solvent was distilled off under reduced pressure. 360 mg of the title compound was obtained as a crude (+)-5-methyl-2-methylaminomethyl-2,3,6,7-tetrahydrofuro [2,3-f] quinoline-7-one (82.9%). The obtained crude was dissolved in methanol. 4N-HCl in 1,4-dioxane solution (0.4 ml) was added to the methanol solution of the crude, and the solution was concentrated. The resultant concentrate was recrystallized from methanol—ether, obtaining 276 mg of the title compound (66.7%) as yellow powder.

mp. 292°–296° C. (dec.).

$^1$H-NMR(CD$_3$OD) δ: 8.07 (1 H, d, J=9.8 Hz), 7.29 (1 H, s), 6.59 (1 H, d, J=9.8 Hz), 5.26 (1 H, m), 3.53 (1 H, dd, J=9.8, 15.6 Hz), 3.41–3.25 (2 H, complex m), 3.05 (1 H, dd, J=6.8, 15.6 Hz), 2.82 (3 H, s), 2.40 (3 H, s).

IR(KBr): 2784, 1663, 1568, 1462, 1311, 1262, 1145, 1085, 834 cm$^{-1}$.

Optical rotation $[\alpha]_D^{22}$=+17.6 (c=0.5, methanol)

Example 223

2-[N-(4-Hydroxybutyryl)-N-methylaminomethyl]-5-methyl-2,3,6,7,8,9-hexahydrofuro-[2,3-f]quinoline-7-one:

A mixture of 5-methyl-2-(methylaminomethyl)-2,3,6,7,8, 9-hexahydrofuro-[2,3-f]quinoline-7-one (1.346 g) and γ-butyrolactone (4.30 g) was stirred in a bath of 150° C. in the stream of nitrogen gas for 4 hours. The solvent was distilled off under reduced pressure. The residual oil was crystallized from ethanol, obtaining 0.575 g of the title compound as white powder (mp. 141°–143° C.).

Yield: 36.7%

$^1$H-NMR(CD$_3$OD) δ: 6.87 (s), 6.83 (s) (altogether, 1 H), 5.00 (1 H, m), 3.80–3.40 (4 H, m), 3.24 (1 H, m), 3.16 (s) ,3.02 (s) (altogether,3 H), 2.09–2.74 (3 H, m), 2.55–2.40 (4 H, m), 2.16 (s), 2.15 (s) (altogether, 3 H), 1.86–1.73 (2 H, m).

IR(KBr): 3399, 3232, 1682, 1660, 1624, 1468, 1203, 1048 cm$^{-1}$.

Example 224

2-(Carbobenzyloxy-L-alanyl)aminomethyl-5-methyl-2,3,6, 7-tetrahydrofuro-[2,3-f]quinoline-7-one:

2-Aminomethyl-5-methyl-2,3,6,7-tetrahydrofuro-[2,3-f] quinoline-7-one (2.3 g, 10 mmol) was dissolved in dimethylformamide (100 ml) while cooled on ice. To the obtained mixture, carbobenzyloxy-L-alanine (2.3 g, 10.5 mmol), a hydrochloric acid salt of 1-ethyl-3-(3-dimethylaminopropyl)carbodiimide (hereinafter referred to as WSC.HCl) (2.3 g, 11.0 mmol), and 1-hydroxybenzotriazol (hereinafter referred to as HOBT) (1.4 g, 11.0 mmol) were added, and the resultant mixture was stirred at room temperature overnight. The reaction mixture was condensed under reduced pressure. The obtained residue was extracted with chloroform, washed with 1N-HCl and saturated aqueous NaCl solution, and dried. The solvent was evaporated. The residue was purified by silica gel column chromatography (chloroform: methanol =20:1) to obtain 3.3 g of the title compound as colorless powdery crystals (76.0%)

mp. 229°–231° C.

$^1$H-NMR(CDCl$_3$) δ: 1.15–1.32 (3 H, m), 2.31 (3 H, s), 2.93 (1 H, m), 3.28 (1 H, m), 3.50–3.80 (2 H, m), 3.93–4.05 (2 H, m), 4.18 (1 H, m), 5.00 (1 H, m), 6.50 (1 H, d, J=10 Hz), 7.12 (1 H, s), 7.29 (5 H, s), 7.91 (1 H, d, J=10 Hz).

Example 225

2-L-Alanylaminomethyl-5-methyl-2,3,6,7-tetrahydrofuro-[2,3-f]quinoline-7-one.HCl The compound obtained in Example 224 (3.0 g, 6.9 mmol) was dissolved in dimethylformamide (200 ml). To the obtained solution, 10% palladium-on-carbon (3.0 g) was added, followed by stirring at room temperature overnight in the atmosphere of hydrogen. The reaction mixture was filtered, and the filtrate was condensed under reduced pressure. The resultant residue was dissolved in methanol (20 ml), and 4N-HCl dioxane (4 ml) was added thereto while cooling on ice. The mixture was condensed under reduced pressure. The resultant residue was recrystallized from methanol—ether to obtain 1.5 g of the title compound as pale yellow powdery crystals (64.4%).

mp. >250° C.

$^1$H-NMR(CDCl$_3$+CD$_3$OD) δ: 1.39–1.5 (3 H, m), 2.42 (3 H, s), 3.05 (1 H, m), 3.49 (1 H, m), 3.60–3.76 (2 H, m), 4.10 (1 H, m), 5.12 (1 H, m), 6.77 (1 H, d, J=9 Hz), 7.27 (1 H, s), 8.23 (1 H, d, J=9 Hz).

IR(KBr): 3395, 2921, 1650, 1558, 1462, 1321, 828 cm$^{-1}$.

Example 226

2-L-Alanylaminomethyl-2,3,6,7,8,9-hexahydro-5-methylmethylfuro-[2,3-f]quinoline-7-one.HCl The compound obtained in Example 225 (600 mg, 1.8 mmol) was dissolved in water (30 ml). To the obtained solution, 10% palladium-on-carbon (600 mg) was added, followed by stirring at 80° C. for 12 hours in the atmosphere of hydrogen. The reaction mixture was filtered, and the filtrate was condensed under reduced pressure. The resultant residue was purified by silica gel column chromatography (chloroform: methanol =5:1). The obtained crystals were dissolved in methanol (5 ml), and 4N-HCl dioxane (1 ml) was added thereto while cooling on ice. The mixture was condensed under reduced pressure. The resultant residue was recrystallized from methanol—ether, to obtain 210 mg of the title compound as colorless powdery crystals (34.0%).

mp. >250° C.

$^1$H-NMR(CDCl$_3$+CD$_3$OD) δ: 1.35–1.51 (3 H, m), 2.15 (3 H, s), 2.58 (2 H, t, J=7 Hz), 2.88 (2 H, t, J=7 Hz), 2.88 (1 H, m), 3.26 (1 H, m), 3.45–3.72 (2 H, m), 4.02 (1 H, m), 4.90 (1 H, m), 6.80 (s), 6.83 (s) (altogether, 2 H).

IR(KBr): 3382, 3218, 2914, 1660, 1558, 1473, 1387, 1204 cm$^{-1}$.

Example 227

2-(Carbobenzyloxy-D-alanyl)aminomethyl-5-methyl-2,3,6, 7-tetrahydrofuro-[2,3-f]quinoline-7-one:

2-Aminomethyl-5-methyl-2,3,6,7-tetrahydrofuro-[2,3-f] quinoline-7-one (2.3 g, 10 mmol) was dissolved in dimethylformamide (100 ml) while cooled on ice. To the obtained mixture, carbobenzyloxy-D-alanine (2.3 g, 10.5 mmol), WSC.HCl (2.3 g, 11.0 mmol), and HOBT (1.4 g, 11.0 mmol) were added, and the resultant mixture was stirred at room temperature for two days. The reaction mixture was condensed under reduced pressure. The obtained residue was extracted with chloroform, washed with 1N-HCl, saturated aqueous NaCl solution, and dried over magnesium sulfate anhydride. The solvent was evaporated. The residue was purified by silica gel column chromatography (chloroform: methanol=15:1) to obtain 4.27 g of the title compound as colorless powdery crystals (98.0%)

mp. 221°–222° C.

$^1$H-NMR (CDCl$_3$) δ: 1.30 (d, J=7 Hz), 1.34 (d, J=7 Hz) (altogether, 3 H), 2.35 (s), 2.36 (s) (altogether, 3 H), 2.96 (1 H, m), 3.30 (1 H, m), 3.55–3.75 (2 H, m), 3.98 (s), 4.00 (s) (altogether, 2 H), 4.17 (1 H, m), 5.02 (1 H, m), 6.54 (1 H, d, J=10 Hz), 7.15 (1 H, s), 7.32 (5 H, s), 7.96 (1 H, d, J=10 Hz).

Example 228

2-D-Alanylaminomethyl-5-methyl-2,3,6,7-tetrahydrofuro-[2,3-f]quinoline-7-one.HCl The compound obtained in Example 227 (4.2 g, 9.7 mmol) was dissolved in dimethylformamide (200 ml). To the obtained solution, 10% palladium-on-carbon (2.0 g) was added, followed by stirring at room temperature overnight in the atmosphere of hydrogen. The reaction mixture was filtered, and the filtrate was condensed under reduced pressure. The resultant residue was dissolved in methanol (20 ml), and 4N-HCl dioxane (5 ml) was added thereto while cooling on ice. The mixture was condensed under reduced pressure. The resultant residue was recrystallized from methanol—ether to obtain 1.3 g of the title compound as pale yellow powdery crystals (40.0%).

mp. 250° C.

$^1$H-NMR(CDCl$_3$-CD$_3$OD) δ: 1.43 (d, J=7 Hz), 1.45 (d, J=7 Hz)(altogether,3 H), 2.39 (3 H, s), 3.02 (1 H, m), 3.49 (1 H, m), 4.00 (1 H, m), 5.10 (1 H, m), 6.69 (1 H, d, J=10 Hz), 7.23 (1 H, s), 8.13 (1 H, d, J=10 Hz).

IR(KBr): 3396, 3213, 2913, 1647, 1556, 1461, 1323, 1257, 830 cm$^{-1}$.

Example 229

2-D-Alanylaminomethyl-2,3,6,7,8,9-hexahydro-5methyl-furo-[2,3-f]quinoline-7-one.HCl The compound obtained in Example 228 (680 mg, 2.0 mmol) was dissolved in water (30 ml). To the obtained solution, 10% palladium-on-carbon (600 mg) was added, followed by stirring at 80° C. for 10 hours in the atmosphere of hydrogen. The reaction mixture was filtered, and the filtrate was condensed under reduced pressure. The resultant residue was purified by silica gel column chromatography (chloroform: methanol =5:1). The obtained crystals were dissolved in methanol (5 ml), and 4N-HCl dioxane (1 ml) was added thereto while cooling on ice. The mixture was condensed under reduced pressure. The resultant residue was recrystallized from methanol—ether, to obtain 300 mg of the title compound as colorless powdery crystals (44.1%).

mp. 242°–245° C. (dec.)

$^1$H-NMR(CDCl$_3$-CD$_3$OD) δ: 1.40–1.49 (3 H, m), 2.15 (3 H, s), 2.57 (2 H, t, J=6 Hz), 2.81–2.96 (3 H, m), 3.26 (1 H, m), 3.40–3.60 (2 H, m), 4.05 (1 H, m), 4.84 (1 H, m), 6.83 (1 H, m).

IR(KBr): 3213, 2997, 1660, 1558, 1473, 1386, 1340, 1247, 1204, 1082, 1050 cm$^{-1}$.

Example 230

2-(N,N-Dimethylglycyl)aminomethyl-5-methyl-2,3,6,7-tetrahydrofuro-[2,3-f]quinoline-7-one.HCl 2-Aminomethyl-5-methyl-2,3,6,7-tetrahydrofuro-[2,3-f]quinoline-7-one (2.3 g, 10 mmol) was dissolved in dimethylformamide (100 ml) while being cooled on ice. To the obtained mixture, a hydrochloric acid salt of N,N-dimethylglycine (1.45 g, 11 mmol), WSC.HCl (2.0 g, 11.0 mmol), and HOBT (1.4 g, 11.0 mmol) were added, and the resultant mixture was stirred at room temperature overnight. The reaction mixture was subjected to distillation under reduced pressure. The resultant residue was recrystallized from ethanol—hexane. As a result, 2.7 g of the title compound was obtained as pale yellow powdery crystals (77.0%)

mp. >250° C.

$^1$H-NMR(CDCl$_3$+CD$_3$OD) δ: 2.34 (3 H, s,), 2.97 (6 H, s), 3.03 (1 H, m), 3.40–3.71 (3 H, m), 4.00 (2 H, s), 5.06 (1 H, m), 6.53 (1 H, d, J=10 Hz), 7.17 (1 H, s), 7.97 (1 H, d, J=10 Hz).

IR(KBr): 3394, 3243, 3021, 2681, 1641, 1562, 1463, 1400, 1309, 1262, 1148, 1076, 828, 777 cm$^{-1}$.

Example 231

2-(N,N-Dimethylglycyl)aminomethyl-2,3,6,7-hexahydro-5-methylfuro-[2,3-f]quinoline-7-one.HCl The compound obtained in Example 230 (2.0 g, 5.7 mmol) was dissolved in water (50 ml). To the obtained solution, 10% palladium-on-carbon (2.0 g) was added, followed by stirring at 80° C. for 12 hours in the atmosphere of hydrogen. The reaction mixture was filtered, and the filtrate was condensed under reduced pressure. The resultant residue was subjected to a recrystallizing procedure using chloroform—methanol—ether to obtain 1.0 g of the title compound as colorless powdery crystals (50.0%).

mp. 208°–209° C.

$^1$H-NMR(CDCl$_3$+CD$_3$OD) δ: 2.15 (3 H, s), 2.57 (2 H, d, J=7 Hz), 2.83–2.94 (3 H, m), 3.27 (1 H, m), 3.46–3.60 (2 H, m), 3.96 (2 H, s),4.91 (1 H, m), 6.83 (1 H, s).

IR(KBr): 3389, 3057, 1661, 1558, 1473, 1387, 1340, 1259, 1204, 1081, 1050, 834 cm$^{-1}$.

Example 232

2-(N-tert-Butoxycarbonyl-N-methylglycyl)aminomethyl-5-methyl-2,3,6,7-tetrahydrofuro-[2,3-f]quinoline-7-one:

2-Aminomethyl-5-methyl-2,3,6,7-tetrahydrofuro-[2,3-f]quinoline-7-one (2.3 g, 10 mmol) was dissolved in dimethylformamide (100 ml) while being cooled on ice. To the obtained mixture, N-tert-butoxycarbonyl-N-methylglycine (2.0 g, 11 mmol), WSC.HCl (2.0 g, 11.0 mmol), and HOBT (1.4 g, 11.0 mmol) were added, and the resultant mixture was stirred at room temperature overnight. The reaction mixture was subjected to distillation under reduced pressure. The resultant residue was extracted with chloroform after the pH was turned to acidic with HCl. The organic phase was washed with saturated aqueous NaCl solution, and dried. The solvent was distilled off under reduced pressure. The resultant residue was recrystallized from chloroform—methanol—ether. As a result, 2.8 g of the title compound was obtained as colorless powdery crystals (69.0%)

mp. 190°–191° C.

$^1$H-NMR(CDCl$_3$) δ: 1.42 (9 H, s), 2.36 (3 H, s), 2.89 (3 H, s), 2.98 (1 H, m), 3.37 (1 H, m), 3.45–3.59 (2 H, m), 3.87 (2 H, s), 5.05 (1 H, m), 6.54 (1 H, d, J=9 Hz), 7.61 (1 H, s), 7.91 (1 H, d, J=9 Hz).

Example 233

2-(N-Methylglycyl)aminomethyl-5-methyl-2,3,6,7-tetrahydrofuro-[2,3-f]quinoline-7-one.HCl:

The compound obtained in Example 232 (2.75 g, 6.9 mmol) was added to trifluoroacetic acid (15 ml) under cooling conditions, and the mixture was stirred for 30 minutes. The reaction mixture was subjected to distillation under reduced pressure, and the residue was purified by silica gel column chromatography (chloroform: methanol =3:1). The obtained crystals were dissolved in chloroform-methanol (3:1, 20 ml), and 5% HCl-methanol (10 ml) was added thereto while cooling on ice. The mixture was condensed under reduced pressure. The resultant residue was recrystallized from methanol—ether. 2.0 g of the title compound was obtained as pale yellow crystals (86.0%).

mp. 188°–191° C.

$^1$H-NMR(CD$_3$OD) δ: 2.43 (3 H, s), 2.72 (3 H, s), 3.06 (1 H, m), 3.41 (1 H, m), 3.54–3.75 (2 H, m), 3.81 (2 H, s), 5.14 (1 H, m), 6.74 (1 H, d, J=10 Hz), 7.36 (1 H, s), 8.25 (1 H, d, J=10 Hz).

IR(KBr): 3411, 3060, 1650, 1564, 1467, 1441, 1399, 1256, 1053, 958, 837 cm$^{-1}$.

Example 234

2-(N-Methylglycyl)aminomethyl-2,3,6,7,8,9-hexahydro-5-methylfuro-[2,3-f]quinoline-7-one.HCl:

The compound obtained in Example 233 (1.2 g, 3.5 mmol) was dissolved in water (40 ml). To the obtained solution, 10% palladium-on-carbon (1.3 g) was added, followed by stirring at 80° C. for 12 hours in the atmosphere of hydrogen. The reaction mixture was filtered, and the filtrate was condensed under reduced pressure. The resultant residue was subjected to a recrystallizing procedure using chloroform—methanol—ether to obtain 690 mg of the title compound as colorless powdery crystals (58.0%).

mp. 253°–255° C. (dec.)

$^1$H-NMR(CDCl$_3$+CD$_3$OD) δ: 2.16 (3 H, s), 2.57 (2 H, t, J=7 Hz), 2.72 (3 H, s), 2.80–2.94 (3 H, m), 3.26 (1 H, m), 3.41–3.67 (2 H, m), 4.88 (1 H, m), 6.84 (1 H, s).

IR(KBr): 3429, 3255, 2925, 2757, 1653, 1563, 1479, 1393, 1347, 1253, 1216, 1056, 837, 727 cm$^{-1}$.

Example 235

2-Iminomethylamino-5-methyl-2,3,5,6-tetrahydrofuro-[2,3-f]quinoline-7-one.HCl:

To a solution of 2-aminomethyl-5-methyl-2,3,6,7-tetrahydrofuro-[2,3-f]quinoline-7-one (500 mg, 2.2 mmol) in methanol (30 ml), a hydrochloric acid salt of benzylformimidate (21 g, 13.2 mmol) was added under cooling conditions, and the mixture was stirred for 1 hour. Thereafter, a hydrochloric acid salt of benzylformimidate (2.1 g, 13.2 mmol) was added every 1 hour, and stirred for 4 hours in total. The reaction mixture was condensed, and the residue was washed with isopropyl alcohol. The resultant crude crystals were purified by silica gel column chromatography (chloroform: methanol: conc. ammonia water= 10:1:0.1). The obtained crystals were dissolved in methanol (5 ml), and 4N-HCl/dioxane (1 ml) was added thereto. The mixture was condensed under reduced pressure. The resultant residue was washed with chloroform and ether. 100 mg of the title compound was obtained as pale yellow powdery crystals (15.5%).

mp. >250° C.

$^1$H-NMR(CDCl$_3$-CD$_3$OD) δ: 2.41 (3 H, s), 3.03 (1 H, m), 3.40–3.95 (3 H, m),5.12 (1 H, m), 6.64 (1 H, d, J=10 Hz), 7.27 (1 H, s), 7.50 (1 H, s), 8.12 (1 H, d, J=10 Hz).

IR(KBr): 3364, 3255, 2993, 1693, 1640, 1462, 1311, 1266, 1151, 1085, 832, 787 cm$^{-1}$.

Example 236

2-(Carbobenzyloxy-α-methylalanyl]aminomethyl-5-methyl-2,3,6,7-tetrahydrofuro-[2,3-f]quinoline-7-one:

2-Aminomethyl-5-methyl-2,3,6,7-tetrahydrofuro-[2,3-f]quinoline-7-one (3.00 g, 13.0 mmol) was dissolved in a solvent mixture of dimethylformamide (200 ml) and pyridine (100 ml). To this solution, N-carbobenzyloxy-α-methylalanine (4.64 g, 19.5 mmol) and WSC-HCl (3.48 g, 19.5 mmol) were added and the mixture was stirred at 50° C. for 48 hours. The reaction mixture was condensed under reduced pressure, and the residue was subjected to extraction using a solvent mixture (chloroform—methanol =4:1) combined with 1N-HCl. The organic phase was washed with saturated aqueous NaCl solution, followed by drying and condensing under reduced pressure. The resultant residue was purified by silica gel column chromatography (chloroform: methanol=25:1). The crude crystals were subjected to a recrystallizing procedure from chloroform—methanol. As a result, 2.55 g of the title compound was obtained as colorless powdery crystals (43.7%).

mp. 220°–222° C.

IR(KBr): 3289, 3023, 1690, 1653, 1614, 1528, 1461, 1266, 1189, 1146, 1081, 831, 692, 666 cm$^{-1}$.

$^1$H-NMR(CDCl$_3$: CD$_3$OD=4:1) δ: 1.45 (3 H, s), 1.47 (3 H, s), 2.34 (3 H, s), 3.00 (1 H, m), 3.33 (1 H, m), 3.65 (1 H, m), 4.90 (1 H, m), 4.95–5.05 (2 H, m), 6.53 (1 H, d, J=9.5 Hz), 7.17 (1 H, s), 7.32 (5 H, s), 7.95 (1 H, d, J=9.5 Hz).

Example 237

5-Methyl2-(α-methylalanyl)aminomethyl-2,3,6,7-tetrahydrofuro-[2,3-f]quinoline-7-one.HCl:

2-(N-Carbobenzyloxy-α-methylalanyl]aminomethyl-5-methyl-2,3,6,7-tetrahydrofuro-[2,3-f]quinoline-7-one (2.46 g, 5.48 mmol) was dissolved in dimethylformamide (190 ml). To the obtained solution, 10% palladium-on-carbon (2.46 g) was added, followed by stirring at room temperature for 3 hours in the atmosphere of hydrogen. The reaction mixture was filtered, and the filtrate was condensed. The resultant residue was dissolved in methanol (70 ml). To the obtained solution, 1.37 N-HCl—methanol (4.39 ml) was added at room temperature, followed by condensing under reduced pressure. The resultant residue was submitted to a recrystallizing procedure using methanol to obtain 1.65 g of the title compound as pale yellow powdery crystals (85.6%).

mp. 265°–268° C.

IR(KBr): 3375, 3203, 2921, 1651, 1622, 1552, 1465, 1403, 1311, 1205, 1168, 1085, 828, 787, 688 cm$^{-1}$.

$^1$H-NMR(CD$_3$OD) δ: 1.45 (3 H, s), 1.50 (3 H, s), 2.36 (3 H, s), 3.05 (1 H, m), 3.35 (1 H, m), 3.59 (2 H, d, J=4.9 Hz), 5.10 (1 H, m), 6.52 (1 H, d, J=9.3 Hz), 7.22 (1 H, s), 8.00 (1 H, d, J=9.3 Hz).

Example 238

2,3,6,7,8,9-Hexahydro-5-methyl(α-methylalanyl)aminomethylfuro-[2,3-f]quinoline-7-one.HCl:

A hydrochloric acid salt of 5-methyl-2-(α-methylalanyl)aminomethyl-2,3,6,7-tetrahydrofuro-[2,3-f]quinoline-7-one (1.15 g, 3.27 mmol) was dissolved in water (30 ml). To the obtained solution, 10% palladium-on-carbon (1.15 g) was added, followed by stirring at 80° C. for 3.5 hours in the atmosphere of hydrogen. The reaction mixture was filtered, and the filtrate was condensed under reduced pressure. The resultant residue was subjected to a recrystallization procedure using methanol—ether to obtain 851 mg of the title compound as colorless powdery crystals (73.5%).

mp. 211°–213° C.

IR(KBr): 3417, 3232, 2920, 1663, 1635, 1473, 1440, 1391, 1345, 1243, 1204, 1056 cm$^{-1}$.

$^1$H-NMR(CD$_3$OD) δ: 1.46 (3 H, s), 1.51 (3 H, s), 2.15 (3 H, s), 2.51 (2 H, t, J=7.6 Hz), 2.80–2.95 (3 H, complex m), 3.25 (1 H, m), 3.52 (2 H, d, J=5.9 Hz), 4.85–4.95 (1 H, m), 6.83 (1 H, s).

Example 239

2-(Carbobenzyloxy-β-alanyl]aminomethyl- 5-methyl-2,3,6,7-tetrahydrofuro-[2,3-f]quinoline-7-one:

2-Aminomethyl-5-methyl-2,3,6,7-tetrahydrofuro-[2,3-f]quinoline-7-one (3.00 g, 13.0 mmol) was dissolved in dimethylformamide (200 ml). To this solution, N-carbobenzyloxy-β-alanine (4.40 g, 19.5 mmol), WSC-HCl (3.50 g, 19.5 mmol), and HOBT (1.00 g, 7.2 mmol) were added, and the mixture was stirred at room temperature for 48 hours. The reaction mixture was condensed under reduced pressure, and the residue was subjected to extraction using a solvent mixture (chloroform—methanol =4:1) combined with 1N-HCl. The organic phase was washed with saturated aqueous NaCl solution, followed by drying and condensing under reduced pressure. The resultant residue was recrystallized from chloroform—methanol—ether. As a result, 2.61 g of the title compound was obtained as colorless powdery crystals (46.2%).

mp. 233°–234° C.

IR(KBr): 3286, 1647, 1536, 1507, 1463, 1265, 1145, 1084, 833 cm$^{-1}$.

$^1$H-NMR(CDCl$_3$: CD$_3$OD=4) δ: 2.37 (3 H, s), 2.45 (2 H, t, J=6.6 Hz), 2.96 (1 H, dd, J=6.8, 14.9 Hz), 3.28–3.50 (4 H, complex m), 3.63 (1 H, dd, J=2.0, 14.9 Hz), 4.97–5.10 (3 H, complex m), 6.54 (1 H, d, J=9.8 Hz), 7.17 (1 H, s), 7.33 (5 H, s), 7.99 (1 H, d, J=9.8 Hz).

Example 240

2-(D-Alanylmethyl)-5-methyl-2,3,6,7-tetrahydrofuro-[2,3-f]quinoline-7-one.HCl:

2-(Carbobenzyloxy-β-alanyl]aminomethyl-5-methyl-2,3, 6,7-tetrahydrofuro-[2,3-f]quinoline-7-one (2.61 g, 6.00 mmol) was dissolved in dimethylformamide (200 ml). To the obtained solution, 10% palladium-on-carbon (2.61 g) was added, followed by stirring at room temperature for 5 hours in the atmosphere of hydrogen. The reaction mixture was filtered, and the filtrate was condensed under reduced pressure. The resultant residue was dissolved in methanol (50 ml). To the obtained solution, 1.37 N-HCl—methanol (4.82 ml) was added at room temperature, followed by being submitted to a recrystallizing procedure using methanol ether to obtain 1.80 g of the title compound as pale yellow powdery crystals (88.8%).

mp. 222°–225° C.

IR(KBr): 3256, 2923, 1645, 1549, 1463, 1310, 1244, 1086, 955, 873, 831, 770, 687 $cm^{-1}$.

$^1$H-NMR(CD$_3$OD) δ: 2.38 (3 H, s), 2.62 (2 H, t, J=6.6 Hz), 3.01 (1 H, dd, J=7.1, 15.9 Hz), 3.17 (2 H, t, J=6.6 Hz), 3.36 (1 H, m), 3.50–3.65 (2 H, m), 5.05 (1 H, m), 6.55 (1 H, d, J=9.5 Hz), 7.25 (1 H, s), 8.05 (1 H, d, J=9.5 Hz).

Example 241

2-(β-Alanylaminomethyl)-2,3,6,7,8,9-hexahydro-5-methyl-furo-[2,3-f]quinoline-7-one.HCl:

A hydrochloric acid salt of 2-(β-Alanylaminomethyl)-5-methyl-2,3,6,7-tetrahydrofuro-[2,3-f]quinoline-7-one (1.10 g, 3.26 mmol) was dissolved in water (50 ml). To the obtained solution, 10% palladium-on-carbon (1.10 g) was added, followed by stirring at 80° C. for 3 hours in the atmosphere of hydrogen. The reaction mixture was filtered, and the filtrate was condensed under reduced pressure. The resultant residue was submitted to a recrystallizing procedure using methanol to obtain 727 mg of the title compound as colorless powdery crystals (66.1%).

mp. 223°–224° C.

IR(KBr): 3278, 3069, 2955, 1668, 1644, 1552, 1479, 1387, 1250, 1201, 1084, 1052 $cm^{-1}$.

$^1$H-NMR(CD$_3$OD) δ: 2.15 (3 H, s), 2.51 (2 H, t, J=7.6 Hz), 2.62 (2 H, t, J=6.5 Hz), 2.81–2.92 (3 H, complex m), 3.17 (2 H, t, J=6.5 Hz), 3.30 (1 H, m), 3.50–3.60 (2 H, m), 4.90 (1 H, m), 6.84 (1 H, s).

Example 242

2-(Carbobenzyloxy-L-prolyl)aminomethyl-5-methyl-2,3,6, 7-tetrahydrofuro-[2,3-f]quinoline-7-one:

2-Aminomethyl-5-methyl-2,3,6,7-tetrahydrofuro-[2,3-f] quinoline-7-one (2.00 g, 8.70 mmol) was dissolved in dimethylformamide (150 ml). To the obtained solution, carbobenzyloxy-L-proline (2.80 g, 11.3 mmol), WSC-HCl (2.00 g, 11.3 mmol) and HOBT (1.53 g, 11.3 mmol) were added, and the mixture was stirred at 50° C. for 48 hours. The reaction mixture was condensed under reduced pressure. The resultant residue was extracted using a solvent mixture (chloroform: methanol=4:1) combined with 1N-HCl. The organic phase was washed with saturated aqueous NaCl solution, followed by drying and condensing under reduced pressure. The resultant residue was purified by silica gel column chromatography (chloroform: methanol=20:1). The crude crystals were subjected to a recrystallizing procedure using chloroform—methanol—ether. As a result, 1.69 g of the title compound was obtained as colorless powdery crystals (42.1%).

mp. 131°–132° C.

IR(KBr): 3273, 1692, 1655, 1615, 1536, 1460, 1435, 1412, 1532, 830 $cm^{-1}$.

$^1$H-NMR(CD$_3$OD) δ: 1.73–1.88 (4 H, complex m), 2.07–2.19 (2 H, m), 2.35 (3 H, s), 3.00 (1 H, m), 3.25 (1 H, m), 3.40–3.60 (2 H, complex m), 4.25 (1 H, m), 4.95–5.10 (3 H, complex m), 6.50 (1 H, d, J=9.8 Hz), 7.22 (1 H, s), 7.25–7.37 (5 H, m), 7.97 (1 H, m).

Example 243

5-Methyl-2-(L-prolylaminomethyl)- 2,3,6,7-tetrahydrofuro-[2,3-f]quinoline-7-one.HCl:

2-(Carbobenzyloxy-L-prolyl)aminomethyl-5-methyl-2,3, 6,7-tetrahydrofuro-[2,3-f]quinoline-7-one (1.04 g, 2.25 mmol) was dissolved in dimethylformamide (130 ml). To the obtained solution, 10% palladium-on-carbon (1.04 g) was added, followed by stirring at room temperature for 4 hours in the atmosphere of hydrogen. The reaction mixture was filtered, and the filtrate was condensed under reduced pressure. The resultant residue was dissolved in methanol (65 ml), to which 1.37 N-HCl—methanol (1.81 ml) was added. The mixture was condensed under reduced pressure. The resultant residue was submitted to a recrystallizing procedure using methanol—ether to obtain 807 mg of the title compound as pale yellow powdery crystals (98.6%).

mp. 236°–239° C.

IR(KBr): 3193, 3024, 2920, 1644, 1558, 1463, 1307, 1243, 1150, 1083, 832, 741, 634 $cm^{-1}$.

$^1$H-NMR(CD$_3$OD) δ: 1.72–1.84 (2 H, m), 1.85–2.05 (2 H, m), 2.20–2.37 (2 H, m), 2.37 (3 H, s), 3.04 (1 H, m), 3.33 (1 H, m), 3.54 (1 H, m), 3.72 (1 H, m), 4.23 (1 H, m), 5.10 (1 H, m), 6.56 (1 H, dd, J=9.8, 2.0 Hz), 7.25 (1 H, d, J=3.4 Hz), 8.04 (1 H, d, J=8.8 Hz).

Example 244

2,3,6,7,8,9-hexahydro-5-methyl-2-(L-prolylaminomethyl) furo-[2,3-f]quinoline-7-one.HCl:

5-Methyl-2-(L-prolylaminomethyl)-2,3,6,7-tetrahydrofuro-[2,3-f]quinoline-7-one.HCl (507 mg, 1.38 mmol) was dissolved in water (25 ml). To the obtained solution, 10% palladium-on-carbon (500 g) was added, followed by stirring at 80° C. for 5 hours in the atmosphere of hydrogen. The reaction mixture was filtered, and the filtrate was condensed under reduced pressure. The resultant residue was submitted to a recrystallizing procedure using ethanol—n-hexane to obtain 320 mg of the title compound as pale yellow powdery crystals (63.4%).

mp. 147°–150° C. (dec.)

IR(KBr): 3377, 3210, 2900, 1662, 1554, 1471, 1367, 1337, 1200, 1073, 1047 $cm^{-1}$.

$^1$H-NMR(CD$_3$OD) δ: 1.72–1.87 (2 H, m), 1.89–2.08 (2 H, m), 2.15 (3 H, s), 2.25–2.38 (2 H, m), 2.45–2.55 (2 H, m), 2.78–2.96 (3 H, complex m), 3.20–3.50 (2 H, complex m), 3.65 (1 H, m), 4.22 (1 H, m), 5.89 (1 H, m), 6.84 (1 H, d, J=4.4 Hz).

Example 244

2-Carbobenzyloxyglycylaminomethyl-5-methyl-2,3,6,7-tetrahydrofuro-[2,3-f]quinoline-7-one:

2-Aminomethyl-5-2,3,6,7-tetrahydrofuro-[2,3-f]quinoline-7-one (1.50 g, 6.52 mmol) was dissolved in a solvent mixture of dimethylformamide (100 ml) and pyridine (50 ml). To the obtained solution, carbobenzyloxyglycine (1.50 g, 7.18 mmol) and WSC-HCl (1.50 g, 7.82 mmol) were added, and the mixture was stirred at room temperature for 24 hours. The reaction mixture was condensed under reduced pressure. The resultant residue was extracted using a solvent mixture (chloroform: methanol =20:1) combined with 1N-HCl. The organic phase was washed with saturated aqueous NaCl solution, followed by drying and condensing under reduced pressure. The resultant residue was purified by silica gel column chromatography (chloroform: methanol =50:1). The crude crystals were subjected to a recrystallizing procedure using chloroform methanol—ether. As a result, 2.05 g of the title compound was obtained as colorless powdery crystals (74.7%).

mp. 204°–205° C. (dec.)

IR(KBr): 3357, 1683, 1659, 1640, 1616, 1539, 1441, 1319, 1254, 1218, 1080, 1062, 828 cm$^{-1}$.

$^1$H-NMR(CDCl$_3$) δ: 2.29 (3 H, s), 2.95 (1 H, m), 3.29 (1 H, m), 3.57. (1 H, m), 3.77 (1 H, ddd, J=3.42, 5.86, 14.16 Hz), 3.90 (2 H, dd, J=1.96, 5.86 Hz), 5.04 (1 H, m), 5.08 (2 H, s), 5.40 (1 H, br.), 6.51 (1 H, d, J=9.77 Hz), 6.59 (1 H, br.), 7.10 (1 H, s), 7.34 (5 H, s), 7.83 (1 H, d, J=9.77 Hz), 8.68 (1 H, br.).

Example 245

2-Glycylaminomethyl-5-methyl-2,3,6,7-tetrahydrofuro-[2,3-f]quinoline-7-one.HCl:

2-Carbobenzyloxyglycylaminomethyl-5-methyl- 2,3,6,7-tetrahydrofuro-[2,3-f]quinoline-7-one (2.00 g, 4.75 mmol) was dissolved in dimethylformamide (250 ml). To the obtained solution, 10% palladium-on-carbon (2.00 g) was added, followed by stirring at room temperature for 3 hours in the atmosphere of hydrogen. The reaction mixture was filtered, and the filtrate was condensed under reduced pressure. The resultant residue was dissolved in methanol (20 ml), to which 4N-HCl/dioxane (1.2 ml) was added, and the mixture was condensed under reduced pressure at room temperature. The resultant residue was submitted to a recrystallizing procedure using methanol—ether to obtain 1.45 g of the title compound as pale yellow powdery crystals (94.6%).

mp. 264°–266° C. (dec.)

IR(KBr): 3412, 3178, 3010, 1684, 1645, 1556, 1459, 1384, 1260, 1218, 1152, 1082, 1063, 852, 789, 683 cm$^{-1}$.

$^1$H-NMR(CD$_3$OD) δ: 2.37 (3 H, s), 3.00 (1 H, dd, J=6.83, 15.62 Hz), 3.36 (1 H, dd, J=9.28, 15.62 Hz), 3.53–3.64 (2 H, complex m), 3.67 (2 H, s), 5.05 (1 H, m), 6.52 (1 H, d, J=9.77 Hz), 7.23 (1 H, s), 8.00 (1 H, d, J=9.77 Hz).

Example 246

2-Glycylaminomethyl-2,3,6,7,8,9-hexahydro-5methylfuro-[2,3-f]quinoline-7-one.HCl:

2-Glycylaminomethyl-5-methyl-2,3,6,7-tetrahydrofuro-[2,3-f]quinoline-7-one.HCl (616.5 mg, 1.91 mmol) was dissolved in water (30 ml). To the obtained solution, 10% palladium-on-carbon (620.0 mg) was added, followed by stirring at 80° C. for 6 hours in the atmosphere of hydrogen. The reaction mixture was filtered, and the filtrate was condensed under reduced pressure. The resultant residue was submitted to a recrystallizing procedure using methanol—ether to obtain 555.1 mg of the title compound as colorless powdery crystals (89.5%).

mp. >300° C.

IR(KBr): 3405, 3238, 3042, 2936, 1663, 1625, 1550, 1469, 1438, 1373, 1206, 1053 cm$^{-1}$.

$^1$H-NMR(CD$_3$OD) δ: 2.15 (3 H, s), 2.50 (2 H, t, J=7.3 Hz), 2.84 (2 H, t, J=7.3 Hz), 2.87 (1 H, dd, J=6.8, 16.1 Hz), 3.22 (1 H, dd, J=9.3, 16.1 Hz), 3.49 (1 H, dd, J=6.8, 14.2 Hz), 3.57 (1 H, dd, J=4.4, 14.2 Hz), 3.67 (2 H, s), 4.87 (1 H, m), 6.84 (1 H, s).

Example 247

5-Fluoro-2-methanesulfonyloxymethyl-2,3,6,7-tetrahydrofuro-[2,3-f]quinoline-2-one:

To a solution of 2-methanesulfonyloxymethyl-7-methanesulfonyloxy-2,3-dihydrofuro-[2,3-f]quinoline (1.20–3.21 mmol) in 1,2-dichloroethane (400 ml), N-fluoro-3,5-dichloropyridiniumtriflate (4.06 g, 12.9 mmol) was added. The mixture was refluxed for 10 hours while stirring. The reaction mixture was washed with water, saturated aqueous sodium bicarbonate, and water in this order, and dried. The solvent was distilled off under reduced pressure. The resultant residue (2.55 g) was purified by silica gel column chromatography (ethyl acetate: chloroform—3:1). As a result, 219 mg of the title compound was obtained as colorless crystals (21.8%).

$^1$H-NMR(CDCl$_3$) δ: 3.06 (3 H, s), 3.15 (1 H, dd, J=15.6, 7.3 Hz), 3.43 (1 H, dd, J=15.6, 9.3 Hz), 4.38–4.51 (2 H, m), 5.23 (1 H, m), 6.63 (1 H, d, J=9.8 Hz), 7.10 (1 H, d, J=9.8 Hz), 7.83 (1 H, dd, J=9.8, 1.5 Hz), 9.33 (1 H, br.s).

Example 248

2-Azidomethyl-5-fluoro-2,3,6,7-tetrahydrofuro-[2,3-f]quinoline-2-one:

To a solution of the compound obtained in Example 247 (219 mg, 0.699 mmol) in N,N-dimethylformamide (10 ml), sodium azide (182 mg, 2.80 mmol) was added, and the mixture was stirred at 100° C. for 2 hours with heat. The reaction mixture was distilled off under reduced pressure. To the resultant residue, water was added, and the mixture was extracted with chloroform, followed by washing with water and drying. The solvent was distilled off under reduced pressure, and the residue was purified by silica gel column chromatography (chloroform) to obtain 109 mg of the title compound as colorless crystals (59.9%)

$^1$H-NMR(COCl$_3$) δ: 3.08 (1 H, dd, J=15.4, 6.8 Hz), 3.39 (1 H, dd, J=15.4, 9.3 Hz), 3.52–3.54 (2 H, m), 5.15 (1 H, m), 6.62 (1 H, d, J=9.8 Hz), 7.10 (1 H, d, J=9.8 Hz), 7.86 (1 H, dd, J=9.8, 1.5 Hz), 9.12 (1 H, br.s).

Example 249-1

2-Aminomethyl-5-fluoro-2,3,6,7-tetrahydrofuro-[2,3-f]quinoline-2-one:

To a solution of the compound obtained in Example 248 (126 mg, 0.484 mmol) in pyridine (7.5 ml), triphenylphosphine (254 mg, 0.968 mmol) was added, and the mixture was stirred at room temperature for 2 hours. Subsequently, 28% ammonia water (5 ml) was added thereto, and the mixture was stirred at room temperature for 10 hours. The reaction mixture was dried to solidity under reduced pressure. The resultant residue was purified by silica gel column chromatography (chloroform: methanol =10:1) to obtain 100 mg of the title compound as pale yellow ncrystals (88.2%)

$^1$H-NMR(CDCl$_3$: CD$_3$OD=10:1) δ: 1.74 (1 H, m), 1.99 (1 H, m), 2.16 (3 H, s), 2.56 (2 H, t, J=7.3 Hz), 2.66–3.06 (6 H, m), 4.06 (1 H, m), 6.75 (1 H, s).

Example 249-2

2-Aminomethyl-5-fluoro-2,3,6,7-tetrahydrofuro-[2,3-f]quinoline-2-one.HCl:

To a solution of the compound obtained in Example 249 (100 mg) in absolute methanol (30 ml), 4N-HCl—methanol (0.5 ml) was added. The mixture was dried to solidity under reduced pressure. The resultant residue was subjected to a recrystallizing procedure using methanol. As a result, 90 mg of the title compound was obtained as pale yellow powdery crystals (77.9%, mp.: >300° C.).

IR(KBr): 3400, 3231, 2944, 1658, 1617, 1484, 1374, 1208, 1117 cm$^{-1}$.

$^1$H-NMR(DMSO-d$_6$) δ: 1.66 (1 H, m), 2.01 (1 H, m), 2.11 (3 H, s), 2.36 (2 H, t, J=7.3 Hz), 2.69 (1 H, m), 2.88 (2 H, br.t, J=7.3 Hz), 3.04 (1 H, dd, J=13.2, 8.8 Hz), 3.18 (1 H, dd, J=13.2, 2.9 Hz), 4.20 (1 H, br.m), 6.71 (1 H, s), 8.18 (1 H, br.s), 9.29 (1 H, s).

Reference Example 13

N-(4-Methoxy-2-methylphenyl)cinnamamide:

2-Nitro-5-methoxytoluene (24.9 g, 149 mmol) was dissolved in a solvent mixture (150 ml) of isopropanol—methanol (2:1). To the solution, 10% palladium-on-carbon (500 mg) was added, followed by stirring at room temperature for 5 hours in the atmosphere of hydrogen. After the reaction, the catalyst was removed by filtration, and the filtrate was condensed. The resultant residue was combined with acetone (150 ml) and pyridine (14.2 ml), and the mixture was cooled to 0° C. and stirred. Cinnamoyl chloride (18.5 g, 111 mmol) was added thereto and the mixture was stirred overnight at room temperature. The reaction mixture was condensed, and the residue was dissolved in chloroform, followed by washing with water, 2N-HCl, and aqueous NaCl solution in this order. The washed material was dried and condensed to obtain 28.33 g of N-(4-methoxy-2methylphenyl)cinnamamide as colorless needles (71.2%).

mp. 202°–203° C.

IR(KBr): 3245, 1648, 1616, 1525, 1490, 1334, 1278, 1220, 1112, 1046, 971, 858 cm$^{-1}$.

$^1$H-NMR(CDCl$_3$) δ: 2.28 (3 H, s), 3.79 (3 H, s), 6.59 (1 H, d, J=15.6 Hz), 6.77 (2 H, d, J=6.8 Hz), 7.07 (1 H, br.s), 7.37 (3 H, br.s), 7.53 (2 H, br.s), 7.68 (1 H, br.d, J=9.3 Hz), 7.74 (1 H, d, J=15.6 Hz).

Reference Example 14

6-Hydroxy-8-methylcarbostyril:

To N-(4-methoxy-2-methylphenyl)cinnamamide (28.33 g, 0.106M), aluminum chloride (70.5 g, 529 mmol) and chlorobenzene (175 ml) were added, and the mixture was stirred in a bath of 125° C. for 1 hour. Thereafter, the mixture was cooled and poured into ice—water, to which n-hexane was added. The insoluble matter was collected by filtration, and washed with chloroform. As a result, 15.0 of 6-hydroxy-8-methylcarbostyril was obtained as brown crystals (80.8%).

IR(KBr): 3313, 1659, 1641, 1605, 1442, 1410, 1383, 1361, 1304, 1136, 849, 616 cm$^{-1}$.

$^1$H-NMR(CD$_3$OD) δ: 2.43 (3 H, s), 6.57 (1 H, d, J=9.7 Hz), 6.85 (1 H, d, J=2.9 Hz), 6.96 (1 H, d, J=2.9 Hz), 7.83 (1 H, d, J=9.7 Hz).

Reference Example 15

6-Allyloxy-8-methylcarbostyril:

A mixture of 6-hydroxy-8-methylcarbostyril (15.0 g, 85.7 mmol), potassium carbonate (23.4 g, 169.5 mmol), allyl iodide (15.6 g, 90.0 mmol), and N,N-dimethylformamide (120 ml) was stirred in a bath of 70° C. for 1.5 hours. The mixture was condensed, and the residue was dissolved in chloroform, followed by washing with water and 2N-NaOH. The washed material was dried and condensed. The resultant residue was recrystallized (chloroform—n-hexane) to obtain 10.11 g of 6-allyloxy-8-methylcarbostyril as pale brown prisms (54.8%).

mp. 188°–190° C.

IR(KBr): 3140, 3000, 1636, 1612, 1438, 1290, 1168, 1126, 1042, 847 cm$^{-1}$.

$^1$H-NMR(CDCl$_3$) δ: 2.48 (3 H, s), 4.56 (2 H, dt, J=4.9, 1.5 Hz), 5.32 (1 H, m), 5.43 (1 H, m), 6.07 (1 H, m), 6.67 (1 H, d, J=9.8 Hz), 6.86 (1 H, d, J=2.9 Hz), 7.03 (1 H, d, J=2.9 Hz), 7.69 (1 H, d, J=9.8 Hz), 9.69 (1 H, br.s).

Reference Example 16

5-Allyl-6-hydroxy-8-methylcarbostyril:

To 6-allyloxy-8-methylcarbostyril (10.11 (47.0 mmol)), N,N-dimethylaniline (25 ml) was added, and the mixture was stirred in a bath of 200° C. for 11 hours. Subsequently, the mixture was cooled. n-Hexane was added to the cooled mixture. The precipitated crystals were collected by filtration, and were washed with chloroform. The washed material was subjected to a recrystallizing procedure (chloroform—methanol—n-hexane) to obtain 9.36 g of 5-allyl-6-hydroxy-8-methylcarbostyril as colorless needles (92.6%).

mp. 270° C.

IR(KBr): 3070, 1644, 1601, 1563, 1445, 1393, 1282, 1259, 1164, 1104, 864 cm$^{-1}$.

$^1$H-NMR(CD$_3$OD) δ: 2.42 (3 H, s), 3.66 (2 H, m), 4.89 (1 H, m), 4.95 (1 H, m), 5.96 (1 H, m), 6.59 (1 H, d, J=9.8 Hz), 7.00 (1 H, s), 8.09 (1 H, d, J=9.8 Hz).

Example 250

2-Bromomethyl-5-methyl-1,2-dihydrofuro-[3,2-f]quinoline-7-one:

5-Allyl-6-hydroxy-8-methylcarbostyril (9.36 g, 43.5 mmol) was dissolved in chloroform (11) with heat. To the obtained solution, N-bromosuccinimide (7.75 g, 43.5 mmol) was added, and the mixture was refluxed for 2 hours. After completion of the reaction, water was added to the reaction mixture, and unreacted 5-allyl-6-hydroxy-8-methylcarbostyril (2.2 g, 23.5%) was separated as an insoluble matter by filtration. The filtrate was washed with water, dried and condensed. The resultant residue was subjected to a recrystallizing procedure using tetrahydrofuran to obtain 4.90 g of 2-bromomethyl-5-methyl-1,2-dihydrofuro-[3,2-f]quinoline-7-one as pale yellow crystals (38.3%).

IR(KBr): 2999, 1664, 1657, 1650, 1643, 1619, 1451, 1340, 1274, 1197, 1073, 855, 831, 667 cm$^{-1}$.

$^1$H-NMR(CDCl$_3$) δ: 2.42 (3 H, s), 3.30 (1 H, dd, J=16.1, 6.4 Hz), 3.48–3.69 (3 H, m), 5.12 (1 H, m), 6.70 (1 H, d, J=9.8 Hz), 6.90 (1 H, s), 7.64 (1 H, d, J=9.8 Hz), 9.04 (1 H, br.s).

Example 251

2-Azidomethyl-5-methyl-1,2-dihydrofuro-[3,2-f]quinoline-7-one:

2-Bromomethyl-5-methyl-1,2-dihydrofuro-[3,2-f]quinoline7-one (4.90 g, 16.7 mmol) and sodium azide (7.5 g, 115 mmol) were added to dimethylformamide (150 ml), and the mixture was stirred in a bath of 100° C. for 1.5 hours, followed by cooling and condensing. The residue was combined with chloroform, and washed with water. The washed material was dried and condensed. The resultant residue was recrystallized from chloroform—n-hexane. As a result, 4.12 g of 2-azidomethyl-5-methyl-1,2-dihydrofuro-[3,2-f]quinoline-7-one was obtained as brown prisms (96.6%).

mp. 183°–185° C.

IR(KBr): 3000, 2088, 1648, 1620, 1449, 1271, 1197, 848 cm$^{-1}$.

$^1$H-NMR(CDCl$_3$) δ: 2.44 (3 H, s), 3.20 (1 H, dd, J=16.1, 6.4 Hz), 3.43–3.55 (2 H, m), 3.60 (1 H, dd, J=13.2, 6.4 Hz), 5.08 (1 H, m), 6.70 (1 H, d, J=9.8 Hz), 6.92 (1 H, s), 7.63 (1 H, d, J=9.8 Hz).

Example 252

2-Aminomethyl-5-methyl-1,2-dihydrofuro-[3,2-f]quinoline-7-one.HCl:

2-Azidomethyl-5-methyl-1,2-dihydrofuro-[3,2-f]quinoline-7-one (2.27 g, 8.87 mmol) was dissolved in tetrahydrofuran (227 ml). To the solution, 10% palladium-on-carbon (2 g) was added, followed by stirring at room temperature for 2.5 hours in the atmosphere of hydrogen. After the catalyst was removed, the mixture was condensed. The resultant residue was treated with activated carbon in methanol. The treated material was condensed and then converted into a hydrochloric acid salt. The salt was subjected to a recrystallizing procedure using methanol—ether to obtain 1.47 g of a hydrochloric acid salt of 2-aminomethyl-5-methyl-1,2-dihydrofuro-[3,2-f]quinoline-7-one as pale yellow prisms (62.6%).

mp. >300° C.

IR(KBr): 3372, 2995, 2900, 1667, 1615, 1496, 1457, 1440, 1213, 1163, 970, 826 cm$^{-1}$.

$^1$H-NMR(CD$_3$OD) δ: 2.45 (3 H, s), 3.13–3.28 (3 H, m), 3.64 (1 H, dd, J=16.1, 9.3 Hz), 5.14 (1 H, m), 6.67 (1 H, d, J=9.8 Hz), 7.02 (1 H, s), 7.88 (1 H, d, J=9.8 Hz).

Example 253

2-Aminomethyl-5-methyl-1,2,8,9-tetrahydrofuro-[3,2-f]quinoline-7-one.HCl:

A hydrochloric acid salt of 2-aminomethyl-5-methyl-1,2-dihydrofuro-[3,2-f]quinoline-7-one (1.0 g) was dissolved in water (50 ml). To the solution, 10% palladium-on-carbon (1 g) was added, followed by stirring at 80° C. for 1.5 hours in the atmosphere of hydrogen. After the catalyst was removed by filtration, the mixture was condensed. The resultant residue was recrystallized from methanol—ether to obtain 642 mg of a hydrochloric acid salt of 2-aminomethyl-5-methyl-1,2,8,9-tetrahydrofuro-[3,2-f]quinoline-7-one as colorless prisms (63.7%).

mp. about 282° C.

IR(KBr): 3214, 2910, 1672, 1490, 1465, 1409, 1207, 991, 961 cm$^{-1}$.

$^1$H-NMR(CD$_3$OD) δ: 2.20 (3 H, s), 2.53 (2 H, br.t, J=7.3 Hz), 2.84 (2 H, br.t, J=7.3 Hz), 2.91 (1 H, dd, J=15.6, 6.4 Hz), 3.03–3.30 (3 H, m), 5.00 (1 H, m), 6.54 (1 H, s).

Reference Example 17

N-(5-ethoxy-2-methylphenyl)-2-oxo-3-methylbutanamide:

A mixture of 2-amino-4-ethoxytoluene (590 mg, 3.99 mmol) and ethyl-2-methylacetoacetate (560 mg, 3.88 mmol) was stirred in a bath of 150° C. for 4 hours. The resultant mixture was subjected to silica gel column chromatography (developer: ethyl acetate—n-hexane), and the fraction containing the target substance was condensed, followed by recrystallizing from a solvent mixture of chloroform—n-hexane. As a result, 252 mg of the title compound was obtained as yellow powder (25.9%).

IR(KBr): 3409, 3237, 1719, 1639, 1582, 1531, 1286, 853, 798 cm$^{-1}$.

$^1$H-NMR(CDCl$_3$) δ: 8.38–8.29 (1 H, br.s), 7.63 (1 H, d, J=2.4 Hz), 7.05 (1 H, d, J=8.3 Hz), 6.62 (1 H, dd, J=2.4, 8.3 Hz), 4.02 (1 H, q, J=7.1 Hz), 3.60 (1 H, q, J=7.2 Hz), 2.34 (3 H, s), 2.22 (3 H, s), 1.55 (3 H, d, J=7.2 Hz), 1.39 (3 H, t, J=7.1 Hz).

Reference Example 18

5-Hydroxy-3,4,8-trimethylcarbostyril:

N-(5-ethoxy-2-methylphenyl)-2-oxo-3-methylbutanamide (8.8 g, 35.3 mmol) was dissolved in m-dichlorobenzene (100 ml). Aluminum chloride (20.6 g, 155 mmol) was added to the solution, and the mixture was placed in a bath of 100° C. and stirred for 1.5 hours. The reaction mixture was poured in ice—water, and the precipitate was collected by filtration. To the filtrate, a mixture of chloroform—methanol (5:1) was added. The organic phase was extracted, and dried. The solvent was distilled off under reduced pressure. The resultant residue was recrystallized from methanol—ether to obtain 3.3 g in total of the title compound as yellow powder (46.2%).

mp. 293°–295° C.

IR(KBr): 3010, 1634, 1544, 1464, 1406, 1380, 1346, 1162 cm$^{-1}$.

$^1$H-NMR(CD$_3$OD) δ: 7.22 (1 H, d, J=8.3 Hz), 6.65 (1 H, d, J=8.3 Hz), 2.73 (3 H, s), 2.37 (3 H, s), 2.21 (3 H, s).

Reference Example 19

5-Allyloxy-3,4,8-trimethylcarbostyril:

5-Hydroxy-3,4,8-trimethylcarbostyril (3.30 g, 16.3 mmol) was dissolved in N,N-dimethylformamide (100 ml), to which potassium carbonate (2.70 g, 19.6 mmol) and allyl iodide (2.91 g, 17.9 mmol) were added. The mixture was stirred in a bath of 75° C. for 8 hours. The reaction mixture was cooled, and the insoluble matter was removed by filtration. The filtrate was subjected to distillation under reduced pressure for removing the solvent. The residue was recrystallized from chloroform—n-hexane. As a result, 2.84 g of the title compound was obtained as pale yellow needles (71.7%).

mp. 193°–196° C.

IR(KBr): 2811, 1643, 1552, 1499, 1410, 1238, 1132, 1006, 829 cm$^{-1}$.

$^1$H-NMR(CDCl$_3$) δ: 9.24 (1 H, br.s), 7.19 (1 H, d, J=7.8 Hz), 6.80 (1 H, d, J=7.8 Hz), 6.13 (1 H, m), 5.44 (1 H, dd, J=1.5, 15.6 Hz), 5.33 (1 H, dd, J=1.5, 10.7 Hz), 4.62 (2 H, d, J=5.4 Hz), 2.69 (3 H, s), 2.38 (3 H, s), 2.26 (3 H, s).

Reference Example 20

6-Allyl-5-hydroxy-3,4,8-trimethylcarbostyril:

5-Allyloxy-3,4,8-trimethylcarbostyril (1.02 g, 420 mmol) was dissolved in N,N-dimethylaniline (20 ml), and the mixture was stirred in a bath of 200° C. for 2 hours. The reaction mixture was condensed under reduced pressure, to which chloroform and aqueous 2N-NaOH solution were added, then extracted into the aqueous phase. The aqueous phase was neutralized with conc. HCl solution, followed by extracting with chloroform—methanol (10:1), drying, and condensing. The resultant residue was recrystallized from chloroform—methanol—ether. As a result, 989 mg of the title compound was obtained as pale yellow needles (97.0%).

mp. 222°–225° C. (dec.)

IR(KBr): 2959, 1638, 1544, 1420, 1366, 1344, 1297, 1176 cm$^{-1}$.

$^1$H-NMR(CDCl$_3$-CD$_3$OD) δ: 7.07 (1 H, s), 6.01 (1 H, m), 5.22–5.08 (2 H, m), 3.43 (2 H, d, J=6.4 Hz), 2.77 (3 H, s), 2.36 (3 H, s), 2.23 (3 H, s).

Example 254

2-Bromomethyl-5,8,9-trimethyl-2,3,6,7-tetrahydrofuro-[2,3-f]quinoline-7-one:

6-Allyl-5-hydroxy-3,4,8-trimethylcarbostyril (1.01 g, 4.16 mmol) was dissolved in chloroform (50 ml). To the obtained solution, N-bromosuccinimide (888 mg, 4.99 mmol) was added. The mixture was refluxed with in a bath of 100° C. for 1.5 hours. The reaction mixture was cooled, washed with saturated aqueous NaCl solution and dried. The solvent was distilled off under reduced pressure. The residue was recrystallized from chloroform—ether to obtain 1.06 g of the title compound as yellow needles (79.8%).

mp. 237°–239° C.

IR(KBr): 3131, 3010, 1621, 1575, 1469, 1444, 1247, 1078, 829, 752 cm$^{-1}$.

$^1$H-NMR(CDCl$_3$) δ: 8.78 (1 H, br.s), 7.08 (1 H, s), 5.13 (1 H, m), 3.62 (1 H, dd, J=5.8, 10.7 Hz), 3.55 (1 H, dd, J=6.3, 10.7 Hz)), 3.39 (1 H, dd, J=9.3, 15.6 Hz), 3.09 (1 H, dd, J=6.4, 15.6, Hz), 2.65 (3 H, s), 2.33 (3 H, s), 2.22 (3 H, s).

Example 255

2-Azidomethyl-5,8,9-trimethyl-2,3,6,7-tetrahydrofuro-[2,3-f]quinoline-7-one:

2-Bromomethyl-5,8,9-trimethyl-2,3,6,7-tetrahydrofuro-[2,3-f]quinoline-7-one (1.07 g, 3.32 mmol) was dissolved in N,N-dimethylformamide (30 ml). To the obtained solution, sodium azide (1.29 g, 19.9 mmol) was added. The mixture was stirred at room temperature for 4 hours. The reaction mixture was subjected to distillation under reduced pressure for removing the solvent. To the resultant residue, chloroform and water were added. The mixture was extracted, dried, and condensed. Recrystallization from chloroform—n-hexane yielded 8.99 mg of the title compound as yellow needles (95.2%).

mp. 187°–189° C.

IR(KBr): 2845, 2095, 1655, 1428, 1347, 1274, 1160, 1046, 825 cm$^{-1}$.

$^1$H-NMR(CDCl$_3$) δ: 7.11 (1 H, s), 5.09 (1 H, m), 3.51 (2 H, d, J=5.9 Hz), 3.34 (1 H, dd, J=9.8, 15.1 Hz), 3.02 (1 H, dd, J=6.8, 15.1 Hz), 2.68 (3 H, s), 2.37 (3 H, s),2.23 (3 H, s).

Example 256

2-Aminomethyl-5,8,9-trimethyl-2,3,6,7-tetrahydrofuro-[2,3-f]quinoline-7-one:

The compound obtained in Example 255 (1.05 g, 3.69 mmol) was dissolved in a solvent mixture of tetrahydrofuran (50 ml) and methanol (20 ml). To the solution, 10% palladium-on-carbon (1 g) was added, followed by stirring at 50° C. for 4 hours in the atmosphere of hydrogen. The catalyst was removed by filtration, and the catalyst was evaporated under reduced pressure. As a result, 658 mg of the title compound was obtained as colorless powder (69.1%). The obtained powder was dissolved in methanol (20 ml), to which 4N-HCl in 1,4-dioxane (0.7 ml) was added. Recrystallization from chloroform—methanol—ether yielded 536 mg of the title compound as pale yellow powder (49.3%).

mp. >300° C.

IR(KBr): 2902, 1633, 1443, 1358, 1219, 1075, 779 cm$^{-1}$.

$^1$H-NMR(CD$_3$OD) δ: 7.21 (1 H, s), 5.15 (1 H, m), 3.45 (1 H, dd, J=9.8, 15.6 Hz), 3.37–3.20 (2 H, m), 3.03 (1 H, dd, J=6.8, 15.6 Hz), 2.71 (3 H, s), 2.37 (3 H, s), 2.18 (3 H, s).

Reference Example 21

6-Dimethylaminomethyl-5-hydroxy-8-methylcarbostyril:

5-Hydroxy-8-methylcarbostyril (10.51 g, 60 mmol) and dimethylamine (aqueous 40% solution, 12.07 g, 66 mmol) were dissolved in N,N-dimethylformamide (30 ml). To this solution, formaldehyde (aqueous 37% solution, 5.36 g, 66 mmol) was added slowly at room temperature, and stirred. After 12 hours, dimethylamine (6 g, 33 mmol), formaldehyde (2.79 g, 33 mmol), and N,N-dimethylformamide (20 ml) were added thereto, and the mixture was stirred at room temperature for further 12 hours. After completion of the reaction, the solvent was distilled off under reduced pressure, and the resultant residue was combined with chloroform and n-hexane. Crystals were collected by filtration, and dried under reduced pressure. As a result, 13.23 g of the title compound was obtained as pale reddish gray crystals (95%).

IR(KBr): 3144, 2822, 1593, 1424, 1279, 1165, 827 cm$^{-1}$.

$^1$H-NMR(CDCl$_3$) δ: 2.30 (3 H, s), 2.35 (6 H, s), 3.65 (2 H, s), 6.56 (1 H, d, J=9.8 Hz), 6.90 (1 H, s), 8.18 (1 H, d, J=9.8 Hz), 8.75 (1 H, br.s).

Example 257

2,3,6,7-Tetrahydro-2-ethoxycarbonyl-5-methyl-furo-[2,3-f]quinoline-7-one:

Ethyl bromoacetate (16.7 g, 100 mmol) was added to dimethylsulfide (6.21 g, 100 mmol), and the mixture was stirred overnight at room temperature. The obtained white solid was thoroughly washed with n-hexane. 21.35 g of an S-ylide compound was obtained as while crystals (93%). The S-ylide compound (9.16 g, 40 mmol) was suspended in N,N-dimethylformamide (20 ml). Potassium carbonate (6.21 g, 45 mmol) was added to the suspension, and stirred at room temperature for 3 hours. To the resultant mixture, the compound obtained in Reference Example 21 (4.64 g, 20 mmol) and N,N-dimethylformamide (20 ml) were added, and the mixture was stirred at room temperature for 12 hours and at 60° C. for further 10 hours. The reaction mixture was diluted with n-hexane. The precipitated crystals and inorganic salts were separated by filtration. The inorganic salts were washed with water and removed. The fraction soluble in chloroform and methanol and the filtrate was combined and condensed. The residue was separated and purified by silica gel column chromatography. 2.62 g of the title compound was obtained as pale yellow powder (48%).

IR(KBr): 3149, 3009, 1731, 1642, 1448, 1219, 1140, 1083, 1037, 837, 642 cm$^{-1}$.

$^1$H-NMR(CDCl$_3$) δ: 1.31 (3 H, t, J=7.3 Hz), 2.33 (3 H, s), 3.38 (1 H, dd, J=15.1, 6.8 Hz), 3.59 (1 H, dd, J=15.1, 10.2 Hz), 4.27 (2 H, q, J=7.3 Hz), 5.30 (1 H, dd, J=10.2, 6.8 Hz), 7.13 (1 H, s), 6.59 (1 H, d, J=9.8 Hz), 7.98 (1 H, d, J=9.8 Hz), 8.68 (1 H, br.s).

Example 258

2,3,6,7,8,9-Hexahydro-2-ethoxycarbonyl-5-methylfuro-[2,3-f]quinoline-7-one:

The compound obtained in Example 257 (3 g, 11 mmol) was dissolved in acetic acid (50 ml). To the solution, 10% palladium-on-carbon (3 g) was added, followed by stirring at 80° C. for 4 hours in the stream of hydrogen to carry out hydrogenation. After completion of the reaction, palladium-on-carbon was removed by filtration. The filtrate was thoroughly washed with chloroform and methanol, and condensed. As a result, 3 g of the title compound was obtained as a white solid (99%).

IR(KBr): 3217, 2956, 1731, 1670, 1627, 1467, 1383, 1339, 1208, 1151, 1082, 1053, 1020, 858, 726, 645 cm$^{-1}$.

$^1$H-NMR(CDCl$_3$) δ: 1.31 (3 H, t, J=7.3 Hz), 2.14 (3 H, s), 2.61 (2 H, t, J=7.3 Hz), 2.89 (1 H, ddd, J=16.6, 7.8, 7.3 Hz), 3.01 (1 H, ddd, J=16.6, 7.8, 7.3 Hz), 3.28 (1 H, dd, J=15.6, 6.8 Hz), 3.49 (1 H, dd, J=15.6, 10.2 Hz), 4.26 (2 H, q, J=7.3 Hz), 5.17 (1 H, dd, J=10.2, 6.8 Hz), 6.83 (1 H, s), 7.33 (1 H, br.s).

Example 259

2,3,6,7,8,9-Hexahydro-2-aminocarbonyl-5-methylfuro-[2,3-f]quinoline-7-one:

The compound obtained in Example 258 (1 g, 3.63 mmol) was dissolved in chloroform (20 ml). To the solution, saturated ammonia—methanol solution (50 ml) was added. The vessel containing the mixture was sealed, and the content was stirred at room temperature for 24 hours. After completion of the reaction, the solvent was distilled off under reduced pressure. 0.88 g of the title compound was obtained as a white solid (99%).

IR(KBr): 3310, 1664, 1630, 1474, 1436, 1386, 1283, 1204, 1088, 1049, 985, 801, 775, 668 cm$^{-1}$.

$^1$H-NMR(CDCl$_3$-CD$_3$OD) δ: 2.17 (3 H, s), 2.61 (2 H, t, J=7.8 Hz), 2.94 (2 H, t, J=7.8 Hz), 3.25–3.65 (2 H, m), 5.13 (1 H, m), 6.87 (1 H, s).

Example 260

2,3,6,7,8,9-Hexahydro-5-methylfuro-[2,3-f]quinoline-7-one-2-ethyl imidate:

The compound obtained in Example 259 (0.87 g, 3.52 mmol) was dissolved in chloroform (100 ml) and ethanol 20 ml). To the obtained solution, ethyl chloroformate (3.34 ml, 35 mmol) was added, and stirred at room temperature for 24 hours. Ethyl chloroformate (5 ml, 52.3 mmol) was further added every 24 hours for 3 days while stirring. After completion of the reaction, the solvent was distilled off under reduced pressure. The residue was washed with ether, and as a result, crude crystals (1.01 g) were collected by filtration (92%). The crude crystals were washed with ethanol and ether. A hydrochloric acid salt of the resultant title compound was dried at 80° C. in vacuo for 2 hours to obtain colorless needles.

mp.: 204°–206° C.

IR(KBr): 3220, 3027, 1739, 1666, 1629, 1481, 1390, 1339, 1209, 1054, 989, 726, 645 cm$^{-1}$.

$^1$H-NMR(CD$_3$OD-CDCl$_3$) δ: 1.32 (3 H, t, J=7.3 Hz), 2.17 (3 H, s), 2.59 (2 H, t, J=7.3 Hz), 2.89 (1 H, ddd, J=16.6, 7.3, 7.3 Hz), 3.01 (1 H, ddd, J=16.6, 7.3, 7.3 HzHz), 3.28 (1 H, dd, J=15.6, 6.8 Hz), 3.52 (1 H, dd, J=15.6, 10.2 Hz), 4.27 (2 H, q, J=7.3 Hz), 5.20 (1 H, dd, J=10.2, 6.8 Hz), 6.85 (1 H, s).

Example 261

2,3,6,7,8,9-Hexahydro-5-methylfuro-[2,3-f]quinoline-7-one-2-amidine:

A hydrochloric acid salt of the compound obtained in Example 260 (652 mg, 2.1 mmol) was dissolved in saturated ammonia—methanol (100 ml) and chloroform (15 ml). The vessel containing the obtained solution was sealed, and the content was stirred at room temperature for 15 hours. After completion of the reaction, the solvent was distilled off under reduced pressure. Chloroform was added to the residue, followed by dilution with ether. The precipitated crystals were separated by filtration, and dried at 80° C. in vacuo for 3 hours. As a result, 570 mg of a hydrochloric acid salt of the title compound (570 mg) was obtained as colorless needles (96%).

mp.: 276°–279° C. (dec.)

IR(KBr): 3319, 3129, 3025, 1665, 1475, 1436, 1386, 1284, 1204, 1087, 666 cm$^{-1}$.

$^1$H-NMR(CD$_3$OD-CDCl$_3$) δ: 2.18 (3 H, s), 2.60 (2 H, t, J=7.8 Hz), 2.95 (1 H, t, J=7.8 Hz), 2.96 (1 H, t, J=7.8 Hz), 3.33 (1 H, m), 3.54 (1 H, dd, J=16.1, 10.7 Hz), 5.13 (1 H, dd, J=10.7, 6.8 Hz), 6.87 (1 H, s).

Example 262

2-Cyano-5-methyl-2,3,6,7,8,9-hexahydrofuro-[2,3-f]quinoline-7-one:

The compound obtained in Example 259 (0.47 g, 1.9 mmol) was dissolved in methylene chloride (40 ml) and pyridine (0.64 ml, 8 mmol). To the obtained solution, trifluoroacetic anhydride (0.56 ml, 4 mmol) was added dropwise while cooling in an ice—water bath, and the mixture was stirred at 0° C. for 1.5 hours. Pyridine (0.64 ml, 8 mmol) and trifluoroacetic anhydride (0.56 ml, 4 mmol) were further added, and stirring was continued at 0° C. for 1 hour. After completion of the reaction, the solvent was distilled off under reduced pressure. To the resultant residue, saturated ammonia—methanol (30 ml) was added, and the mixture was stirred at room temperature for 1.5 hours. The solvent was distilled off under reduced pressure. The residue was combined with chloroform, and extracted. The organic phase was washed with water, aqueous 5% potassium hydrogensulfate, saturated aqueous sodium bicarbonate solution, and saturated aqueous NaCl solution in this order, and dries over magnesium sulfate. The solvent was reduced under reduced pressure, and the residue was subjected to silica gel column chromatography for separation and purification. As a result, 0.41 g of the title compound was obtained as pale yellow powder (94%).

IR(KBr): 3225, 3093, 2910, 1673, 1630, 1470, 1490, 1370, 1197, 1071, 1050, 932, 747 cm$^{-1}$.

$^1$H-NMR(CDCl$_3$) δ: 2.16 (3 H, s), 2.62 (2 H, t, J=7.3 Hz), 2.85 (1 H, ddd, J=16.1, 7.8, 7.3 Hz), 2.97 (1 H, ddd, J=16.1, 7.8, 7.3 Hz), 3.46 (1 H, dd, J=15.6, 5.8 Hz), 3.55 (1 H, dd, J=15.6, 9.8 Hz), 5.38 (1 H, dd, J=9.8, 5.8 Hz), 6.89 (1 H, s), 7.39 (1 H, br.s).

Example 263

2,3,6,7,8,9-Hexahydro-5-methylfuro-[2,3-f]quinoline-7-one-2-amidoxime:

The compound obtained in Example 262 (0.63 g, 2.76 mmol) was dissolved in ethanol (50 ml), to which hydroxylamine hydrochloride (0.38 g, 5.5 mmol) and triethylamine (1.15 ml, 8.3 mmol) were added. The mixture was refluxed with heat at 90° C. for 1 hour. The solvent was distilled off under reduced pressure. To the residue, water and chloroform were added. The precipitate was collected by filtration, and washed with water and chloroform. Subsequently, the washed material was dissolved in hot methanol and chloroform, followed by drying over magnesium sulfate. When the solvent was distilled off under reduced pressure, 0.47 g of the title compound was obtained as a white solid (65%). This solid was recrystallized from methanol—ether to obtain colorless crystals (mp.: 251°–254° C.).

IR(KBr): 3443, 3317, 3215, 3091, 2908, 1665, 1625, 1469, 1367, 1307, 1201, 1075, 927, 743 cm$^{-1}$.

$^1$H-NMR(DMSO-d$_6$) δ: 2.11 (3 H, s), 2.39 (2 H, t, J=7.8 Hz), 2.74 (2 H, t, J=7.8 Hz), 3.26 (2 H, m), 5.02 (1 H, t, J=8.7 Hz), 5.49 (2 H, br.s), 6.82 (1 H, s), 9.30 (1 H, s), 9.35 (1 H, s).

Reference Example 22

N-(5-Ethoxy-2-methylphenyl)-3,3-dimethylacrylamide:

2-Amino-5-ethoxytoluene (23.3 g, 0.153 mol) was dissolved in pyridine (200 ml). While cooling the solution, 3,3-dimethylacroylchloride (20 g, 0.119 mol) was added thereto and stirred at room temperature for 3 hours.

After the solvent was evaporated, the condensed mixture was dissolved in chloroform, washed with water, and dried and condensed. The resultant residue was purified by silica gel column chromatography (chloroform: methanol =20:1), then recrystallized (chloroform—n-hexane). As a result, 36.7 g of the title compound was obtained as colorless crystals (100%).

$^1$H-NMR(CDCl$_3$) δ: 1.38 (3 H, t, J=6.8 Hz), 1.90 (3 H, s), 2.18 (3 H, s), 2.22 (3 H, s), 4.02 (2 H, q, J=6.8 Hz), 5.73 (1 H, s), 6.60 (1 H, dd, J=2.4, 8.7 Hz), 7.03 (1 H, d, J=8.7 Hz).

Reference Example 23

5-Hydroxy-4,4,8-trimethyl-1,2,3,4-tetrahydrocarbostyril:

To the compound obtained in Reference Example 22 (36.7 g, 0.158 mol), chlorobenzene (350 ml) and aluminum chloride (105.19 g, 0.788 mol) were added. The mixture was stirred in a hot bath of 125° C. for 90 minutes. After cooling, the mixture was poured into ice—water, and then dissolved in a solvent mixture of chloroform—methanol (10:1). The resultant solution was extracted with 1N caustic soda. The aqueous phase was neutralized with conc. HCl, and crystals precipitated were collected by filtration and washed.

The washed crystals were dried, and recrystallized (chloroform—n-hexane). As a result, 20.55 g of the title compound was obtained as pale yellow crystals (64%).

mp. 171°–173° C.

IR(KBr): 3228, 1639, 1605, 1506, 1457, 1425, 1389, 1329, 1291, 1052, 806 cm$^{-1}$.

$^1$H-NMR(CDCl$_3$) δ: 1.46 (6 H, s), 2.14 (3 H, s), 2.48 (2 H, s), 4.91 (1 H, s), 6.33 (1 H, d, J=8.3 Hz), 6.85 (1 H, d, J=8.3 Hz).

Reference Example 24

5-Allyloxy-4,4-8-trimethyl-1,2,3,4-tetrahydrofurocarbostyril:

The compound obtained in Reference Example 23 (19.78 g, 96.4 mmol) and allyl iodide (17.83 g, 106 mmol) were dissolved in N,N-dimethylformamide (200 ml), to which potassium carbonate (20 g, 144 mmol) was added. The mixture was stirred in a bath of 50° C. for 4 hours. The solvent was distilled off under reduced pressure. The residue was dissolved in chloroform and washed with water. After being dried and condensed, the residue was purified by silica gel column chromatography (chloroform), and then recrystallized (chloroform—n-hexane). 13.27 g of the title compound was obtained as colorless crystals (56%).

mp. 174°–178° C.

IR(KBr): 2036, 1553, 1345, 1302, 1234, 1209, 1051, 964, 905 cm$^{-1}$.

$^1$H-NMR(CDCl$_3$) δ: 1.43 (6 H, s), 2.16 (3 H, s), 2.46 (3 H, s), 4.51–4.54 (2 H, m), 5.25–5.42 (2 H, m), 6.07 (1 H, m), 6.51 (1 H, d, J=8.7 Hz), 6.94 (1 H, d, J=8.7 Hz).

Reference Example 25

6-Allyl-5-hydroxy-4,4-8-trimethyl-1,2,3,4-tetrahydrofurocarbostyril:

To the compound obtained in Reference Example 24 (13 g, 53.0 mmol), N-dimethylaniline (13 ml) was added. The mixture was stirred in a bath of 203° C. for 48 hours. After the mixture was cooled, n-hexane was added to allow crystals to precipitate. Filtration and recrystallization yielded 12.27 g of the title compound as colorless crystals (94%).

mp. 174°–177° C.

$^1$H-NMR(CDCl$_3$) δ: 1.44 (6 H, s), 2.14 (3 H, s), 2.46 (2 H, s), 3.33–3.35 (2 H, m), 5.16 (1 H, s), 5.20–5.27 (2 H, m), 5.91–6.06 (1 H, m), 6.77 (1 H, s).

Example 264

2-Hydroxymethyl-5,9,9-trimethyl-2,3,6,7,8,9hexahydrofuro-[2,3-f]quinoline-7-one:

The compound obtained in Reference Example 25 (12.2 g, 49.6 mmol) was dissolved in pyridine (20 ml), to which acetic anhydride (10.23 g, 100 mmol) was added dropwise while cooling on ice. Subsequently, the mixture was stirred at room temperature for 1 hour. The solvent was evaporated and the residue was dissolved in chloroform, then washed with water, dried and condensed. The resultant residue was dissolved in chloroform (150 ml). m-Perbenzoic acid (16.5 g, 95.9 mmol) was added thereto. The mixture was stirred at room temperature overnight. The reaction mixture was washed with water, dried, condensed, and dissolved in methanol (100 ml). 1N caustic soda was added and stirred for 3 hours.

The solvent was evaporated and the resultant residue was condensed. Water was added for allowing crystals to precipitate. The crystals were dissolved in a solvent mixture of chloroform and methanol (10:1), and purified by silica gel column chromatography (chloroform). Recrystallization using chloroform—n-hexane yielded 5.7 g of the title compound as colorless crystals (40%).

mp. 165°–166° C.

IR(KBr): 3430, 3211, 2915, 1645, 1604, 1447, 1361, 1284, 1123, 1070, 871, 828 cm$^{-1}$.

$^1$H-NMR(CDCl$_3$) δ: 1.39 (3 H, s), 1.42 (3 H, s), 2.14 (3 H, s), 2.45 (2 H, s), 2.86–3.20 (2 H, m), 3.68–3.83 (2 H, m), 4.89 (1 H, m), 6.84 (1 H, s).

Example 265

2-Azidomethyl-5,9,9-trimethyl-2,3,6,7,8,9hexahydrofuro-[2,3-f]quinoline-7-one:

The compound obtained in Example 264 (2.42 g, 9.27 mmol) was dissolved in pyridine (10 ml), to which methanesulfonyl chloride (1.67 g, 10.2 mmol) was added and stirred at room temperature for 3 hours.

The solvent was evaporated and the residue was dissolved in chloroform, then washed with water, dried and condensed. The resultant residue was purified by silica gel column chromatography (chloroform). 3 g of 2-methanesulfonyloxymethyl-5,9,9-trimethyl-2,3,6,7,8,9 hexahydrofuro-[2,3-f]quinoline-7-one was obtained as colorless powder. This product was dissolved in N,N-dimethylformamide (40 ml), to which sodium azide (2.9 g, 44.2 mmol) was added and stirred in a bath of 150° C. for 3 hours. The solvent was evaporated, and the residue was dissolved in chloroform, washed with water, dried, and condensed. The resultant residue was purified by silica gel chromatography (chloroform), and then recrystallized (chloroform—n-hexane). 2.7 g of the title compound was obtained as colorless crystals (98%).

mp. 181°–183° C.

IR(KBr): 3206, 2915, 2076, 1657, 1604, 1448, 1363, 1295, 1266, 1124, 1070, 875, 824 cm$^{-1}$.

$^1$H-NMR(CDCl$_3$) δ: 1.41 (6 H, s), 2.14 (3 H, s), 2.45 (2 H, s), 2.88–3.38 (2 H, m), 3.43–3.49 (2 H, m), 4.94 (1 H, m), 6.84 (1 H, s).

Example 266

2-Aminomethyl-5,9,9-trimethyl-2,3,6,7,8,9hexahydrofuro-[2,3-f]quinoline-7-one.HCl:

The compound obtained in Example 265 (2.69 g, 9.41 mmol) was dissolved in N,N-dimethylformamide (40 ml). To the resultant solution, 10% palladium-on-carbon (1.2 g) was added, followed by stirring at room temperature for 3 hours in the atmosphere of hydrogen.

After the catalyst was removed by filtration, the filtrate was condensed, and the residue was purified by silica gel chromatography (chloroform: methanol =25:1), then dissolved in methanol. HCl—dioxane was added to for converting into a hydrochloric acid salt. The salt was recrystallized (methanol—ether). 1.33 g of the title compound was obtained as colorless crystals.

mp. 296°–298° C.

$^1$H-NMR(CD$_3$OD) δ: 1.41 (6 H, s), 2.18 (3 H, s), 2.40 (2 H, s), 2.91 (1 H, dd, J=7.8, 16.1 Hz), 3.15–3.38 (3 H, m), 4.96 (1 H, m), 6.91 (1 H, s).

Reference Example 26

5-Acetoxy-6-[1-(tert-butyldimethylsilyloxy)methyl- 2-propenyl]-8-methylcarbostyril:

6-(1-Hydroxymethyl-2-propenyl)-5-hydroxy-8-methylcarbostyril (8.40 g, 34.3 mmol) was dissolved in pyridine (120 ml), to which tert-butyldimethylsilylchloride (7.5 g, 49.8 mmol) was added. The mixture was stirred at room temperature for 3 hours. Acetic anhydride (20 ml, 0.212 mol) was added to the reaction mixture, followed by stirring at room temperature for 90 minutes, then condensing under reduced pressure. The resultant residue was subjected to an azeotropic distillation along with toluene. The residue was extracted from chloroform—1N-HCl. The organic phase was washed with saturated aqueous NaCl solution, dried, and condensed under reduced pressure. The residue was purified by silica gel chromatography (chloroform: ether= 1:1), and then the obtained crude crystals was recrystallized from chloroform—n-hexane. As a result, 6.00 g of the title compound was obtained as colorless powdery crystals (43.6%).

mp. 169°–171° C.

IR(KBr): 2915, 1757, 1653, 1601, 1468, 1445, 1252, 1192, 1148, 1097, 852, 831, 778 cm$^{-1}$.

$^1$H-NMR(CDCl$_3$) δ: 0.02 (6 H, s), 0.85 (9 H, s), 2.42 (3 H, s), 2.43 (3 H, s), 3.59 (1 H, Br.q, J=6.8 Hz), 3.80 (1 H, d, J=4.9 Hz), 3.81 (1 H, d, J=6.8 Hz), 5.06 (1 H, dt, J=1.5, 17.1 Hz), 5.15 (1 H, dr, J=1.5, 10.7 Hz), 6.01 (1 H, ddd, J=6.3, 10.7, 17.1 Hz), 6.65 (1 H, d, J=9.8 Hz), 7.31 (1 H, s), 7.65 (1 H, d, J=9.8 Hz), 9.14 (1 H, br.s).

Reference Example 27

5-Acetoxy-6-[1-(tert-butyldimethylsilyloxy)methyl-2,3epoxypropyl]-8-methylcarbostyril:

5-Acetoxy-6-[1-(tert-butyldimethylsilyloxy)methyl-2propenyl]-8-methylcarbostyril (6.00 g, 15.0 mmol) was dissolved in chloroform (100 ml), to which m-perbenzoic acid (13.0 g, 52.7 mmol) was added. The mixture was stirred for hours. Saturated aqueous sodium sulfite solution was added to the reaction mixture, followed by stirring for 90 minutes. The organic phase was washed with saturated NaCl solution, dried over sodium sulfate and condensed under reduced pressure. The resultant residue was recrystallized from chloroform—n-hexane. As a result, 6.10 g of the title compound (mixtures of diastereomers, 3:1) was obtained as colorless powdery crystals (97.8%).

mp. 168°–170° C.

IR(KBr): 3411, 2990, 1757, 1653, 1602, 1467, 1446, 1387, 1253, 1190, 1148, 1191, 834, 775 cm$^{-1}$.

$^1$H-NMR(CDCl$_3$) δ: 0.03 (s), 0.01 (s), 0.02 (s) (altogether, 6 H), 0.87 (s), 0.88 (s) (altogether, 9 H), 2.41 (s), 2.43 (s), 2.44 (s), 2.45 (s) (altogether, 6 H), 2.56 (m), 2.63 (m), 2.77 (m), 3.01 (m) (altogether, 2 H), 3.34 (1 H, m), 3.76–3.95 (2 H, m), 6.55 (d, J=9.8 Hz), 6.66 (d, J=9.8 Hz) (altogether, 1 H), 7.38 (s), 7.51 (s)(altogether, 1H), 7.64 (1 H, d, J=9.8 Hz), 9.34 (1 H, br.s).

Example 267

(2RS,2SR)-3-(tert-Butyldimethylsilyloxy)methyl-2-diallylaminomethyl-5-methyl-2,3,6,7-tetrahydrofuro-[2,3-f] quinoline-7-one:

3-(tert-Butyldimethylsilyloxy)methyl-2-hydroxymethyl-5-methyl-2,3,6,7-tetrahydrofuro-[2,3-f]quinoline-7-one (2.30 g, 6.13 mmol) was dissolved in pyridien (50 ml), to which methanesulfonyl chloride (0.7 ml, 9.04 mmol) was added, followed by stirring at room temperature for 3 hours. Methanol (30 ml) was added to the reaction mixture, and stirred for 15 minutes. Subsequently, the reaction mixture was condensed under reduced pressure. The residue was extracted from chloroform—1N-HCl. The organic phase was dried over sodium sulfate, and condensed under reduced pressure. The residue was suspended in diallylamine (20 ml), and refluxed with heat for 18 hours. The reaction mixture was condensed under reduced pressure. The residue was suspended in chloroform—ether. The insoluble matter was separated by filtration.

The filtrate was condensed under reduced pressure, and the resultant residue was extracted (partition extraction) from chloroform—1N-HCl. The organic phase was dried over sodium sulfate, and condensed under reduced pressure. The residue was recrystallized from ethyl acetate. 2.17 g of the title compound was obtained as pale yellow powdery crystals (75.3%).

mp. 197°–199° C.

IR(KBr): 3400, 3173, 2922, 2845, 1664, 1652, 1636, 1612, 1403, 1088, 833, 776 cm$^{-1}$.

$^1$H-NMR(CDCl$_3$) δ: 0.02 (3 H, s), 0.05 (3 H, s), 0.88 (9 H, s), 2.34 (3 H, s), 2.70 (1 H, dd, J=4.9, 14.2 Hz), 2.81 (1 H, dd, J=7.3, 14.2 Hz), 3.16–3.28 (4 H, m), 3.35 (1 H, dd, J=6.4, 12.7 Hz), 3.67 (1 H, dd, J=7.3, 9.8 Hz), 3.77 (1 H, dd, J=6.4, 9.8 Hz), 4.82 (1 H, dd, J=5.4, 12.7 Hz), 5.12 (2 H, d, J=8.8 Hz), 5.16 (2 H, d, J=17.1 Hz), 5.85 (2 H, m), 6.55 (1 H, d, J=9.8 Hz), 7.16 (1 H, s), 7.92 (1 H, d, J=9.8 Hz), 8.94 (1 H, br.s).

Reference Example 28

3-(tert-Butyldimethylsilyloxy)methyl-2-hydroxymethyl-5-methyl-2,3,6,7-tetrahydrofuro-[2,3-f]quinoline-7-one:

5-Acetoxy-6-[1-(tert-butyldimethylsilyloxy)methyl-2,3-epoxypropyl]-8-methylcarbostyril (6.10 g, 14.6 mmol) was dissolved in a solvent mixture (150 ml) of tetrahydrofuran methanol (1:1), to which aqueous 1N-NaOH solution (25 ml) was added. The mixture was stirred at 50° C. for 30 minutes. Concentrated HCl was added to adjust the pH to about 5. Extraction was carried out using chloroform—water. The organic phase was dried over sodium sulfate and condensed under reduced pressure. The resultant residue was recrystallized from chloroform—ether—n-hexane. As a result, 5.10 g the title compound (mixture of diasteromers, 3.1) was obtained as colorless powdery crystals (93.0%).

mp. 182°–184° C.

IR(KBr): 3396, 3265, 3170, 3038, 2924, 1656, 1615, 1464, 1271, 1227, 1153, 1088, 1061, 833, 773 cm$^{-1}$.

$^1$H-NMR(CDCl$_3$) δ: 0.04 (s), 0.07 (s), 0.09 (s), 0.11 (s) (altogether, 6 H), 0.89 (s), 0.91 (s) (altogether, 9 H), 2.30 (s), 2.34 (s) (altogether, 3 H), 3.47–3.55 (m), 3.64–3.72 (m) (altogether, 2 H), 3.95–3.79 (m), 4.08 (m) (altogether,3 H), 4.78 (m), 5.01 (m) (altogether, 1 H), 6.53 (d, J=9.8 Hz), 6.57 (d, J=9.8 Hz) (altogether, 1 H), 7.09 (1 H, s), 7.89 (d, J=9.8 Hz), 7.90 (d, J=9.8 Hz) (altogether, 1 H), 8.8 (1 H, br.s).

Example 268

(2RS,3SR)-2-Aminomethyl-3-hydroxymethyl-5-methyl-2, 3,6,7-tetrahydrofuro-[2,3-f]quinoline-7-one.HCl:

(2RS,3SR)-3-(tert-Butyldimethylsilyloxy)methyl-2-diallylaminomethyl-5-methyl-2,3,6,7-tetrahydrofuro-[2,3-f]quinoline-7-one (2.17 g, 4.62 mmol) was dissolved in a solvent mixture (60 ml) of tetrahydrofuran—N,N-dimethylformamide (5:1), to which tetra-n-butylammonium chloride (1.0 M tetrahydrofuran solution, 10 ml, 10.0 mmol) was added, followed by stirring at room temperature for 8 hours. The reaction mixture was condensed under reduced pressure, and the resultant residue was separated by silica gel column chromatography (chloroform—methanol =50:1). All the fractions that contain spots in the vicinity of Rf=0.4 were collected, and condensed under reduced pressure. The resultant residue was dissolved in ethanol (100 ml). To the solution, Wilkinson catalyst (140.0 mg, 0.15 mmol), 1,4-diazabicyclo[2,2,2]octane (200.0 mg, 1.78 mmol) and water (10 ml) were added, and the mixture was refluxed with heat for 2 hours. The reaction mixture was condensed under reduced pressure, and the residue was purified by silica gel column chromatography (chloroform: saturated ammonia—methanol=50:1). Crude crystals were obtained (500 The crude crystals were dissolved in a solvent mixture of chloroform and methanol (4:1), to which 4N-HCl—dioxane (0.6 ml, 2.40 mmol) was added. The resultant mixture was condensed under reduced pressure, then subjected to azeotropic distillation along with methanol (twice). The residue was recrystallized from methanol—ether. 521.7 mg of the title compound was obtained as pale yellow powdery crystals (38.1%).

mp. >300° C.

IR(KBr): 3383, 2994, 2869, 2559, 2540, 1663, 1655, 1635, 1573, 1446, 1394, 1078, 1054, 1023, 838 cm$^{-1}$.

$^1$H-NMR(CD$_3$OD) δ: 2.39 (3 H, s), 3.23–3.36 (2 H, m), 3.43 (1 H, m), 3.67 (1 H, dd, J=8.8, 10.7 Hz), 3.90 (1 H, dd, J=4.9, 10.7 Hz), 5.01 (1 H, ddd, J=3.9, 5.9, 9.3 Hz), 6.57 (1 H, d, J=9.3 Hz), 7.3 (1 H, s), 8.08 (1 H, d, J=9.3 Hz).

Example 269

(2RS,3SR)-2-Aminomethyl-3-hydroxymethyl-5-methyl-2,3,6,7,8,9-hexahydrofuro-[2,3-f]quinoline-7-one.HCl:

(2RS,3SR)-2-Aminomethyl-3-hydroxymethyl-5-methyl-2,3,6,7-tetrahydrofuro-[2,3-f]quinoline-7-one (550.0 mg, 2.12 mmol) was dissolved in water (50 ml). To the solution, 10% palladium-on-carbon (500 mg) was added, followed by stirring at 80° C. for 2 hours in the atmosphere of hydrogen. The reaction mixture was filtered, and the filtrate was condensed under reduced pressure, and the residue was dissolved in methanol. HCl—methanol solution was added thereto to convert the mixture to a hydrochloric acid salt. The salt was condensed, and recrystallized from methanol—ether. As a result, 430.1 mg of the title compound was obtained as colorless powdery crystals (78.2%).

mp. >300° C.

IR(KBr): 3383, 2994, 2870, 2743, 2700, 2561, 2520, 2453, 1676, 1630, 1469, 1444, 1376, 1204, 1075, 1054, 1021 cm$^{-1}$.

$^1$H-NMR(DMSO-d$_6$) δ: 2.12 (3 H, s), 2.40 (2 H, t, J=7.3 Hz), 2.70 (2 H, t, J=7.3 Hz), 2.90 (1 H, m), 3.1 (1 H, m), 3.3 (1 H, m), 3.45 (1 H, m), 3.70 (1 H, dd, J=4.9, 10.7 Hz), 4.73 (1 H, m), 6.86 (1 H, s), 8.35 (3 H, br.s), 9.32 (1 H, s).

Example 270

2-Diallylaminomethyl-3-fluoromethyl-5-methyl-2,3,6,7-tetrahydrofuro-[2,3-f]quinoline-7-one:

(2RS,3SR)-3-(tert-Butyldimethylsilyl)oxymethyl-2-diallylaminomethyl-5-methyl-2,3,6,7-tetrahydrofuro-[2,3-f]quinoline-7-one (2.30 g, 4.89 mmol) was dissolved in a solvent mixture (60 ml) of tetrahydrofuran—N,N-dimethylformamide (5:1). Tetra-n-butylammonium fluoride (1.0 M tetrahydrofuran solution, 10 ml, 10.0 mmol was added thereto. The resultant mixture was stirred at room temperature for 8 hours. Subsequently, the reaction mixture was condensed under reduced pressure. The residue was separated by silica gel chromatography (chloroform: methanol= 50:1). All the fractions that contain spots in the vicinity of Rf=0.4 (silica gel column chromatography: developer=chloroform: methanol (10:1)) were collected, and condensed under reduced pressure. The resultant residue was dissolved in pyridine (50 ml). To the solution, methanesulfonyl chloride (2.5 ml, 32.0 mmol) was added, and stirred at room temperature for 5 hours. Subsequently, methanol (20 ml) was added and stirred for 15 minutes. The reaction mixture was condensed under reduced pressure. The resultant residue was subjected to silica gel column chromatography (developer: chloform: methanol (50:1)) for separation and purification. 1.45 g of pale yellow oily material was obtained. This material was suspended in toluene (70 ml). To the suspension, tetrabutylammonium fluoride (10. M teterahydrofuran solution, 15 ml) was added, and the mixture was refluxed with heat for 40 minutes. The reaction mixture was condensed under reduced pressure, and the residue was subjected to extraction using chloroform—water. The organic phase was washed with saturated aqueous NaCl solution, dried, and condensed under reduced pressure. The resultant residue was purified by silica gel column chromatography (chloroform). As a result, 0.61 g of the title compound (cis: trans =1:1) was obtained as pale yellow amorphous substance (36.4%). mp. 68°–71° C. IR(Cap): 3155, 2998, 1653, 1615, 1462, 1445, 1419, 1331, 1260, 1216, 1142, 1084, 992, 918, 835, 754 cm$^{-1}$.

$^1$H-NMR(CD$_3$OD) δ: 2.46 (s), 2.48 (s) (altogether,3 H), 2.81–3.05 (4 H, complex m), 3.27–34.0 (complex m), 3.94 (m) (altogether, 5 H), 5.14–5.37 (4 H, complex m), 4.92 (m), 5.51 (m)(altogether, 1 H), 5.85–6.04 (2 H, complex m), 6.66 (d, J=9.8 Hz), 6.67 (d, J=9.8 Hz) (altogether, 1 H), 7.33 (s), 7.38 (s) (altogether, 1 H), 8.05 (1 H, d, J=9.8 Hz), 9.34 (br.), 9.55 (br.) (altogether, ill).

Example 271

2-Aminomethyl-3-fluoromethyl-5-methyl-2,3,6,7-tetrahydrofuro-[2,3-f]quinoline-7-one.HCl:

2-Diallylaminomethyl-3-fluoromethyl-5-methyl-2,3,6,7-tetrahydrofuro-[2,3-f]quinoline-7-one (609.8 mg, 1.78 mmol) was dissolved in ethanol (50 ml). To the solution, Wilkinson catalyst (100.0 mg, 0.108 mmol), 1,4diazabicyclo [2,2,2]octane (100.0 mg, 0.891 mmol) and water (10 ml) were added, and the mixture was refluxed with heat for 90 minutes. The reaction mixture was condensed under reduced pressure, and the residue was purified by silica gel column chromatography (chloroform: saturated ammonia—methanol=50:1). Pale yellow crude crystals were obtained. The crude crystals were dissolved in a solvent mixture of chloroform and methanol (4:1), to which 1.37N-HCl—methanol solution (1.0 ml, 1.37 mmol) was added. The resultant mixture was condensed under reduced pressure, then subjected to azeotropic distillation along with methanol (twice). The residue was recrystallized from methanol—ethanol—ether. 265.0 mg of the title compound was obtained as pale yellow powdery crystals (49.8%).

mp. 288°–291° C. (dec.)

IR(KBr): 3384, 2911, 1652, 1602, 1456, 1425, 1354, 1332, 1257, 1237, 1148, 1083, 1010, 830, 776 cm$^{-1}$.

$^1$H-NMR(CD$_3$OD) δ: 2.37 (3 H, s), 2.96–3.16 (2 H, complex m), 3.21–3.41 (2 H, complex m), 3.56 (m), 3.92 (m) (altogether, 1 H), 4.75 (m), 5.20 (m) (altogether, 1 H), 6.55 (1 H, d, J=9.8 Hz), 7.41 (s), 7.59 (s) (altogether, 1 H), 8.08 (1 H, d, J=9.8 Hz).

Example 272

2-(1,2-Dihydroxyethyl)-5-methyl-2,3,6,7-tetrahydrofuro-[2,3-f]quinoline-7-one:

5-Methyl-2-vinyl-2,3,6,7-tetrahydrofuro-[2,3-f]-quinoline-7-one (1.5 g, 6.61 mmol) was dissolved in a solvent mixture of t-butanol (200 ml), acetone (200 ml) and water (100 ml). A solution (14 ml) of 0.16 N osmium tetraoxide and t-butanol, and N-methyl morpholine N-oxide hydrate (3.57 g, 3.46 mmol) were added to the mixture, and stirred at room temperature for 10 hours. The reaction mixture was condensed under reduced pressure, and the residue was purified by silica gel column chromatography (eluent=chloroform: methanol m 4:1) to obtain crude crystals. The obtained crude crystals were recrystallized from chloroform—methanol—ether to obtain 1.38 g of the title compound as colorless powdery crystals (80.0%).

mp. 259°–261° C.

IR(KBr): 3259, 2908, 1643, 1564, 1462, 1328, 1146, 886, 830, 791, 65 8cm$^{-1}$.

$^1$H-NMR(CDCl$_3$:CD$_3$OD=4:1)δ: 2.37(3H,s), 3.31(2H,d, J=8.3 Hz), 3.71(1H,dd,J=11.2,6.4 Hz), 3.78(1H,d,J=3.9 Hz), 3.85(1H,m), 4.95(1H,m), 6.55(1H,d,J=9.8 Hz), 7.21(1H,s), 7.98(1H,d,J=9.8 Hz).

Example 273

2-(1-Hydroxy-2-methanesulfonyoxyethyl)-5-methyl-2,3,6,7-tetrahydrofuro-[2,3-f]quinoline-7-one 2-(1,2-dihydroxyethyl)-5-methyl-2,3,6,7-tetrahydrofuro[2,3-f]quinoline-7-one (1.38 g, 5.29 mmol) was dissolved in pyridine (130 ml). Methanesulfonylchloride (411 μl, 5.29 mmol) was added to the mixture while cooling in an ice bath, and the mixture was stirred at room temperature for 16 hours. While cooling in an ice bath, methanol (10ml) was added to the mixture, which was then stirred for 30 minutes. The reaction mixture was condensed under reduced pressure, and the residue was extracted from chloroform-1N-HCl. The organic phase was washed with aqueous sodium bicarbonate solution, and aqueous saturated NaCl solution in this order, dried, and condensed under reduced pressure. The resultant residue was recrystallized from chloroform-methanol to obtain 1.68 g of the title compound as colorless powdery crystals (93.8%).

mp. 173°–175° C.

IR(KBr): 3473, 1656, 1616, 1465, 1349, 1173, 1083, 954, 837, 793, 528 cm$^{-1}$.

$^1$H-NMR(CDCl$_3$:CD$_3$OD=4:1)δ: 2.38(3H,s), 3.11(3H,s), 3.32–3.40(2H,m), 4.39(1H,dd,J=10.7,5.6 Hz), 4.49(1H,dd, J=10.7,3.4 Hz), 4.93(1H,m), 6.57(1H,d,J=9.5 Hz), 7.21(1H, s), 7.97(1H,d,J=9.5 Hz).

Example 274

2-(2-Azido-1-hydroxyethyl)-5-methyl-2,3,6,7-tetrahydrofuro[2,3-f]quinoline-7-one 2-(1-Hydroxy-2-methanesulfonyloxyethyl)-5-methyl-2,3,6,7-tetrahydrofuro[2,3-f]quinoline-7-one (1.66 g, 4.90 mmol) was dissolved in dimethylformamide (50 ml). Sodium azide (1.91 g, 29.4 mmol) was added to the mixture, and the mixture was stirred at 100° C. for 2.5 hours. The reaction mixture was condensed under reduced pressure, and the residue was extracted from chloroform-water. The organic phase was dried over sodium sulfate, and condensed under reduced pressure. The resultant residue was purified by silica gel column chromatography (eluent=chloroform: methanol=10:1) to obtain 1.19 g of the title compound as pale yellow powdery crystals (85.0%).

mp. 173°–175 ° C.

IR(KBr): 3345, 3100, 2096, 1648, 1464, 1268, 836 cm$^{-1}$.

$^1$H-NMR(CDCl$_3$)δ: 2.30(3H,s), 3.31(2H,d,J=7.8 Hz), 2.53–2.59(2H,m,complex m), 4.03(1H,m), 4.89(1H,m), 6.54(1H,d,J=9.3 Hz), 7.13(1H,s), 7.85(1H,d,J=9.3 Hz), 8.62(1H,br.).

Example 275

2-(2-Amino-1-hydroxyethyl)-5-methyl-2,3,6,7-tetrahydrofuro[2,3-f]quinoline-7-one·HCl 2-(2-Azido-1-hydroxyethyl)-5-methyl-2,3,6,7-tetrahydrofuro[2,3-f]quinoline-7-one (1.01 g, 3.53 mmol) was dissolved in tetrahydrofuran (100 ml), to which 10% palladium-on-carbon (1.01 g) was added for hydrogen replacement and stirred at room temperature for 3 hours. The reaction mixture was filtered, and the filtrate was condensed under reduced pressure. The residue was dissolved in a solvent mixture of methanol (40 ml) and chloroform (10 ml), to which 4N-HCl-dioxane (0.94 ml) was added while cooling in a water bath, followed by condensing under reduced pressure. The resultant residue was recrystallized from methanol-ether to obtain 749 mg of the title compound as pale yellow powdery crystals (71.6%).

mp. 276°–279° C.

IR(KBr): 3206, 2903, 1654, 1630, 1558, 1461, 1324, 1262, 1150, 1083, 923, 832, 791 cm$^{-1}$.

$^1$H-NMR(CDCl$_3$: CD$_3$OD=4:1)δ: 2.41(3H,s), 2.98(1H, m), 3.23–3.40(2H,m,complex m), 3.51(1H,m), 4.07(1H,m), 4.86(1H,m), 6.70(1H,d,J=9.3 Hz), 7.27(1H,s), 8.10(1H,d,J= 9.3 Hz).

Example 276

2-(2-Amino-1-hydroxyethyl)-5-methyl-2,3,6,7,8,9-hexahydro-5-methylfuro[2,3-f]quinoline-7-one·HCl A hydrochloric acid salt of 2-(2-amino-1-hydroxyethyl)-5-methyl-2,3,6,7-tetrahydrofuro[2,3-f]quinoline-7-one (699 mg, 2.36 mmol) was dissolved in water (60 ml), to which 10% palladium-on-carbon (100 mg) was added for hydrogen replacement and stirred at 80° C. for 2 hours. The reaction mixture was filtered, and the filtrate was condensed under reduced pressure. The residue was recrystallized from methanol-ether to obtain 390 mg of the title compound as colorless powdery crystals (55.3%).

mp. 276°–278° C.

IR(KBr): 3387, 3228, 3009, 1674, 1628, 1471, 1441, 1377, 1330, 1206, 1052 cm$^{-1}$.

$^1$H-NMR(CDCl$_3$:CD$_3$OD=4:1)δ: 2.17(3H,s), 2.56(2H,t, J=7.6 Hz), 2.82–2.90(3H,complex m), 3.11–3.27(4H,complex m), 3.95(1H,m), 4.70(1H,m), 6.73(1H,d,J=3.9 Hz).

Reference Example 29

N-(5-Methoxy-2-methylphenyl)α-methylcinnamamide

2-Amino-4-methoxytoluene (13.2 g, 89.7 mmol) and pyridine (10 ml) were dissolved in acetone (112 ml), to which α-methylcinnamoylchloride (19.4 g, 107.6 mmol) was added while cooling and stirring. The mixture was stirred overnight at room temperature. The solvent was evaporated, and the residue was dissolved in chloroform, washed with water, dried, and condensed. The residue was purified by alumina chromatography (chloroform), and subjected to recrystallization with chloroform—n-hexane to obtain 21.27 g of the title compound as colorless crystals (84.4%).

mp. 125°–126° C.

IR(KBr): 3273, 1641, 1614, 1587, 1520, 1485, 1459, 1304, 1251, 1031, 838, 761, 705 cm$_{-1}$.

$^1$H-NMR(CDCl$_3$)δ: 2.24(3H,d,J=1.5 Hz), 2.25(3H,s), 3.82(3H,s), 6.66(1H,dd,J=2.7,8.3 Hz), 7.09(1H,d,J=8.3 Hz), 7.30–7.55(7H,complex m), 7.76(1H,d,J=2.7 Hz).

Reference Example 30

5-Hydroxy-3,8-dimethylcarbostyril

N-(5-Methoxy-2-methylphenyl)α-methylcinnamamide (21.3 g, 75.8 mmol) and aluminum chloride (50.4 g, 378 mmol) were combined with chlorobenzene (158 ml), and heated in a bath at 125° C. for 45 minutes while stirring. After cooling, the mixture was poured into ice-water, to which hexane was added. Precipitated crystals were collected by filtration, and dissolved in chloroform-methanol (4:1). After drying and condensing, the resultant residue was washed with chloroform to obtain 12.22 g of the title compound as pale brown crystals (85.3%).

mp. >270° C.

IR(KBr): 3126, 1628, 1608, 1573, 1502, 1443, 1438, 1247, 1066, 778 cm$^{-1}$.

$^1$H-NMR(CDCl$_3$:CD$_3$OD 3:1)δ: 2.14(3H,s), 2.25(3H,s), 6.46(1H,d,J=8.1 Hz), 7.00(1H,d,J=8.1 Hz), 8.02(1H,s).

Reference Example 31

5-Allyloxy-3,8-dimethylcarbostyril

5-Hydroxy-3,8-dimethylcarbostyril (4 g, 21.16 mmol) and allyl iodide (3.73 g, 22.2 mmol) were dissolved in dimethylformamide (44 ml), to which potassium carbonate (6.1 g, 44.2 mmol) was added, and stirred for 2 hours in a bath at 70° C. The solvent was distilled off, and the residue was dissolved in chloroform, and washed with water. After drying and condensing, the resultant residue was purified by silica gel chromatography (chloroform), and was subjected to recrystallization (chloroform-n-hexane) to obtain 4.32 g of the title compound as pale yellow prisms (89.2%).

mp. 208°–210° C.

IR(KBr): 3103, 2991, 1640, 1619, 1588, 1496, 1259, 1237, 1087, 993, 787 cm$^{-1}$.

$_1$H-NMR(CDCl$_3$)δ: 2.26(3H,s), 2.35(3H,s), 4.63(2H,d,J=4.9 Hz), 5.33(1H,dd,J=1.5,9.7 Hz), 5.46(1H,dd,J=1.5,16.1 Hz), 6.13(1H,m), 6.53(1H,d,J=7.8 Hz), 7.15(1H,d,J=7.8 Hz), 8.07(1H,s), 8.85(1H,s).

Reference Example 32

6-Allyl-5-hydroxy-3,8-dimethylcarbostyril

N,N-dimethylaniline (10 ml) was added to 5-allyloxy-3,8-dimethylcarbostyril (4.32 g, 18.9 mmol), and stirred for 2 hours and 40 minutes in a bath of 200° C. in the atmosphere of argon. After cooling, hexane was added. Precipitated crystals were collected by filtration, and purified by silica gel chromatography (chloroform:methanol =10:1). The purified product was subjected to recrystallization (chloroform-n-hexane) to obtain 3.86 g of the title compound as colorless crystals (89.4%).

mp. 227°–229° C.

IR(KBr): 3264, 1632, 1603, 1579, 1484, 1448, 1353, 1264, 1215, 1163, 917, 786, 587 cm$^{-1}$.

$^1$H-NMR(CDCl$_3$:CD$_3$OD 3:1)δ: 2.24(3H,s), 2.36(3H,s), 3.43(2H,d,J=6.4 Hz), 5.02–5.13(2H,complex m), 5.99(1H, m), 7.05(1H,s), 8.15(1H,s).

Example 277

2-(2-Bromomethyl-5,8-dimethyl-2,3,6,7-tetrahydrofuro[2,3-f]quinoline-7-one

To 6-allyl-5-hydroxy-3,8-dimethylcarbostyril (3.86 g, 16.68 mmol), N-bromsuccinimide (3.0 g, 16.68 mmol) and chloroform (140 ml) were added, and stirred for 25 minutes in a bath at 75° C. After cooling, the mixture was washed with water, dried, and condensed. The resultant residue was subjected to recrystallization (chloroform-methanol-ether) to obtain 3.36 g of the title compound as pale yellow prisms (64.7%).

mp. 277°–278° C.

IR(KBr): 3142, 2996, 1631, 1611, 1586, 1476, 1434, 1246, 1222, 1087, 1068, 975, 858, 826 cm$^{-1}$.

$^1$H-NMR(CDCl$_3$)δ: 2.23(3H,s), 2.38(3H,s), 3.18(1H,dd, J=6.6,15.4 Hz), 3.45(1H,dd,J=9.0,15.4 Hz), 3.55–3.74(2H, complex m), 5.17(1H,m), 7.13(1H,s), 7.83(1H,s).

Example 278

2-Azidomethyl-5,8-dimethyl-2,3,6,7-tetrahydrofuro[2,3-f]quinoline-7-one

To 2-Bromomethyl-5,8-dimethyl-2,3,6,7-tetrahydrofuro[2,3-f]quinoline-7-one (3.36 g, 10.9 mmol) and sodium azide (5.1 g, 78.5 mmol), dimethylformamide (73.2 ml) were added, and stirred for 1 hour in a bath at 100° C. After cooling, the mixture was condensed, and the resultant residue was dissolved in chloroform, which was washed with water and dried. After condensation, the precipitated crystals were subjected to recrystallization (chloroform-ether) to obtain 2.76 g of the title compound as colorless crystals (93.8%).

mp. 184°–186° C.

IR(KBr): 3156, 3015, 2915, 1641, 1613, 1590, 1483, 1437, 1262, 1091, 1005, 900, 837 cm$^{-1}$.

$^1$H-NMR(CDCl$_3$)δ: 2.24(3H,s), 2.34(3H,s), 3.04(1H,dd, J=6.9,15.6 Hz), 3.36(1H,dd,J=9.3,15.6 Hz), 3.52(2H,d,J=4.9 Hz), 5.11(1H,m), 7.07(1H,m), 7.76(1H,s), 8.88(1H,s).

Example 279

2-Aminomethyl-5,8-dimethyl-2,3,6,7-tetrahydrofuro[2,3-f]quinoline-7-one·HCl

2-Azidomethyl-5,8-dimethyl-2,3,6,7-tetrahydrofuro[2,3-f]quinoline-7-one (2.76 g, 10.2 mmol) was dissolved in tetrahydrofuran (200 ml), to which 10% palladium-on-carbon (2.76 g) was added. The mixture was stirred at room temperature for 2 hours in the atmospher of hydrogen. The catalyst was filtered off, and the filtrate was condensed. The residue was converted to a hydrochloric acid salt, and then subjected to recrystallization (methanol-ether) to obtain 2.10 g of the title compound as yellow crystals (73.4%).

mp. >300° C.

IR(KBr): 3385, 3000, 1643, 1615, 1590, 1477, 1439, 1261, 1089, 997, 973, 938, 862, 832 cm$^{-1}$.

¹H-NMR(CD₃OD)δ: 2.18(3H,s), 2.37(3H,s), 3.04(1H,dd, J=6.8,15.6 Hz), 3.20(1H,dd,J=9.3,13.2 Hz), 3.35(1H,m), 3.49(1H,dd,J=9.3,15.6 Hz), 5.19(1H,m), 7.19(1H,s), 7.88(1H,s).

Example 280

2-Aminomethyl-5,8-dimethyl-2,3,6,7,8,9-tetrahydrofuro[2,3-f]quinoline-7-one·HCl

2-Aminomethyl-5,8-dimethyl-2,3,6,7-tetrahydrofuro[2,3-f]quinoline-7-one·HCl (1.25 g, 4.46 mmol) was dissolved in water (40 ml), to which 10% palladium-on-carbon (1.3 g) was added. The mixture was stirred in a bath at 80° for 16 hours in the atmosphere of hydrogen. The catalyst filtered off, and the filtrate was condensed. The residue was subjected to recrystallization (methanol-ether) to obtain 725 mg of the title compound as colorless crystals (57.5%).

mp. 270°–273° C.

IR(KBr): 3411, 3221, 2947, 1675, 1631, 1482, 1446, 1392, 1340, 1272, 1078, 951 cm⁻¹.

¹H-NMR(CD₃OD)δ: 1.22(3H,d,J=6.3 Hz), 2.17(3H,s), 2.46–2.65(2H,complex m), 2.88–3.44(5H,complex m), 5.01(1H,m), 6.89(1H,s).

Reference Example 33

5-(2-Methyl-2-propenyl)oxy-3,8-dimethylcarbostyril

Reaction, post-treatment, and recrystallization (chloroform-n-hexane) were performed in a manner similar to that described in Reference Example 31 using 5-hydroxy-3,8-dimethylcarbostyril (3 g, 15.87 mmol) and 3-chloro-2-methyl-1-propene (1.58 g, 17.46 mmol). As a result, 3.48 g of the title compound was obtained as pale brown crystals (90.2%).

mp. 201°–202° C.

IR(KBr): 2997, 1653, 1624, 1498, 1357, 1297, 1259, 1239, 1090, 997, 891, 785 cm⁻¹.

¹H-NMR(CDCl₃)δ: 1.88(3H,s), 2.26(3H,s), 2.34(3H,s), 4.53(2H,s), 5.04(1H,s), 5.13(1H,s), 6.52(1H,d,J=8.3 Hz), 7.15(1H,d,J=8.3 Hz), 8.06(1H,s), 8.72(1H,s).

Reference Example 34

6-(2-Methyl-2-propenyl)-5-hydroxy-3,8-dimethylcarbostyril

Reaction, post-treatment, and recrystallization (chloroform-n-hexane) were performed in a manner similar to that described in Reference Example 32 using 5-(2-methyl-2-propenyl)oxy-3,8-dimethylcarbostyril (3.48 g, 14.3 mmol). As a result, 3.29 g of the title compound was obtained as colorless needles (94.5%).

mp. 237°–240° C.

IR(KBr): 3273, 3176, 2902, 1636, 1606, 1582, 1448, 1432, 1348, 1318, 1249, 1162, 888 cm⁻¹.

¹H-NMR(CDCl₃:CD₃OD 2:1)δ: 1.74(3H,s), 2.24(3H,s), 2.37(3H,s), 3.38(2H,s), 4.68(1H,s), 4.83(1H,s), 7.05(1H,s), 8.17(1H,s).

Example 281

2-Bromomethyl-2,5,8-trimethyl-2,3,6,7-tetrahydrofuro[2,3-f]quinoline-7-one

Reaction, past-process, and recrystallization (chloroform-methanol-ether) were performed in a manner similar to that described in Example 277 using 6-(2-methyl-2-propenyl)-5-hydroxy-3,8-dimethylcarbostyril (3.29 g, 13.54 mmol) and N-bromsuccinimide (2.41 g, 13.54 mmol). As a result, 3.93 g of the title compound was obtained as pale yellow prisms (90.1%).

mp. 257°–259° C.

IR(KBr): 3148, 3002, 2950, 1635, 1612, 1588, 1479, 1447, 143, 111, 1259, 837 cm⁻¹.

¹H-NMR(CDCl₃:CD₃OD 5:1)δ: 1.68(3H,s), 2.23(3H,s), 2.38(3H,s), 3.10(1H,d,J=15.6 Hz), 3.42(1H,d,J=15.6 Hz), 3.61(2H,s), 7.12(1H,s), 7.83(1H,s).

Example 282

2-Azidomethyl-2,5,8-trimethyl-2,3,6,7-tetrahydrofuro[2,3-f]quinoline-7-one

To 2-bromomethyl-2,5,8-trimethyl-2,3,6,7-tetrahydrofuro-[2,3-f]quinoline-7-one (3.93 g, 12.2 mmol) and sodium azide (5.15 g, 79.3 mmol), dimethylformamide (85 ml) was added, and the mixture was stirred for 3 hours in a bath at 150° C. After cooling, post-treatment and recrystallization (chloroform-n-hexane) were performed in a manner similar to that described in Example 278 to obtain 3.28 g of the title compound as colorless crystals (94.7%).

mp. 232°–234° C.

IR(KBr): 3153, 3009, 2955, 2905, 2081, 1635, 1614, 1589, 1480, 1437, 1260, 1079, 869, 820c m⁻¹.

¹H-NMR(CDCl₃)δ: 1.56(3H,s), 2.24(3H,s), 2.33(3H,s), 3.01(1H,d,J=15.6 Hz), 3.22(1H,d,J=15.6 Hz), 3.40(1H,d,J=13.2 Hz), 3.42(1H,d,J=13.2 Hz), 7.05(1H,s), 7.76(1H,s), 8.68(1H,s).

Example 283

2-Aminomethyl-2,5,8-trimethyl-2,3,6,7-tetrahydrofuro-[2,3-f]quinoline-7-one·HCl

Reduction, post-treatment and recrystallization (methanol-ether) were performed in a manner similar to that described in Example 279 using 2-azidomethyl-2,5,8-trimethyl-2,3,6,7-tetrahydrofuro[2,3-f]quinoline-7-one (3.28 g, 11.55 mmol). As a result, 3.36 g of the title compound was obtained as colorless prisms (98.7%).

mp. >250° C.

IR(KBr): 3368, 2915, 1640, 1612, 1589, 1477, 1440, 1307, 1261, 1082 cm⁻¹.

¹H-NMR(CD₃OD)δ: 1.60(3H,s), 2.18(3H,s), 2.38(3H,s), 3.16(1H,d,J=16.1 Hz), 3.24–3.35(3H,complex m), 7.18(1H, s), 7.88(1H,s).

Example 284

2-Aminomethyl-2,5,8-trimethyl-2,3,6,7,8,9-hexahydrofuro[2,3-f]quinoline-7-one·HCl A hydrochloric acid salt of 2-Aminomethyl-2,5,8-trimethyl-2,3,6,7-tetrahydrofuro-[2,3-f]quinoline-7-one (1.18 g, 4.0 mmol) was suspended in a mixture of water (200 ml) and methanol (40 ml), to which 10% palladium-on-carbon (1.2 g) was added. The mixture was then stirred in a bath at 80° C. for 16 hours in the atmosphere of hydrogen. Post-treatment and recrystallization (methanol-ether) were performed in a manner similar to that described in Example 280 to obtain 957 mg of the title compound as colorless crystals (80.6%).

mp. 287°–288° C.

IR(KBr): 3394, 3196, 2930, 1663, 1627, 1484, 1469, 1446, 1391, 1381, 1276, 1249, 1078 cm$^{-1}$.

$^1$H-NMR(CD$_3$OD)δ: 1.22(3H,d,J=6.4 Hz), 1.53(3H,s), 2.17(3H,s), 2.35–2.65(2H,complex m), 2.98–3.26(5H,complex m), 6.88(1H,s).

Reference Example 35

5-(3-Methyl-2-butenyl)oxy-3,8-dimethylcarbostyril

Reaction, post-treatment, and recrystallization (chloroform-n-hexane) were performed in a manner similar to that described in Reference Example 31 using 5-hydroxy-3,8-dimethylcarbostyril (1.4 g, 7.41 mmol) and 4-bromo-2-methyl-2-butene (1.21 g, 8.15 mmol). As a result, 1.41 g of the title compound was obtained as colorless crystals (74.1%).

mp. 175°–177° C.

IR(KBr): 2905, 1654, 1589, 1495, 1453, 1382, 1258, 1237, 1085, 779 cm$^{-1}$.

$^1$H-NMR(CDCl$_3$)δ: 1.76(3H,s), 1.82(3H,s), 2.25(3H,s), 2.34(3H,s), 4.60(2H,d,J=6.8 Hz), 5.54(1H,m), 6.54(1H,d,J=8.3 Hz), 7.15(1H,d,J=8.3 Hz), 8.05(1H,s), 8.73(1H,s).

Reference Example 36

6-(2,3-Dimethyl-2-propenyl)-5-hydroxy-3,8dimethylcarbostyril

Reaction and post-treatment were performed in a manner similar to that described in Reference Example 32 with 5-(3-methyl-2-butenyl)oxy-3,8-dimethylcarbostyril (1.41 g, 5.49 mmol). Subsequently, purification by silica gel chromatography (chloroform:ethyl acetate=10:1) was performed to obtain 1.35 g of the title compound as a colorless powder (95.7%).

IR(KBr): 3154, 2960, 1636, 1578, 1483, 1431, 1370, 1260, 1208, 1162, 885, 583 cm$^{-1}$.

$^1$H-NMR(CDCl$_3$)δ: 1.45(3H,d,J=7.3 Hz), 1.67(3H,s), 2.25(3H,s), 2.35(3H,s), 3.50(1H,q,J=7.3 Hz), 5.11(1H,s), 5.20(1H,s), 6.19(1H,s), 7.01(1H,s), 8.00(1H,s), 8.90(1H,s).

Example 285

2-Iodomethyl-2,3,5,8-tetramethyl-2,3,6,7-tetrahydrofuro[2,3-f]quinoline-7-one

Iodine (1.53 g, 6.02 mmol) and potassium iodide (1.01 g, 6.08 mmol) were dissolved in a mixture (105 ml) of chloroform and methanol (4:1), and the resultant mixture was maintained cool. Separately, 6-(2,3-dimethyl-2-propenyl)-5-hydroxy-3,8-dimethylcarbostyril (1.35 g, 5.25 mmol) was dissolved in a mixture (21 ml) of chloroform and methanol (4:1), to which potassium carbonate (1.13, 8.19 mmol) was added. While stirring at −20° C., the above-mentioned cooled solution of iodine and potassium iodide was added thereto, followed by stirring overnight at −20° C. Excessive amounts of aqueous sodium sulfite solution were added to the mixture, followed by stirring at room temperature. Thereafter, extraction was performed with chloroform, and drying and condensing followed. To the resultant pale brown crystals, ethyl acetate was added, which was then ground with heat. After spontaneous cooling, precipitated crystals were collected by filtration to obtain 1.75 g of the title compound (87.0%).

mp. 212°–214° C.

IR(KBr): 3154, 3009, 2945, 1651, 1616, 1591, 1481, 1449, 1371, 1258, 1158, 1098, 872, 830 cm$^{-1}$.

$^1$H-NMR(CDCl$_3$)δ: 1.32(3H,d,J=7.3 Hz), 1.67(3H,s), 2.25(3H,s), 2.34(3H,s), 3.34(1H,d,J=10.7 Hz), 3.42(1H,q,J=7.3 Hz), 3.53(1H,d,J=10.7 Hz), 6.98(1H,s), 7.77(1H,s), 8.72(1H,s).

Example 286

2-Azidomethyl-2,3,5,8-tetramethyl-2,3,6,7-tetrahydrofuro[2,3-f]quinoline-7-one

To a mixture of 2-iodomethyl-2,3,5,8-tetramethyl-2,3,6,7-tetrahydrofuro[2,3-f]quinoline-7-one (1.75 g, 4.57 mmol) and sodium azide (3.5 g, 53.8 mmol), dimethylformamide (24 ml) was added, and the mixture was stirred for 3 hours in a bath at 150° C. After cooling, post-treatment and recrystallization (chloroform-n-hexane) were performed in a manner similar to that described in Example 278 to obtain 1.13 g of the title compound as pale yellow crystals (83.0%).

mp. 189°–192° C.

IR(KBr): 3153, 2949, 2083, 1642, 1613, 1589, 1477, 1436, 1259 cm$^{-1}$.

$^1$H-NMR(CDCl$_3$)δ: 1.29(3H,d,J=7.3 Hz), 1.59(3H,s), 2.24(3H,s), 2.35(3H,s), 3.21(1H,d,J=13.2 Hz), 3.39(1H,q,J=7.3 Hz), 3.54(1H,d,J=13.2 Hz), 6.98(1H,s), 7.78(1H,s), 8.74(1H,s).

Example 287

2-Aminomethyl-2,3,5,8-tetramethyl-2,3,6,7-tetrahydrofuro[2,3-f]quinoline-7-one·HCl Reduction, post-treatment and recrystallization (methanol-ether) were performed in a manner similar to that described in Example 279 using 2-azidomethyl-2,3,5,8-tetramethyl-2,3,6,7-tetrahydrofuro[2,3-f]quinoline-7-one (1.13 g, 3.79 mmol). As a result, 804 mg of the title compound was obtained as colorless prisms (68.7%).

mp. >250° C.

IR(KBr): 3349, 3180, 2923, 1647, 1615, 1590, 1507, 1478, 1438, 1258, 1069, 1019, 891 cm$^{-1}$.

$^1$H-NMR(CD$_3$OD)δ: 1.32(3H,d,J=7.3 Hz), 1.63(3H,s), 2.20(3H,s), 2.40(3H,s), 3.13(1H,d,J=13.2 Hz), 3.24(1H,q,J=13.2 Hz), 3.49(1H,q,J=7.3 Hz), 7.16(1H,s), 7.92(1H,s).

Example 288

2-Aminomethyl-2,3,5,8-tetramethyl-2,3,6,7,8,9-hexahydrofuro[2,3-f]quinoline-7-one·HCl Reduction, post-treatment and recrystallization (methanol-ether) were performed in a manner similar to that described in Example 280 using 2-aminomethyl-2,3,5,8-tetramethyl-2,3,6,7-tetrahydrofuro[2,3-f]quinoline-7-one (510 mg, 1.65 mmol). As a result, 415 mg of the title compound was obtained as colorless prisms (80.8%).

mp. 293°–295° C.

IR(KBr): 3406, 3202, 2955, 1669, 1627, 1470, 1378, 1338, 1269, 1244, 1068, 1048, 876 cm$^{-1}$.

¹H-NMR(CD₃OD)δ: 1.22(3H,d,J=6.3 Hz), 1.27(3H,d,J= 7.3 Hz), 1.53(3H,s), 2.18(3H,s), 2.38–2.65(2H,complex m), 2.97–3.18(4H,complex m), 6.84(1H,s).

Reference Example 37

3,8-Dimethyl-5-(Z-2-pentenyloxy)carbostyril

Z-2-Penten-1-ol (5.0 g, 58.1 mmol), trimethylamine (6.45 g, 63.9 mmol), methanesulfonylchloride (7.0 g, 61.1 mmol) and ether (30 ml) were allowed to react at ambient temperature for 1 hour. After the completion of the reaction, the insoluble matter was removed and washed with water. The washed substance was dried over sodium sulfate. The solvent was distilled off to obtain 7.95 g of Z-1-mesyloxy-2-pentene as pale yellow oily material (83.4%). This material was added to a mixture of 3,8-dimethyl-5-hydroxycarbostyril (7.0 g, 37.0 mmol), potassium carbonate (10.2 g, 74.0 mmol) and dimethylformamide (210 ml), and allowed to react at 70° C. for 1 hour. The reaction mixture was condensed under reduced pressure, and the residue was poured into water to obtain 7.36 g of the title compound as a brown solid (77.3%).

IR(KBr): 1637, 1585, 1493, 1258 cm⁻¹.

¹H-NMR(CDCl₃)δ: 1.05(3H,t,J=7.7 Hz), 2.10–2.32(2H, m), 2.27(3H,s), 2.37(3H,s), 4.70(2H,d,J=4.3 Hz), 5.70–5.84(2H,m), 6.57(1H,d,J=8.0 Hz), 7.20(1H,d,J=8.0 Hz), 8.07(1H,s), 8.90(1H,br).

Reference Example 38

3,8-Dimethyl-5-hydroxy-6-(1-methyl-2-butenyl)carbostyril

A mixture of the compound obtained in Reference Example 37(7.2 g, 28.0 mmol) and dimethylaniline (10 ml) was allowed to react at 200° C. for 2 hours. After cooling, ether was poured into the reaction mixture to obtain 5.90 g of the title compound as a pale brown solid (80.6%).

IR(KBr): 1634, 1577, 1434, 1350, 1307 cm⁻¹.

¹H-NMR(CDCl₃)δ: 1.39(3H,d,J=7.3 Hz), 1.76(3H,d,J= 4.1 Hz), 2.25(3H,s), 2.34(3H,s), 3.52(1H,m), 5.65–5.82(2H, m), 5.93(1H,br), 7.01(1H,s), 8.01(1H,s), 8.80(1H,br).

Example 289

2-(1-Bromoethyl)-3,5,8-trimethyl-2,3,6,7-tetrahydrofuro[2,3-f]quinoline-7-one

The compound obtained in Reference Example 38(3.18 g, 12.4 mmol) was dissolved in chloroform (30 ml). To the obtained solution, N-bromosuccinimide (2.42 g, 13.6 mmol) was added, and allowed to react for 1 hour. The reaction mixture was washed with water, and dried. The solvent was distilled off, and the residue was washed with ethyl acetate to obtain 3.51 g of the title compound as a pale brown solid (84.5%).

IR(KBr): 1642, 1615, 1590, 1481, 1443 cm⁻¹.

¹H-NMR(CDCl₃)δ: 1.20–2.03(6H,m), 2.25(3H,s), 2.35(3H,s), 3.52(1H,m), 4.15–4.82(2H,m), 7.03(s), 7.06(s)(9D1H), 7.72(s), 7.76(s)(altogether,1H), 8.82(1H,br).

Example 290

2-(1-Azidoethyl)-3,5,8-trimethyl-2,3,6,7-tetrahydrofuro[2,3-f]quinoline-7-one

A mixture of the compound obtained in Example 289 (3.30 g, 9.9 mmol), sodium azide (3.84 g, 59 mmol) and dimethylformamide (30 ml) was allowed to react at 120° C. for 4 hours. The reaction mixture was poured into water to obtain 2.13 g of the title compound as a pale brown solid (72.7%).

IR(KBr): 2075, 1641, 1618, 1589, 1479, 1450, 1371, 1255 cm⁻¹.

¹H-NMR(CDCl₃)δ: 1.20–1.81(6H,m), 2.20(3H,s), 2.38(3H,s), 3.34–4.74(3H,m), 7.04(s), 7.10(s)(altogether, 1H), 7.81(1H,s), 8.90(1H,br).

Example 291

2-(1-Aminoethyl)-3,5,8-trimethyl-2,3,6,7-tetrahydrofuro[2,3-f]quinoline-7-one

The compound obtained in Example 290 (2.08 g, 7.0 mmol) was dissolved in a mixture of methanol (30 ml), tetrahydrofuran (30 ml) and dimethylformamide (30 ml). To the obtained solution, 10% palladium-on-carbon (0.70 g) was added, and allowed to react at ambient temperature for 4 hours in the stream of hydrogen gas. The insoluble matter was removed by filtration, and the solvent was distilled off under reduced pressure. The residue was purified by silica gel column chromatography (benzene:methanol=2:1) to obtain 1.25 g of the title compound as a colorless solid (66.0%, mp.: 195°–207° C.)

IR(KBr): 1644, 1614, 1590, 1478, 1438, 1372, 1257 cm⁻¹.

¹H-NMR(CD₃OD)δ: 1.08–1.44(6H,m), 2.19(3H,s), 2.37(3H,s), 3.04–4.42(3H,m), 7.14(s), 7.19(s)(altogether, 1H), 7.91(1H,s), 7.93(s)(altogether,1H).

Reference Example 39

3,8-Dimethyl-5-(E-2-pentenyloxy)carbostyril 3,8-Dimethyl-5-hydroxycarbostyril (1.72 g, 9.1 mmol), potassium carbonate (2.51 g, 18.1 mmol), E-1-Bromo-2-pentene (2.0 g, 13.4 mmol) and dimethylformamide (30 ml) were allowed to react at 60° C. for 1 hour. After the completion of the reaction, the procedure described in Reference Example 31 was followed to obtain 0.60 g of the title compound as a colorless solid (25.6%).

IR(KBr): 1635, 1584, 1495, 1363, 1330, 1260 cm⁻¹.

¹H-NMR(CDCl₃)δ: 1.07(3H,t,J=7.3 Hz), 2.16(2H,m), 2.29(3H,s), 2.38(3H,s), 4.58(2H,d,J=5.8 Hz), 5.76(H,dt,J= 15.7,5.8 Hz), 5.96(1H,dt,J=15.7,5.8 Hz), 6.56(1H,d,J=8.0 Hz), 7.18(1H,d,J=8.0 Hz), 8.10(1H,s), 9.11(1H,br).

Reference Example 40

3,8-Dimethyl-6-(1-ethyl-2-propenyl)-5-hydroxycarbostyril

The compound obtained in Reference Example 39 (0.20 g, 0.78 mol) was heated at 200° C. for 15 minutes, and purified by silica gel column chromatography (chloroform:methanol=30:1) to obtain 94 mg of the title compound as a pale brown solid (46.8%)

IR(KBr): 1636, 1483, 1433, 1374, 1301, 1258, 1211, 1162 cm$^{-1}$.

$^1$H-NMR(CDCl$_3$)δ: 0.95(3H,t,J=7.3 Hz), 1.74–1.95(2H, m), 2.30(3H,s), 2.39(3H,s), 3.33(2H,q,J=7.3 Hz), 5.20–6.16(3H,m), 7.05(1H,s), 8.09(1H,s), 9.15(1H,br).

Example 292

2-Bromomethyl-5,8-dimethyl-3-ethyl-2,3,6,7-tetrahydrofuro[2,3-f]quinoline-7-one

The title compound was prepared in a manner similar to that described in Example 277 using the compound obtained in Reference Example 40 (88 mg, 0.34 mol), N-bromosuccinimide (67 mg, 0.38 mol) and chloroform (2 ml). 49 mg of the title compound was obtained as a pale yellow solid (42.6%).

IR(KBr): 1653, 1616, 1590, 1480, 1439, 1258 cm$^{-1}$.

$^1$H-NMR(CDCl$_3$)δ: 0.95–1.08(3H,m), 2.50–2.90(2H,m), 2.27(3H,s), 2.39(3H,s), 3.26–5.10(4H,m), 7.12(s), 7.16(s)(altogether,1H), 7.88(1H,s), 9.32(1H,br).

Example 293

2-Azidomethyl-5,8-dimethyl-3-ethyl-2,3,6,7-tetrahydrofuro[2,3-f]quinoline-7-one

The title compound was prepared in a manner similar to that described in Example 274 using the compound obtained in Example 292 (46 mg, 0.14 mmol), sodium azide (53 mg, 0.82 mmol) and dimethylformamide (1.0 ml). 24 mg of the title compound was obtained as a pale yellow solid (58.8%).

IR(KBr): 2082, 1641, 1612, 1590, 1479, 1438, 1265 cm$^{-1}$.

$^1$H-NMR(CDCl$_3$)δ: 0.92–1.90(5H,m), 2.26(3H,s), 2.39(3H,s), 3.12–5.08(4H,m), 7.12(s), 7.14(s)(altogether, 1H), 7.87(1H,s), 9.34(1H,br).

Example 294

2-Aminomethyl-5,8-dimethyl-3-ethyl-2,3,6,7-tetrahydrofuro[2,3-f]quinoline-7-one

The title compound was prepared in a manner similar to that described in Example 275 using the compound obtained in Example 293 (21 mg, 0. 070 mmol), 10% palladium-on-carbon (10 mg) and dimethylformamide (0.6 ml). 11 mg of the title compound was obtained as colorless crystals (57.4%). The crystals were purified by silica gel column chromatography to obtain the cis- form of the title compound as colorless powdery crystals (mp. 209°–225° C.) and the trans- form of the title compound as colorless powdery crystals (mp. 142°–155° C.).

Cis Compound

IR(KBr): 1646, 1616, 1590, 1479, 1439 cm$^{-1}$.

$^1$H-NMR(CDCl$_3$—CD$_3$OD 2:1)δ: 1.01(3H,t,J=7.4 Hz), 1.54–1.90(2H,m), 2.19(3H,s), 2.40(3H,s), 2.92–4.76(4H,m), 7.15(1H,s), 7.91(1H,s).

Trans Compound

IR(KBr): 1644, 1615, 1588, 1475, 1437 cm$^{-1}$.

$^1$H-NMR(CDCl$_3$—CD$_3$OD 10:1)δ: 1.05(3H,t,J=7.4 Hz), 1.50–1.85(2H,m), 2.26(3H,s), 2.39(3H,s), 2.90–4.96(4H,m), 7.13(1H,s), 7.84(1H,s).

Reference Example 41

3,8-Dimethyl-5-(2-butenyloxy)carbostyril 3,8-Dimethyl-5-hydroxycarbostyril (3 g, 15.86 mmol) was dissolved in dimethylformamide (30 ml). To the solution, crotyl bromide (2.06 ml, 20.45 mmol) and potassium carbonate (4.4g, 31.84 mmol) were added. The mixture was stirred at 70° C. for 2 hours. After spontaneous cooling, water (90 ml) was added to the mixture. Precipitated crystals were collected by filtration. The obtained crystals were dissolved in chloroform, washed with water and saturated aqueous NaCl solution in this order, and dried. The solvent was distilled off under reduced pressure, and the residue was recrystallized from chloroform-n-hexane. As a result, 2.43 g of the title compound was obtained as colorless crystals (63%).

mp. 210°–214° C.

IR(KBr): 3161, 3005, 2848, 1657, 1590, 1496, 1472, 1374, 1297, 1259, 1237, 1182, 1090, 995, 963, 908, 786 cm$^{-1}$.

$^1$H-NMR(CDCl$_3$)δ: 1.79(3H,d,J=6.4 Hz), 2.26(3H,s), 2.35(3H,s), 4.54(2H,d,=5.9 Hz), 5.75–5.89(2H,complex m), 6.53(1H,d,=8.3 Hz), 7.15(1H,d,J=8.3 Hz), 8.06(1H,s), 8.88(1H,br).

Reference Example 42

3,8-Dimethyl-5-hydroxy-6-(1-methylallyl)carbostyril

To the compound obtained in Reference Example 41 (2.24 g, 9.21 mmol), dimethylaniline (8 ml) was added, and the mixture was stirred at 200° C. for 2 hours. After cooling, ethyl acetate (20 ml) was added to the mixture. The mixture was washed with aqueous potassium hydrogensulfate and saturated aqueous NaCl solution in this order, and dried. The solvent was distilled off under reduced pressure, and the residue was recrystallized from ethyl acetate-n-hexane. As a result, 1.57 g of the title compound was obtained as colorless crystals (70%).

mp.169°–171° C.

IR(KBr): 3256, 2954, 1635, 1579, 1482, 1435, 1346, 1309, 1244, 1163, 908, 783 cm$^{-1}$.

$^1$H-NMR(CDCl$_3$)δ: 1.44(3H,d,J=6.8 Hz), 2.25(3H,s), 2.34(3H,s), 3.59(1H,m), 5.26(1H,s), 5.32(1H,dd,J=1.5,3.9 Hz), 5.80(1H,br), 6.11(1H,m), 7.02(1H,s), 8.02(1H,s), 8.77(1H,br).

Example 295

2-(Bromomethyl)-3,5,8-trimethyl-2,3,6,7-tetrahydrofuro[2,3-f]quinoline-7-one

The compound obtained in Reference Example 42 (1.4 g, 5.75 mmol) was dissolved in chloroform (10 ml), to which N-bromosuccinimide (1.13 g, 6.35 mmol) was added. The mixture was refluxed for 1 hour. After cooling, the precipitate was removed by filtration. The filtrate was washed with water and saturated aqueous NaCl solution in this order, and dried. The solvent was distilled off under reduced pressure, and the residue was washed with ethyl acetate to obtain 1.56 g of the title compound as crystals (84%).

mp. 205°–208° C. (dec.)

IR(KBr): 3155, 3012, 1652, 1616, 1590, 1481, 1450, 1257, 1163, 1102, 1003, 948, 869 cm$^{-1}$.

¹H-NMR(CDCl₃)δ: 1.26(d,J=6.8 Hz), 1.40(d,J=6.8 Hz) (altogether,3H), 2.24(s), 2.25(s)(altogether,3H), 2.35(3H,s), 3.42–3.72(3H,complex m), 4.62(q,J=6.4 Hz), 5.04(q,J=6.8 Hz) (altogether,1H), 7.03(1H,s), 7.77(1H,s), 8.83(1H,br).

Example 296

2-(Azidomethyl)-3,5,8-trimethyl-2,3,6,7-tetrahydrofuro[2,3-f]quinoline-7-one

The compound obtained in Example 295 (1.49 g, 4.62 mmol) was dissolved in dimethyformamide (20 ml). Sodium azide (1.8 g, 27.69 mmol) was added to the mixture, and stirred at 150° C. for 3 hours. After cooling, ethyl acetate and water were added to the mixture for phase separation. The organic phase was washed with water and saturated aqueous NaCl solution in this order, and dried. The solvent was distilled off under reduced pressure to obtain 1.43 g (assayed quantitatively) of the title compound as crude crystals.

mp. 198°–202° C. (dec.)

IR(CHCl₃) 3387, 2959, 2091, 1646, 1616, 1590, 1474, 1439, 1246, 1086, 909 cm⁻¹.

¹H-NMR(CDCl₃)δ: 1.26(d,J=7.3 Hz), 1.37(d,J=7.3 Hz)(altogether,3H), 2.24(s), 2.25(s)(altogether,3H), 2.35(3H,s), 3.32–3.68(3H,complex m), 4.57(m), 5.01(dt,J= 4.0,7.9 Hz) (altogether,1H), 7.03(1H,s), 7.77(1H,s), 8.76(1H,br).

Example 297

2-(Aminomethyl)-3,5,8-trimethyl-2,3,6,7-tetrahydrofuro[2,3-f]quinoline-7-one·HCl The compound obtained in Example 296 (1.3 g, 4.57 mmol) was dissolved in tetrahydrofuran (20 ml), to which 10% palladium-on-carbon (650 mg) was added. The mixture was stirred at room temperature for 2 hours in the stream of hydrogen. After removing the catalyst by filtration, the filtrate was distilled off under reduced pressure, and the residue was purified by silica gel column chromatography (chloroform:methanol=20:1). The resultant material was subjected to a further silica gel column chromatography (benzene:methanol=10:1) to obtain 496 mg of the first eluate (trans form). The component was converted to a hydrochloric acid salt to obtain 540 mg of the trans form of the title compound as colorless crystals (40%). The last eluate (cis form) was processed in a similar manner to obtain 300 mg of the cis form of the title compound as colorless crystals (yield: 22%).
Trans compound·HCl
  mp. >300° C.
  IR(KBr): 3399, 3175, 3049, 1644, 1590, 1473, 1433, 1256, 1086, 981, 953, 790, 624 cm⁻¹.
  ¹H-NMR(D₂O)δ: 1.40(3H,d,J=6.8 Hz), 2.14(3H,s), 2.29(3H,s), 3.28–3.49(3H,complex m), 4.79(1H,m), 7.23(1H,s), 7.81(1H,s).
  ¹H-NMR(CDCl₃—CD₃OD)δ: 1.38(3H,d,J=6.8 Hz), 2.24(3H,s), 2.39(3H,s), 2.96(1H,dd,J=7.3,13.7 Hz), 3.04(1H,dd,J=3.9,13.7 Hz), 3.25(1H,quint,J=6.8 Hz), 4.45(1H,dt,J=3.9,7.3 Hz), 7.09(1H,s), 7.86(1H,s).
Cis compound·HCl
  mp. >230° C.
  IR(KBr): 3400, 2910, 1665 1616, 1473 cm⁻¹.
  ¹H-NMR(D₂O)δ: 1.26(3H,d,J=7.3 Hz), 2.11(3H,s), 2.22(3H,s), 3.30(1H,dd,J=13.5,10.8 Hz), 3.44(1H,dd,J=13.5,2.7 Hz), 3.80(1H,m), 5.19(1H,m), 7.14(1H,s), 7.68(1H,s).

Example 298

2-(Aminomethyl)-3,5,8-trimethyl-2,3,6,7,8,9-hexahydrofuro[2,3-f]quinoline-7-one·HCl The trans compound obtained in Example 297 (380 mg, 1.29 mmol) was dissolved in water (30 ml). To the solution, 10% palladium-on-carbon (400 mg) was added. The mixture was stirred at 80° C. for 2 days in the stream of hydrogen. After removing the catalyst by filtration, the filtrate was distilled off under reduced pressure, and the residue was subjected to recrystallization from methanol-ether to obtain 227 mg of the title compound in a trans form as colorless crystals (59%). By a similar procedure using the cis compound obtained in Example 297 (165 mg, 0.56 mmol), 85 mg of the title compound in a cis form was obtained as colorless crystals (51%).
Trans Compound
  mp. 246°–250° C. (dec.)
  IR(KBr): 3399, 3215, 2952, 1672, 1630, 1472, 1389, 1339, 1268, 1084, 1045, 968 cm⁻¹.
  ¹H-NMR(CD₃OD)δ: 1.22(3H,d,J=6.4 Hz), 1.35(3H,d,J=6.8 Hz), 2.18(3H,s), 2.54(2H,m), 3.01–3.30(4H,complex m), 4.49(1H,m), 6.87(1H,s).
Cis Compound
  mp. >230° C.
  IR(KBr): 3400, 2900, 1674, 1630, 1470 cm⁻¹.
  1H-NMR(D₂O)δ: 1.19(6H,m), 2.17(3H,s), 2.61(2H,m), 2.90(1H,m), 3.25(1H,m), 3.35–3.41(1H,m), 3.70(1H,m), 5.03(1H,m), 6.99(1H,s).

Reference Example 43

3,4-Dihydro-5-hydroxy-8-methylcarbostyril

5-Hydroxy-8-methylcarbostyril (20.0 g, 0.114M) was dissolved in acetic acid (800 ml). To the solution, 10% palladium-on-carbon (10.0 g) was added. The mixture was stirred at 80° C. for 4 hours in the stream of hydrogen. The reaction mixture was filtered, and the filtrate was distilled off under reduced pressure. The residue was extracted from a mixture of chloroform-methanol (10:1) and saturated aqueous sodium bicarbonate solution. The organic phase was washed with saturated aqueous NaCl solution, dried, and condensed under reduced pressure. The resultant residue was recrystallized from methanol-ether to obtain 20.2 g of the title compound as pale yellow powdery crystals (99.9%).

mp. 161°–168° C.

IR(KBr): 3284, 1645, 1605, 1504, 1467, 1438, 1397, 1322, 1285, 1192, 1056, 792, 709, 481 cm⁻¹.

¹H-NMR(CD₃OD)δ: 2.13(3H,s), 2.49(2H,t,J=7.3 Hz), 2.88(2H,t,J=7.3 Hz), 6.41(1H,d,J=8.3 Hz), 6.81(1H,d,J=8.3 Hz).

Reference Example 44

1-N-Benzyl-5-benzyloxy-3,4-dihydro-8-methylcarbostyril

To a solution of 5-hydroxy-3,4-dihydro-8-methylcarbostyril (20.2 g, 0.114 mol) in dimethylformamide (150 ml), sodium hydride (55%, 10 g, 0.229 mol) was added while cooling in an ice bath, and the mixture was stirred for 10 minutes. Subsequently, benzylchloride (30 ml, 0.261 mol) was added thereto. The temperature of the mixture was raised to 70° C., and the mixture was stirred for 45 minutes. Methanol (20 ml) was added to the reaction mixture while cooling in an ice bath, followed by condensing under reduced pressure. The residue was extracted from chloroform-water. The organic phase was washed with saturated aqueous NaCl solution, dried, and condensed under reduced pressure. The residue was purified by silica gel column chromatography (hexane:ethyl acetate=2:1) to obtain pale yellow crude crystals. The crude crystals were recrystallized from ethyl acetate-hexane. As a result, 26.3 g of the title compound was obtained as colorless flakes (64.6%).

mp. 115°–118° C.

IR(KBr): 3410, 1665, 1602, 1491, 1475, 1438, 1379, 1360, 1310, 1262, 1245, 1170, 1151, 1122 cm$^{-1}$.

$^1$H-NMR(CDCl$_3$)δ: 2.22(s), 2.28(s)(altogether,2H), 2.54(t,J=7.3 Hz), 2.59(t,J=7.3 Hz), (altogether,2H), 2.83(t,J=7.3 Hz), 3.02(t,J=7.3 Hz) (altogether,2H), 5.04(1H,br.s), 5.06(br.s), 5.11(br.s)(altogether,1H), 6.56(d,J=8.3 Hz), 6.66(d,J=8.3 Hz)(altogether,1H), 6.95(d,J=8.3 Hz), 6.96(d,J=8.3 Hz)(altogether,1H), 7.09 –7.40(10H,complex m).

Reference Example 45

3,4-Dihydro-5-hydroxy-3,3,8-trimethylcarbostyril

1-N-benzyl-5-benzyloxy-3,4-dihydro-8-methylcarbostyril (2.62 g, 73.4 mmol) was dissolved in anhydrous tetrahydrofuran (300 ml). To the solution, lithium diisopropylamide (LDA) (as a 1.50M cyclohexane solution, 100 ml, 150 mmol) and methyl iodide (9.4 ml, 151 mmol) were alternately added each three times every 10 minutes while cooling in an ice bath. Methanol (50 ml) was added to the reaction solution to neutralize excessive LDA, followed by extraction from ethyl acetate-water. The organic phase was washed with saturated aqueous NaCl solution, dried, and condensed under reduced pressure. The resultant residue was purified by silica gel column chromatography (hexane-:ethyl acetate=3:1). Subsequently, the residue was dissolved in acetic acid (500 ml). To the solution, 10% palladium-on-carbon (50.0 g) and 1.8N HCl-acetic acid (4 ml, 73.8 mmol) were added, and the resultant mixture was stirred at 30° C. for 45 minutes in the atmosphere of hydrogen. The reaction mixture was filtered, and the filtrate was condensed under reduced pressure. The residue was extracted from a mixture of chloroform-methanol (10:1) and saturated aqueous sodium bicarbonate solution. The organic phase was washed with saturated aqueous NaCl solution, dried, and condensed under reduced pressure. The resultant residue was purified by silica gel column chromatography (chloroform-methanol =50:1) to obtain pale yellow crude crystals, which were recrystallized from methanol-ether-hexane to obtain 12.9 g of the title compound as colorless powdery crystals (85.7%).

mp. 188°–189° C.

IR(KBr): 3287, 2859, 1651, 1640, 1610, 1508, 1472, 1395, 1370, 1314, 1283, 1233, 1168, 1052, 814, 780, 653, 598 cm$^{-1}$.

$^1$H-NMR(CD$_3$OD)δ: 1.13(6H,s), 2.13(3H,s), 2.74(2H,s), 6.42(1H,d,J=8.3 Hz), 6.81(1H,d,J=8.30 Hz).

Reference Example 46

5-Allyloxy-3,3,8-trimethylcarbostyril

Using 5-hydroxy-3,3,8-trimethylcarbostyril (2.0 g, 9.77 mmol), allyl iodide (1.72 g, 10.2 mmol), and potassium carbonate (3 g, 21.7 mmol), the procedure of Reference Example 41 was followed (reaction, post-treatment, and recrystallization from chloroform-n-hexane). 2.2 g of the title compound was obtained as colorless flakes (92.0%).

mp. 132°–134° C.

IR(KBr): 3197, 2950, 1669, 1615, 1500, 1457, 1389, 1353, 1313, 1272, 1234, 1217, 1084, 793 cm$^{-1}$.

$^1$H-NMR(CDCl$_3$)δ: 1.21(6H,s), 2.16(3H,s), 2.83(2H,s), 4.35(2H,dt,J=1.5,5.4 Hz), 5.28(1H,dt,J=1.5,10.3 Hz), 5.40(2H,ddd,J=1.5,3.4,17.1 Hz), 6.06(1H,m), 6.49(1H,d,J=8.3 Hz), 6.94(1H,d,J=8.3 Hz), 7.23(12H,s).

Reference Example 47

6-Allyl-5-hydroxy-3,3,8-trimethylcarbostyril

Using 5-allyloxy-3,3,8-trimethylcarbostyril (2.2 g, 8.98 mmol), the procedure of Reference Example 32 was followed (reaction, post-treatment, and recrystallization from ether-n-hexane). 1.54 g of the title compound was obtained as colorless prisms (70.0%).

mp. 155°–156° C.

IR(KBr): 3338, 2955, 1636, 1610, 1481, 1434, 1399, 1280, 1234, 1168, 1125, 923 cm$^{-1}$.

$^1$H-NMR(CDCl$_3$)δ: 1.22(6H,s), 2.13(3H,s), 2.78(2H,s), 3.35(2H,d,J=6.4 Hz), 5.07(1H,s), 5.19(1H,d,J=1.5 Hz), 5.24(1H,dd,J=1.5,5.4 Hz), 6.00(1H,m), 6.75(1H,s), 7.20(1H,s).

Example 299

2-Bromomethyl-5,8,8-trimethyl-2,3,6,7,8,9-hexahydrofuro[2,3-f]quinoline-7-one

Using 6-allyl-5-hydroxy-3,3,8-trimethylcarbostyril (1.36 g, 3.28 mmol) and N-bromosuccinimide (1.12 g, 6.28 mmol), the procedure of Example 277 was followed (reaction, post-treatment, and recrystallization from chloroform-ether-n-hexane). 1.93 g of the title compound was obtained as colorless needles (94.9%).

mp. 188°–190° C.

IR(KBr): 3192, 2947, 1663, 1626, 1404, 1389, 1353, 1323, 1241, 1216, 1076, 946, 822, 796 cm$^{-1}$.

$^1$H-NMR(CDCl$_3$)δ: 1.20(3H,s), 1.22(3H,s), 2.14(3H,s), 2.73(2H,s), 3.07(1H,dd,J=6.4,15.6 Hz), 3.34(1H,dd,J=9.3,15.6 Hz), 3.51(1H,dd,J=6.8,10.7 Hz), 3.60(1H,dd,J=4.9,10.7 Hz), 5.02(1H,m), 6.82(1H,s), 7.22(1H,s).

Example 300

2-Azidomethyl-5,8,8-trimethyl-2,3,6,7,8,9-hexahydrofuro[2,3-f]quinoline-7-one

Using the compound obtained in Example 299 (1.93 g 5.96 mmol) and sodium azide (2.8 g, 43.1 mmol), the procedure of Example 278 was followed (reaction, post-treatment, and recrystallization from chloroform-ether). 1.47 g of the title compound was obtained as colorless crystals (86.2%).

mp. 154°–156° C.

IR(KBr): 3196, 2087, 1653, 1627, 1471, 1390, 1296, 1281, 1240, 1079, 1048 cm$^{-1}$.

$^1$H-NMR(CDCl$_3$)δ: 1.21(6H,s), 2.14(3H,s), 2.75(2H,s), 2.96(1H,dd,J=6.8,15.6 Hz), 3.28(1H,dd,J=9.3,15.6 Hz), 3.41(1H,dd,J=6.3,13.2 Hz), 3.48(1H,dd,J=3.9,13.2 Hz), 5.00(1H,m), 6.83(1H,s), 7.21(1H,s).

Example 301

2-Aminomethyl-5,8,8-trimethyl-2,3,6,7,8,9-hexahydrofuro[2,3-f]quinoline-7-one·HCl

Using 2-azidomethyl-5,8,8-trimethyl-2,3,6,7,8,9-hexahydrofuro[2,3-f]quinoline-7-one (1.47 g, 5.14 mmol), the procedure of Example 279 was followed (reduction, post-treatment, and recrystallization from methanol-ether). 1.16 g of the title compound was obtained as pale yellow crystals (76.0%).

mp. 157°–179° C.

IR(KBr): 3375, 3202, 2951, 1665, 1475, 1389, 1354, 1334, 1291, 1239, 1078 cm$^{-1}$.

$^1$H-NMR(CD$_3$OD)δ: 1.14(3H,s), 1.17(3H,s), 2.17(3H,s), 2.73(1H,d,J=16.1 Hz), 2.77(1H,d,J=16.1 Hz), 2.94(1H,dd,J=7.3,15.6 Hz), 3.15(1H,dd,J=7.3,13.7 Hz), 3.29(1H,dd,J=3.4,13.7 Hz), 3.39(1H,dd,J=9.3,15.6 Hz), 5.00(1H,m), 6.90(1H,s).

Reference Example 48

6-(2-Methyl-2-propenyl)-5-hydroxy-3,3,8-trimethylcarbostyril

Using 5-hydroxy-3,3,8-trimethylcarbostyril (1.99 g, 9.69 mmol), 3-chloro-2-methyl-1-propene (1.08 g, 12.0 mmol), and potassium carbonate (2.67 g, 19.38 mmol), the procedure of Reference Example 41 was followed (reaction and post-treatment) to obtain 2.43 g of a crude ether. The obtained crude (2.43 g) was allowed to react and post-treated in a manner similar to that Reference Example 47, followed by purifying by silica gel column chromatography(ether:hexane =1:1). As a result, 1.37 g of the title compound was obtained as a colorless solid (54.4%).

mp. 183° C.

IR(KBr): 3450, 3400, 2950, 1668, 1620, 1484, 1388 cm$^{-1}$.

$^1$H-NMR(CDCl$_3$)δ: 1.21(6H,s), 1.61(3H,s), 2.13(3H,s), 2.78(2H,s), 3.31(2H,s), 4.91(1H,s), 4.96(1H,s), 6.73(1H,s), 7.23(1H,br.s).

Example 302

2-Bromomethyl-2,5,8,8-tetramethyl-2,3,6,7,8,9-hexahydrofuro[2,3-f]quinoline-7-one

Using 5-hydroxy-6-(2-methyl-2-propenyl)-3,3,8-trimethyl-3,4-dihydrocarbostyril (1.35 g, 5.18 mmol) and N-bromosuccinimide (968 mg, 5.44 mmol), the procedure of Example 299 was followed (reaction, post-treatment, and recrystallization from chloroform-hexane) to obtain 1.30 g of the title compound as colorless needles (74%).

mp. 158°–160° C.

IR(CHCl$_3$): 3400, 2950, 1668, 1474, 1380, 1296 cm$^{-1}$.

$^1$H-NMR(CDCl$_3$)δ: 1.20(3H,s), 1.21(3H,s), 1.62(3H,s), 2.13(3H,s), 2.71(2H,s), 2.97(1H,d,J=15.6 Hz), 3.30(1H,d,J=15.6 Hz), 3.51(2H,s), 6.79(1H,s), 7.23(1H,br.s).

Example 303

2-Azidomethyl-2,5,8,8-tetramethyl-2,3,6,7,8,9-hexahydrofuro[2,3-f]quinoline-7-one

Using 2-bromomethyl-2,5,8,8-tetramethyl-2,3,6,7,8,9-hexahydrofuro[2,3-f]quinoline-7-one (1.28 g, 3.78 mmol) and sodium azide (1.96 g, 30.1 mmol), the procedure of Example 300 was followed (reaction, post-treatment, and recrystallization from ethyl acetate-hexane) to obtain 921 mg of the title compound as colorless needles (81%).

mp. 169°–170° C.

IR(CHCl$_3$): 3600, 3400, 2920, 2092, 1667, 1628, 1474, 1388, 1292 cm$^{-1}$.

$^1$H-NMR(CDCl$_3$)δ: 1.18(3H,s), 1.22(3H,s), 1.51(3H,s), 2.14(3H,s), 2.73(3H,s), 2.92(1H,d,J=15.6 Hz), 3.12(1H,d,J=15.6 Hz), 3.29(1H,d,J=12.7 Hz), 3.35(1H,d,J=12.7 Hz), 6.80(1H,s), 7.25(1H,br.s).

Example 304

2-Aminomethyl-2,5,8,8-tetramethyl-2,3,6,7,8,9-hexahydrofuro[2,3-f]quinoline-7-one·HCl

Using 2-azidomethyl-2,5,8,8-tetramethyl-2,3,6,7,8,9-hexahydrofuro[2,3-f]quinoline-7-one (1.03 g, 3.43 mmol), the procedure of Example 301 was followed (reaction, post-treatment, and recrystallization from methanol-ether) to obtain 864 mg of the title compound as colorless needles (81%).

mp. 156°–157° C.

IR(KBr): 3417, 3200, 2910, 1661, 1626, 1475, 1390 cm$^{-1}$.

$^1$H-NMR(CDCl$_3$—CD$_3$OD(5:1))δ: 1.18(3H,s), 1.20(3H,s), 1.56(3H,s), 2.15(3H,s), 2.69(1H,d,J=16.1 Hz), 2.77(1H,d,J=16.1 Hz), 3.01(1H,d,J=16.1 Hz), 3.19(2H,s), 3.22((1H,d,J=16.1 Hz), 6.82(1H,s).

Reference Example 49

5-(2-Butenyloxy)-3,3,8-trimethyl-3,4-dihydrocarbostyril

To a solution of 5-hydroxy-3,3,8-trimethyl-3,4-dihydrocarbostyril (23 g, 11.2 mmol) and potassium carbonate (3.1 g, 22.4 mmol) in dimethylformamide (20 ml), crotyl bromide (1.8 g, 13.4 mmol) was added and stirred at 70° C. for 2 hours. The reaction mixture was poured into ice-water, and precipitated crystals were collected by filtration. The collected crude crystals were dissolved in chloroform, washed with water, and dried. The solvent was evaporated, and the residue was recrystallized from chloroform-hexane. 1.9 g of the title compound was obtained as colorless needles (65.4%).

mp. 154°–155° C.

IR(CHCl$_3$): 1671, 1617, 1497, 1388, 1309, 1267, 1085 cm$^{-1}$.

$^1$H-NMR(CDCl$_3$)δ: 1.21(6H,s), 1.76(3H,d,J=6 Hz), 2.16(3H,s), 2.81(2H,s), 4(2H,d,J=6 Hz), 5.63–5.91(2H,m), 6.49(1H,d,J=8 Hz), 6.93(1H,d,J=8 Hz).

Reference Example 50

5-Hydroxy-6-(1-methyl-2-propenyl)-3,3,8-trimethyl-3,4-dihydrocarbostyril

A solution of 5-(2-butenyloxy)-3,3,8-trimethyl-3,4-dihydrocarbostyril (1.9 g, 7.3 mmol) in N,N-dimethylaniline (5 ml) was stirred at 210° C. for 7 hours in the stream of argon gas. After spontaneous cooling, the reaction mixture was diluted with hexane, and the precipitated crystals were collected by filtration. The obtained crude crystals were recrystallized from ethyl acetate-hexane to obtain 1.7 g of the title compound as colorless needles (89.3%).

mp. 137°–138° C.

IR(CHCl$_3$): 2957, 1667, 1483, 1388 cm$^{-1}$.

$^1$H-NMR(CDCl$_3$)δ: 1.21(6H,s), 1.40(3H,d,J=5 Hz), 2.15(3H,s), 2.78(2H,s), 3.50(1H,quintet,J=2 Hz), 5.20–5.30(2H,m), 6.06(1H,m), 6.78(1H,s).

Example 305

2-Bromomethyl-3,5,8,8-tetramethyl-2,3,6,7,8,9-hexahydrofuro[2,3-f]quinoline-7-one A solution of 5-hydroxy-6-(1-methyl-2-propenyl)-3,3,8-trimethyl- 3,4-dihydrocarbostyril (1.6 g, 6.2 mmol) and N-bromosuccinimide (1.2 g, 6.5 mmol) in chloroform (20 ml) was refluxed while stirring for 1 hour. Chloroform was added to the reaction mixture, followed by washing with water, and drying. The solvent was evaporated, and the residue was recrystallized from ethyl acetate-hexane. 1.9 g of the title compound was obtained as colorless crystals (90.6%).

mp. 192°–193° C.

IR(KBr): 1669, 1473 cm$^{-1}$.

$^1$H-NMR(CDCl$_3$)δ: 1.22(6H,s), 1.21(d,J=7 Hz), 1.37(d, J=7 Hz)(altogether,3H), 2.15(3H,s), 2.73(2H,s), 3.32(m), 3.54(m)(altogether,3H), 4.48(m), 4.89(m)(altogether,1H), 7.19(1H,s), 7.26(1H,s).

Example 306

2-Azidomethyl-3,5,8,8-tetramethyl-2,3,6,7,8,9-hexahydrofuro[2,3-f]quinoline-7-one A solution of 2-bromomethyl-3,5,8,8-tetramethyl-2,3,6,7,8,9-hexahydrofuro[2,3-f]quinoline-7-one (1.8 g, 5.3 mmol) and 90% sodium azide (3.1 g, 42 mmol) in dimethylformamide (30 ml) was stirred at 150° C. for 2 hours. The reaction mixture was poured in water, followed by extracting with ethyl acetate. The extract was washed with water, and dried. The solvent was evaporated, and the residue was recrystallized from ethyl acetate-hexane. 1.2 g of the title compound was obtained as colorless needles (75.5%).

mp. 181°–182° C.

IR(KBr): 2090, 1669, 1473, 1389, 1290 cm$^{-1}$.

$^1$H-NMR(CDCl$_3$)δ: 1.22(6H,s), 1.23(d,J=7 Hz), 1.33(d, J=7 Hz)(altogether,3H), 2.16(3H,s), 2.76(2H,s), 3.34(m), 3.52(m)(altogether,3H), 4.45(m), 4.89(m)(altogether,1H), 6.77(1H,s,4-H).

Example 307

Trans-2-aminomethyl-3,5,8,8-tetramethyl-2,3,6,7,8,9-hexahydrofuro[2,3-f]quinoline-7-one·HCl Cis-2-aminomethyl-3,5,8,8-tetramethyl-2,3,6,7,8,9-hexahydrofuro[2,3-f]quinoline-7-one·HCl 2-Azidomethyl-3,5,8,8-tetramethyl-2,3,6,7,8,9-hexahydrofuro[2,3-f]quinoline-7-one (1.2 g, 3.8 mmol) was dissolved in tetrahydrofuran (20 ml). To the resultant solution, methanol (20 ml) and 10% palladium-on-carbon (400 mg) were added, followed by stirring for 1 hour in the stream of hydrogen. The catalyst was filtered off and the solvent was evaporated. 980 mg of crude crystals were obtained, and they were separated and purified by silica gel column chromatography (chloroform-methanol=10:1). The resultant crystals were separately dissolved in methanol, followed by adding 1.37 N-HCl/methanol. The solvent was evaporated, and the residue was recrystallized from methanol-ether. 320 mg of the title compound in a trans- form and 230 mg of the title compound in a cis- form were obtained.

Trans Compound mp. 222°–223° C.

IR(KBr): 3411, 2953, 1656, 1476, 1389, 1241 cm$^{-1}$.

$^1$H-NMR(CD$_3$OD+CDCl$_3$)δ: 1.20(6H,s), 1.37(3H,d,J=7 Hz), 2.17(3H,s), 2.73(2H,s), 3.08–3.33(3H,m), 4.54(1H,m), 6.80(1H,s).

Cis Compound mp. 271°–273° C.

IR(KBr): 3401, 2954, 1660, 1473, 1389, 1239, 1060 cm$^{-1}$.

$^1$H-NMR(CD$_3$OD+CDCl$_3$)δ: 1.18(6H,s), 1.21(3H,d,J=6 Hz), 2.18(3H,s), 2.75(2H,s), 3.05–3.30(3H,m), 4.97(1H,m), 6.80(1H,s).

Reference Example 51

N-(2-Methyl-5-methoxyphenyl)butylamide

5-Methoxy-2-methylaniline (12.3 g, 89.8 mmol) was dissolved in pyridine (100 ml). To the resultant solution, butyl anhydride (17.0 g, 107.7 mmol) was added, and the mixture was stirred at room temperature for 1 hour and 30 minutes. Methanol (10 ml) was added thereto and stirred for 20 minutes. Subsequently, The reaction mixture was condensed under reduced pressure. The resultant residue was extracted from ethyl acetate-aqueous 1N-HCl solution. The organic phase was washed with aqueous 50% NaCl solution, and dried over sodium sulfate, followed by condensing under reduced pressure. The residue was recrystallized from ethyl acetate-hexane to obtain 15.8 g of the title compound as colorless needles (85.0%).

mp. 85°–86° C.

IR(KBr): 3278, 1653, 1615, 1586, 1528, 1494, 1455, 1412, 1312, 1219, 1039 cm$^{-1}$.

$^1$H-NMR(CDCl$_3$)δ: 1.03(3H,t), 1.72–1.85(2H,m), 2.19(3H,s), 2.38(2H,t,J=7.6 Hz), 3.79(3H,s), 6.63(1H,d,J= 8.3 Hz), 6.91(1H,br.s), 7.06(1H,d,J=8.3 Hz), 7.65(1H,br.s).

Reference Example 52

2-Chloro-3-ethyl-5-methoxy-8-methylquinoline

To the compound obtained in Reference Example 51 (15.8 g, 76.3 mmol), dimethylformamide (10 ml) was added. while cooling on ice, phosphorus oxychloride (70 ml) was added to the resultant mixture and dissolved. After completely dissolved, the solution was heated to 70° C., and stirred for 30 minutes. The reaction mixture was cooled to 0° C., and thereafter, ice was added to the mixture until generation of gas is no more observed. Extraction was performed using ethyl acetate. The organic phase was washed with aqueous 50% NaCl solution, and dried over sodium sulfate, followed by condensing under reduced pressure. The residue was separated and purified by silica gel column chromatography (hexane:ethyl acetate=10:1) to obtain 6.24 g of the title compound as colorless powdery crystals (34.7%).

mp. 101°–102° C.

IR(KBr): 2956, 1611, 1587, 1477, 1381, 1314, 1265, 1215, 1100, 926, 806, 727 cm$^{-1}$.

$^1$H-NMR(CDCl$_3$)δ: 1.35(3H,t,J=7.5 Hz), 2.66(3H,s), 2.91(2H,q,J=7.5 Hz), 3.97(3H,s), 6.75(1H,d,J=7.8 Hz), 7.39(1H,d,J=7.8 Hz), 8.36(1H,s).

Reference Example 53

3-Ethyl-5-methoxy-8-methylcarbostyril

Acetic acid (50 ml) and water (10 ml) were added to the compound obtained in Reference Example 52 (6.24 g, 26.5 mmol), and the mixture was stirred at 120° C. for 19 hours. The reaction mixture was condensed under reduced pressure, and the resultant residue was recrystallized from chloroform-methanol-hexane. As a result, 4.88 g of the title compound was obtained colorless powdery crystals (86.8%).

mp. 195°–197° C.

IR(KBr): 3162, 2997, 1652, 1607, 1497, 1450, 1388, 1293, 1254, 1099, 910, 792 cm$^{-1}$.

$^1$H-NMR(CDCl$_3$)δ: 1.28(3H,t,J=7.4 Hz), 2.34(3H,s), 2.67(2H,q,J=7.4 Hz), 3.92(3H,s), 6.54(1H,d,J=8.3 Hz), 7.18(1H,d,J=8.3 Hz), 8.00(1H,s), 8.70(1H,br.s).

Reference Example 54

3-Ethyl-5-hydroxy-8-methylcarbostyril

The compound obtained in Reference Example 53 (4.88 g, 22.5 mmol) was suspended in chlorobenzene (80 ml). Anhydrous aluminum chloride (9.00 g, 67.5 mmol) was added to the suspension, and stirred at 100° C. for 2 hours. The reaction mixture was cooled on ice. When ic was added to the mixture, crystals were precipitated. The precipitated crystals were collected by filtration, followed by washing with hexane. 4.43 g of colorless powdery crystals were obtained (96.9%).

mp. 267°–270° C.

IR(KBr): 3357, 3059, 1634, 1608, 1579, 1379, 1356, 1259, 1161, 1074, 820 cm$^{-1}$.

$^1$H-NMR(CD$_3$OD)δ: 1.26(3H,t,J=7.4 Hz), 2.35(3H,s), 2.62(2H,q,J=7.4 Hz), 6.54(1H,d,J=7.8 Hz), 7.11(1H,d,J=7.8 Hz), 8.10(1H,s).

Reference Example 55

5-Allyoxy-3-ethyl-8-methylcarbostyril

To a solution of the compound obtained in Reference Example 54 (3.00 g, 14.8 mmol) in dimethylformamide (50 ml), anhydrous potassium carbonate (4.07 g, 29.5 mmol) and allyl iodide (2.00 ml, 22.1 mmol) were added. The mixture was stirred at 70° C. for 90 minutes. The reaction mixture was condensed under reduced pressure. The resultant residue was extracted from chloroform-aqueous caustic soda solution. The organic phase was washed with saturated aqueous NaCl solution, dried over sodium sulfate, and condensed under reduced pressure. The residue was recrystallized from chloroform-ether to obtain 2.58 g of the title compound as colorless powdery crystals (71.8%).

mp. 184°–185° C.

IR(KBr): 3161, 3003, 2867, 1653, 1607, 1498, 1451, 1420, 1391, 1260, 1235, 1091, 999, 926, 785 cm$^{-1}$.

$^1$H-NMR(CDCl$_3$)δ: 1.28(3H,t,J=7.3 Hz), 2.36(3H,s), 2.67(2H,q,J=7.3 Hz), 5.34(1H,dd,J=1.5,10.7 Hz), 5.47(1H, dd,J=1.5,17.1 Hz), 6.12(1H,m), 6.53(1H,d,J=8.3 Hz), 7.16(1H,d,J=8.3 Hz), 8.04(1H,s), 8.96(1H,br.s).

Reference Example 56

6-Allyl-3-ethyl-5-hydroxy-8-methylcarbostyril

The compound obtained in Reference Example 55 (2.58 g 10.6 mmol) was suspended in N,N-dimethylaniline (18 ml). The suspension was heated and dissolved while stirring at 200° C. for 90 minutes. The reaction mixture was cooled to room temperature, and n-hexane was added thereto. Precipitated crystals were collected, and recrystallized from chloroform-hexane. 2.45 g of the title compound was obtained as colorless needles (94.8 g).

mp. 226°–229° C. (dec.)

IR(KBr): 3272, 3066, 2954, 1630, 1579, 1485, 1447, 1355, 1305, 1246, 1214, 1165, 994, 925, 803, 772, 568 cm$^{-1}$.

$^1$H-NMR(CD$_3$OD)δ: 1.26(3H,t,J=7.5 Hz), 2.34(3H,s), 2.62(2H,q,J=7.5 Hz), 3.40(2H,d,J=6.4 Hz), 4.92(1H,m), 5.03(1H,s), 5.96(1H,m), 7.05(1H,s), 8.13(1H,s).

Example 308

2-Bromomethyl-8-ethyl-5-methyl-6,7-dihydrofuro[2,3-f]quinoline-7-one

To a solution of the compound obtained in Reference Example 56 (2.37 g, 7.74 mmol) in chloroform (60 ml), N-bromosuccinimide (1.82 g, 10.2 mmol) was added, and the solution was stirred at room temperature for 20 minutes. The reaction liquid was extracted from chloroform-water. The organic phase was dried over sodium sulfate, and condensed under reduced pressure. The resultant residue was recrystallized from chloroform-hexane. 3.07 g of the title compound was obtained as pale yellow powdery crystals (97.7%).

mp. 237°–240° C.

IR(KBr): 3155, 3017, 1645, 1613, 1588, 1480, 1447, 1258, 1212, 1085, 939, 916, 880, 828, 616 cm$^{-1}$.

$^1$H-NMR(CDC$_3$)δ: 1.27(3H,t,J=7.4 Hz), 2.33(3H,s), 2.65(2H,q,J=7.4 Hz), 3.17(1H,dd,J=6.8,15.4 Hz), 3.43(1H, dd,J=9.7,15.4 Hz), 3.57(1H,dd,J=6.8,10.4 Hz), 3.67(1H,dd, J=4.6,10.4 Hz), 5.14(1H,m), 7.07(1H,s), 7.27(1H,s), 7.71(1H,br.s).

Example 309

2-Azidomethyl-8-ethyl-5-methyl-6,7-dihydrofuro[2,3-f]quinoline-7-one

To a solution of the compound obtained in Example 308 (3.04 g, 9.45 mmol) in dimethylformamide (150 ml), sodium azide (1.54 g, 26.6 mmol) was added, and the solution was stirred at 120° C. for 100 minutes. The reaction liquid was condensed under reduced pressure, and the residue was extracted from a solvent mixture of chloroform-methanol (4:1). The organic phase was washed with saturated aqueous NaCl solution, dried over sodium sulfate, and condensed under reduced pressure. The resultant residue was recrystallized from chloroform-methanol-hexane. 2.28 g of the title compound was obtained as colorless needles (84.6%).

mp. 182°–183° C.

IR(KBr): 2938, 2089, 1643, 1614, 1589, 1482, 1451, 1258 cm$^{-1}$.

$^1$H-NMR(CDCl$_3$)δ: 1.26(3H,t,J=7.4 Hz), 2.33(3H,s), 2.65(2H,q,J=7.4 Hz), 3.04(1H,dd,J=6.6,15.4 Hz), 3.38(1H, dd,J=9.5,15.4 Hz), 3.52(2H,dd,J=4.9 Hz), 5.12(1H,m), 7.08(1H,s), 7.72(1H,s), 8.60(1H,br.s).

Example 310

2-Aminomethyl-2-ethyl-5-methyl-6,7-dihydrofuro[2,3-f]quinoline-7-one·HCl

To a solution of the compound obtained in Example 309 (2.27 g, 7.98 mmol) in dimethylformamide (100 ml), 10% palladium-on-carbon (2.27 g) was added, followed by stirring at room temperature for 1 hour in the atmosphere of hydrogen. The reaction liquid was condensed under reduced pressure, and the residue was recrystallized from chloroform-methanol-hexane. The resultant colorless powdery crystals (1.38 g) were suspended in methanol (80 ml). 1.37N HCl-methanol (4.08 ml, 5.60 mmol) was added thereto and the mixture was dissolved, The reaction mixture was condensed under reduced pressure. The residue was recrystallized from methanol-hexane. 1.08 g of the title compound was obtained as pale yellow powdery crystals (45.8%).

mp. >270° C.

IR(KBr): 3389, 2949, 1640, 1615, 1589, 1478, 1451, 1264, 1089, 941, 827, 639 cm$^{-1}$.

$^1$H-NMR(CD$_3$OD)δ: 1.25(3H,t,J=7.5 Hz), 2.38(3H,s), 2.61(2H,q,J=7.5 Hz), 3.04(1H,dd,J=7.3,15.6 Hz), 3.25(2H, br.), 3.50(1H,dd,J=9.3,15.6 Hz), 5.17(1H,m), 7.20(1H,s), 7.87(1H,s).

Example 311

2-Aminomethyl-8-ethyl-5-methyl-6,7,8,9-tetrahydrofuro[2,3-f]quinoline-7-one·HCl The compound obtained in Example 310 (619 mg, 2.10 mmol) was dissolved in water (40 ml) and methanol (10 ml). To the solution, 10% palladium-on-carbon (620 mg) was added, followed by stirring at 80° C. for 5 hours in the atmosphere of hydrogen. The reaction mixture was filtered, and the filtrate was condensed under reduced pressure. The residue was recrystallized from methanol-hexane. 447 mg of the title compound was obtained as pale red powdery crystals (71.7%).

mp. 274°–276° C.

IR(KBr): 3193, 2947, 1670, 1628, 1479, 1443, 1393, 1341, 1312, 1214, 1101, 967, 930 cm$^{-1}$.

$^1$H-NMR(CD$_3$OD)δ: 0.98–1.04(3H,m), 1.43–1.53(1H,m), 1.77–1.85(1H,m), 2.16(3H,s), 2.36–2.41(1H,m), 2.67–2.72(1H,m), 2.89–3.04(2H,m), 3.12–3.20(1H,m), 3.32–3.41(1H,m), 5.01(1H,br.), 6.89(1H, s), 7.86(1H,s).

Reference Example 57

3-Ethyl-8-methyl-5-(3-methyl-2-butenyl)oxycarbostyril

The compound obtained in Reference Example 54 (1.70 g, 8.36 mmol) was dissolved in dimethylformamide (40 ml). To the solution, potassium carbonate (2.31 g, 16.7 mmol) and 1-bromo-3-methyl-butene (1.31 g, 8.78 mmol) were added, and stirred at 70° C. for 3 hours. The reaction mixture was condensed under reduced pressure, and the residue was extracted from chloroform-aqueous 1N-caustic soda solution. The organic phase was washed with saturated aqueous NaCl solution, dried, and condensed under reduced pressure. The resultant residue was recrystallized from chloroform-ether. 1.88 g of the title compound was obtained as colorless powdery crystals (80.0%).

mp. 178°–179° C.

IR(KBr): 3158, 3000, 1639, 1583, 1498, 1445, 1386, 1334, 1297, 1259, 1090, 997, 924, 836, 791 cm$^{-1}$.

$^1$H-NMR(CDCl$_3$)δ: 1.27(3H,t,J=7.3 Hz), 1.77(3H,s), 1.82(3H,s), 2.35(1H,s), 2.67(2H,q,J=7.3 Hz), 4.62(2H,d,J= 6.4 Hz), 5.55(1H,m), 6.54(1H,d,J=8.3 Hz), 7.16(1H,d,J=8.3 Hz), 8.02(1H,s), 8.82(1H,br.s).

Reference Example 58

3-Ethyl-5-hydroxy-8-methyl-6-(1,2-dimethyl-2-propenyl)carbostyril

The compound obtained in Reference Example 57 (1.81 g 6.67 mmol) was suspended in N,N-dimethylaniline (12 ml). The suspension was heated and dissolved while stirring at 200° C. for 2 hours and 30 minutes. The reaction system was cooled to room temperature, and hexane was added thereto. Precipitated crystals were collected by filtration, and recrystallized from chloroform-hexane. 1.62 g of the title compound was obtained as pale yellow powdery crystals (89.5 %).

mp. 146°–147° C.

IR(KBr): 3149, 2953, 1636, 1585, 1444, 1389, 1295, 1261, 1176, 1112, 1077, 919, 880, 806, 650, 584 cm$^{-1}$.

$^1$H-NMR(CDCl$_3$)δ: 1.27(3H,t,J=7.3 Hz), 1.46(3H,t,J=7.2 Hz), 1.68(3H,s), 2.33(3H,s), 2.66(2H,q,J=7.3 Hz), 3.48(1H, q,J=7.2 Hz), 5.13(1H,s), 5.21(1H,s), 6.13(1H,br.s), 7.02(1H, s), 7.97(1H,s), 8.61(1H,br.s).

Example 312

2-Azidomethyl-8-ethyl-2,3,5-trimethyl-6,7-dihydrofuro[2,3-f]quinoline-7-one

To a solution of the compound obtained in Reference Example 58 (1.53 g, 5.64 mmol) in a solvent mixture of chloroform-methanol (4:1) (30 ml), potassium carbonate (3.89 g, 28.2 mmol) was added and cooled to −20° C. Iodine (1.58 g, 6.21 mmol) and potassium iodide (1.03 g, 6.21 mmol) were dissolved in chloroform-methanol (4:1), and this solution was added to the cooled mixture, followed by stirring at −20° C. for 18 hours. The reaction mixture was extracted from chloroform-aqueous sodium sulfite. The organic phase was washed with saturated aqueous NaCl solution, dried, and condensed under reduced pressure. The resultant residue was separated and purified by silica gel column chromatography (chloroform:methanol=10:1) to obtain an iodide (229 mg, 0.58 mmol, 10.3%). The iodide was dissolved in dimethylformamide (10 ml), to which sodium azide (375 mg, 5.77 mmol) was added, followed by stirring at 150° C. for 4 hours. The reaction mixture was condensed under reduced pressure, and the resultant residue was extracted from chloroform-water. The organic phase was washed with saturated aqueous NaCl solution, dried over sodium sulfate, and condensed under reduced pressure. The resultant residue was separated and purified by silica gel chromatography (chloroform:ethyl acetate=3:1) to obtain 73 mg of the title compound (syn:anti=3:2) as pale yellow powdery crystals (40.5%).

mp. 174°–176° C.

IR(KBr): 3156, 3008, 2868, 2090, 1640, 1616, 1588, 1479, 1448, 1380, 1322, 1286, 1092, 1065, 850, 818 cm$^{-1}$.

$^1$H-NMR(CDCl$_3$)δ: 1.25(3H,t,J=7.3 Hz), 1.27(3H,t,J=7.3 Hz), 1.44(s), 1.60(s)(altogether,3H), 2.33(3H,s), 2.65(2H,q, J=7.3 Hz), 3.18(d,J=13.2 Hz), 3.31(d,J=12.7 Hz),(altogether,1H), 3.34(1H,m), 3.46(d,J=12.7 Hz), 3.54(d,J=13.2

Hz)(altogether,1H), 6.98(s), 7.02(s)(altogether,1H), 7.74(s), 7.75(s)(altogether,1H), 8.50(1H,br.s).

Example 313

2-Aminomethyl-2-ethyl-2,3,5-trimethyl-6,7-dihydrofuro[2,3-f]quinoline-7-one·HCl

To a solution of the compound obtained in Example 312 (70.0 mg, 0.22 mmol) in tetrahydrofuran (15 ml), 10% palladium-on-carbon (70.0 mg) was added, followed by stirring at room temperature for 2 hours in the atmosphere of hydrogen. The reaction mixture was filtered, and the filtrate was condensed under reduced pressure. The residue was separated and purified by silica gel chromatography (chloroform:methanol=15:1) to obtain 52.0 mg of an amino compound (0.18 mmol). The amino compound was dissolved in methanol (5 ml), to which 1.37N HCl -methanol (146 μl, 0.20 mmol) was added. The reaction mixture was condensed under reduced pressure, and the residue was recrystallized from methanol-ether. As a result, 52.7 mg of the title compound was obtained as pale yellow powdery crystals (syn: anti=3:2) (72.9%).

mp. 272°–275° C. (dec.)

IR(KBr): 3396, 3152, 2955, 1646, 1615, 1588, 1495, 1448, 1382, 1261, 1097, 1037, 879, 816 cm$^{-1}$.

$^1$H-NMR(CD$_3$OD)δ: 1.26(3H,t,J=7.4 Hz), 1.32(3H,d,J= 6.8 Hz), 1.47(s), 1.63(s)(altogether,3H), 2.40(3H,s), 2.62(2H,q,7.4 Hz), 3.06–3.37(2H,complex), 3.49–3.62(1H, m), 7.16(s), 7.18(s)(altogether,1H), 7.88(s), 7.90(s)(altogether,1H).

Reference Example 59

3-Ethyl-5-(2-methyl-2-propenyl)oxy-8-methylcarbostyril

Using 3-ethyl-5-hydroxy-8-methylcarbostyril (0.91 g, 4.87 mmol) and 3-chloro-2-methyl-1-propene (0.485 g, 5.36 mmol), the procedure of Reference Example 31 was followed (reaction, post-treatment, and recrystallization from chloroform-n-hexane) to obtain 0.94 g of the title compound as pale brown crystals (75.1%).

mp. 181°–182° C.

IR(KBr): 3159, 2905, 1637, 1605, 1583, 1497, 1453, 1257, 1232, 1086, 795 cm$^{-1}$.

$^1$H-NMR(CDCl$_3$):1.28(3H,t,J=7.3 Hz), 1.88(3H,s), 2.36(3H,s), 2.66(2H,dq,J=7.3,1.0 Hz), 4.54(2H,s), 5.04(1H, s), 5.14(1H,s), 6.53(1H,d,J=8.3 Hz), 7.15(1H,d,J=8.3 Hz), 8.04(1H,d,J=8.3 Hz), 8.92(1H,s).

Reference Example 60

3-Ethyl-6-(2-methyl-2-propenyl)-5-hydroxy-8-methylcarbostyril

Using 3-ethyl-5-(2-methyl-2-propenyl)oxy-8-methylcarbostyril (0.94 g, 3.66 mmol), the procedure of Reference Example 32 was followed (reaction, post-treatment, and recrystallization from chloroform-methanol-n-hexane) to obtain 710 mg of the title compound as pale yellow crystals (75.5%).

mp. 222°–224° C.

IR(KBr): 3310, 1635, 1605, 1578, 1444, 1351, 1247, 1219 cm$^{-1}$.

$^1$H-NMR (CDCl$_3$) δ: 1.27(3H,t,J=7.3 Hz), 1.74(3H,s), 2.36(3H,s), 2.67(2H,q,J=7.3 Hz), 3.40(2H,s), 4.97(1H,s), 5.00(1H,s), 5.47(1H,s), 6.98(1H,s), 7.98(1H,s), 8.66(1H,s).

Example 314

2-Bromomethyl-8-ethyl-2,5-dimethyl-2,3,6,7-tetrahydrofuro[2,3-f]quinoline-7-one

Using 3-ethyl-6-(2-methyl-2-propenyl)-5-hydroxy-8-methylcarbostyril (710 mg, 2.76 mmol) and N-bromosuccinimide (516 mg, 2.90 mmol), the procedure of Example 227 was followed (reaction, post-treatment, and recrystallization from chloroform-n-hexane) to obtain 920 mg of the title compound as pale yellow crystals (99.2%).

mp. 231°–232° C.

IR(KBr): 3170, 2960, 1639, 1587, 1477, 1444, 1310, 1262, 1244, 1074, 1047, 817 cm$^{-1}$.

$^1$H-NMR(CDCl$_3$)δ: 1.28(3H,t,J=7.3 Hz), 1.68(3H,s), 2.34(3H,s), 2.64(2H,dq,J=7.3,1.0 Hz), 3.06(1H,d,J=15.6 Hz), 3.41(1H,d,J=15.6 Hz), 3.58(2H,s), 7.05(1H,s), 7.70(1H,d,J=1.0 Hz), 8.76(1H,s).

Example 315

2-Azidomethyl-8-ethyl-2,5-dimethyl-2,3,6,7-tetrahydrofuro[2,3-f]quinoline-7-one

Dimethylformamide (21 ml) was added to a mixture of 2-bromomethyl-8-ethyl-2,5-dimethyl-2,3,6,7-tetrahydrofuro[2,3-f]quinoline-7-one (920 mg, 2.74 mmol) and sodium azide (1.30 g, 19.9 mmol). The procedure of Example 278 was followed (reaction, post-treatment, and recrystallization from chloroform-n-hexane) to obtain 740 mg of the title compound as colorless needles (80.9%).

mp. 211°–212° C.

IR(KBr): 2950, 2900, 1078, 1636, 1587, 1480, 1447, 1297, 1258, 1079, 813 cm$^{-1}$.

$^1$H-NMR(CDCl$_3$)δ: 1.26(3H,t,J=7.3 Hz), 1.57(3H,s), 2.34(3H,s), 2.66(2H,dq,J=7.3,1.0 Hz), 3.02(1H,d,J=15.6 Hz), 3.21(1H,d,J=15.6 Hz), 3.42(2H,s), 7.05(1H,s), 7.71(1H,d,J=1.0 Hz), 8.73(1H,s).

Example 316

2-Aminomethyl-8-ethyl-2,5-dimethyl-2,3,6,7-tetrahydrofuro[2,3-f]quinoline-7-one·HCl Using 2-azidomethyl-8-ethyl-2,5-dimethyl-2,3,6,7-tetrahydrofuro[2,3-f]quinoline-7-one (740 mg, 2.48 mmol), the procedure of Example 279 was followed (reduction, post-treatment, and recrystallization from methanol-ether) to obtain 650 mg of the title compound as pale yellow crystals (85.0%).

mp. >250° C.

IR(KBr): 2960, 1640, 1613, 1588, 1480, 1450, 1263, 1086, 815 cm$^{-1}$.

$^1$H-NMR(CD$_3$OD)δ: 1.26(3H,t,J=7.3 Hz), 1.61(3H,s), 2.39(3H,s), 2.62(2H,dq,J=7.3,1.0 Hz), 3.17(1H,d,J=15.6 Hz), 3.27(1H,d,J=15.6 Hz), 3.29(2H,s), 7.18(1H,s), 7.84(1H,d,J=1.0 Hz).

Example 317

2-Aminomethyl-8-ethyl-2,5-dimethyl-2,3,6,7,8,9-hexahydrofuro[2,3-f]quinoline-7-one·HCl A hydrochloric aid salt (400 mg, 1.30 mmol) of 2-aminomethyl-8-ethyl-2,5-dimethyl-2,3,6,7-tetrahydrofuro[2,3-f]quinoline-7-one was suspended in a mixture of water (70 ml) and methanol (15 ml). To the suspension, 10% palladium-on-carbon (400 mg) was added, followed by stirring in a bath at 80° C. for 13 hours in the atmosphere of hydrogen. The procedure of Example 280 was followed (post-treatment, and recrystallization from methanol-ether) to obtain 279 mg of the title compound as colorless crystals (69.1%).

mp. 273°–274° C.

IR(KBr): 3197, 2914, 1659, 1625, 1474, 1447, 1391, 1379, 1338, 1279, 1254, 1081 cm$^{-1}$.

$^1$H-NMR(CD$_3$OD)δ: 1.01(3H,t,J=7.8 Hz), 1.46(1H,m), 1.53(3H,s), 1.80(1H,m), 2.17(3H,s), 2.39(1H,m), 2.66(1H, dd,J=16.1,8.3 Hz), 3.02(1H,dd,J=16.1,6.9 Hz), 3.05(1H,d, J=16.1 Hz), 3.18(1H,d,J=16.1 Hz), 3.21(2H,s), 6.87(1H,s).

Reference Example 60

N-(2-Methyl-5-methoxyphenyl)isovalerylamide

To a solution of 5-methoxy-2-methylaniline (12.1 g, 83.3 mmol) in dichloromethane (100 ml), pyridine (8 ml, 99.8 mmol) and isovaleroyl chloride (11.9 g, 98.4 mmol) were added. The mixture was heated up to room temperature with stirring for 3 hours. Methanol (5 ml) was added to the reaction mixture while cooling in an ice bath. After 10 minutes of stirring, extraction was performed from chloroform-water. The organic phase was washed with saturated aqueous NaCl solution, dried, and condensed under reduced pressure. The residue was recrystallized from ether-hexane to obtain 12.4 g (63.5%) of the title compound as colorless powdery crystals.

mp. 110°–111° C.

IR(KBr): 3391, 3214, 2950, 1639, 1583, 1539, 1498, 1464, 1424, 1365, 1290, 1246, 1213, 1159, 1130, 1132, 853, 803, 718 cm$^{-1}$.

$^1$H-NMR(CDCl$_3$)δ: 1.04(6H,d,J=5.86 Hz), 2.19(3H,s), 2.22(1H,m), 2.25(2H,br.s), 3.79(3H,s), 6.63(1H,br.d,J=8.30 Hz), 6.89(1H,br.), 7.06(1H,d,J=8.30 Hz), 7.63(1H,br.s).

Reference Example 61

2-Chloro-3-isopropyl-5-methoxy-8-methylquinoline

Dimethylformamide (14 ml) was added to N-(2-methyl-5-methoxyphenyl)isovalerylamide (12.4 g, 56.1 mmol). Phosphorus oxychloride (90 ml) was added to the mixture until dissolved while stirring in an ice bath. Subsequently, the solution was stirred at room temperature for 1 hour, followed by heating at 70° C. and stirring for 2 hours. The reaction mixture was condensed under reduced pressure. Ice-water was poured into the resultant residue, followed by extracting from chloroform-water. The organic phase was washed with saturated aqueous NaCl solution, dried over sodium sulfate, and condensed under reduced pressure. The residue was separated and purified by silica gel column chromatography (hexane:ethyl acetate=4:1) to obtain pale yellow crude crystals. They were recrystallized from chloroform-hexane to obtain 2.65 g of the title compound as colorless needles (18.9%).

mp. 74°–76° C.

IR(KBr): 2951, 1724, 1701, 1613, 1587, 1500, 1476, 1460, 1436, 1384, 1370, 1320, 1265, 1213, 1140, 1104, 1035, 935, 810, 729 cm$^{-1}$.

$^1$H-NMR(CDCl$_3$)δ: 1.36(6H,d,J=6.84 Hz), 2.65(3H,s), 3.48(1H,septet,J=6.84 Hz), 3.98(3H,s), 6.74(1H,d,J=7.82 Hz), 7.38(1H,d,J=7.82 Hz), 8.41(1H,s).

Reference Example 62

3-Isopropyl-5-methoxy-8-methylcarbostyril

2-Chloro-3-isopropyl-5-methoxy-8-methylquinoline (2.65 g, 10.6 mmol) was dissolved in acetic acid (70 ml), and the solution was stirred at 120° C. for 15 hours. The reaction solution was condensed under reduced pressure, and the resultant residue was recrystallized from chloroform-ethyl acetate. 2.10 g of the title compound was obtained as pale yellow powdery crystals (85.6%).

mp. 248°–250° C.

IR(KBr): 3159, 2941, 1632, 1620, 1578, 1498, 1452, 1386, 1262, 1240, 1103, 1082, 991, 801, 788 cm$^{-1}$.

$^1$H-NMR(CDCl$_3$)δ: 1.27(6H,d,J=6.84 Hz), 2.39(3H,s), 3.28(1H,septet,J=6.84 Hz), 3.93(3H,s), 6.55(1H,d,J=8.30 Hz), 7.19(1H,d,J=8.30 Hz), 8.04(1H,s), 9.68(1H,br.).

Reference Example 63

5-Hydroxy-3-isopropyl-8-methylcarbostyril

3-Isopropyl-5-methoxy-8-methylcarbostyril (2.10 g, 9.90 mmol) was suspended in chlorobenzene (50 ml), to which aluminum chloride (4.20 g, 31.5 mmol) was added. The mixture was stirred at 110° C. for 1 hour. The reaction mixture was cooled on ice, and methanol (30 ml) was added thereto. After stirring for 10 minutes, the reaction mixture was condensed under reduced pressure. The resultant residue was recrystallized from water to obtain 1.60 g of the title compound as pale yellow powdery crystals (81.1%).

mp. 258°–261° C. (dec.)

IR(KBr): 3175, 2950, 1630, 1608, 1569, 1504, 1440, 1403, 1352, 1250, 1235, 1086, 806, 798 cm$^{-1}$.

$^1$H-NMR(CD$_3$OD)δ: 1.27(6H,d,J=6.83 Hz), 2.35(3H,s), 3.21(1H,septet,J=6.83 Hz), 6.53(1H,d,J=8.06 Hz), 7.10(1H, d,J=8.06 Hz), 8.09(1H,s).

Reference Example 64

5-Allyloxy-3-isopropyl-8-methylcarbostyril

5-Hydroxy-3-isopropyl-8-methylcarbostyril (1.60 g, 7.37 mmol) was dissolved in dimethylformamide (30 ml), to which potassium carbonate (2.50 g, 18.1 mmol) and allyl iodide (0.71 ml, 7.76 mmol) were added. The mixture was stirred at 70° C. for 90 minutes. The reaction mixture was condensed under reduced pressure. The resultant residue was extracted from chloroform-water. The organic phase was washed with saturated aqueous NaCl solution, dried, and condensed under reduced pressure. The residue was recrystallized from chloroform-ether to obtain 1.85 g of the title compound as pale yellow powdery crystals (97.9%).

mp. 211°–212° C. (dec.)

IR(KBr): 3396, 3162, 3004, 2900, 1641, 1608, 1586, 1497, 1449, 1391, 1299, 1253, 1240, 1081, 924 cm$^{-1}$.

$^1$H-NMR(CDCl$_3$)δ: 1.28(6H,d,J=6.84 Hz), 2.34(3H,s), 3.27(1H,septet,J=6.84 Hz), 4.65(2H,d,J=5.31 Hz), 5.34(1H, dd,J=1.22,10.50 Hz), 5.47(1H,dd,J=1.22,17.33 Hz), 6.13(1H,m), 6.53(1H,d,J=8.30 Hz), 7.16(1H,d,J=8.30 Hz), 8.04(1H,s), 8.66(1H,br.).

Synthetic Example 65

6-Allyl-5-hydroxy-3-isopropyl-8-methylcarbostyril

5-Allyloxy-3-isopropyl-8-methylcarbostyril (1.85 g, 7.20 mmol) was suspended in N,N-dimethylaniline (20 ml). The suspension was heated and dissolved while stirring at 202° C. for 90 minutes. The reaction system was heated under reduced pressure until condensed. The resultant residue was recrystallized from methanol-ether-hexane to obtain 1.50 g of the title compound as pale yellow powdery crystals (81.1%).

mp. 210°–212° C. (dec.)

IR(KBr): 3250, 3183, 2947, 1626, 1571, 1485, 1438, 1387, 1354, 1301, 1265, 1250, 1213, 1180, 1128, 1080, 925, 791, 591 cm$^{-1}$.

$^1$H-NMR(CDCl$_3$) δ: 1.28(6H,d,J=6.84 Hz), 2.33(3H,s), 3.28(1H,septet,J=6.84 Hz), 3.44(2H,d,J=5.86 Hz), 5.24(1H, dd,J=1.47,17.58 Hz,overlapped with 1H, dd, J=1.47,9.76 Hz), 5.67(1H,br.), 6.02(1H,m), 7.08(1H,s), 7.99(1H,s), 8.82(1H,br.).

Example 318

2-Bromomethyl-8-isopropyl-5-methyl-6,7-dihydrofuro[2,3-f]quinoline-7-one

6-Allyl-5-hydroxy-3-isopropyl-8-methylcarbostyril (1.50 g, 5.34 mmol) was dissolved in chloroform (100 ml). N-bromosuccinimide (1.10 g, 6.18 mmol) was added to the solution, and the mixture was stirred at 75° C. for 90 minutes. The reaction mixture was extracted from chloroform-water, and the organic phase was washed with saturated aqueous NaCl solution, dried, and condensed under reduced pressure. The residue was recrystallized from chloroform -ethyl acetate-ether to obtain 1.95 g of the title compound as pale yellow needles (99.4%).

mp. 242°–244° C. (dec.)

IR(KBr): 3405, 3156, 3009, 2900, 1643, 1617, 1587, 1481, 1449, 1390, 1330, 1260, 1241, 1212, 1193, 1080, 977, 920, 861, 827, 800, 662 cm$^{-1}$.

$^1$H-NMR(CDCl$_3$)δ: 1.27(3H,d,J=6.83 Hz), 1.28(3H,d,J= 6.83 Hz) 2.34(3H,s), 3.18(1H,dd,J=7.08,15.87 Hz), 3.26(1H,septet,J=6.83 Hz), 3.43(1H,dd,J=9.25,15.87 Hz), 3.57(1H,dd,J=6.84,10.49 Hz), 3.69(1H,dd,J=4.64,10.49 Hz), 5.13(1H,s), 7.07(1H,s), 7.69(1H,s), 8.87(1H,br.).

Example 319

2-Azidomethyl-8-isopropyl-5-methyl-6,7-dihydrofuro[2,3-f]quinoline-7-one

2-Bromomethyl-8-isopropyl-5-methyl-6,7-dihydrofuro [2,3f]quinoline-7-one (1.95 g, 5.80 mmol) was dissolved in dimethylformamide (100 ml), to which sodium azide (1.00 g, 15.4 mmol) was added. The mixture was stirred at 120° C. for 1 hour. The reaction mixture was condensed under reduced pressure, and the resultant residue was extracted from chloroform-water. The organic phase was washed with saturated aqueous NaCl solution, dried, and condensed under reduced pressure. The residue was separated and purified by silica gel column chromatography (chloroform) to obtain pale yellow crude crystals. They were recrystallized from chloroform-ether-hexane to obtain 1.45 g of the title compound as pale yellow powdery crystals (83.8%).

mp. 206°–208° C. (dec.)

IR(KBr): 3391, 3150, 2900, 2087, 1631, 1585, 1481, 1448, 1299, 1267, 1249, 1093, 1080, 894, 872 cm$^{-1}$.

$^1$H-NMR(CDCl$_3$)δ: 1.26(6H,d,J=6.84 Hz), 2.34(3H,s), 3.03(1H,dd,J=6.35,15.14 Hz), 3.26(1H,septet,J=6.84 Hz), 3.38(1H,dd,J=9.77,15.14 Hz), 3.49(1H,dd,J=4.39,13.18 Hz), 3.55(1H,dd,J=6.34,13.18 Hz), 5.12(1H,m), 7.07(1H,s), 7.72(1H,s), 8.77(1H,br.).

Example 320

2-Aminomethyl-8-isopropyl-5-methyl-6,7-dihydrofuro[2,3-f]quinoline-7-one·HCl 2-Azidomethyl-8-isopropyl-5-methyl-6,7-dihydrofuro[2, 3-f]quinoline-7-one (1.45 g, 4.87 mmol) was dissolved in dimethylformamide (200 ml). To the solution, 10% palladium-on-carbon (1.45 g) was added, followed by stirring at room temperature for 90 minutes in the atmosphere of hydrogen. The reaction mixture was filtered, and the filtrate was condensed under reduced pressure. The resultant residue was recrystallized from methanol-ether to obtain 1.32 g of the title compound as pale yellow powdery crystals (87.9%).

mp. >300° C.

IR(KBr) 3397, 2948, 1643, 1585, 1476, 1447, 1255, 1080 cm$^{-1}$.

$^1$H-NMR(CD$_3$OD)δ: 1.26(6H,d,J=6.84 Hz), 2.39(3H,s), 3.05(1H,dd,J=6.84,15.63 Hz), 3.18–3.37(3H,complex m), 3.50(1H,dd,J=9.77,15.63 Hz), 5.19(1H,m), 7.20(1H,s), 7.89(1H,s).

Reference Example 66

3-Isopropyl-8-methyl-5-prenyloxycarbostyril

5-HYdroxy-3-isopropyl-8-methylcarbostyril (1.50 g, 6.91 mmol) was dissolved in dimethylformamide (30 ml). To the solution, potassium carbonate (3.00 g, 21.7 mmol) and prenyl bromide (0.90 ml, 7.67 mmol) were added, and the mixture was stirred at 70° C. for 7 hours. The reaction mixture was condensed under reduced pressure, and the resultant residue was extracted from chloroform-water. The organic phase was washed with saturated aqueous NaCl solution, dried, and condensed under reduced pressure. The residue was recrystallized from chloroform-ethyl acetate to obtain 1.85 g of the title compound as pale yellow needles (97.9%).

mp. 175°–177° C.

IR(KBr): 3403, 3165, 2900, 1644, 1606, 1583, 1495, 1450, 1379, 1340, 1293, 1270, 1236, 1095, 1028, 984, 924, 837, 801, 792 cm$^{-1}$.

$^1$H-NMR(CDCl$_3$)δ: 1.28(6H,d,J=6.83 Hz), 1.77(3H,s), 1.83(1H,s), 2.34(3H,s), 3.27(1H,septet,J=6.83 Hz), 4.63(2H, d,J=6.34 Hz), 5.55(1H,t,J=6.34 Hz), 6.54(1H,d,J=8.30 Hz), 7.16(1H,d,J=8.30 Hz), 8.01(1H,s), 8.69(1H,br.).

Reference Example 66

6-(1,2-Dimethylallyl)-5-hydroxy-3-isopropyl-8-methylcarbostyril

3-Isopropyl-8-methyl-5-prenyloxycarbostyril (1.90 g, 6.67 mmol) was suspended in N,N-dimethylaniline (30 ml). The suspension was heated and dissolved while stirring at 202° C. for 2 hours. The reaction system was heated under reduced pressure until condensed. The resultant residue was recrystallized from chloroform-hexane to obtain 1.70 g of the title compound as pale yellow powdery crystals (89.5%).

mp. 162°–164° C.

IR(KBr): 3430, 3155, 2951, 1636, 1608, 1547, 1485, 1444, 1374, 1348, 1294, 1265, 1209, 1132, 1139, 1084, 1043, 925, 894, 791, 581, 540 cm$^{-1}$.

$^1$H-NMR(CDCl$_3$)δ: 1.27(6H,d,J=6.83 Hz), 1.46(3H,d,J=7.33 Hz), 1.63(3H,s), 2.35(3H,s), 3.27(1H,septet,J=6.83 Hz), 3.49(1H,t,J=7.33 Hz), 5.13(1H,s), 5.21(1H,s), 6.22(1H, br), 7.01(1H,s), 7.98(1H,s), 8.87(1H,br).

Example 321

6-(1,2-Dimethylallyl)-2-iodomethyl-8-isopropyl-2,3,5-trimethyl-6,7-dihydrofuro[2,3-f]quinoline-7-one 5-Hydroxy-3-isopropyl-8-methylcarbostyril (1.60 g, 5.61 mmol) was dissolved in a solvent mixture of chloroform-methanol (4:1). To the resultant solution, potassium carbonate (5.00 g, 36.2 mmol) was added, and the mixture was stirred at −20° C. During stirring, a solution of iodine (1.70 g, 6.70 mmol) and potassium iodide (1.15 g, 6.93 mmol) in a solvent mixture (130 ml, cooled at −20° C.) of chloroform and methanol (4:1) was added thereto. The temperature was maintained at −20° C., and stirring was continued for 18 hours. The reaction mixture was extracted from chloroform-water, and the organic phase was washed with saturated aqueous sodium chloride solution, dried, and condensed under reduced pressure. The residue was recrystallized from ethyl acetate-ether-hexane to obtain 2.10 g of the title compound (syn:anti=6:1) as pale yellow powdery crystals (91.0%).

mp. 191°–192° C.

IR(KBr) 3397, 3151, 3008, 2950, 2856, 1637, 1616, 1588, 1479, 1447, 1390, 1379, 1325, 1305, 1261, 1220, 1082, 1058, 1043, 1030, 915, 874, 853, 814, 616 cm$^{-1}$.

$^1$H-NMR(CDCl$_3$)δ: 1.28(6H,d,J=6.84 Hz), 1.32(3H,d,J=7.33 Hz), 1.69(3H,s), 2.38(3H,s), 3.27(1H,septet,J=6.84 Hz), 3.35(d,J=10.7 Hz), 3.42(d,J=10.74 Hz)(altogether,1H), 3.41(q,J=7.33 Hz), 3.44(q,J=7.33 Hz), (altogether,1H), 3.45(d,J=10.74 Hz), 3.52(d,J=10.74 Hz)(altogether,1H), 6.98(s), 7.01(s)(altogether,1H), 7.69(s), 7.22(s)(altogether, 1H), 9.31(1H,br).

Example 322

2-Azidomethyl-8-isopropyl-2,3,5-trimethyl-6,7-dihydrofuro[2,3-f]quinoline-7-one

2-Iodomethyl-8-isopropyl-2,3,5-trimethyl-6,7-dihydrofuro[2,3-f]quinoline-7-one (2.10 g, 5.11 mmol) was dissolved in dimethylformamide (75 ml). To the solution, sodium azide (4.50 g, 69.2 mmol) was added, and the mixture was stirred at 150° C. for 4 hours. The reaction mixture was condensed under reduced pressure, and the residue was extracted from chloroform-water. The organic phase was washed with saturated aqueous sodium chloride solution, dried, and condensed under reduced pressure. The residue was separated and purified by silica gel column chromatography (chloroform) to obtain pale yellow crude crystals. The obtained crude was recrystallized from chloroform-ether-hexane to obtain 1.25 g of the title compound (syn:anti=1) as a colorless powder (75.0%).

mp. 185°–187° C.

IR(KBr): 3412, 3246, 3014, 2950, 2864, 2089, 1636, 1586, 1478, 1447, 1382, 1326, 1282, 1260, 1225, 1091, 1080, 1065, 1033, 923, 896, 876, 857, 812, 646, 604, 569 cm$^{-1}$.

$^1$H-NMR(CDCl$^3$)δ: 1.24(3H,d,J=6.84 Hz), 1.26(3H,d,J=6.84 Hz), 1.29(3H,d,J=7.33 Hz), 1.46(s), 1.62(s)(altogether, 3H), 2.37(3H,s), 3.14(d,J=12.70 Hz), 3.28(d,J=12.70 Hz)(altogether,1H), 3.26(1H,septet,J=6.84 Hz), 3.39(1H,q,J=7.33 Hz), 3.47(d,J=12.70 Hz), 3.54(d,J=12.70 Hz)(altogether, 1H), 6.98(s), 7.01(s)(altogether,1H), 7.71(s), 7.75(s)(altogether,1H), 9.02(1H,br).

Example 323

2-Aminomethyl-8-isopropyl-2,3,5-trimethyl-6,7-dihydrofuro[2,3-f]quinoline-7-one·HCl 2-Azidomethyl-8-isopropyl-2,3,5-trimethyl-6,7-dihydrofuro[2,3-f]quinoline-7-one (1.25 g, 3.83 mmol) was dissolved in dimethylformamide (200 ml). To the solution, 10% palladium-on-carbon (1.45 g) was added, followed by stirring at room temperature for 90 minutes in the atmosphere of hydrogen. The reaction mixture was filtered, and the filtrate was condensed under reduced pressure. The resultant residue was suspended in methanol (50 ml), and the suspension was dissolved with 1.37 N HCl-methanol (4 ml, 5.31 mmol). The reaction mixture was condensed under reduced pressure, and the residue was recrystallized from methanol-ether to obtain 1.08 g of the title compound as colorless powdery crystals (83.7%).

mp. >300° C.

IR(KBr): 3404, 3152, 2948, 2910, 2860, 1645, 1615, 1589, 1505, 1480, 1449, 1390, 1379, 1263, 1227, 1096, 1082, 1060, 1029, 881, 847, 811, 606 cm$^{-1}$.

$^1$H-NMR(CD$_3$OD)δ: 1.26(3H,d,J=6.84 Hz), 1.27(3H,d,J=6.84 Hz), 1.32(3H,d,J=7.33 Hz), 1.49(s), 1.64(s)(altogether, 3H), 2.40(3H,s), 3.14–3.27(3H,complex m), 3.39(q,J=7.33 Hz), 3.50(q,J=7.33 Hz)(altogether,1H), 7.16(1H,s), 7.85(s), 7.00(s)(altogether,1H).

Reference Example 67

3-Isopropyl-8-methyl-5-(2-methylallyl)oxycarbostyril

Using 5-hydroxy-3,3,8-trimethylcarbostyril (1.0 g, 46 mmol) and β-methallylchloride (500 mg, 5.5 mmol), the procedure of Reference Example 64 was followed (reaction, post-treatment, and recrystallization from chloroform-hexane). 1.19 g of the title compound was obtained as colorless needles (88.1%).

mp. 212°–213° C.

IR(KBr): 3003, 1638, 1496, 1448, 1237, 1098 cm$^{-1}$.

$^1$H-NMR(CDCl$_3$)δ: 1.28(6H,d,J=7.0 Hz), 1.89(3H,s), 2.34(3H,s), 3.27(1H,m), 4.54(2H,s), 5.04(1H,s) 5.15(1H,s), 6.53(1H,d,J=8.0 Hz), 7.15(1H,d,J=8.0 Hz), 8.05(1H,s).

Reference Example 68

5-Hydroxy-3-isopropyl-8-methyl-6-(2-methylallyl)carbostyril

Using 3-isopropyl-8-methyl-5-(2-methylallyl)oxycarbostyril (1.0 g, 3.7 mmol), the procedure of Reference Example 65 was followed (reaction, post-treatment, recrystallization from ethyl acetate-hexane). 930 mg of the title compound was obtained as colorless needles (92.6%).

mp. 205°–206° C.

IR(KBr): 3365, 3210, 2953, 1629, 1570, 1442, 1355, 1254, 1221 cm$^{-1}$.

$^1$H-NMR(CDCl$_3$)δ: 1.27(6H,d,J=7.0 Hz), 1.75(3H,s), 2.34(3H,s), 3.25(1H,m), 3.39(2H,s), 4.85(1H,s), 4.93(1H,s), 7.10(1H,s), 8.05(1H,s).

Example 324

2-Bromomethyl-8-isopropyl-2,5-dimethyl-2,3,6,7-tetrahydrofuro[2,3-f]quinoline-7-one Using 5-hydroxy-3-isopropyl-8-methyl-6-(2-methylallyl-)carbostyril (900 mg, 3.3 mmol), the procedure of Example 318 was followed (reaction, post-treatment, recrystallization of crude crystals from ethyl acetate-hexane). 820 mg of the title compound was obtained as colorless crystals (70.5%).

mp. 231°–232° C.

IR(KBr): 3154, 3007, 1638, 1477, 1448, 1261, 1076, 810 cm$^{-1}$.

$^1$H-NMR(CDCl$_3$)δ: 1.27(6H,d,J=7.0 Hz), 1.68(3H,s), 2.32(3H,s), 3.05(1H,d,J=16.2 Hz), 3.26(1H,m), 3.41(1H,d,J=16.2 Hz), 3.58(2H,s), 7.05(1H,s), 7.68(1H,s), 8.62(1H,s).

Example 325

2-Azidomethyl-8-isopropyl-2,5-dimethyl-2,3,6,7-tetrahydrofuro[2,3-f]quinoline-7-one Using 2-bromomethyl-8-isopropyl-2,5-dimethyl-2,3,6,7-tetrahydrofuro[2,3-f]quinoline-7-one (700 mg, 2.2 mmol), the procedure of Example 319 was followed (reaction, post-treatment, purification of crude crystals by silica gel column chromatography (chloroform-methanol=20:1), followed by recrystallization from ethyl acetate-hexane). 520 mg of the title compound was obtained as colorless crystals (74.3%).

mp. 171°–172° C.

IR(KBr): 3006, 2095, 1638, 1479, 1448, 1260, 1079 cm$^{-1}$.

$^1$H-NMR(CDCl$_3$)δ: 1.25(6H,d,J=7.2 Hz), 1.58(3H,s), 2.33(3H,s), 3.02(1H,d,J=15.4 Hz), 3.20(1H,d,J=15.4 Hz), 3.25(1H,m), 3.41(2H,s), 7.05(1H,s), 7.70(1H,s), 8.64(1H,s).

Example 326

2-Aminomethyl-8-isopropyl-2,5-dimethyl-2,3,6,7-tetrahydrofuro[2,3-f]quinoline-7-one·HCl Using 2-azidomethyl-8-isopropyl-2,5-dimethyl-2,3,6,7-tetrahydrofuro[2,3-f]quinoline-7-one (480 mg, 1.54 mmol), the procedure of Example 320 was followed (reaction, post-treatment, followed by recrystallization of the resultant crude crystals of a hydrochloric acid salt from methanol-ether). 300 mg of the title compound was obtained as colorless crystals (62.0%).

mp. >300° C.

IR(KBr): 3397, 2950, 1642, 1478, 1449, 1260, 1080 cm$^{-1}$.

$^1$H-NMR(CDCl$_3$—CD$_3$OD)δ: 1.26(6H,d,J=7 Hz), 1.63(3H,s), 2.38(3H,s), 3.13(1H,d,J=16 Hz), 3.16–3.31(4H, m), 7.13(1H,s), 7.81(1H,s).

Reference Example 69

5-(2-Butenyloxy)-3-isopropyl-8-methylcarbostyril

3-Isopropyl-5-hydroxy-8-methyl-1,2-dihydrocarbostyril (2.2 g, 10.13 mmol) was dissolved in dimethylformamide (25 ml). Crotylbromide (1.22ml, 12.11 mmol) and potassium carbonate (2.8 g, 20.26 mmol) were added to the solution, and the mixture was stirred at 70° C. for 2.5 hours. After the mixture was cooled, chloroform-water was added for phase separation. The organic phase was washed with water, and saturated aqueous sodium chloride solution in this order, and dried. The solvent was distilled off under reduced pressure, and the residue was recrystallized from chloroform-n-hexane. As a result, 1.88 g of the title compound was obtained as colorless needles (68%).

mp. 210°–213° C.

IR(KBr): 3159, 3005, 1641, 1584, 1497, 1448, 1375, 1237, 962, 924, 799 cm$^{-1}$.

$^1$H-NMR(CDCl$_3$):1.29(6H,d,J=6.8 Hz), 1.79(3H,d,J=5.9 Hz), 2.34(3H,s), 3.27(1H,septet,J=6.8 Hz), 4.57(2H,d,J=5.4 Hz), 5.73–5.94(2H,complex m), 6.54(1H,d,J=8.3 Hz), 7.15(1H,d,J=8.3 Hz), 8.02(1H,s), 8.82(1H,bs).

Reference Example 70

5-Hydroxy-3-isopropyl-6-(1-methyl-allyl)-8-methylcarbostyril

Dimethylaniline (6 ml) was added to the compound obtained in Reference Example 69 (1.805 g, 6.65 mmol), and the mixture was stirred at 200° C. for 1.5 hour. After the mixture was cooled, ethyl acetate was added thereto, followed by washing with saturated aqueous potassium hydrogensulfate solution and saturated aqueous sodium chloride solution, and drying. The solvent was distilled off under reduced pressure, and the residue was recrystallized from ethyl acetate-hexane. 1.66 g of the title compound was obtained as pale purple crystals (92%).

mp. 157°–159° C.

IR(KBr): 3186, 2950, 1628, 1575, 1483, 1440, 1408, 1298, 1271, 1210, 929, 884, 793 cm$^{-1}$.

$^1$H-NMR(CDCl$_3$)δ: 1.27(6H,d,J=6.8 Hz), 1.44(3H,d,J=6.8 Hz), 2.34(3H,s), 3.28(1H,septet,J=6.8 Hz), 3.60(1H,m), 5.28(1H,d,J=1.5 Hz), 5.33(1H,dd,J=1.5,5.4 Hz), 5.86(1H, bs), 6.12(1H,m), 7.02(1H,s), 7.99(1H,s), 8.81(1H,bs).

Example 327

2-Bromomethyl-8-isopropyl-3,5-dimethyl-2,3,6,7-tetrahydrofuro[2,3-f]quinoline-7-one The compound obtained in Reference Example 70 (1.62 g, 5.97 mmol) was dissolved in chloroform (10 ml). To the resultant solution, N-bromosuccinimide (1.17 g, 6.57 mmol) was added and refluxed for 1 hour. Subsequently, N-bromosuccinimide (53 mg) was further added, and refluxed for 20 minutes. After the system was cooled, chloroform-water was added for phase separation. The organic phase was washed with saturated aqueous sodium chloride solution, and dried. The solvent was distilled off under reduced pressure. The residue was washed with ethyl acetate, obtaining 2.01 g of the title compound (96%).

mp. 221°–224° C.

IR(KBr): 3154, 3012, 2858, 1642, 1588, 1481, 1449, 1261, 1218, 948, 917, 848 cm$^{-1}$.

¹H-NMR(CDCl₃)δ: 1.26(d,J=6.8 Hz), 1.40(d,J=6.8 Hz) (altogether,3H), 1.27(6H,d,J=6.8 Hz), 2.35(3H,s), 3.26(1H, septet,J=6.8 Hz), 3.43–3.75(3H,complex m), 4.63(m), 5.04(m)(altogether,1H), 7.03(s), 7.04(s)(altogether,1H), 7.70(1H,s), 8.78(1H,bs).

Example 328

2-(Azidomethyl)-8-isopropyl-3,5-dimethyl-2,3,6,7-tetrahydrofuro[2,3-f]quinoline-7-one The compound obtained in Example 327 (1.97 g, 5.62 mmol) was dissolved in dimethylformamide (25 ml). To the resultant solution, sodium azide (2.2 g, 33.84 mmol) was added, and the mixture was stirred at 150° C. for 3 hours. After the mixture was cooled, ethyl acetate-water was added for phase separation. The organic phase was washed with water, and saturated aqueous sodium chloride solution in this order, and dried. The solvent was distilled off under reduced pressure, and the residue was washed with hexane. 1.3 g of the title compound was obtained (78%).

mp. 186°–190° C. (dec.)

IR(KBr): 3156, 3015, 2082, 1641, 1586, 1480, 1447, 1262, 1081, 849 cm⁻¹.

¹H-NMR(CDCl₃)δ: 1.26(d,J=6.8 Hz), 1.36(d,J=6.8 Hz) (altogether,3H), 1.27(6H,d,J=6.8 Hz), 2.36(3H,s), 3.26(1H, septed,J=6.8 Hz), 3.29–3.69(3H,complex m), 4.59(m), 5.03(dt,J=4.4,8.8 Hz)(altogether,1H), 7.03(1H,s), 7.73(s), 7.75(s)(altogether,1H), 8.82(1H,bs).

Example 329

2-(Aminomethyl)-8-isopropyl-3,5-dimethyl-2,3,6,7-tetrahydrofuro[2,3-f]quinoline-7-one·HCl The compound obtained in Example 328 (1.3 g, 4.16 mmol) was dissolved in tetrahydrofuran (25 ml) and dimethylformamide (5 ml). To the solution, 10% palladium-on-carbon (650 mg) was added, followed by stirring at room temperature for 3 hours in the stream of hydrogen. The catalyst was filtered off, and the filtrate was distilled off under reduced pressure. The residue was subjected to silica gel column chromatography to obtain 1.16 g of an amine compound from the eluent of chloroform: methanol=3:1. The amine compound was purified with a Rober column (benzene:methanol=3:1) to obtain 363 mg of a first component (trans form of the title compound), and 237 mg of the last component (cis form of the title compound). The components were converted into hydrochloric acid salts to obtain 363 mg of a trans compound as pale yellow crystals (27%), and 215 mg of a cis compound as colorless crystals (16%).

Trans Compound·HCl mp. >250° C.

IR(KBr): 3383, 2943, 1641, 1586, 1477, 1448, 1261, 1079, 965 cm⁻¹.

¹H-NMR(CD₃CD)δ: 1.26(6H,d,J=6.8 Hz), 1.41(3H,d,J=6.8 Hz), 2.40(3H,s), 3.20–3.41(4H,complex m), 4.67(1H, m), 7.19(1H,s), 7.88(1H,s).

Free Base of the Trans Compound

¹H-NMR(CDCl₃)δ: 1.27(3H,d,J=6.8 Hz), 1.28(3H,d,J=6.8 Hz), 1.35(3H,d,J=6.8 Hz), 2.33(3H,s), 3.00(1H,dd,J=6.8,13.7 Hz), 3.10(1H,dd,J=3.9,13.7 Hz), 3.22–3.32(2H, complex m), 4.43(1H,dt,J=3.9,6.8 Hz), 7.02(1H,s), 7.73(1H, s), 8.63(1H,bs).

Cis Compound·HCl mp. >250° C.

IR(KBr): 3399, 2946, 1640, 1585, 1477, 1448, 1262, 1080, 965, 935, 825 cm⁻¹.

¹H-NMR(DMSO-d₆)δ: 1.17(3H,s), 1.21(6H,d,J=6.8 Hz), 2.34(3H,s), 3.08–3.25(3H,complex m), 3.68(1H,m), 5.06(1H,m), 7.13(1H,s), 7.74(1H,s).

Free Base of the Cis Compound

¹H-NMR(CDCl₃)δ: 1.21(3H,d,J=7.3 Hz), 1.27(6H,d,J=6.8 Hz), 2.33(3H,s), 2.99(1H,dd,J=3.9,13.7 Hz), 3.13(1H, dd,J=8.8,13.7 Hz), 3.27(1H,septet,J=6.8 Hz), 3.56(1H,quintet,J=7.3 Hz), 4.81(1H,dt,J=3.9,8.8 Hz), 7.03(1H,s), 7.73(1H,s), 8.58(1H,bs).

Reference Example 71

6-Bromo-3-methoxyaniline

4-Bromo-3-nitroanisole (19.8 g, 85.1 mmol) was dissolved in methanol (150 ml). Conc. HCl (40 ml) was added to the resultant solution, and the mixture was stirred while cooling. During stirring, reduced iron (14.3 g) was added to the mixture by small portions, and the mixture was stirred at room temperature for 4 hours. The reaction mixture was condensed under reduced pressure. 2N-Caustic soda solution (100 ml) was added to the condensate, and the insoluble matter was filtered off. The filtrate was extracted with chloroform. The organic phase was dried and condensed under reduced pressure to obtain 16.0 g of the title compound, 3-methoxyaniline, as a brown oil (93.0%).

IR(KBr): 3444, 3363, 1610, 1489, 1460, 1299, 1262, 1207, 1169, 1045, 1008, 825, 601 cm⁻¹.

¹H-NMR(CDCl₃)δ: 7.29(1H,d,J=8.8 Hz), 6.34(1H,d,J=2.5 Hz), 6.25(1H,dd,J=2.5,8.8 Hz), 4.16–3.95(2H,br), 3.76(3H,s).

Reference Example 72

N-(2-Brom-5-methoxyphenyl)-3,3-dimethylacrylamide

6-Bromo-3-methoxyaniline (13.8 g, 68.3 mmol) was dissolved in pyridine (200 ml). To the resultant solution, 3,3-dimethylacroylchloride (7.71 g, 65.0 mmol) was added dropwise while cooling on ice. After the addition was completed the mixture was stirred at room temperature for 2 hours. The reaction mixture was condensed under reduced pressure, and the residue was dissolved in chloroform, followed by washing with aqueous 2N-HCl solution, water, aqueous 2N-caustic soda solution in this order. The organic phase was dried, and condensed under reduced pressure. As a result, the title compound was obtained as an red oil.

IR(KBr): 3286, 1660, 1636, 1585, 1518, 1451, 1298, 1234, 1170, 1150, 1016, 846 cm⁻¹.

¹H-NMR(CDCl₃)δ: 8.21(1H,d,J=2.9 Hz), 7.59–7.48(1H, br), 7.33(1H,d,J=8.8 Hz), 6.50(1H,dd,J=2.9,8.8 Hz), 5.73(1H,s), 3.77(3H,s), 2.20(3H,s), 1.89(3H,s).

Reference Example 73

4,4-Dimethyl-5-hydroxy-3,4-dihydrocarbostyril

N-(2-Brom-5-methoxyphenyl)-3,3-dimethylacrylamide (530 mg, 1.87 mmol) was dissolved in m-dichlorobenzene (10 ml). To the resultant solution, aluminum chloride (1.24 g, 9.33 mmol) was added, and the mixture was stirred at 120° C. for 40 minutes. The reaction mixture was poured into ice-water, followed by extracting with chloroform-methanol (10:1), and drying. Subsequently, the residue was subjected to silica gel column chromatography (developer= chloroform-methanol =30:1). From the first eluate, 152 mg of 4,4-dimethyl-5-hydroxy-3,4-dihydrocarbostyril (152 mg, 42.5%) was obtained as pale yellow needles. From the second eluate, 4,4-dimethyl-7-hydroxy-3,4-dihydrocarbostyril (63 mg, 17.6%) was obtained as pale yellow needles.

mp. 245°–246° C.

IR(KBr): 3185, 1591, 1587, 1490, 1407, 1287, 1219, 1069, 807, 781 $cm^{-1}$.

$^1$H-NMR(CDCl$_3$—CD$_3$OD)δ: 6.96(6H,t,J=7.8 Hz), 6.49(1H,d,J=7.8 Hz), 6.34(1H,d,J=7.8 Hz), 2.43(2H,s), 1.45(6H,s).

Reference Example 74

5-Allyloxy-4,4-dimethyl-3,4-dihydrocarbostyril 4,4-Dimethyl-5-hydroxy-3,4-dihydrocarbostyril (3.45 g, 18.0 mmol) was dissolved in dimethylformamide (100 ml). To the solution, potassium carbonate (2.99 g, 21.7 mmol) and allyl iodide (3.33 g, 19.9 mmol) were added, and the mixture was stirred at 100° C. for 24 hours. Subsequently, potassium carbonate (1.5 g, 10.9 mmol) and allyl iodide (1.65 g, 9.82 mmol) were added and stirring was continued for 24 hours. The reaction mixture was condensed under reduced pressure. Chloroform and water were added to the residue, and extracted. After the extract was dried and condensed, the residue was purified by silica gel column chromatography (developer=chloroform:methanol=50:1). Recrystallization from a solvent mixture of chloroform-hexane-ether yielded 2.06 g of the title compound as pale yellow needles (52.3%).

mp. 141°–142° C.

IR(KBr): 2917, 1676, 1592, 1507, 1467, 1389, 1268, 1234, 1088, 987, 925, 729 $cm^{-1}$.

$^1$H-NMR(CDCl$_3$)δ: 7.80–7.69(1H,br), 7.08(1H,t,J=7.8 Hz), 6.58(1H,d,J=7.8 Hz), 6.36(1H,d,J=7.8 Hz), 6.07(1H,m), 5.40(1H,dd,J=1.5,15.7 Hz), 5.29(1H,dd,J=1.5,10.4 Hz), 4.56(2H,d,J=5.4 Hz), 2.48(2H,s), 1.44(6H,s).

Reference Example 75

6-Allyl-4,4-dimethyl-5-hydroxy-2,3-dihydrocarbostyril

5-Allyloxy-4,4-dimethyl-3,4-dihydrocarbostyril (817 mg, 3.73 mmol) was dissolved in dimethylaniline (15 ml), and the resultant solution was stirred in a bath at 205° C. for 5 hours. The reaction solution was condensed under reduced pressure, followed by extracting with chloroform and 2N-aqueous caustic soda solution. The aqueous phase was neutralized with conc. HCl. Subsequently, the neutralized phase was extracted with a mixture of chloroform-methanol (10:1), dried, and condensed under reduced pressure. Recrystallization from a mixture of chloroform-methanol-ether yielded 710 mg of the title compound as pale yellow needles (86.9%).

mp. 210°–212° C.

IR(KBr): 3122, 2959, 1638, 1544, 1457, 1421, 1366, 1398, 1177, 875 $cm^{-1}$.

$^1$H-NMR(CDCl$_3$—CD$_3$OD)δ: 6.61(1H,d,J=7.8 Hz), 6.32(1H,d,J=7.8 Hz), 5.94(1H,m), 4.96(1H,dd,J=1.5,16.1 Hz), 4.90–4.86(1H,m), 3.51(2H,m), 2.36(1H,s), 1.42(6H,s).

Example 330

5-Bromo-2-bromomethyl-9,9-dimethyl-2,3,6,7,8,9-hexahydrofuro[2,3-f]quinoline-7-one To 6-allyl-4,4-dimethyl-5-hydroxy-2,3-dihydrocarbostyril (489 mg, 2.23 mmol) in chloroform (30 ml), N-bromosuccinimide (873 mg, 4.91 mmol) was added, and the mixture was refluxed with heat for 2.5 hours. The reaction mixture was cooled, and then washed with saturated aqueous sodium chloride solution, dried and condensed under reduced pressure. The residue was recrystallized from chloroform-ether to obtain 670 mg of the title compound as yellow needles (77.1%).

mp. 237°–239° C.

IR(KBr): 3150, 1620, 1468, 1443, 1288, 1248, 1199, 1120, 1077, 865, 626 $cm^{-1}$.

$^1$H-NMR(CDCl$_3$)δ: 7.85–7.73(1H,br), 7.18(1H,s), 5.09–4.97(1H,m), 3.59–3.48(2H,m), 3.33(1H,dd,J=9.3,15.6 Hz), 3.04(1H,dd,J=5.9,15.6 Hz), 2.47(2H,s), 1.41(3H,s), 1.40(3H,s).

Example 331

2-Azidomethyl-5-bromo-9,9-dimethyl-2,3,6,7,8,9-hexahydrofuro[2,3-f]quinoline-7-one 5-Bromo-2-bromomethyl-9,9-dimethyl-2,3,6,7,8,9-hexahydrofuro[2,3-f]quinoline-7-one (1.25 g, 3.21 mmol) was dissolved in dimethylformamide (50 ml). To the resultant solution, sodium azide (1.25 g, 19.3 mmol) was added, and the mixture was stirred at room temperature for 17 hours. The reaction mixture was condensed under reduced pressure, and the residue was extracted along with chloroform and water. The organic phase was dried, and condensed under reduced pressure. Recrystallization from chloroform-n-hexane-ether yielded 997 mg of the title compound as pale yellow needles (88.4%).

mp. 187°–189° C.

IR(KBr): 3211, 2086, 1675, 1605, 1461, 1421, 1357, 1232, 1122, 1028, 744 $cm^{-1}$.

$^1$H-NMR(CDCl$_3$)δ: 7.84–7.73(1H,br), 7.20(1H,s), 5.04–4.91(1H,m), 3.48(2H,m), 3.25(1H,dd,J=9.8,15.1 Hz), 2.97(1H,dd,J=6.8,15.1 Hz), 2.47(2H,s), 1.42(3H,s), 1.41(3H,s).

Example 332

2-Aminomethyl-9,9-dimethyl-2,3,6,7,8,9-hexahydrofuro[2,3-f]quinoline-7-one

2-Azidomethyl-5-bromo-9,9-dimethyl-2,3,6,7,8,9-hexahydrofuro[2,3-f]quinoline-7-one (997 mg, 2.84 mmol) was dissolved in methanol (50 ml). To the solution, 10% palladium-on-carbon (1.0 g) was added, followed by stirring in a bath at 50° C. for 1 hour in the atmosphere of hydrogen. The catalyst was filtered off, and the filtrate was condensed under reduced pressure. Recrystallization from a solvent mixture of methanol-ether yielded 560 mg of the title compound as a yellow powder (80.4%).

mp. 230°–233° C.

IR(KBr): 3045, 1669, 1472, 1428, 1373, 1210, 1055, 915, 843, 804 $cm^{-1}$.

¹H-NMR(CDCl₃—CD₃OD)δ: 6.95(1H,d,J=7.8 Hz), 6.34(1H,d,J=7.8 Hz), 4.93–4.79(1H,m), 3.24(1H,dd,J=9.3, 15.1 Hz), 2.92(2H,m), 2.81(1H,dd,J=6.8,15.1 Hz), 2.44(2H, s), 1.42(3H,s), 1.39(3H,s).

Example 333

The compound obtained in Example 332 (550 mg) was dissolved in methanol, to which HCl in 1,4-dioxane (4N) was added to convert the compound into a hydrochloric acid salt. Subsequently, the salt was condensed under reduced pressure. Recrystallization from a mixture of methanol-ether yielded 541 mg of a hydrochloric acid salt of the compound of example 332 as a yellow powder (84.1%).

mp. 292°–294° C. (dec.)

IR(KBr): 3406, 2943, 1653, 1471, 1427, 1385, 1211, 1054, 977, 809 cm⁻¹.

¹H-NMR(CD₃OD)δ: 7.01(1H,d,J=7.8 Hz), 6.46(1H,d,J= 7.8 Hz), 5.06(1H,m), 3.40–3.21(3H,complex m), 2.93(1H, dd,J=7.8,15.6 Hz), 2.40(2H,s), 1.41(6H,s).

Example 334-1

2-Aminomethyl-5-bromo-9,9-dimethyl-2,3,6,7,8,9-hexahydrofuro[2,3-f]quinoline-7-one 2-Azidomethyl-5-bromo-9,9-dimethyl-2,3,6,7,8,9-hexahydrofuro[2,3-f]quinoline-7-one (492 mg, 1.40 mmol) was dissolved in tetrahydrofuran (10 ml). To the solution, triphenylphosphine (404 mg, 1.54 mmol) was added, and the mixture was stirred in a bath at 50° C. for 2 hours. After completion of the reaction, aqueous 2N-caustic soda solution (2 ml) was added to the reaction mixture, followed by stirring a further 1 hour at room temperature. The reaction mixture was condensed under reduced pressure, and extracted with chloroform and 2N-HCl. The aqueous phase was neutralized with aqueous 2N-caustic soda solution, and then extracted with a solvent mixture of chloroform-methanol (10:1), dried, and condensed under reduced pressure. The condensate was purified by silica gel column chromatography (developer=chloroform). Recrystallization from chloroform-methanol-ether yielded 330 mg of the title compound as pale yellow needles (72.1%).

mp. 252°–255° C.

IR(KBr): 2989, 1685, 1605, 1470, 1429, 1350, 1267, 1195, 1146, 1065, 984, 925 cm⁻¹.

¹H-NMR(CDCl₃)δ: 7.82–7.73(1H,br), 7.18(1H,s), 4.87(1H,m), 3.22(1H,dd,J=8.8,15.1 Hz), 3.03–2.82(3H, complex m), 2.47(2H,s), 1.43(3H,s), 1.39(3H,s).

Example 334-2

The compound obtained in Example 334 (330 mg) was dissolved in methanol, to which 1.37N HCl in methanol (0.8 ml) was added to convert the compound into a hydrochloric acid salt. Subsequently, the salt was recrystallized from methanol-ether to obtain 311 mg of a hydrochloric acid salt of this compound as pale yellow needles (85.1%).

mp. 276°–278° C. (dec.)

IR(KBr): 3400, 2945, 1669, 1625, 1467, 1364, 1266, 1197, 1062, 742 cm⁻¹.

¹H-NMR(CD₃OD)δ: 7.31(1H,s), 5.08(1H,m), 3.42–3.20(3H,complex m), 2.97(1H,dd,J=7.8,16.1 Hz), 2.46(2H,s), 1.43(6H,s).

Example 335

2-(2'-Boc-amino-3'-tritylmercaptopropionyl)aminomethyl-5-methyl-2,3,6,7-tetrahydrofuro[2,3-f]quinoline-7-one Boc-S-trytyl-L-cysteine (6.04 g, 13.03 mmol) and WSC·HCl (2.43 g, 15.65 mmol) were suspended in tetrahydrofuran (200 ml). To the resultant suspension, a suspension of 2-aminomethyl-5-methyl-2,3,6,7-tetrahydrofuro[2,3-f] quinoline-7-one (3.30 g, 14.33 mmol) in tetrahydrofuran (400 ml) was added dropwise at room temperature. The mixture was stirred at room temperature overnight. The solvent was distilled off under reduced pressure. The residue was dissolved in chloroform (500 ml), and washed with water (500 ml), saturated aqueous sodium bicarbonate solution (500 ml), and saturated aqueous sodium chloride solution (500 ml) in this order, followed by drying. The solvent was distilled off under reduced pressure, and the residue was purified by silica gel column chromatography (eluent=chloroform:methanol=50:1). As a result, 7.60 g of the title compound was obtained as a pale brown powder (80.2%).

IR(KBr): 3265, 3045, 2970, 2920, 1655, 1615, 1515, 1485, 1465, 1445, 1390, 1365, 1310, 1245, 1215, 1160, 1080, 1065, 1030, 830, 790, 740, 700 cm⁻¹.

¹H-NMR(CDCl₃)δ: 8.83(1H,br), 7.84(d,J=9.8 Hz), 7.81(d,J=9.8 Hz), (altogether,1H), 7.42–7.35(5H,m), 7.25(1H,m), 7.02(1H,s), 6.61–6.42(2H,m), 4.98(1H,m), 3.97–3.45(3H,m), 3.24(1H,m), 2.96(1H,m), 2.77(1H,m), 2.47(1H,m), 2.28(s), 2.27(s)(altogether,3H), 1.38(s), 1.34(s)(altogether,9H).

Example 336

2-(2'-Amino-3'-tritylmercaptopropionyl)aminomethyl-5-methyl-2,3,6,7-tetrahydrofuro[2,3-f]quinoline-7-one 2-(2'-Boc-amino-3'-tritylmercaptopropionyl)aminomethyl-5-methyl-2,3,6,7-tetrahydrofuro[2,3-f]quinoline-7-one (8.01 g) was dissolved in methanol (30 ml). To the solution, 5% HCl/methanol (20 ml) was added, and the mixture was stirred at room temperature overnight. The solvent was distilled off under reduced pressure, and the residue, dissolved in chloroform, was washed with saturated aqueous sodium bicarbonate solution and saturated aqueous sodium chloride solution in this order, and dried. When the solvent was distilled off under reduced pressure, 6.61 g of the title compound was obtained as a pale brown powder (96.9%).

Separation and Purification of Diastereomers by Silica Gel Column Chromatography When a diastereomer mixture (6.61 g) was subjected to silica gel column chromatography (eluent=chloroform-methanol =80:1–50:1) for separation, 1.07 g of a first component, 691 mg of a last component, and 3.68 g of an unseparated material were obtained.

First Component: Pale Brown Powder

IR(KBr): 3260, 3165, 3040, 3000, 2915, 1650, 1615, 1570, 1511, 1485, 1460, 1440, 1310, 1265, 1245, 1215, 1145, 1080, 1065, 1030, 875, 830, 740, 700, 675, 635, 615 cm⁻¹.

¹H-NMR(CDCl₃)δ: 8.84(1H,br), 7.85(1H,d,J=8.7 Hz), 7.55(1H,br), 7.43–7.38(5H,m), 7.29–7.19(5H,m), 6.98(1H, s), 6.54(1H,d,J=9.8 Hz), 4.99(1H,m), 3.62(1H,m), 3.52(1H, m), 3.26(1H,m), 3.08(1H,m), 2.95(1H,m), 2.72(1H,m), 2.58(1H,m), 2.23(3H,s), 1.45(1H,br).

Last Component: Pale Brown Powder

IR(KBr): 3345, 3270, 3165, 3040, 3000, 2910, 1650, 1635, 1615, 1510, 1485, 1465, 1440, 1310, 1265, 1240, 1210, 1145, 1080, 1065, 1030, 830, 740, 695, 675, 615 cm$^{-1}$.

$^1$H-NMR(CDCl$_3$)δ: 8.79(1H,br), 7.86(1H,d,J=9.8 Hz), 7.44–7.38(6H,m), 7.32–7.18(10H,m), 7.06(1H,s), 6.58(1H, d,J=9.8 Hz), 4.97(1H,m), 3.65(1H,m), 3.46(1H,m), 3.26(1H, m), 2.98–2.89(2H,m), 2.69(1H,m), 2.60(1H,m), 2.30(3H,s), 1.56(2H,br).

Example 337

2-(2'-Amino-3'-tritylmercaptopropionyl)aminomethyl-5-methyl-2,3,6,7-tetrahydrofuro[2,3-f]quinoline-7-one·HCl (1) Hydrochloric acid salt of the first component separated by silica gel column chromatography:

2-(2'-Amino-3'-tritylmercaptopropionyl)aminomethyl-5-methyl-2,3,6,7-tetrahydrofuro[2,3-f]quinoline-7-one (1.05 g, 1.82 mmol) was dissolved in a mixture of methanol (5 ml) and chloroform (5 ml). To the resultant solution, 5% HCl/methanol (1.50 ml, 2.06 mmol) was added dropwise while cooling with ice-water. The mixture was stirred at room temperature for 20 minutes. The solvent was distilled off under reduced pressure. When the residue was recrystallized from methanol-ether, 879 mg of a hydrochloric acid salt of the first component was obtained as pale yellow crystals (78.8%).

mp. 234.7°–239.2° C. (dec.)

IR(KBr): 3375, 3195, 3035, 2950, 2910, 2850, 1650, 1615, 1555, 1485, 1460, 1440, 1315, 1265, 1245, 1215, 1150, 1080, 1065, 1045, 830, 740, 700, 675, 620 cm$^{-1}$.

$^1$H-NMR(CD$_3$OD)δ: 7.99(1H,d,J=9.8 Hz), 7.87–7.21(16H,m), 6.54(1H,d,J=9.8 Hz), 5.09(1H,m), 3.80(1H,m), 3.54–3.40(2H,m), 3.34(1H,m), 3.04(1H,m), 2.64(1H,m), 2.56(1H,m), 2.37(3H,s).

(2) Hydrochloric acid salt of the last component separated by silica gel column chromatography:

2-(2'-Amino-3'-tritylmercaptopropionyl)aminomethyl-5-methyl-2,3,6,7-tetrahydrofuro[2,3-f]quinoline-7-one (640 mg, 1.11 mmol) was treated in a manner similar to the above. Recrystallization from methanol-ether yielded 512 mg of a hydrochloric acid salt of the last component as pale yellow crystals (76.6%).

mp. 236.5°–239.7° C. (dec.)

IR(KBr): 3370, 3185, 3035, 2905, 1650, 1615, 1560, 1485, 1460, 1440, 1400, 1315, 1265, 1245, 1210, 1150, 1080, 1065, 1030, 830, 740, 700, 670, 615 cm$^{-1}$.

$^1$-HNMR(CD$_3$OD)δ: 7.99(1H,d,J=9.8 Hz), 7.32–7.23(15H,m), 7.60(1H,s), 6.50(1H,d,J=9.8 Hz), 5.08(1H,m), 3.88(1H,m), 3.53–3.46(2H,m), 3.28(1H,m), 3.07(1H,m), 2.64(1H,m), 2.56(1H,m), 2.28(3H,s).

Example 338

2-Bromomethyl-5-methyl-2,3,6,7,8,9-hexahydrofuro[2,3-f]quinoline-7-one

2-Bromomethyl-5-methyl-2,3,6,7-tetrahydrofuro[2,3-f]quinoline-7-one (4.0 g, 13.6 mmol) was dissolved in acetic acid (100 ml). To the resultant solution, 10% palladium-on-carbon (4 g) was added, followed by stirring at 70° C. for 7 hours in the stream of hydrogen. The palladium-on-carbon was filtered off, and the filtrate was condensed under reduced pressure. Ether was added to the residue, obtaining 3.15 g of the title compound as a colorless solid (78.2%).

IR(KBr): 1666, 1627, 1471, 1375, 1203 cm$^{-1}$.

$^1$H-NMR(CDC$_3$)δ: 2.16(3H,s), 2.54–2.96(4H,m), 3.09(1H,dd,J=6.5,15.7 Hz), 3.35(1H,dd,J=9.2,15.7 Hz), 3.52(1H,dd,J=6.8,10.3 Hz), 3.63(1H,dd,J=4.9,10.3 Hz), 5.02(1H,m), 6.86(1H,s), 7.45(1H,br).

Example 339

2-Benzoxycarbonylhydrazinomethyl-5-methyl-2,3,6,7,8,9-hexahydrofuro[2,3-f]quinoline-7-one The compound obtained in Example 338 (1.5 g, 5.1 mmol) was dissolved in dimethylformamide (40 ml), to which carbobenzoxy hydrazine (4.2 g, 25.3 mmol) was added, and stirred at 150° C. for 5 hours. The reaction mixture was poured into water, and then extracted with chloroform. The organic phase was washed with water, dried, and condensed under reduced pressure. As a result, 0.744 g of the title compound was obtained as a colorless solid (40.0%).

IR(KBr): 1670, 1627, 1471, 1377, 1270 cm$^{-1}$.

$^1$H-NMR(DMSO-d$_6$)δ: 2.11(3H,s), 2.34–3.56(8H,m), 4.82(1H,m), 5.07(2H,s), 6.83(1H,s), 7.37(5H,s), 8.76(1H, br), 9.32(2H,br).

Example 340

2-Hydrazinomethyl-5-methyl-2,3,6,7,8,9-hexahydrofuro[2,3-f]quinoline-7-one

The compound obtained in Example 339 (0.77 g, 2.0 mmol) was dissolved in a mixture of dimethylformamide (6 ml), methanol (11 ml), and 5% HCl-methanol solution (2 ml). To the resultant solution, 10% palladium-on-carbon (0.30 g) was added, followed by stirring at ambient temperature for 2 hours in the stream of hydrogen. The palladium-on-carbon was filtered off, and the solvent was distilled off under reduced pressure. 0.438 g of the title compound was obtained as pale yellow crystals (76.5%).

IR(KBr): 1669, 1626, 1470, 1439, 1372, 1054 cm$^{-1}$.

$^1$H-NMR(D$_2$O)δ: 2.15(3H,s), 2.50–3.48(8H,m), 5.14(1H, m), 7.01(1H,s).

Example 341

2-(1,1-Bisethoxycarbonylmethylidenhydrazino)methyl-5-methyl-2,3,6,7,8,9-hexahydrofuro[2,3-f]quinoline-7-one The compound obtained in Example 340 (0.43 g, 1.5 mmol), triethylamine (0.23 g, 2.3 mmol) and diethylketomalonic acid (1.1 g, 6.0 mmol) were dissolved in chloroform (8 ml), and the resultant solution was stirred at ambient temperature for 15 hours. The reaction mixture was washed with water, dried over sodium sulfate, and condensed under reduced pressure. Ether was added to the residue, and 0.315 g of the title compound was obtained as colorless needles (52.0%, mp.: 137°–139° C.).

IR(KBr): 1714, 1684, 1650, 1523, 1472, 1377, 1282 cm$^{-1}$.

$^1$H-NMR(CDCl$_3$)δ: 1.36(6H,t,J=7.1 Hz), 2.16(3H,s), 2.56–2.98(5H,m), 3.32(1H,dd,J=9.4,15.6 Hz), 3.81–3.93(2H,m), 4.28(2H,q,J=7.1 Hz), 4.32(2H,q,J=7.1 Hz), 5.03(1H,m), 6.83(1H,s), 7.35(1H,br), 11.42(1H,br).

Example 342

2-Cyanoaminomethyl-5-methyl-2,3,6,7-tetrahydrofuro[2,3-f]quinoline-7-one

2-Aminomethyl-5-methyl-2,3,6,7-tetrahydrofuro[2,3-f]quinoline-7-one (1.0 g, 4.34 mmol) was dissolved in tetrahydrofuran (120 ml), to which cyanogen bromide (2.76 g, 26 mmol) was added and the mixture was stirred at 40° C. for 4 hours. After completion of the reaction, the precipitated crystals were collected by filtration, and washed with water. As a result, 0.427 g of the title compound was obtained as yellow crystals (38.5%). Recrystallization from chloroform-methanol yielded the title compound as pale yellow needles (mp: 227°–230° C. (dec.)).

IR(KBr): 2206, 1628, 1564, 1464, 1438, 1326 cm$^{-1}$.

$^1$H-NMR(DMSO-d$_6$)δ: 2.32(3H,s), 2.95(1H,dd,J=6.8, 15.6 Hz), 3.08–3.50(3H,m), 5.03(1H,m), 6.45(1H,d,J=9.7 Hz), 7.07(1H,br), 7.20(1H,s), 7.82(1H,d,J=9.7 Hz), 10.78(1H ,br).

Example 343

2-Cyanoaminomethyl-5-methyl-2,3,6,7,8,9-hexahydrofuro[2,3-f]quinoline-7-one

Using 2-aminomethyl-5-methyl-2,3,6,7,8,9-hexahydrofuro[2,3-f]quinoline-7-one (1.30 g, 5.6 mmol), cyanogen bromide (3.56 g, 33.6 mmol), and tetrahydrofuran (150 ml), the procedure of Example 342 was followed. 0.631 g of the title compound was obtained as yellow crystals (43.8%). Recrystallization from chloroform-methanol yielded the title compound as colorless needles (mp.: 209°–210° C.).

IR(KBr): 2210, 1662, 1628, 1472, 1439, 1373 cm$^{-1}$.

$^1$H-NMR(DMSO-d$_6$)δ: 2.11(3H,s), 2.35–3.40(8H,m), 4.85(1H,m), 6.83(1H,s), 7.00(1H,br), 9.32(1H,br).

Example 344

2-(1-Iminoethylaminomethyl)-5-methyl-2,3,6,7-tetrahydrofuro[2,3-f]quinoline-7-one (a) and N,N'-bis(5-methyl-7-oxy-2,3,6,7-tetrahydrofuro[2,3-f]quinoline-2-ylmethyl)acetamidine (b)

To a solution of 2-aminomethyl-5-methyl-2,3,6,7-tetrahydrofuro[2,3-f]quinoline-7-one (1.15 g, 5.0 mmol) in methanol (20 ml), a hydrochloric acid salt of ethylacetamidate (620 mg, 5.0 mmol) was added while cooling on ice, followed by stirring for 4 hours. The reaction mixture was condensed under reduced pressure, and the residue was purified by silica gel column chromatography. As a result, 560 mg of the title compound (a) (42.5%) was obtained as pale yellow crystals, and compound (b) was obtained.

The obtained compound (b) was dissolved in methanol. To the resultant solution, 1.37N-HCl/methanol (1 ml) was added, and the mixture was condensed under reduced pressure. The residue was recrystallized from methanol-ether to obtain a hydrochloric acid salt of the compound (b) as pale yellow crystals (15.4%).

(a)
mp. 150°–154° C. (dec.)
IR(KBr): 3220, 1660 cm$^{-1}$.
$^1$H-NMR(CD$_3$OD+CDCl$_3$)δ: 2.24(3H,s), 2.36(3H,s), 3.06(1H,m), 3.45(1H,m), 3.50–3.75(2H,m), 5.15(1H,m), 6.53(1H,d,J=9 Hz), 7.20(1H,s), 7.93(1H,d,J=9 Hz).
Hydrochloric Acid Salt of (b)
mp. 229°–233° C. (dec.)
IR(KBr): 3393, 3222, 1661, 1473, 1372 cm$^{-1}$.
$^1$H-NMR(CD$_3$OD+CDCl$_3$)δ: 2.05(3H,s), 2.35(6H,s), 3.00(1H,m), 3.30(1H,m), 3.40–3.65(2H,m), 5.10(1H,m), 6.53(1H,d,J=10 Hz), 7.16(1H,s), 7.92(1H,d,J=10 Hz).

Example 345

2-(1-Iminoethylaminomethyl)-5-methyl-2,3,6,7,8,9-hexahydrofuro[2,3-f]quinoline-7-one (a) and N,N'-bis(5-methyl-7-oxy-2,3,6,7,8,9-hexahydrofuro[2,3-f]quinoline-2ylmethyl)acetamidine (b)

2-Aminomethyl-5-methyl-2,3,6,7,8,9-hexahydrofuro[2,3-f]quinoline-7-one (1.15 g, 5.0 mmol) was processed in a manner similar to that described in Example 344. 700 mg of the title compound (a) (51.4%) and 350 mg of the title compound (b) (14.4%) were obtained both as colorless crystals.

(a):
mp. 149°–153° C. (dec.)
IR(KBr): 3211, 3060, 1667, 1472, 1382 cm$^{-1}$.
$^1$H-NMR(CD$_3$OD+CDCl$_3$)δ: 2.17(3H,s), 2.26(3H,s), 2.56(2H,t,J=7 Hz), 2.85(2H,t,J=7 Hz), 2.93(1H,m), 3.33(1H,m), 3.43–3.71(2H,m), 5.00(1H,m), 7.40(1H,s).
(b):
mp. 210°–214° C. (dec.)
IR(KBr): 3394, 1652, 1402 cm$^{-1}$.
$^1$H-NMR(CD$_3$OD+CDCl$_3$)δ: 2.07(3H,s), 2.35(6H,s), 2.50(2H,t,J=7 Hz), 2.84(2H,t,J=7 Hz), 3.05(1H,m), 3.50(1H,m), 3.40–3.70(2H,m), 5.15(1H,m), 7.35(1H,s).

Reference Example 76

N-(2-methyl-4,5-dimethoxyphenyl)cinnamamide

To a solution of 4,5-dimethoxy-2-methylaniline (40.1 g), pyridine (48.5 ml), and acetone (350 ml), cinnamoyl chloride (44.0 g) was added dropwise at room temperature over 15 minutes. After allowing to react at room temperature for 2 hours, water (15 ml) was added and the mixture was stirred for 20 minutes. The solvent was distilled off under reduced pressure, and the residue was dissolved in chloroform, followed by washing with 1N HCl, 1N caustic soda and water in this order, and drying. Chloroform was evaporated. Precipitated crystals were collected by filtration with ether. 69.8 g of the title compound was obtained as yellow crystals (97.8%).

$^1$H-NMR(CDCl$_3$)δ: 2.24(3H,s), 3.86(6H,s), 6.60(1H,d,J=15.1 Hz), 6.69(1H,s), 7.20(1H,bs), 7.37(3H,bs), 7.53(3H,bs), 7.75(1H,d,J=15.1 Hz).

Reference Example 77

5,6-Dihydroxy-8-methylcarbostyril

The compound obtained in Reference Example 76 (69.8 g) was suspended in m-dichlorobenzene (420 ml). To the resultant suspension, aluminum chloride powder was added while stirring. Subsequently, reaction was allowed to proceed in a bath at 110° C. for 1 hour. The reaction product was added into ice-water (1.5 l), and then conc. HCl (60 ml) was added thereto. Precipitated crystals were collected by filtration. The collected material was washed with ether, and dried at 60° C. under reduced pressure. 37.5 g of the title compound was obtained as yellowish brown crystals (83.5%).

¹H-NMR(DMSO-d₆)δ: 2.26(3H,s), 6.36(1H,d,J=9.8 Hz), 6.86(1H,s), 8.02(1H,d,J=9.8 Hz), 9.01(1H,s), 9.03(1H,bs), 10.51(1H,bs).

Example 345

2-Hydroxycarbonyl-5-methyl-6,7-dihydro-1,3-dioxo[4,5-f]quinoline-7-one

To a solution of the 5,6-dihydro-8-methylcarbostyril (9.58 g, 50.1 mmol) obtained in Reference Example 77 in dimethylformamide (150 ml), potassium carbonate (26.3 g, 0.20 mol) and methyldichloroacetate (12.9 g, 90.2 mmol) were added. The mixture was stirred at 60° C. for 15 hours in the stream of argon gas. The solvent was distilled off under reduced pressure. HCl was added to the residue. The insoluble matter was collected, and then washed with water. 5.36 g of the title compound was obtained (43.3%).

mp. 246°–250° C. (dec.)

IR(KBr): 1651, 1463, 1320, 1200, 1080 cm⁻¹.

¹H-NMR(DMSO-d₆)δ: 2.36(3H,s), 6.53(1H,d,J=9.6 Hz), 6.64(1H,s), 7.83(1H,d,J=9.6 Hz).

Example 346

2-Hydroxymethyl-5-methyl-6,7-dihydro-1,3-dioxo[4,5-f]quinoline-7-one

To a mixture of the dimethylformamide (50 ml) and tetrahydrofuran (150 ml), the compound obtained in Example 345 (5.65 g, 22.9 mmol) was suspended. To the suspension, triethylamine (6.94 g, 68.6 mmol) was added, and the mixture was stirred for 1 hour while adding ethyl chlorocarbonate (7.44 g, 68.6 mmol) dropwise in a bath of ice-water. The insoluble mater was filtered off, and the solution was added dropwise into an aqueous solution of sodium borohydride (8.65 g, 0.23 mol) in water (50 ml) while cooling in a bath of ice-aqueous NaCl solution and stirring for 1 hour. Diluted HCl was added to the reaction mixture, followed by extracting with chloroform-methanol (8:1). The extract was dried and distilled off under reduced pressure. The residue was purified by silica gel column chromatography to obtain 1.40 g of the title compound as pale yellowish brown crystals (20.2%).

mp. 243°–245° C. (dec.)

IR(KBr): 1648, 1614, 1496, 1466, 1416, 1319, 1205 cm⁻¹.

¹H-NMR(CDCl₃—CD₃OD)δ: 2.38(3H,s), 3.97(2H,d,J=4.0 Hz), 6.34(1H,t,J=4.0 Hz), 6.63(1H,d,J=9.5 Hz), 6.95(1H,s), 7.90(1H,d,J=9.5 Hz).

Example 347

2-Azidomethyl-5-methyl-6,7-dihydro-1,3-dioxo[4,5-f]quinoline-7-one

The compound obtained in Example 346 (1.05 g, 4.51 mmol) was dissolved in pyridine (20 ml), to which mesylchloride (1.03 g, 9.0 mmol) was added. The mixture was stirred at ambient temperature for 2 hours. The reaction mixture was condensed under reduced pressure. The residue was dissolved in a solvent mixture of chloroform-methanol (8:1), followed by washing with diluted HCl, saturated aqueous sodium bicarbonate solution, and water in this order, and drying. The solvent was distilled off under reduced pressure. The residue was dissolved in dimethylformamide (40 ml). Sodium azide (1.46 g, 22.5 mmol) was added to the solution, and the mixture was stirred at 100° C. for 2 hours. The reaction mixture was distilled under reduced pressure, and the resultant residue was combined with water, followed by extracting with chloroform-methanol (10:1). The extract was dried, and the solvent was distilled off under reduced pressure. The residue was washed with ether to obtain 1.00 g of the title compound as pale brown crystals (85.9%).

mp. 188°–190° C. (dec.)

IR(KBr): 2092, 1652, 1495, 1461, 1320, 1204, 1105, 832 cm⁻¹.

¹H-NMR(CDCl₃)δ: 2.37(3H,s), 3.63(2H,m), 6.38(1H,t,J=3.9 Hz), 6.63(1H,d,J=9.7 Hz), 6.93(1H,s), 7.80(1H,d,J=9.7 Hz).

Example 348

2-Aminomethyl-5-methyl-6,7-dihydro-1,3-dioxo[4,5-f]quinoline-7-one

The compound obtained in Example 347 (1.33 g, 5.15 mmol) was dissolved in pyridine (45 ml), to which triphenylphosphine (2.70 g, 10.3 mmol) was added. The mixture was stirred at ambient temperature for 1 hour. Subsequently, 29% ammonia water (90 ml) was added to the reaction mixture, and the resultant mixture was allowed to react at ambient temperature for 4 hours. The reaction mixture was distilled off under reduced pressure, and the residue was washed with ether. As a result, 1.13 g of the title compound was obtained (94.5%).

mp. 218°–221° C. (dec.)

IR(KBr): 1653, 1615, 1492, 1457, 1318, 1215, 1066 cm⁻¹.

¹H-NMR(CDCl₃)δ: 1.64(2H,br), 2.35(3H,s), 3.22(2H,d, J=3.4 Hz), 6.22(1H,t,J=3.4 Hz), 6.65(1H,d,J=9.8 Hz), 6.91(1H,s), 7.83(1H,d,J=9.8 Hz), 8.93(1H,br).

Example 349

2-Aminomethyl-5-methyl-6,7,8,9-tetrahydro-1,3-dioxo[4,5-f]quinoline-7-one

The compound obtained in Example 348 (0.45 g, 1.94 mmol) was dissolved in 0.15N HCl (14 ml). To the solution, 10% palladium-on-carbon (0.45 g) was added, and the mixture was stirred at 80° C. for 2 hours in the stream of hydrogen. The catalyst was filtered off from the reaction mixture. Distillation under reduced pressure yielded 0.37 g of the title compound as colorless crystals (70.5%).

mp. 265°–267° C. (dec.)

IR(KBr): 1664, 1490, 1467, 1373, 1323, 1273, 1114, 1028 cm⁻¹.

¹H-NMR(D₂O)δ: 2.16(3H,s), 2.52–3.00(4H,m), 3.59(2H, d,J=2.6 Hz), 6.46(1H,t,J=2.6 Hz), 6.73(1H,s).

TEST Example 1

Action on Mouse Arrhythmia Induced by Chloroform

Test compounds (100 mg/kg) were given to mice, and 20 minutes thereafter, the mice were confined in a pot filled with chloroform. Upon respiratory stoppage, the mice were immediately taken out of the pot, and electrocardiodiagram (lead II) was recorded to obtain ventricular tachycardia, ventricular fibrillation, and period until the cardiac arrest. The results were expressed by % inhibition of ventricular fibrillation, which are shown in Table 30.

TABLE 30

| Example No. | % Inhibition |
|---|---|
| Example 15 | 100 |
| Example 16 | 100 |
| Example 20 | 100 |
| Example 22 | 90 |
| Example 77 | 100 |
| Example 94 | 100 |
| Example 120 | 90 |
| Example 121 | 100 |

TEST Example 2

Inotropic Action and Action Against Time-dependent Action on Guinea Pig Atrium Samples Guinea pigs were smashed at the head, and were exsanguinated through a cut in the carotid artery. Their hearts were taken out. From each heart, the right and left atria were obtained. The atria were suspended in Krebs-Henzereit solution at 32° C. through which a gas containing 95% oxygen and 5% carbon dioxide was passed. The tensile strength was measured with a strain gauge, and was amplified and recorded. Beats of right atria were counted using a tachometer, and the counts were regarded as the cardiac rate. Electric pulses (1 Hz, 5 msec) having twice the magnitude of the threshold were applied onto the left atria. The samples were given to the guinea pigs in an accumulative manner at intervals of 5 minutes.

The results are expressed by the increment of contraction of the left atrium when $10^{-7}M$ of a sample was administered. The results are shown in Table 31.

TABLE 31

| Example No. | Increment of Contraction (%) |
|---|---|
| Example 13 | 31.8 |
| Example 50 | 11.1 |
| Example 103 | 13.1 |
| Example 106 | 46.8 |
| Example 109 | 20.3 |
| Example 114 | 18.8 |

TEST Example 3

Action on the Blood Flow of a Hind Leg of Anesthetic Dog

Adult crossbred dogs were put under anesthesia with pentobarbital-Na (30 mg/kg) by intravenous injection, Heparin was administered to each dog, and an extracorporeal circulation circuit was established in the femoral artery, The blood flow in the hind leg was measured with an electromagnetic hemodromometer placed on the circuit, The samples were administered at a dose of 100 μg into the feromal artery through a rubber tube provided on the circuit.

The results were expressed by the increment of blood flow, which are shown in Table 32.

TABLE 32

| Example No. | Increment of Blood Flow (%) |
|---|---|
| Example 16 | 92.6 |
| Example 17 | 80.8 |
| Example 21 | 35.7 |
| Example 50 | 26.7 |
| Example 82 | 31.0 |
| Example 99 | 97.0 |
| Example 103 | 66.7 |
| Example 106 | 39.5 |
| Example 107 | 54.1 |
| Example 108 | 54.8 |
| Example 120 | 110.0 |

Industrial Applicability

The compound (1) according to the present invention has positive inotropic action and antiarrhythmic action, and can dilate blood vessels without extremely increasing the heart rate. Therefore, a medicine for cardiac diseases containing the compound as the active component is remarkably useful for treating cardiac insufficiency, arrhythmia, and so forth.

We claim:

1. A quinoline derivative having formula selected from the group consisting of formulas (1a)–(1d):

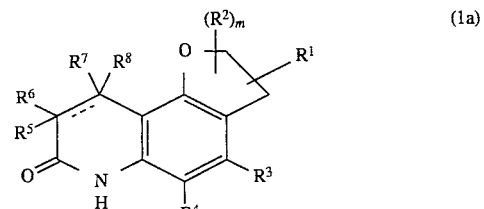
(1a)

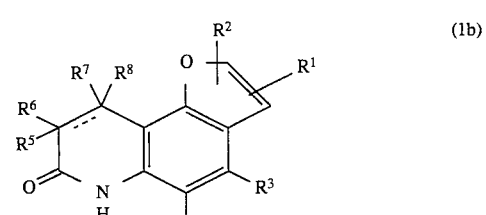
(1b)

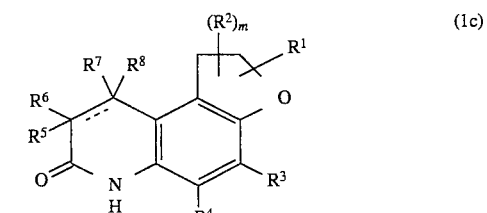
(1c)

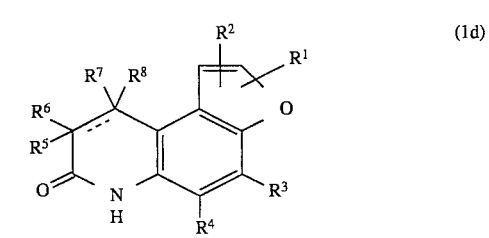
(1d)

$R^1$ is hydroxy, carboxy, alkoxycarbonyl, carbamoyl, alkenyl, formyl, cyano, alkyl optionally having an operative substituent, or a group

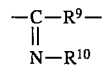

(wherein $R^9$ is amino or alkyl, and $R^{10}$ is hydrogen or hydroxy);

each $R^2$ is the same or different, and represents hydrogen, alkyl optionally having an operative substituent, alkenyl, acyl, or hydroxy;

$R^3$, $R^4$ are the same or different, and represent hydrogen, halogen, alkyl optionally having an operative substituent, amino optionally having an operative substituent, alkoxy, alkylthio, carboxy, alkoxycarbonyl, acyl, carbamoyl, cyano or nitro;

$R^5$, $R^6$, $R^7$, $R^8$ are the same or different, and represent hydrogen or alkyl;

m is a whole number from 0 to 3;

- - - means optionally having a double bond formed by $R^6$ and $R^8$; or a medicinally acceptable salt thereof.

2. The quinoline derivative according to claim 1 or a medicinally acceptable salt thereof, wherein $R^1$ in formula (1) is one of the following substituents:

$R^1$ is hydroxy, carboxy, C2–C9 alkoxycarbonyl, carbamoyl, C2–C8 alkenyl, formyl, cyano, a group

(wherein $R^9$ is amino or C1–C8 alkyl, and $R^{10}$ is hydrogen or hydroxy), or C1–C8 alkyl optionally substituted by halogen, hydroxy, alkoxy optionally having an operative substituent, alkylthio optionally having an operative substituent, acyloxy, alkylsulfonyl, alkylsulfonyloxy, nitroxy, azido, cyano, thiocyanato, amino optionally having an operative substituent, and cyclic amino optionally having an operative substituent.

3. A therapeutic method for treating heart disease comprising administering to a patient suffering from heart disease, an effective amount of a composition comprising a quinoline derivative having a formula selected from the group consisting of formulas (1a)–(1d):

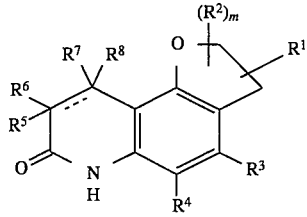

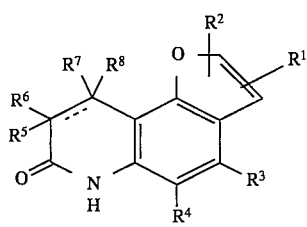

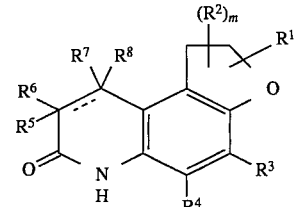

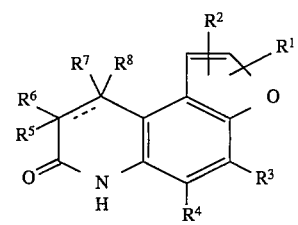

$R^1$ is hydroxy, carboxy, alkoxycarbonyl, carbamoyl, alkenyl, formyl, cyano, alkyl optionally having an operative substituent, or a group

(wherein $R^9$ is amino or alkyl, and $R^{10}$ is hydrogen or hydroxy);

each $R^2$ is the same or different, and represents hydrogen, alkyl optionally having an operative substituent, alkenyl, acyl, or hydroxy;

$R^3$, $R^4$ are the same or different, and represent hydrogen, halogen, alkyl optionally having an operative substituent, amino optionally having an operative substituent, alkoxy, alkylthio, carboxy, alkoxycarbonyl, acyl, carbamoyl, cyano, or nitro;

$R^5$, $R^6$, $R^7$, $R^8$ are the same or different, and represent hydrogen or alkyl;

m is a whole number from 0 to 3;

- - - means optionally having a double bond formed by $R^6$ and $R^8$; or a medicinally acceptable salt thereof.

4. The therapeutic method according to claim 3, wherein the patient is suffering from cardiac insufficiency or arrhythmia.

5. The method of claim 3, wherein said composition acts as a cardiotonic, antiarrhythmic agent or a vasodilator.

6. The method of claim 3, wherein said effective amount is 1 mg to 1 g per day.

7. A pharmaceutical composition for the treatment of heart diseases comprising an effective amount of a quinoline derivative according to claim 1 or a medicinally acceptable salt thereof, in admixture with a pharmaceutically acceptable carrier.

* * * * *